United States Patent
Pell et al.

(10) Patent No.: US 10,368,854 B2
(45) Date of Patent: *Aug. 6, 2019

(54) METHODS AND DEVICES TO DECREASE TISSUE TRAUMA DURING SURGERY

(71) Applicant: Physcient, Inc., Durham, NC (US)

(72) Inventors: Charles Anthony Pell, Durham, NC (US); Hugh Charles Crenshaw, Durham, NC (US)

(73) Assignee: Physcient, Inc., Durham, NC (US)

(*) Notice: Subject to any disclaimer, the term of this patent is extended or adjusted under 35 U.S.C. 154(b) by 168 days.

This patent is subject to a terminal disclaimer.

(21) Appl. No.: 15/495,248

(22) Filed: Apr. 24, 2017

(65) Prior Publication Data

US 2018/0035992 A1 Feb. 8, 2018

Related U.S. Application Data

(63) Continuation of application No. 13/111,762, filed on May 19, 2011, now abandoned, which is a
(Continued)

(51) Int. Cl.
*A61B 17/02* (2006.01)
*A61M 25/10* (2013.01)
(Continued)

(52) U.S. Cl.
CPC ........ *A61B 17/0218* (2013.01); *A61B 5/0051* (2013.01); *A61B 5/442* (2013.01);
(Continued)

(58) Field of Classification Search
CPC . A61B 17/02; A61B 17/0206; A61B 17/0218; A61B 17/025;
(Continued)

(56) References Cited

U.S. PATENT DOCUMENTS

| 1,156,440 A | 10/1915 | Smith |
| 2,013,892 A | 9/1935 | Lucas |

(Continued)

FOREIGN PATENT DOCUMENTS

| EP | 0980674 A3 | 3/2000 |
| EP | 1642536 A2 | 4/2006 |

(Continued)

OTHER PUBLICATIONS

Examination Report No. 1 for Australian Patent Application No. 2015202794, dated Mar. 21, 2016, 3 pages.
(Continued)

*Primary Examiner* — Samuel S Hanna
(74) *Attorney, Agent, or Firm* — Withrow & Terranova, P.L.L.C.

(57) ABSTRACT

Methods and devices are disclosed to reduce tissue trauma when a physician retracts a patient's tissues for surgery. A device includes a tissue engager adapted to engage a patient's tissue, a control system adapted to control the tissue engager to deform the patient's tissue, and a sensor adapted to produce a first signal based on the deformation. The control system is further adapted to receive the first signal, perform a plurality of measurements based on the first signal over time; and compare a substantially instantaneous measurement of the first signal to a variance in the plurality of measurements over an interval of time preceding the instantaneous measurement, and detect a state of the patient's tissue based on the comparison.

20 Claims, 166 Drawing Sheets

Related U.S. Application Data continuation-in-part of application No. 12/422,584, filed on Apr. 13, 2009, now Pat. No. 8,845,527.

(60) Provisional application No. 61/395,915, filed on May 19, 2010.

(51) Int. Cl.
    *A61B 5/00* (2006.01)
    *A61B 7/00* (2006.01)
    *A61B 17/12* (2006.01)
    *A61B 90/00* (2016.01)
    *A61B 17/00* (2006.01)

(52) U.S. Cl.
    CPC .............. *A61B 5/7239* (2013.01); *A61B 7/00* (2013.01); *A61B 17/02* (2013.01); *A61B 17/025* (2013.01); *A61B 17/0206* (2013.01); *A61B 17/0293* (2013.01); *A61B 17/12136* (2013.01); *A61B 90/03* (2016.02); *A61M 25/104* (2013.01); *A61B 2017/00022* (2013.01); *A61B 2017/00172* (2013.01); *A61B 2017/00181* (2013.01); *A61B 2017/00314* (2013.01); *A61B 2017/00323* (2013.01); *A61B 2017/00398* (2013.01); *A61B 2017/00539* (2013.01); *A61B 2017/00544* (2013.01); *A61B 2017/00557* (2013.01); *A61B 2017/00734* (2013.01); *A61B 2017/0225* (2013.01); *A61B 2017/0256* (2013.01); *A61B 2017/0262* (2013.01); *A61B 2090/064* (2016.02); *A61B 2090/065* (2016.02); *A61B 2090/0809* (2016.02); *A61B 2562/0219* (2013.01)

(58) Field of Classification Search
    CPC ........... A61B 2017/00022; A61B 2017/00172; A61B 2017/00181; A61B 2017/00398; A61B 2090/064; A61B 2090/065; A61B 2090/0809; A61B 5/442; A61B 2017/0256
    See application file for complete search history.

(56) References Cited

U.S. PATENT DOCUMENTS

| | | |
|---|---|---|
| 2,313,164 A | 3/1943 | Nelson |
| 2,460,470 A | 2/1949 | Rogers |
| 3,008,239 A | 11/1961 | Lange |
| 3,572,326 A | 3/1971 | Jensen |
| 3,665,925 A | 5/1972 | Dersookian |
| 3,766,909 A | 10/1973 | Ozbey |
| 3,785,381 A | 1/1974 | Lower et al. |
| 3,789,849 A | 2/1974 | Laufe et al. |
| 3,888,117 A | 6/1975 | Lewis |
| 3,965,890 A | 6/1976 | Gauthier |
| 4,041,937 A | 8/1977 | Diaz |
| 4,066,082 A | 1/1978 | Arcan et al. |
| 4,155,355 A | 5/1979 | Yamamoto |
| 4,254,763 A | 3/1981 | McCready et al. |
| 4,263,904 A | 4/1981 | Judet |
| 4,297,884 A | 11/1981 | Leveque et al. |
| 4,364,382 A | 12/1982 | Mennen |
| 4,424,724 A | 1/1984 | Bookwalter et al. |
| 4,432,376 A | 2/1984 | Huszar |
| 4,622,955 A | 11/1986 | Fakhrai |
| 4,777,943 A | 10/1988 | Chvapil |
| 4,784,150 A | 11/1988 | Voorhies et al. |
| 4,899,761 A | 2/1990 | Brown et al. |
| 4,945,896 A | 8/1990 | Gade |
| 4,989,587 A | 2/1991 | Farley |
| 5,020,933 A | 6/1991 | Salvestro et al. |
| 5,184,601 A | 2/1993 | Putman |
| 5,201,325 A | 4/1993 | McEwen et al. |
| 5,213,112 A | 5/1993 | Niwa et al. |
| 5,359,995 A | 11/1994 | Sewell, Jr. |
| 5,578,043 A | 11/1996 | Galstian |
| 5,679,245 A | 10/1997 | Manica |
| 5,735,791 A | 4/1998 | Alexander, Jr. et al. |
| 5,769,781 A | 6/1998 | Chappuis |
| 5,782,746 A | 7/1998 | Wright |
| 5,885,244 A | 3/1999 | Leone et al. |
| 5,957,950 A | 9/1999 | Mockros et al. |
| 6,007,552 A | 12/1999 | Fogarty et al. |
| 6,139,493 A | 10/2000 | Koros et al. |
| 6,200,318 B1 | 3/2001 | Har-Shai et al. |
| 6,241,706 B1 | 6/2001 | Leschinsky et al. |
| 6,251,093 B1 | 6/2001 | Valley et al. |
| 6,312,377 B1 | 11/2001 | Segermark et al. |
| 6,517,563 B1 | 2/2003 | Paolitto et al. |
| 6,730,021 B2 | 5/2004 | Vassiliades, Jr. et al. |
| 6,767,324 B2 | 7/2004 | D-Alessandro et al. |
| 6,837,851 B1 | 1/2005 | Valentini et al. |
| 7,059,182 B1 | 6/2006 | Ragner |
| 7,695,501 B2 | 4/2010 | Ellis et al. |
| 7,775,974 B2 | 8/2010 | Buckner et al. |
| 8,579,806 B2 | 11/2013 | Buckner et al. |
| 8,845,527 B2 | 9/2014 | Crenshaw et al. |
| 8,915,845 B2 | 12/2014 | Pell et al. |
| 9,049,989 B2 | 6/2015 | Crenshaw et al. |
| 9,402,610 B2 | 8/2016 | Pell et al. |
| 2002/0022770 A1 | 2/2002 | Borsody |
| 2002/0193734 A1 | 12/2002 | Moenning |
| 2003/0060685 A1 | 3/2003 | Houser et al. |
| 2003/0083648 A1 | 5/2003 | Wang et al. |
| 2003/0181800 A1 | 9/2003 | Bonutti |
| 2003/0216619 A1 | 11/2003 | Scirica et al. |
| 2003/0236472 A1 | 12/2003 | Van Hoeck et al. |
| 2004/0073301 A1 | 4/2004 | Lamard |
| 2004/0077931 A1 | 4/2004 | Lamard |
| 2004/0087955 A1 | 5/2004 | Bordi |
| 2004/0102806 A1 | 5/2004 | Broome et al. |
| 2004/0143166 A1 | 7/2004 | Lamard |
| 2004/0206365 A1 | 10/2004 | Knowlton |
| 2004/0225197 A1 | 11/2004 | Roux et al. |
| 2004/0230101 A1 | 11/2004 | Martin et al. |
| 2004/0260229 A1 | 12/2004 | Meir |
| 2005/0043592 A1 | 2/2005 | Boyd et al. |
| 2005/0043621 A1 | 2/2005 | Perlin |
| 2005/0119568 A1 | 6/2005 | Salcudean et al. |
| 2005/0137460 A1 | 6/2005 | Bertolero et al. |
| 2005/0175872 A1 | 8/2005 | Trabold et al. |
| 2005/0215866 A1 | 9/2005 | Kim |
| 2006/0025656 A1* | 2/2006 | Buckner ................. A61B 1/32 600/202 |
| 2006/0084843 A1 | 4/2006 | Sommerich et al. |
| 2006/0095032 A1 | 5/2006 | Jackson et al. |
| 2006/0184095 A1 | 8/2006 | Ott |
| 2006/0247500 A1 | 11/2006 | Voegele et al. |
| 2006/0273135 A1 | 12/2006 | Beetel |
| 2007/0032783 A1 | 2/2007 | Abboud et al. |
| 2007/0179408 A1 | 8/2007 | Soltz |
| 2007/0225558 A1 | 9/2007 | Hauck et al. |
| 2007/0250172 A1 | 10/2007 | Moskowitz et al. |
| 2007/0270685 A1 | 11/2007 | Kang et al. |
| 2009/0192360 A1 | 7/2009 | Riess et al. |
| 2009/0259107 A1 | 10/2009 | Crenshaw et al. |
| 2009/0259109 A1 | 10/2009 | Bucefari et al. |
| 2009/0287060 A1 | 11/2009 | Pell et al. |
| 2011/0201893 A1 | 8/2011 | O'Prey et al. |
| 2011/0295290 A1 | 12/2011 | Whitfield |
| 2012/0130180 A1 | 5/2012 | Pell et al. |
| 2012/0203070 A1 | 8/2012 | Crenshaw et al. |
| 2013/0090695 A1 | 4/2013 | Bernstein et al. |
| 2013/0197521 A1 | 8/2013 | Seykora et al. |
| 2013/0237766 A1 | 9/2013 | Pell et al. |
| 2015/0141906 A1 | 5/2015 | Pell et al. |
| 2015/0209093 A1 | 7/2015 | Dallis |

(56) References Cited

U.S. PATENT DOCUMENTS

| | | | |
|---|---|---|---|
| 2015/0351734 | A1 | 12/2015 | Crenshaw et al. |
| 2016/0000419 | A1 | 1/2016 | Weisshaupt et al. |

FOREIGN PATENT DOCUMENTS

| | | | |
|---|---|---|---|
| FR | 2211851 A5 | 7/1974 | |
| GB | 1520832 | 8/1978 | |
| WO | 8908425 A1 | 9/1989 | |
| WO | 2007099576 A2 | 9/2007 | |
| WO | 2008030256 A1 | 3/2008 | |
| WO | 2008030935 A3 | 3/2008 | |
| WO | 2009086402 A1 | 7/2009 | |
| WO | 2009126953 A2 | 10/2009 | |
| WO | 2009140495 A2 | 11/2009 | |
| WO | 2014170825 A2 | 10/2014 | |

OTHER PUBLICATIONS

Patent Examination Report No. 2 for Australian Patent Application No. 2015202794, dated Oct. 31, 2016, 3 pages.
Notice of Acceptance for Australian Patent Application No. 2015202794, dated Mar. 9, 2017, 3 pages.
First Office Action and Examination Search Report for Canadian Patent Application No. 2,724,336, dated Sep. 10, 2015, 5 pages.
International Preliminary Report on Patentability for International Patent Application No. PCT/US2009/040348, dated Oct. 21, 2010, 7 pages.
Office Action and Examination Search Report for Canadian Patent Application No. 2,799,772, dated Sep. 7, 2016, 3 pages.
International Preliminary Report on Patentability for International Patent Application No. PCT/US2009/043954, dated Dec. 16, 2010, 6 pages.
International Search Report and Written Opinion for International Patent Application No. PCT/US2016/036130, dated Sep. 16, 2016, 12 pages.
Communication pursuant to Article 94(3) EPC for European Patent Application 09729202.3, dated May 23, 2017, 5 pages.
Examination Report for European Patent Application No. 12829774. 4, dated Dec. 21, 2016, 4 pages.
First Examination Report for Indian Patent Application No. 2661/MUMNP/2010, dated Mar. 19, 2018, 5 pages.
Albin, M.D. et al., "Brain Retraction Pressure During Intracranial Procedures," Surg. Forum., 1975, pp. 499-500, vol. 26.
Albin, MS et al., "Clinical and Experimental Brain Retraction Pressure Monitoring," Acta Neurol Scand Suppl 1977; 64:522-3.
Andrews RJ et al., "Retraction Brain Ischaemia: Cerebral Blood Flow, Evoked Potentials, Hypotension and Hyperventilation in a New Animal Model," Neurol Res Mar. 1992; 14(1):12-8.
Andrews, RJ et al., "Retraction Brain Ischaemia: Mannitol Plus Nimodipine Preserves Both Cerebral Blood Flow and Evoked Potentials During Normoventilation and Hyperventilation," Neurol Res Mar. 1992; 14(1):19-25.
Andrews, RJ, et al. "A Review of Brain Retraction and Recommendations for Minimizing Intraoperative Brain Injury," Neurosurgery 1993; 33(6):1052-64.
Baisden, CE et al., "Occult Rib Fractures and Brachial Plexus Injury Following Median Sternotomy for Open-Heart Operations," Ann Thorac Surg Sep. 1984; 38(3):192-4.
Benedetti et al., "Postoperative Pain and Superficial Abdominal Reflexes after Posterolateral Thoracotomy," Ann. Thorac. Surg., Jul. 1997, 64(1): 207-210.
Bennett, M et al., "Evoked potential changes during brain retraction in dogs," Stroke Jul.-Aug. 1977; 8(4):487-92.
Bolotin et al., "A Novel Instrumented Retractor to Monitor Tissue-Disruptive Forces during Lateral Thoracotomy", J. Thorac. Cardiovasc. Surg., Apr. 2007, 133(4):949-954.
Bonfils-Roberts, EA, "The Rib Spreader: A Chapter in the History of Thoracic Surgery," Chest 1972 May 1, 1972; 61(5):469-74.

Bromage, P.R., "The Control of Post-Thoracotomy Pain," Anesthesia, May 1989, 44(5):445-446.
Candaele et al., "Chest Pain After Partial Upper Versus Complete Sternotomy for Aortic Value Surgery," Acta Cardiol, Feb. 2003, 58(1): 17-21.
Cerfolio et al., "Intercostal Muscle Flap Reduces the Pain of Thoracotomy: A Prospective Randomized Trial," J. Thorac. Cardiovasc. Surg., Oct. 2005, 130(4): 987-993.
Chaudhuri, O et al., "Reversible Stress Softening of Actin Networks," Nature 2007; 445(7125):295-8.
Clark, JD et al., "Blockade of the Complement C5A Receptor Reduces Incisional Allodynia, Edema, and Cytokine Expression," Anesthesiology Jun. 2006; 104(6):1274-82.
Clark, JD et al., "Morphine Reduces Local Cytokine Expression and Neutrophil Infiltration After Incision," Mol Pain 2007; 3:28.
Dajczman, E., et al. "Long-Term Postthoracotomy Pain", Chest, Feb. 1991, 99(2): 270-274.
Datta et al., "Back Pain and Disability after Lumbar Laminectomy: Is There a Relationship to Muscle Retraction?", Neurosurgery, Jun. 2004, 54(6): 1413-1420, discussion 20.
Davidson, RI et al., "Compression-Expansion Forceps for Intracranial Dissection and Retraction," Technical note. J Neurosurg Oct. 1986; 65(4):563.
De Silva, RJ, et al., "Apt070 Inhibits Complement Activation During in Vitro Cardiopulmonary Bypass," Eur J Cardiothorac Surg Jul. 2006; 30(1):72-6.
Defalque et al., "Long-Term Postthoracotomy Pain", Chest, Mar. 1992, 101(3): 884.
Dorfmann, A, et al. "A Constitutive Model for Muscle Properties in a Soft-Bodied Arthropod," Journal of the Royal Society Interface 2007; 4(13):257-69.
Dowling et al., "Improved Pain Control After Cardiac Surgery: Results of a Randomized, Double-Blind, Clinical Trial", J. Thorac. Cardiovasc. Surg., Nov. 2003, 126(5): 1271-1278.
Eisenberg, E, et al., "Prevalence and Characteristics of Post Coronary Artery Bypass Graft Surgery Pain (PCP)," Pain May 2001; 92(1-2):11-7.
Eng, J. et al., "Post-Thoracotomy Analgesia," J R Coll Surg Edinb Apr. 1993; 38(2):62-8.
Erdek, MA et al., "Chronic Pain and Thoracic Surgery," Thorac Surg Clin Feb. 2005; 15(1):123-30.
Erdogan, M. et al., "Prospective, Randomized, Placebo-Controlled Study of the Effect of Tens on Postthoracotomy Pain and Pulmonary Function," World J Surg Dec. 2005; 29(12)1563-70.
Evans, Krista, "The Hole-N-Ator: An Analysis of the Relation Between the Forces Applied to the Retracted Tissue and the Reactions Applied at the Crank Mechanism," 1999, http://em-ntserver.unl.edu:80/Mechanics-Pages/KristaEvans/holenator%20revised.htm.
Fanning, NF et al., "Inhibition of Neutrophil Apoptosis After Elective Surgery," Surgery Sep. 1999; 126(3):527-34.
Flatters, SJ., "Characterization of a Model of Persistent Postoperative Pain Evoked by Skin/Muscle Incision and Retraction (smir)," Pain Jun. 20, 2007.
Fleck, C., et al., "Deformation Behaviour and Damage Accumulation of Cortical Bone Specimens from the Equine Tibia Under Cyclic Loading," J Biomech Feb. 2003; 36(2)179-89.
Foering, K. et al., "Percutaneous Transluminal Angioplasty Balloon Inflation with Syringes: Who Needs an Inflator?" Journal of Vascular and Interventional Radiology, vol. 20, May 2009, pp. 629-633.
Fonseca, P., "Postthoracotomy Pain," J. Thorac. Cardiovasc. Surg., Dec. 1998; 116(6): 1081-2.
Greenwald, L.V., et al., "Rib Fractures in Coronary Bypass Patients: Radionuclide Detection," Radiology, Aug. 1993; 148(2): 553-4.
Harada, S., et al., "Retraction induced brain edema," Acta. Neurochir. Suppl. (Wien), 1994; 60: 449-51.
Hazelrigg, S.R., et al., "Acute and Chronic Pain Syndromes After Thoracic Surgery," Surg. Clin. North. Am., Aug. 2002; 82(4): 849-65.
Ho, S.C., et al., "Persistent Pain After Cardiac Surgery: An Audit of High Thoracic Epidural and Primary Opioid Analgesia Therapies," Anesth. Analg., Oct. 2002; 95(4): 820-3, table of contents.

(56) References Cited

OTHER PUBLICATIONS

Hong, K., et al., "Monitoring Retraction Pressure on the Brain. An Experimental and Clinical Study," J. Neurosurg., Feb. 1987; 66(2): 270-5.
Horgan, C.O., et al., "A Theory of Stress Softening of Elastomers Based on Finite Chain Extensibility," Proceedings of the Royal Society A: Mathematical, Physical and Engineering Sciences 2004; 460(2046): 1737-54.
Kalso, E., et al., "Chronic Post-Sternotomy Pain," Acta Anaesthesiol Scand, Sep. 2001; 45(8): 935-9.
Karmakar, M.K., et al., "Postthoracotomy Pain Syndrome," Thorac Surg Clin, Aug. 2004; 14(3): 345-52.
Katz, J., et al., "Acute Pain After Thoracic Surgery Predicts Long-term Post-Thoracotomy Pain," Clin J Pain, Mar. 1996; 12(1): 50-5.
Kavanagh, B.P., et al., "Pain control after thoracic surgery. A review of current techniques," Anesthesiology, Sep. 1994; 81(3): 737-59.
Kawaguchi, Y., et al., "Back muscle injury after posterior lumbar spine surgery. Part 1: Histologic and histochemical analyses in rats," Spine Nov. 15, 1994; 19(22):2590-7.
Kawaguchi M.D. et al., "Back Muscle Injury After Posterior Lumbar Spine Surgery," Spine, 1996, pp. 2683-2688, vol. 21, No. 22.
Kawaguchi, M.D. et al., "Back Muscle Injury After Posterior Lumbar Spine Surgery," Spine, 1996, pp. 941-944, vol. 21, No. 8.
Kawaguchi, M.D. et al., "Preventative Measures of Back Muscle Injury After Posterior Lumbar Spine Surgery in Rats," Spine, 1998, 2282-2287, vol. 23, No. 21.
Kirton, R.S., et al., "Strain softening behaviour in nonviable rat right-ventricular trabeculae, in the presence and the absence of butanedione monoxime," Exp Physiol, Sep. 1, 2004; 89(5): 593-604.
Kirton, R.S., et al., "Strain softening is not present during axial extensions of rat intact right ventricular trabeculae in the presence or absence of 2,3-butanedione monoxime," Am J Physiol Heart Circ Physiol, Feb. 1, 2004; 286(2): H708-15.
Koehler, R.P., et al., "Management of postthoracotomy pain: Acute and chronic." Thorac Surg Clin, Aug. 2006; 16(3): 287-97.
International Preliminary Report on Patentability for International Patent Application No. PCT/US2016/036130, dated Dec. 21, 2017, 8 pages.
Examination Report for Indian Patent Application No. 2354/MUMNP/2010, dated Feb. 27, 2018, 5 pages.
Final Office Action for U.S. Appl. No. 14/734,661, dated Jul. 26, 2017, 26 pages.
Office Action and Examination Search Report for Canadian Patent Application No. 2,799,772, dated Jun. 6, 2017, 4 pages.
Kruger, M., et al., "Pain management in cardiothoracic practice," Surg Clin North Am., Apr. 1999; 79(2): 387-400.
Lewis, R.J., "The advent of vats. In My Opinion," CTSNet, Jun. 19, 2007, http://www.ctsnet.org/sections/newsandviews/inmyopinion/articles/article-62.html.
Long, J.H., Jr., "Stiffness and damping forces in the intevertebral joints of blue marlin (*Makaira nigricans*)," J exp Biol, 1992; 162: 131-55.
Long, J.H., Jr., et al., "Locomotor design of dolphin vertebral columns: Bending mechanics and morphology of delphinus delphis," J Exp Biol, Jan. 1997; 200(Pt 1): 65-81.
Magnano, D., et al., "Ineffectiveness of local wound anesthesia to reduce postoperative pain after median sternotomy," J Card Surg, Jul.-Aug. 2005; 20(4): 314-8.
Minor, A.A., "Alternative management for post-thoracotomy pain syndrome," Can J Surg, Oct. 1996; 39(5): 430-1.
Moss, E., "Effect of propofol on brain retraction pressure and cerebral perfusion pressure," Br J Anaesth, Dec. 1, 1990; 65(6): 823-5.
Murphy, G.S., et al., "The effects of morphine and fentanyl on the inflammatory response to cardiopulmonary bypass in patients undergoing elective coronary artery bypass graft surgery," Anesth Analg, Jun. 2007; 104(6): 1334-42, table of contents.

Ochroch, E.A., et al., "Women suffer more short and long-term pain than men after major thoracotomy," Clin J Pain, Jun. 2006; 22(5): 491-8.
Ochroch, E.A., et al., "Impact of acute pain and its management for thoracic surgical patients," Thorac Surg Clin, Feb. 2005; 15(1): 105-21.
Peeters-Asdourian, C., et al., "Choices in pain management following thoracotomy," Chest, May 1999; 115(5 Suppl): 122S-4S.
Perkins, F.M., et al., "Chronic pain as an outcome of surgery. A review of predictive factors," Anesthesiology, Oct. 2000; 93(4): 1123-33.
Perttunen, K., et al., "Chronic pain after thoracic surgery: A follow-up study," Acta Anaesthesiol Scand, May 1999; 43(5): 563-7.
Pluijms, W.A., et al., "Chronic post-thoracotomy pain: A retrospective study," Acta Anaesthesiol Scand, Aug. 2006; 60(7): 804-8.
Provenzano, P., et al., "Nonlinear ligament viscoelasticity," Ann Biomed Eng, Oct. 2001; 29(10): 908-14.
Richardson, J., et al., "Postthoracotomy pain," Ann Thorac Surg, Jan. 1998; 65(1): 300-2.
Rogers, M.L, et al., "Preliminary findings in the neurophysiological assessment of intercostal nerve injury during thoracotomy," Eur J Cardiothorac Surg, Feb. 1, 2002; 21(2): 298-301.
Rosenorn, J., et al., "Reduction of regional cerebral blood flow during brain retraction pressure in the rat." J Neurosurg, Jun. 1982; 56(6): 826-9.
Rosenorn, J., et al., "The risk of cerebral damage during graded brain retractor pressure in the rat," J Neurosurg, Oct. 1985;63(4): 608-11.
Sabanathan, S., et al., "Management of pain in thoracic surgery," Br J Hosp Med, Jul. 14-Aug. 17, 1993; 50(2-3): 114-20.
Sandler, A.N., "Post-thoracotomy analgesia and perioperative outcome," Minerva Anestesiol, May 1999; 65(5): 267-274, abstract only.
Savage, C., et al., "Postthoracotomy pain management," Chest Surg Clin N. Am, May 2002; 12(2): 251-63.
Sihoe, A.D., et al. "The use of gabapentin for post-operative and post-traumatic pain in thoracic surgery patients," Eur J Cardiothorac Surg, May 2006; 29(5): 795-9.
Speich, J.E., et al., "Rok-induced cross-link formation stiffens passive muscle: Reversible strain-induced stress softening in rabbit detrusor," Am J Physiol Cell Physiol, Jul. 1, 2005; 289(1): C12-21.
Strebel, B.M., et al., "Chronic post-thoracotomy pain syndrome," CMAJ, 2007; 177(9): 1029.
Styf, M.D. et al., "The Effects of External Compression by Three Different Retractors on Pressure in the Erector Spine Muscles During and After Posterior Lumbar Spine Surgery in Humans," Spine, 1998, pp. 354-358, vol. 23, No. 3.
Takamori, S., et al., "Intraoperative intercostal nerve blockade for postthoracotomy pain," Ann Thorac Surg, Aug. 2002; 74(2): 338-41.
Taylor, H., et al., "The impact of self-retaining retractors on the paraspinal muscles during posterior spinal surgery," Spine, Dec. 15, 2002; 27(24): 2758-62.
Thiex, R., et al., "Technical pitfalls in a porcine brain retraction model. The impact of brain spatula on the retracted brain tissue in a porcine model: A feasibility study and its technical pitfalls," Neuroradiology, Oct. 2005; 47(10): 765-73.
Tiippana, E., et al., "Post-thoracotomy pain after thoracic epidural analgesia: A prospective follow-up study," Acta Anaesthesiol Scand, Apr. 2003; 47(4): 433-8.
Vander Salm, T.J., et al., "Brachial plexus injury following median sternotomy. Part II," J Thorac Cardiovasc Surg, Jun. 1982; 83(6): 914-7.
Vanderby, R., et al., "Collagen in connective tissue: From tendon to bone," J Biomech, Oct. 2003; 36(10): 1523-7.
Vincent, J.F.V., "Locust oviposition: Stress softening of the extensible intersegmental membranes," Proceedings of be Royal Society of London Series B, Biological Sciences (1934-1990), 1975; 188(1091): 189-201.
Wainwright, et al., 1976, Mechanical Design in Organisms, John Wiley & Sons.

(56) References Cited

OTHER PUBLICATIONS

Wang, et al., "A Compound Sensor for Biomechanical Analyses of Bullock Soft Tissue in vivo," Journal of Rehabilitation Research and Development, vol. 37, No. 4, Aug. 2000, pp. 433-443.
Weisman, G., et al., "Cyclic loading in knee ligament injuries," Am J Sports Med, Jan.-Feb. 1980; 8(1): 24-30.
White et al., "Use of a continuous local anesthetic infusion for pain management after median sternotomy", Anesthesiology, Oct. 2003, 99(4): 918-923.
Woo et al., 1999, Animal Models in Orthopaedic Research, CRC Press. pp. 175-196.
Woodring, J.H., et al., "Upper rib fractures following median sternotomy," Ann Thorac Surg, Apr. 1985;39(4): 355-7.
Yin, L., et al., "A biphasic and transversely isotropic mechanical model for tendon: Application to mouse tail fascicles in uniaxial tension," J Biomech, Jun. 2004; 37(6): 907-16.
Yokoh, A., et al., "Intermittent versus continuous brain retraction. An experimental study," J Neurosurg, Jun. 1983; 58(6): 918-23.
Non-final Office Action for U.S. Appl. No. 12/832,378 dated Mar. 30, 2012, 7 pages.
Final Office Action for U.S. Appl. No. 12/832,378 dated Oct. 17, 2012, 17 pages.
Advisory Action for U.S. Appl. No. 12/832,378 dated Feb. 26, 2013, 3 pages.
Notice of Allowance for U.S. Appl. No. 12/832,378 dated Aug. 28, 2013, 12 pages.
Non-final Office Action for U.S. Appl. No. 12/422,584 dated Apr. 24, 2012, 13 pages.
Advisory Action for U.S. Appl. No. 12/422,584 dated Mar. 15, 2012, 2 pages.
Final Office Action for U.S. Appl. No. 12/422,584 dated Dec. 21, 2011, 14 pages.
Non-final Office Action for U.S. Appl. No. 12/422,584 dated Apr. 27, 2011, 12 pages.
Non-final Office Action for U.S. Appl. No. 12/422,584 dated Mar. 7, 2013, 13 pages.
Advisory Action for U.S. Appl. No. 14/577,323, dated Aug. 18, 2017, 14 pages.
Final Office Action for U.S. Appl. No. 12/422,584 dated Sep. 9, 2013, 11 pages.
Advisory Action for U.S. Appl. No. 12/422,584, dated Jan. 27, 2014, 7 pages.
Advisory Action for U.S. Appl. No. 12/422,584 dated Mar. 24, 2014, 3 pages.
Final Office Action for U.S. Appl. No. 12/465,978 dated Jan. 5, 2012, 12 pages.
Non-final Office Action for U.S. Appl. No. 12/465,978 dated Apr. 14, 2011, 10 pages.
Non-final Office Action for U.S. Appl. No. 12/465,978 dated Sep. 18, 2012, 11 pages.
Final Office Action for U.S. Appl. No. 12/465,978 dated Apr. 22, 2013, 14 pages.
Advisory Action for U.S. Appl. No. 12/465,978 dated Jul. 26, 2013, 3 pages.
Non-final Office Action for U.S. Appl. No. 12/465,978 dated May 8, 2014, 18 pages.
Notice of Allowance for U.S. Appl. No. 12/465,978 dated Sep. 5, 2014, 12 pages.
Notice of Allowance for U.S. Appl. No. 11/187,207 dated Apr. 12, 2010, 6 pages.
Final Office Action for U.S. Appl. No. 11/187,207 dated Dec. 8, 2009, 6 pages.
Non-final Office Action for U.S. Appl. No. 11/187,207 dated Feb. 2, 2009, 9 pages.
Final Office Action for U.S. Appl. No. 11/187,207 dated Oct. 9, 2007, 5 pages.
Non-Final Office Action for U.S. Appl. No. 13/608,458 dated Dec. 29, 2014, 11 pages.
Non-Final Office Action for U.S. Appl. No. 13/111,577 dated Oct. 23, 2013, 22 pages.
Notice of Allowance for U.S. Appl. No. 13/111,577 dated Jan. 14, 2015, 10 pages.
Non-Final Office Action for U.S. Appl. No. 13/111,762 dated Aug. 8, 2013, 8 pages.
Final Office Action for U.S. Appl. No. 13/111,762 dated Mar. 26, 2014, 8 pages.
Non-Final Office Action for U.S. Appl. No. 13/111,762 dated Feb. 11, 2015, 16 pages.
Notice of Acceptance for Australian Patent Application No. 2009234286, dated Jan. 29, 2015, 2 pages.
Notice of Acceptance for Australian Patent Application No. 2009246299, dated Feb. 17, 2015, 2 pages.
International Search Report for PCT/US09/40348 dated Oct. 4, 2010, 9 pages.
International Search Report for PCT/US2011/037191 dated Aug. 29, 2011, 12 pages.
International Search Report for PCT/US09/43954 dated Nov. 8, 2010, 13 pages.
International Search Report and Written Opinion for PCT/US2012/054442 dated Nov. 26, 2012, 9 pages.
International Preliminary Report on Patentability for PCT/US2012/054442 dated Mar. 20, 2014, 8 pages.
International Preliminary Report on Patentability for PCT/US2011/037191 dated Nov. 29, 2012, 10 pages.
Extended European Search Report for Patent Application 09729202.3, dated Oct. 14, 2014, 7 pages.
Extended European Search Report for European Patent Application 09747577.6 dated Sep. 3, 2013, 12 pages.
Final Office Action for U.S. Appl. No. 13/608,458, dated Jul. 16, 2015, 9 pages.
Final Office Action for U.S. Appl. No. 13/111,762, dated Aug. 13, 2015, 14 pages.
Notice of Allowance for U.S. Appl. No. 12/422,584, dated Jun. 6, 2014, 9 pages.
Final Office Action for U.S. Appl. No. 13/111,577 dated Aug. 7, 2014, 12 pages.
Advisory Action for U.S. Appl. No. 13/111,762 dated Jul. 3, 2014, 3 pages.
Patent Examination Report No. 1 for Australian Patent Application No. 2009234286, dated Jul. 31, 2014, 3 pages.
Patent Examination Report No. 1 for Australian Patent Application No. 2009246299, dated Jul. 17, 2014, 3 pages.
Extended European Search Report for European Patent Application 12829774.4 dated Jul. 2, 2015, 7 pages.
Non-Final Office Action for U.S. Appl. No. 14/577,323, dated Oct. 28, 2016, 12 pages.
Final Office Action for U.S. Appl. No. 14/577,323, dated May 5, 2017, 15 pages.
Advisory Action and Examiner-Initiated Interview Summary for U.S. Appl. No. 13/608,458, dated Nov. 9, 2015, 4 pages.
Notice of Allowance for U.S. Appl. No. 13/608,458, dated Feb. 12, 2016, 10 pages.
Corrected Notice of Allowance for U.S. Appl. No. 13/608,458, dated May 18, 2016, 4 pages.
Advisory Action for U.S. Appl. No. 13/111,762, dated Nov. 30, 2015, 3 pages.
Non-Final Office Action for U.S. Appl. No. 13/111,762, dated Apr. 7, 2016, 23 pages.
Final Office Action for U.S. Appl. No. 13/111,762, dated Nov. 22, 2016, 21 pages.
Examination Report No. 1 for Australian Patent Application No. 2012304320, dated Mar. 2, 2016, 3 pages.
Notice of Acceptance for Australian Patent Application No. 2012304320, dated Aug. 31, 2016, 2 pages.
Examination Report No. 1 for Australian Patent Application No. 2015202539, dated Jul. 6, 2016, 5 pages.
Office Action and Examination Search Report for Canadian Patent Application No. 2,721,075, dated Nov. 3, 2015, 4 pages.

* cited by examiner

MOTION CONTRACTING B207 (INFLATION PHASE)   MOTION EXPANDING B207 (DEFLATION PHASE)

Variables and inputs:
$F_n$     most recent measure of force
$T_S$     first threshold (input by user)
$T_V$     second threshold (input by user)
N     number of seconds, where N > 0.5
$RMS_x$     root mean square (an estimate of noise in the $d^2F/dt^2$ signal) over the last x seconds Calculating RMS ($D_n$ = nth discrete measurement of $d^2F/dt^2$):

$$RMS = \sqrt{\frac{D_1^2 + D_2^2 + ... + D_n^2}{n}}$$

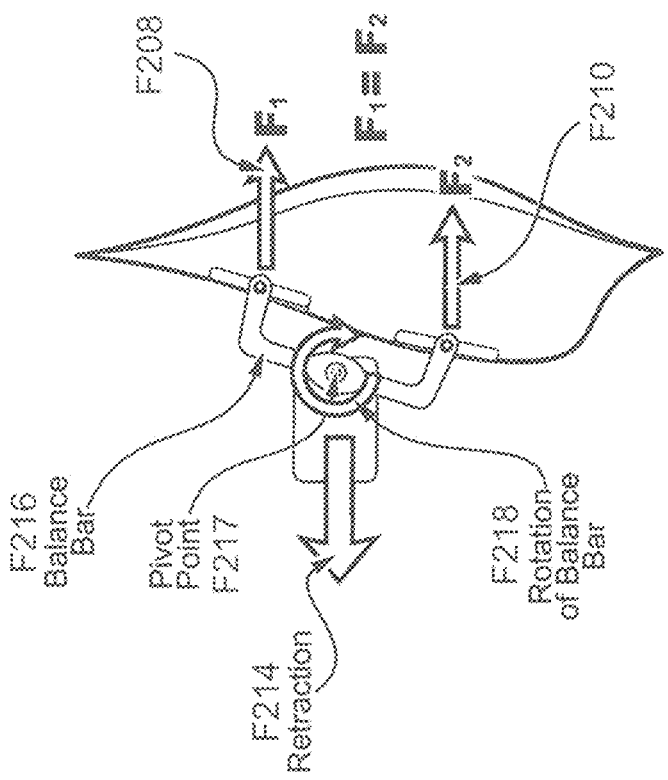
FIG. 49B.2
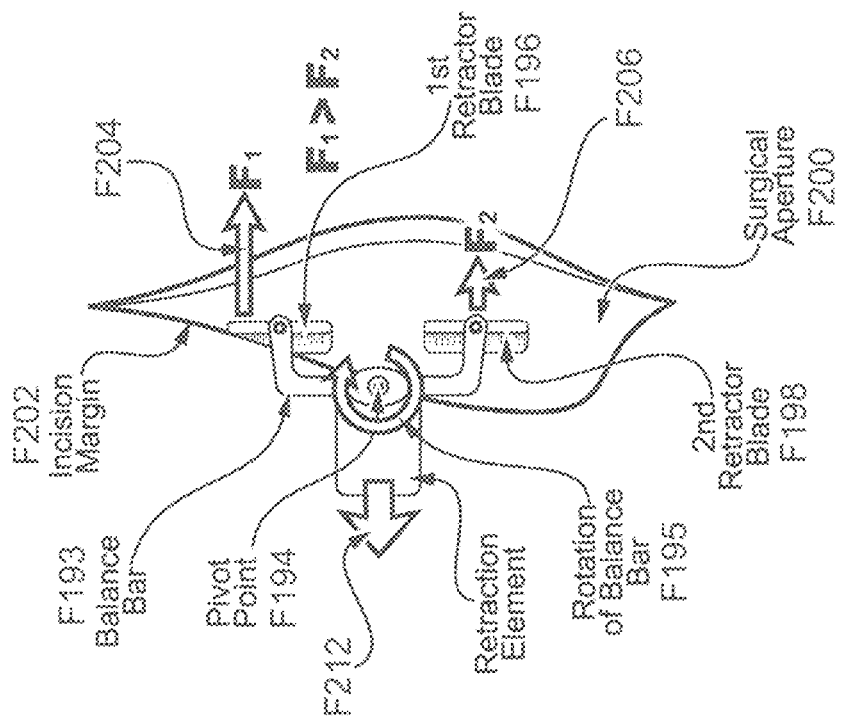
FIG. 49B.1

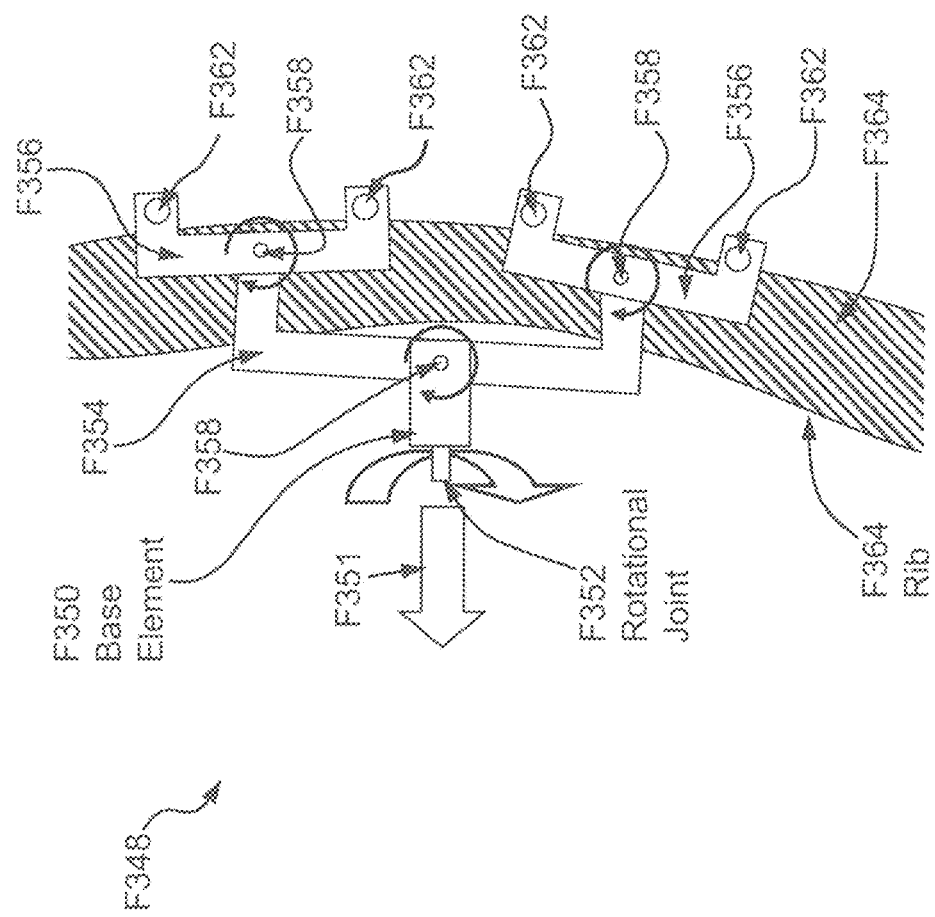
FIG. 55A — top view

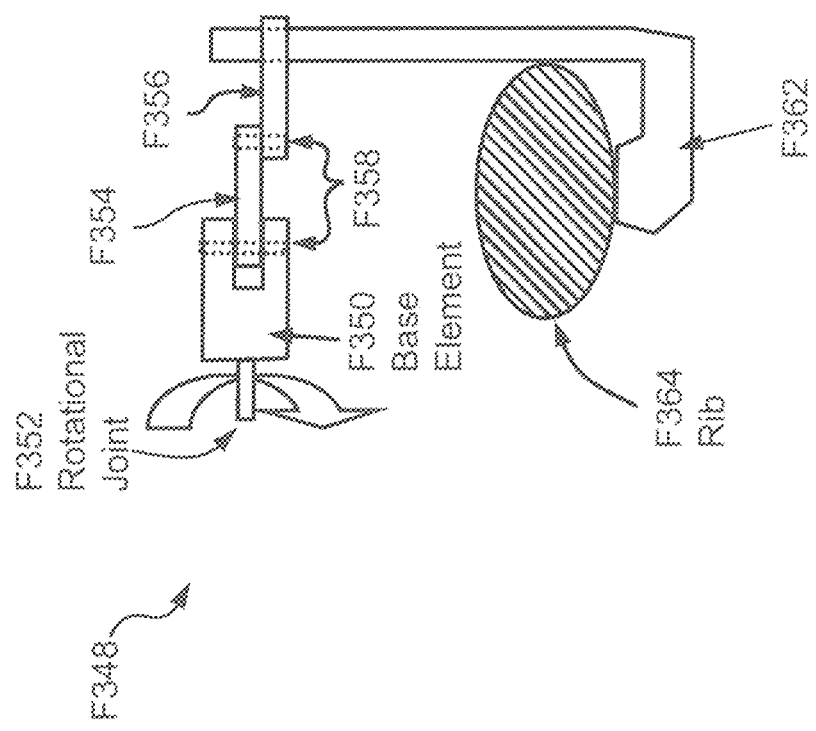
FIG. 55B – side view

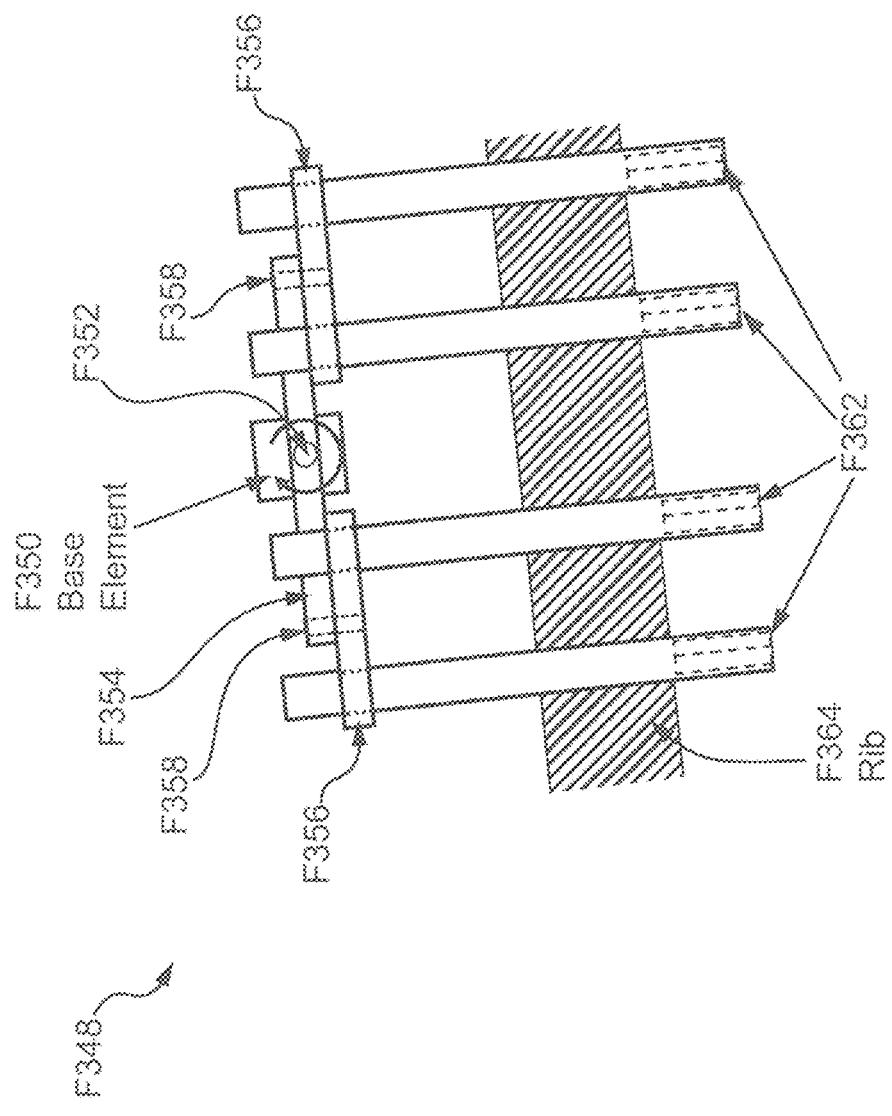

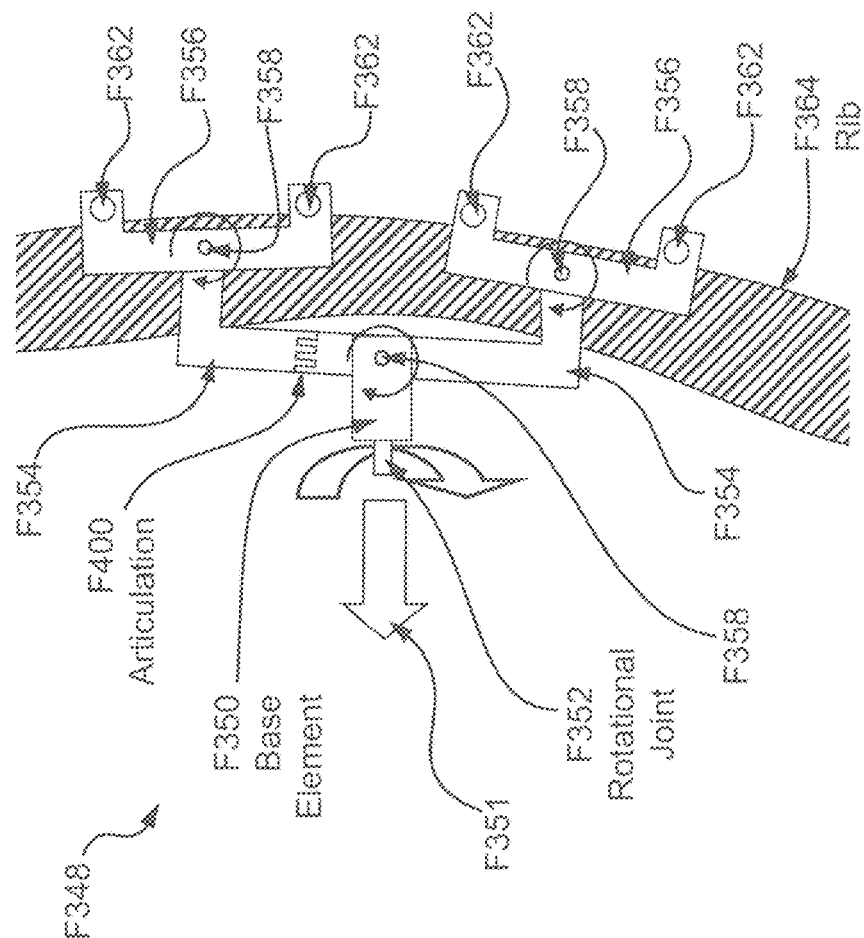
FIG. 56A – top view

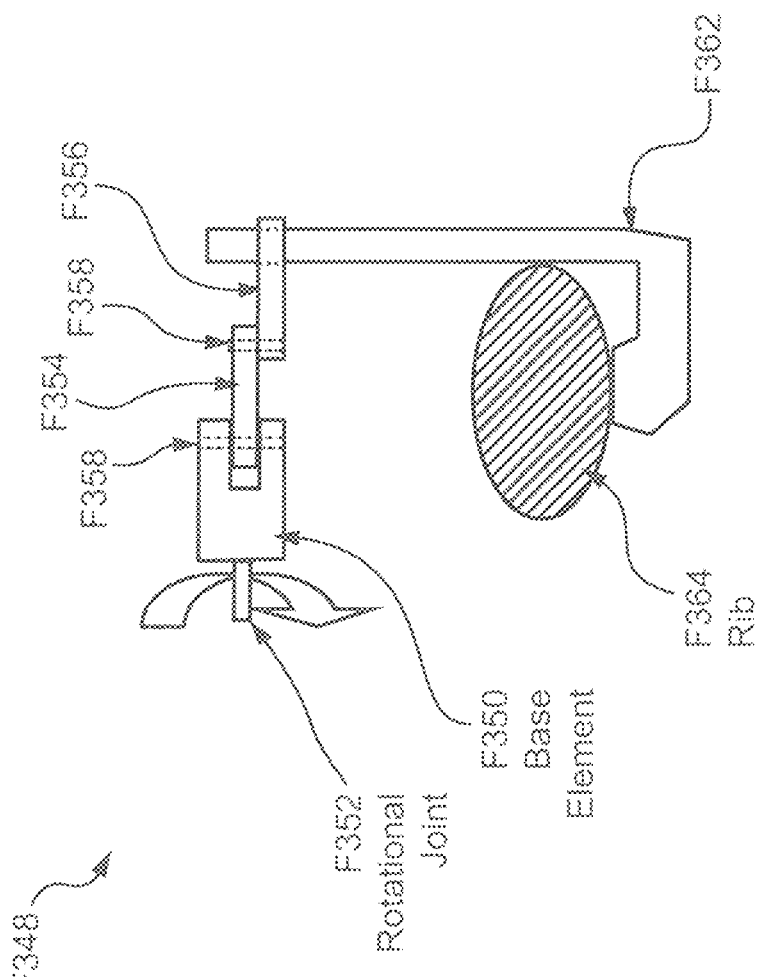
FIG. 56B – side view

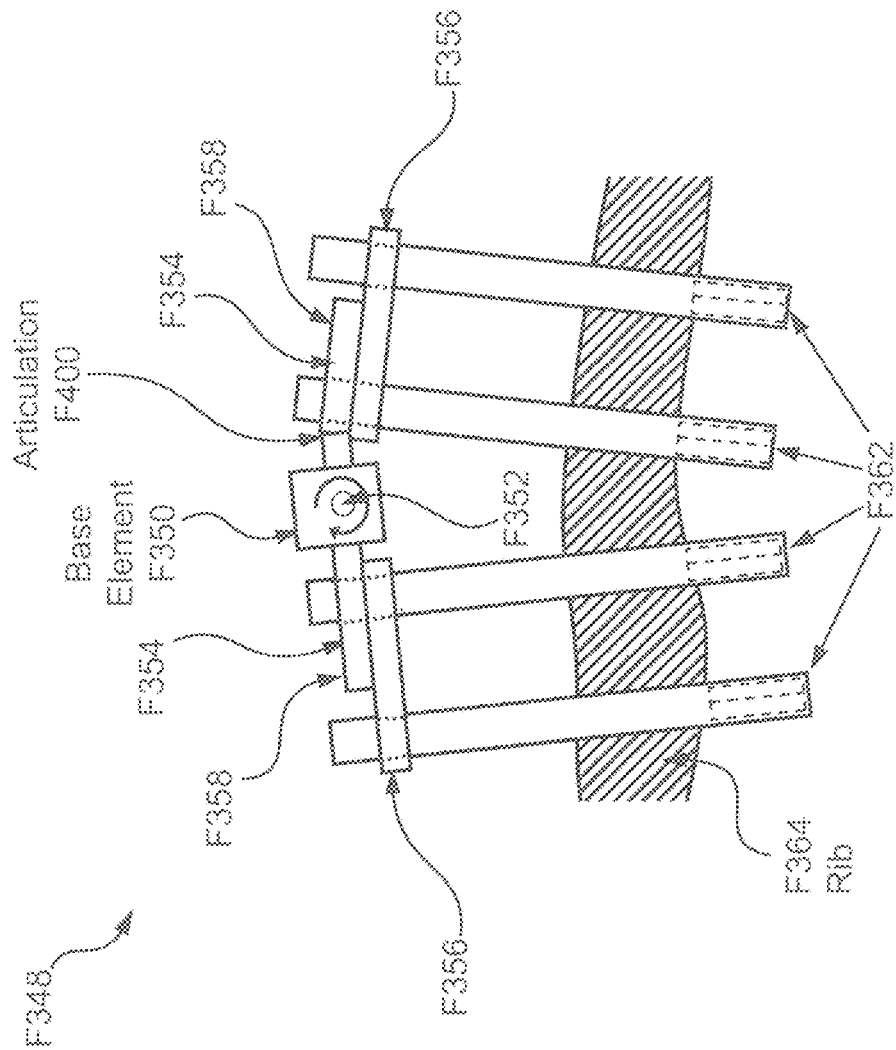

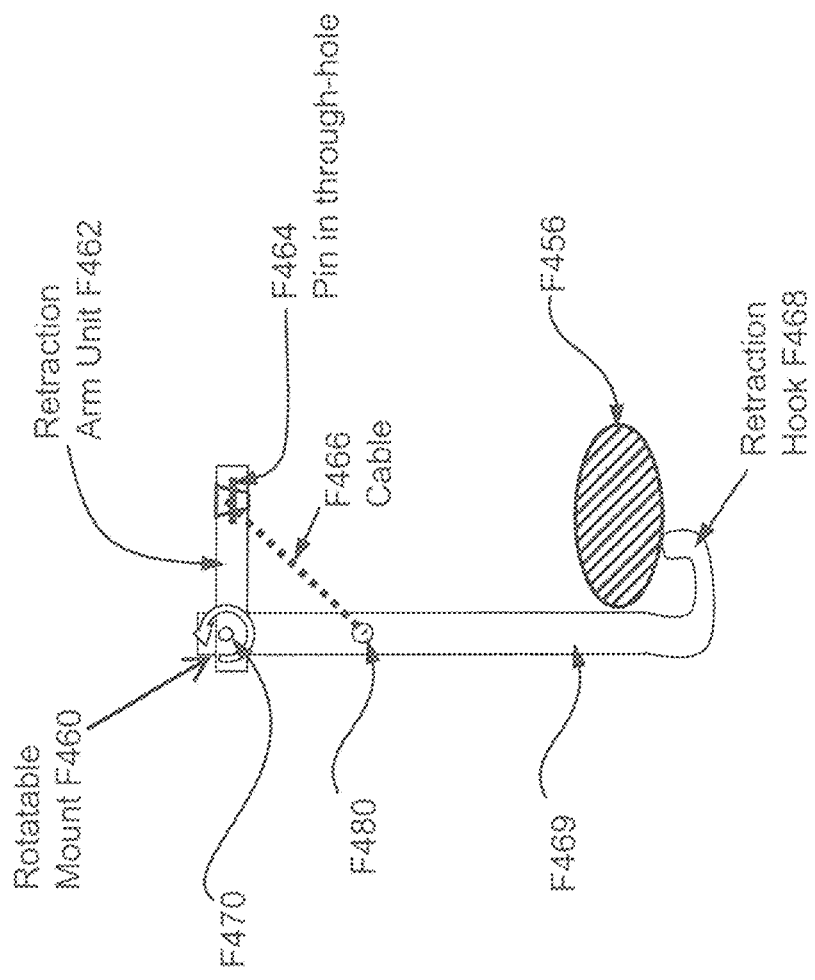
FIG. 59A – side view

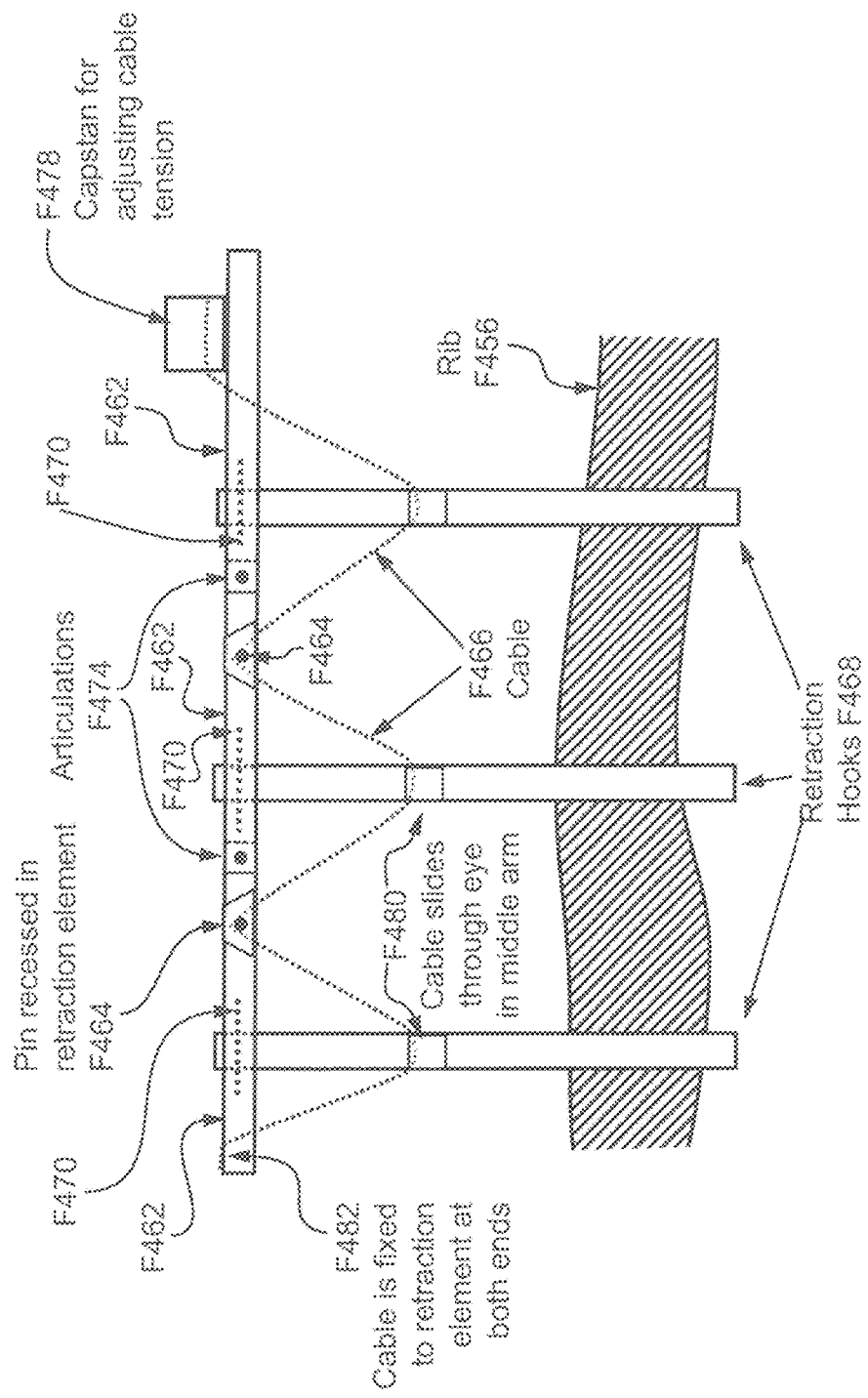
FIG. 59B – front view

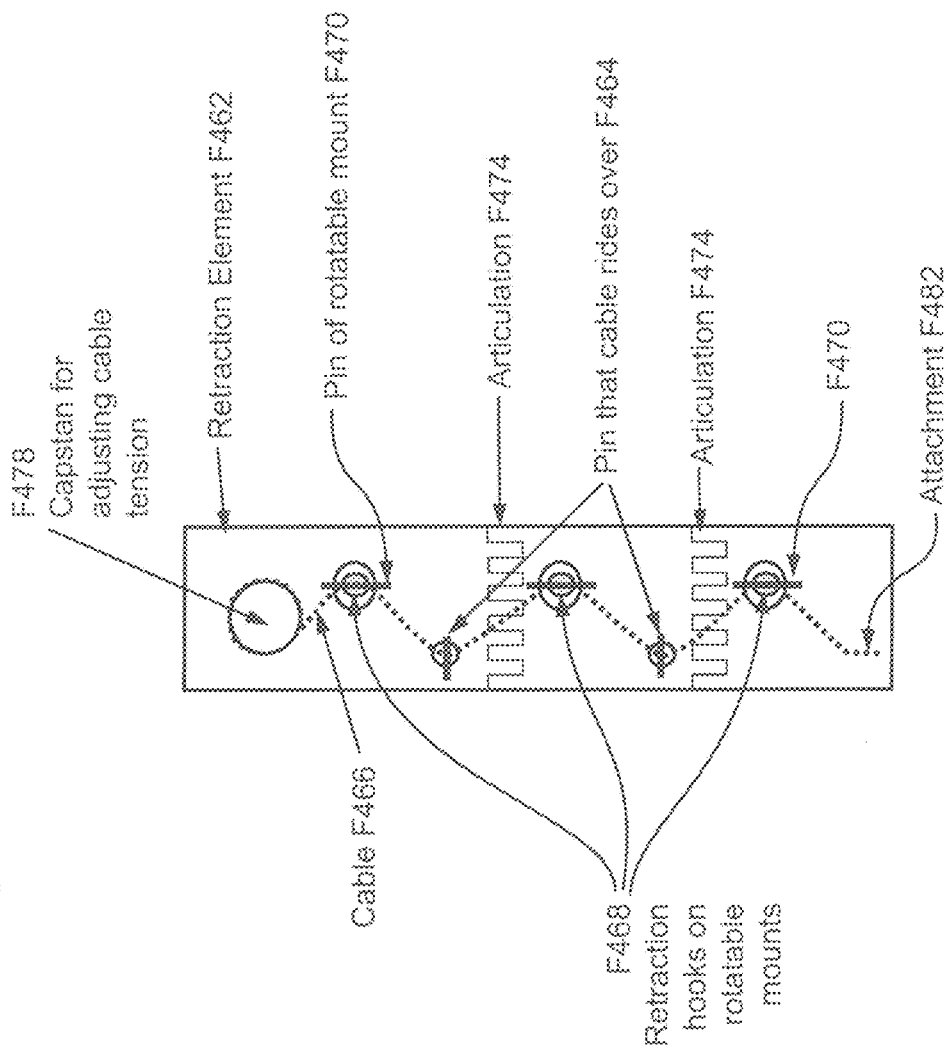
FIG. 59C – top view

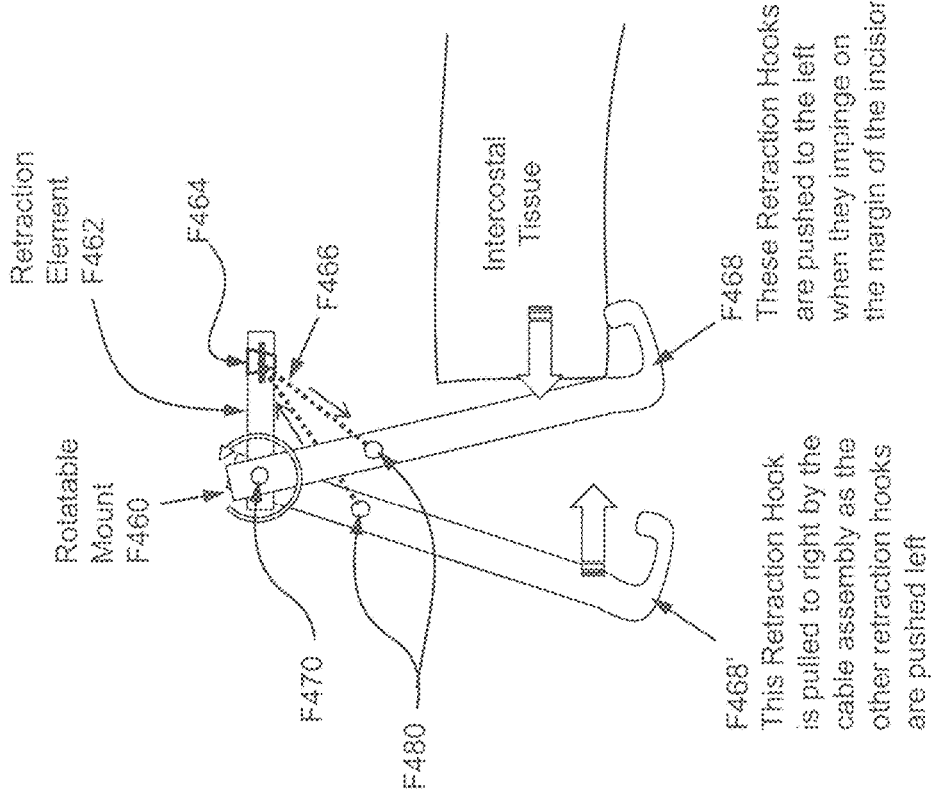
FIG. 59D – side view

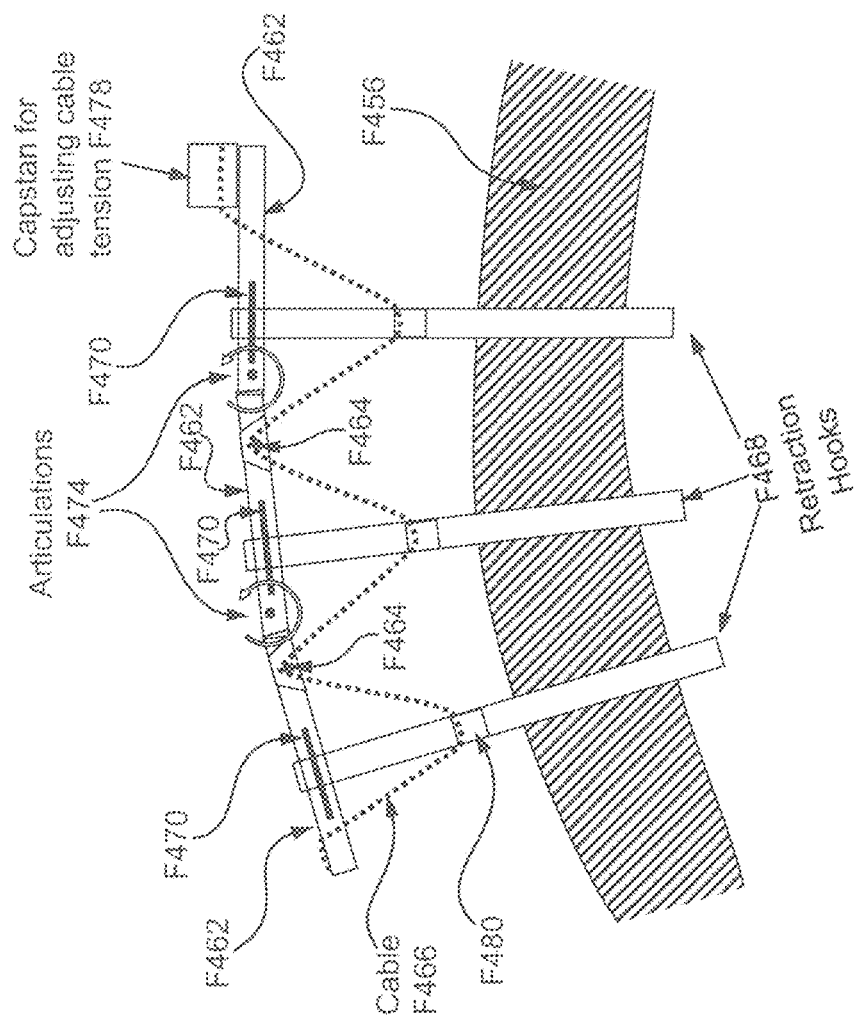
FIG. 59E – front view

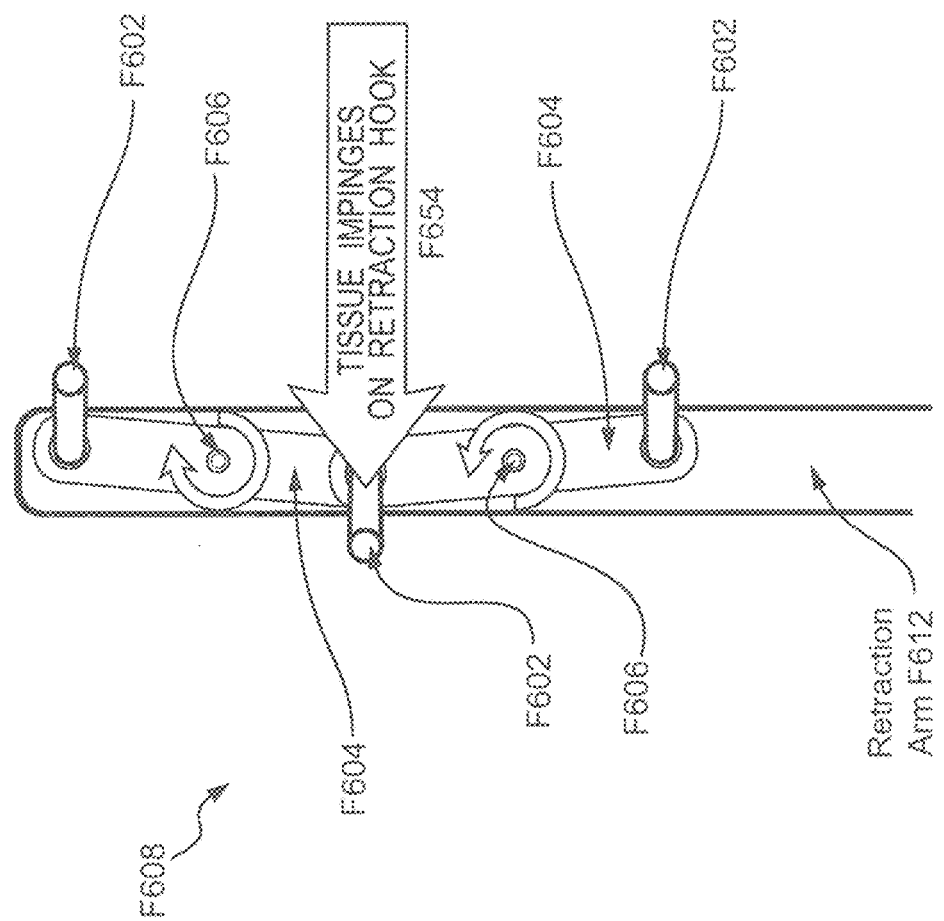

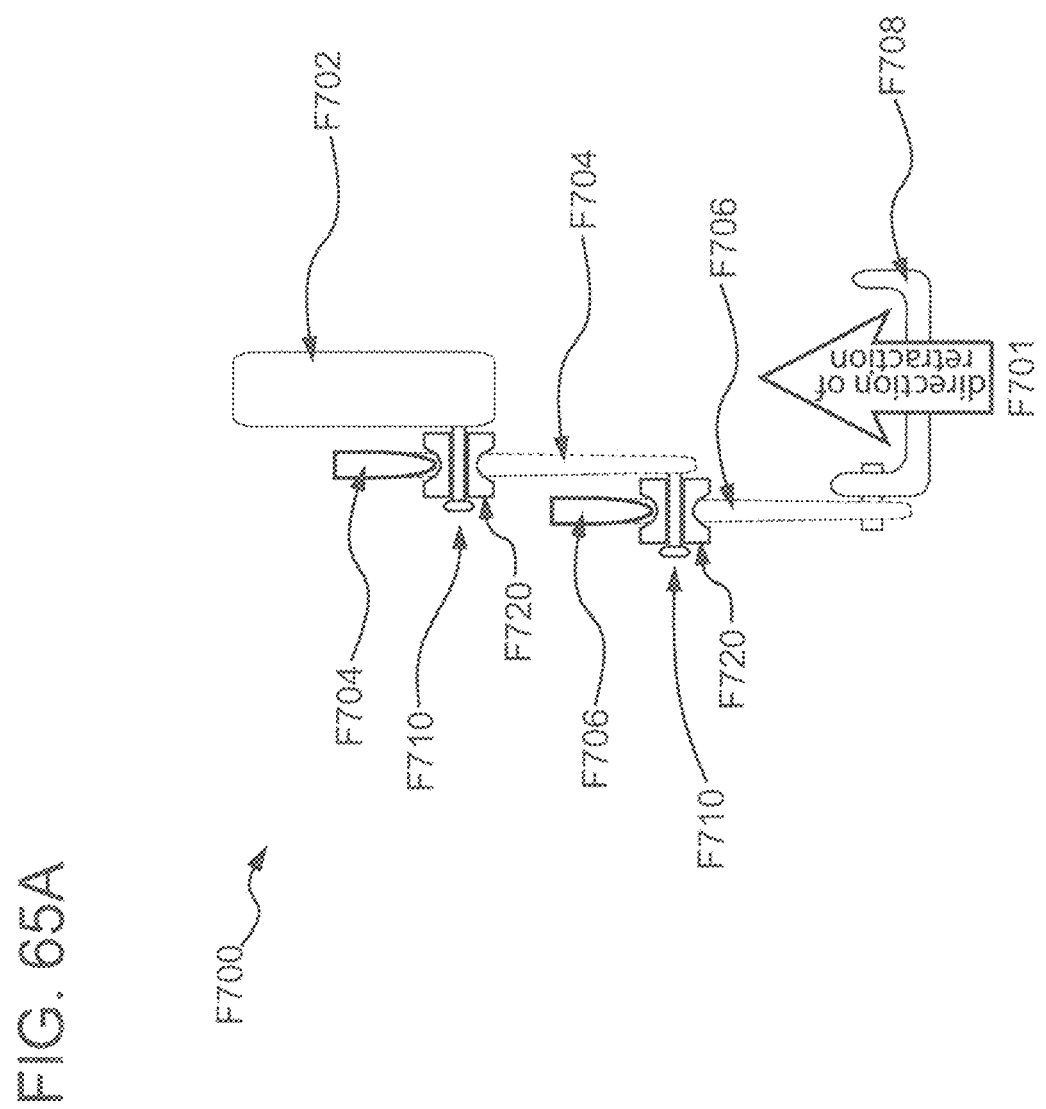

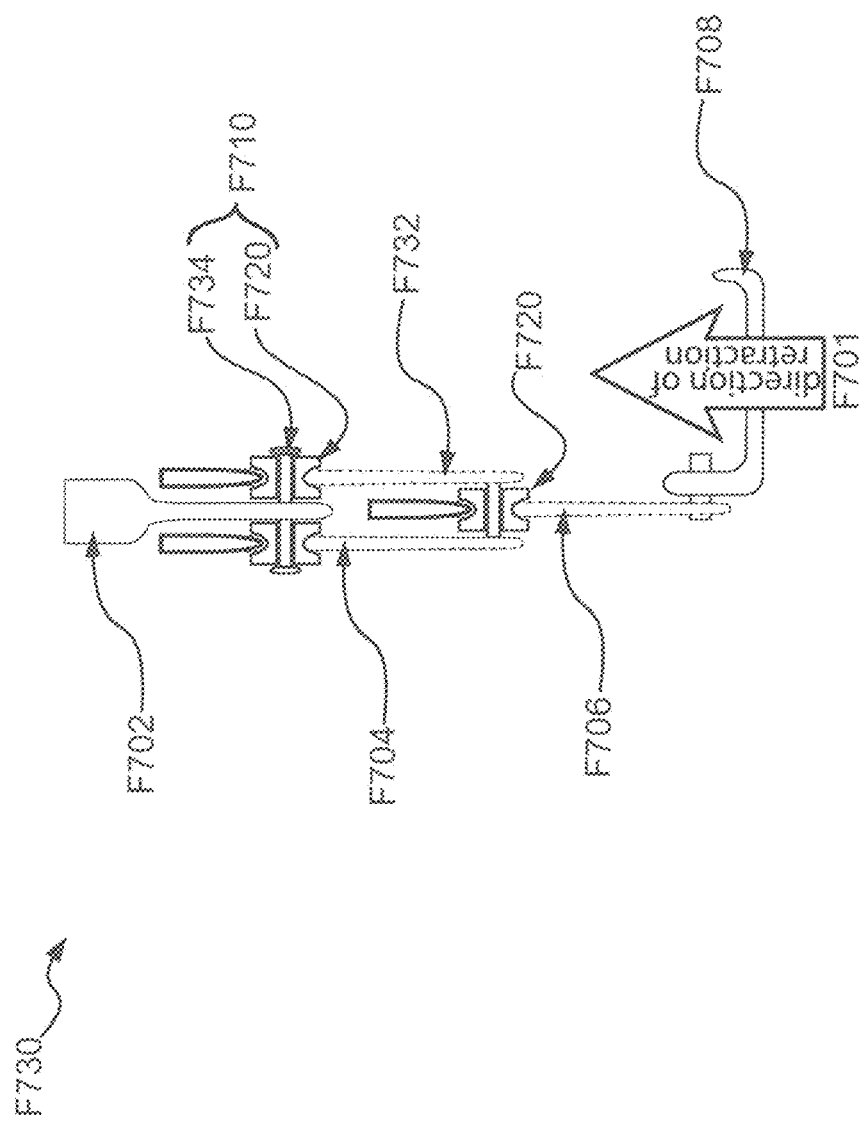

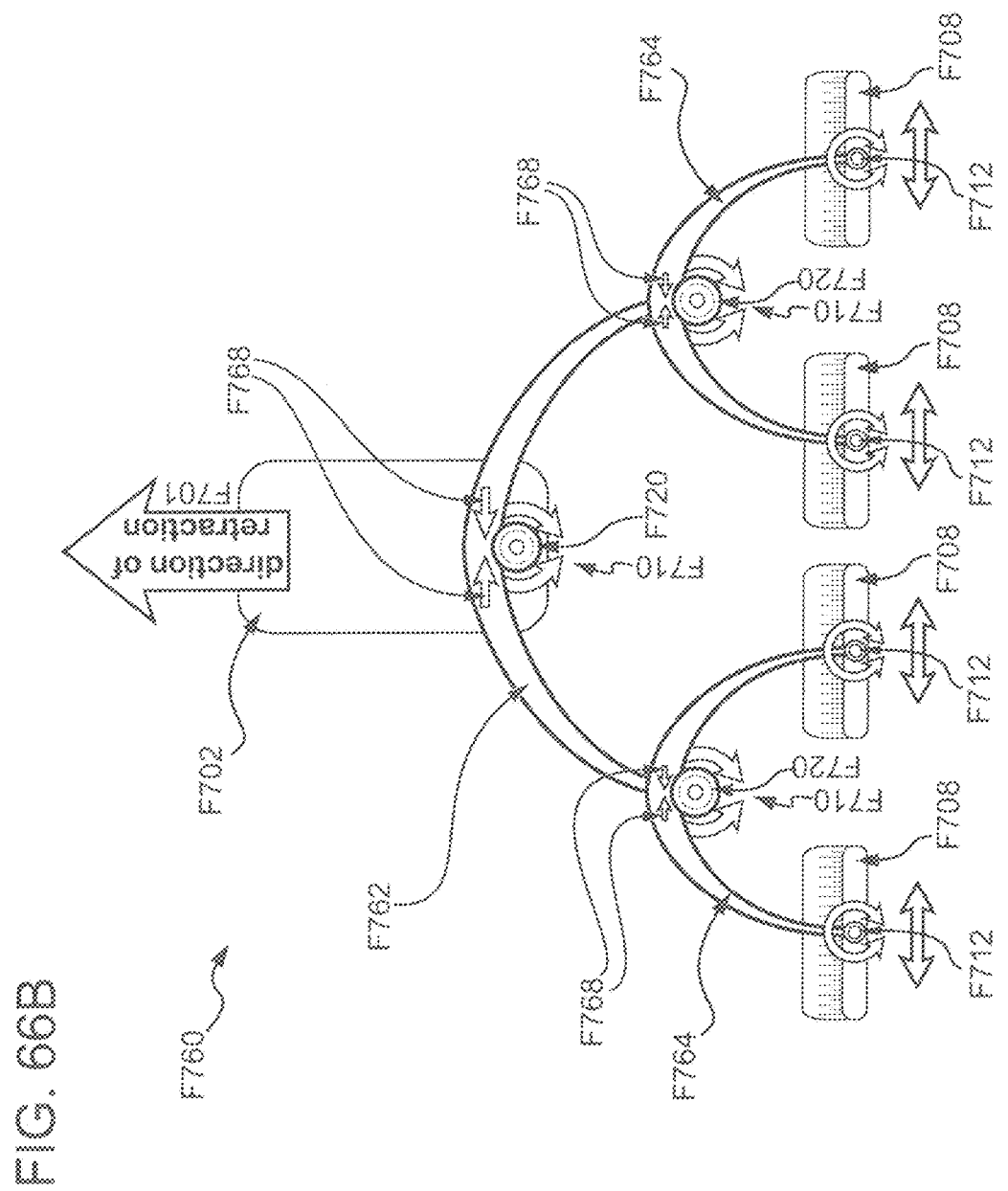

$$\vec{F}_1 = -\vec{F}_2$$

Cooley retractor, available for sale in 2008

Sauerbruch Rib Spreader, circa 1911

De Quervain chest retractor, circa 1913

Meyer retractor, circa 1909

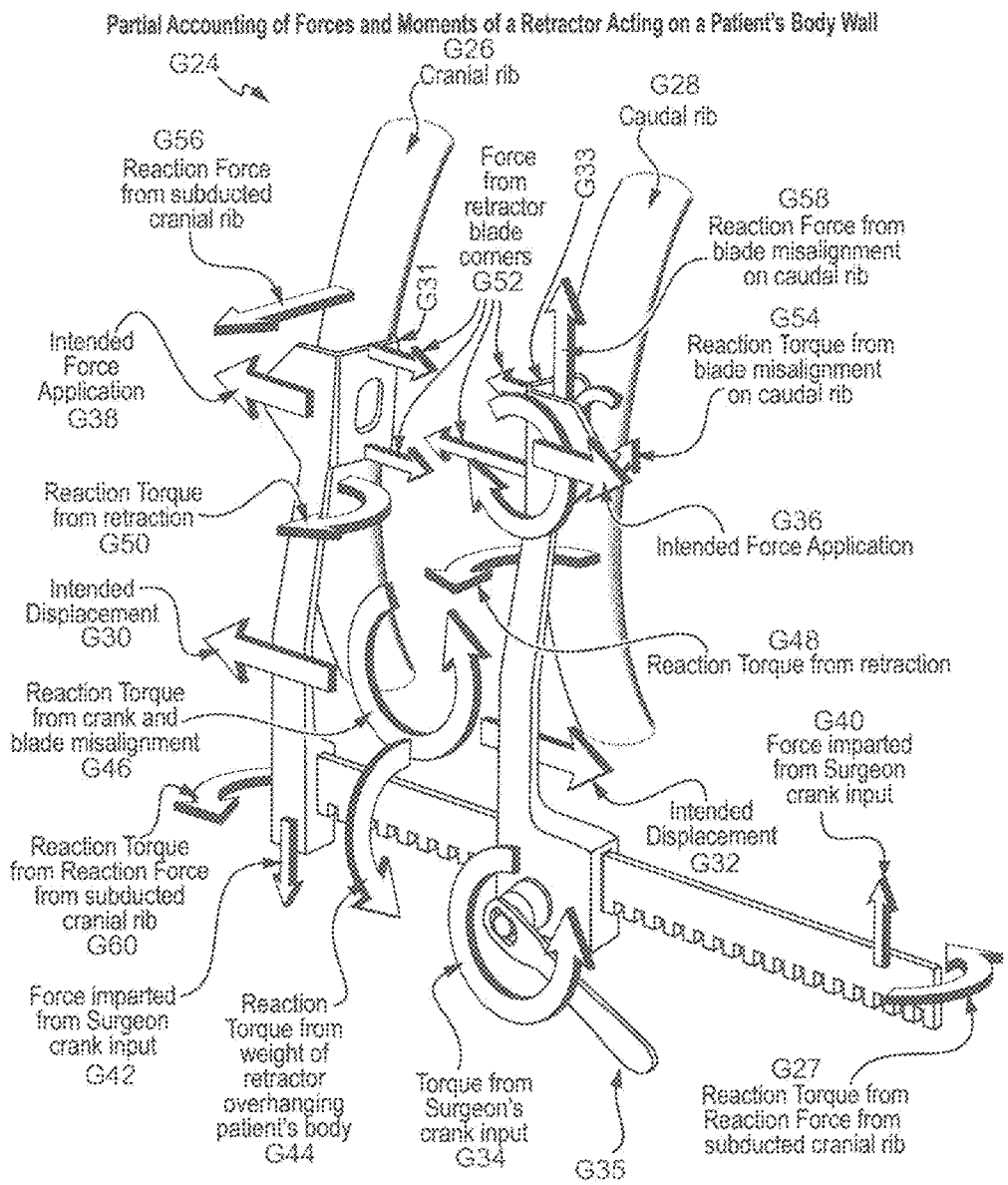

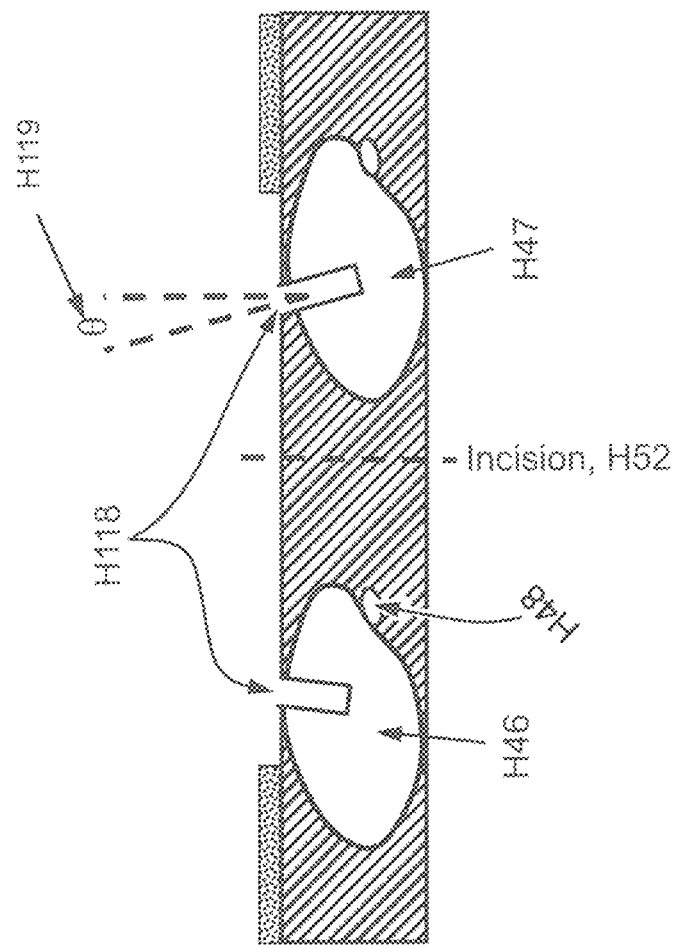

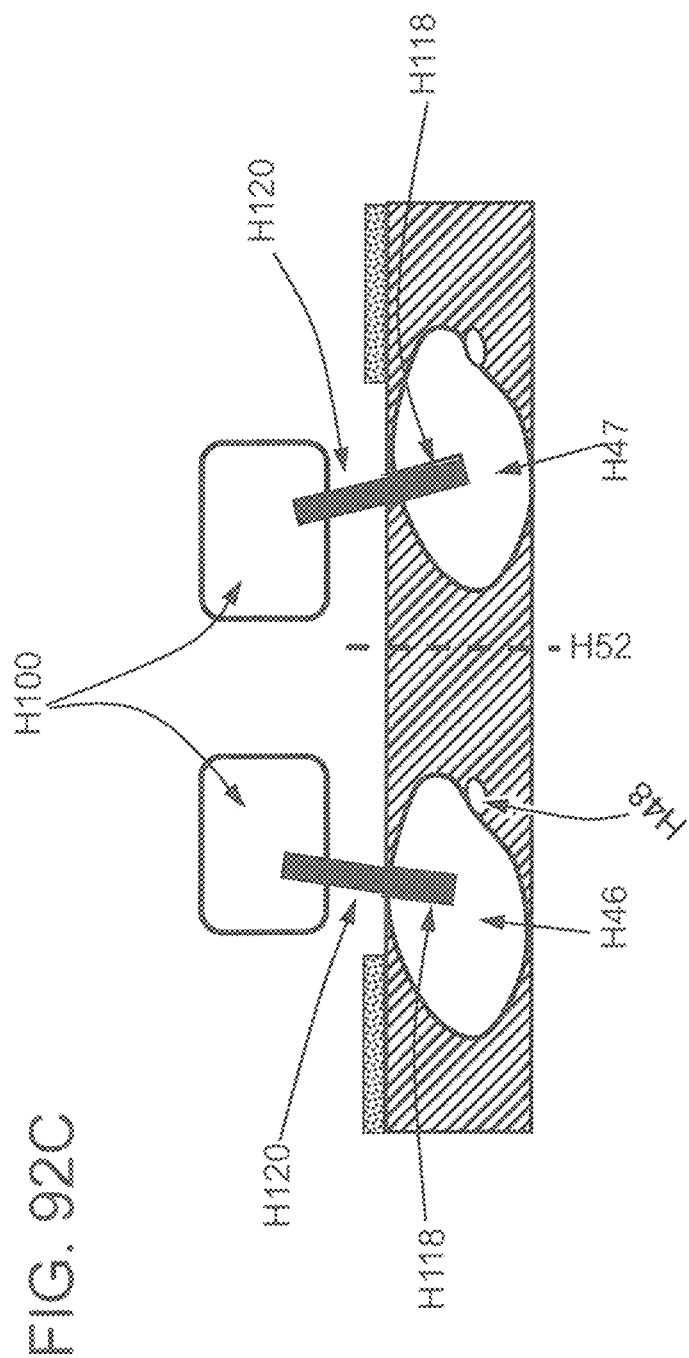

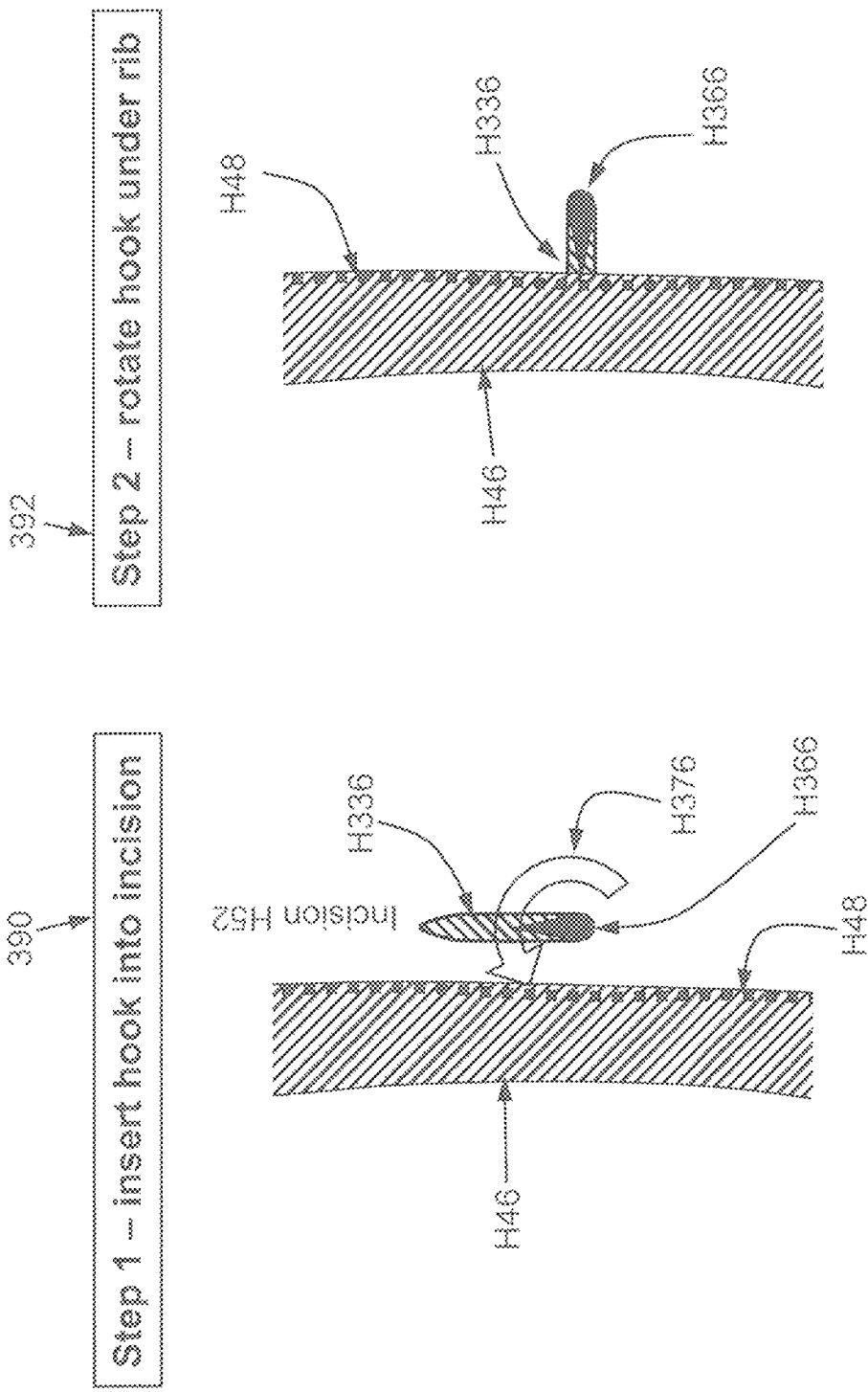

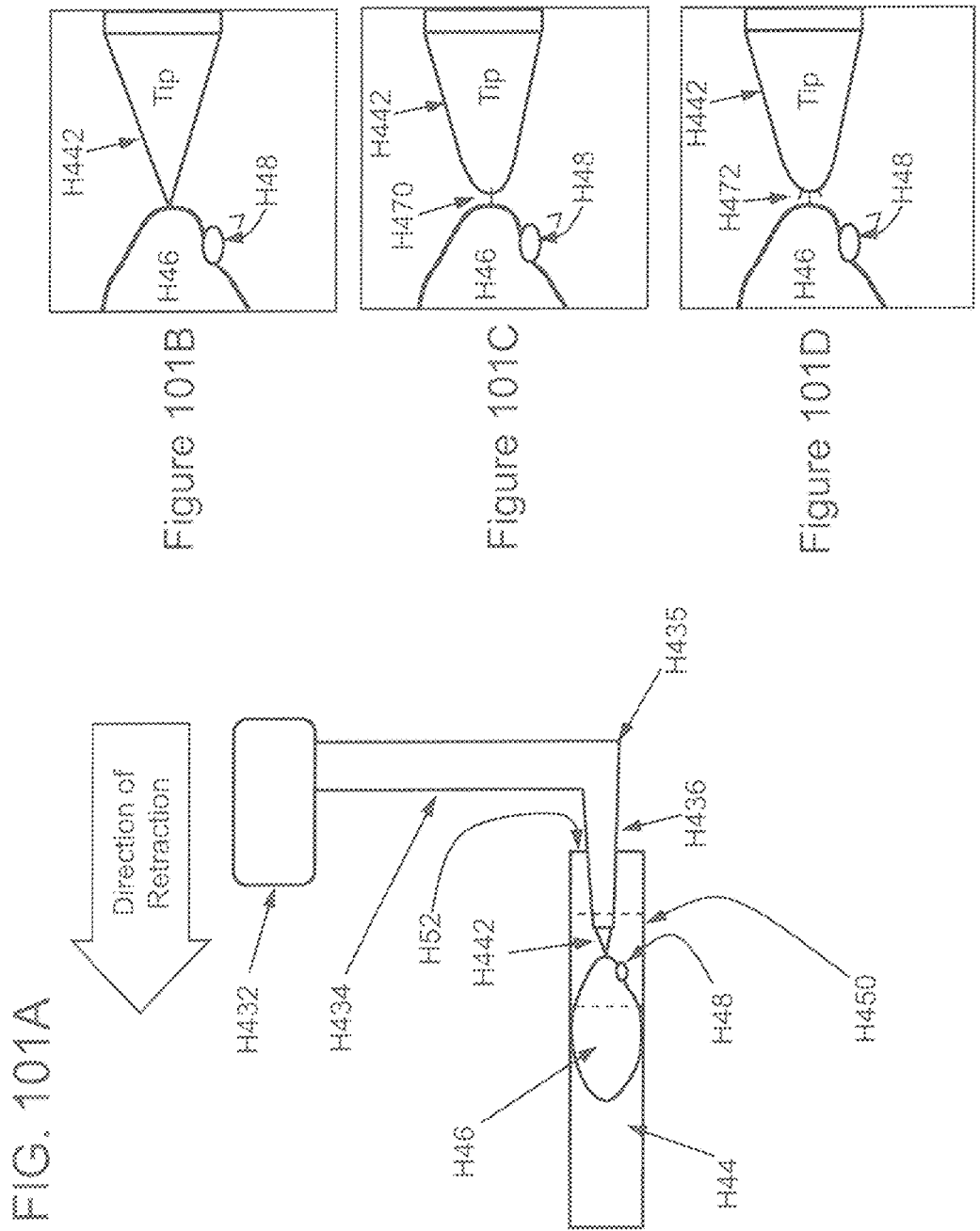

FIG. 120A
FIG. 120B1 (Prior Art)
FIG. 120B2
FIG. 120C
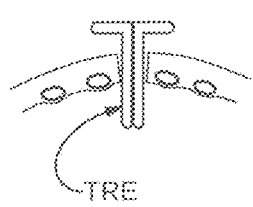
TRE
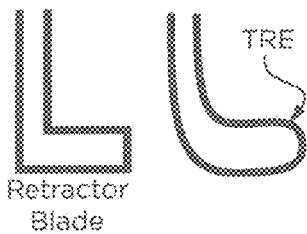
Retractor Blade
TRE
TRE
FIG. 120D
FIG. 120E
FIG. 120F
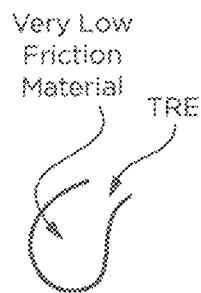
Very Low Friction Material
TRE
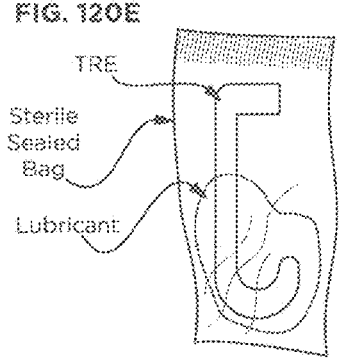
TRE
Sterile Sealed Bag
Lubricant
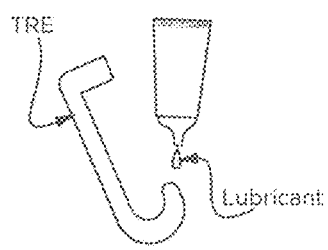
TRE
Lubricant
FIG. 120G
FIG. 120H
FIG. 120I
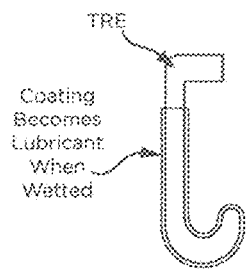
TRE
Coating Becomes Lubricant When Wetted
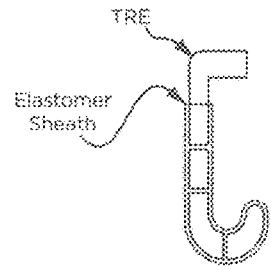
TRE
Elastomer Sheath
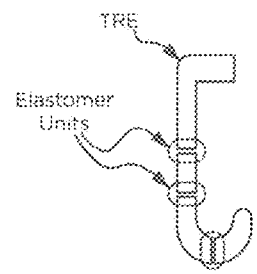
TRE
Elastomer Units Engagement 3. Ready for Retraction 2. Engaging Action of the Finger Flexing Lever on the Articulating Safety Finger 1. Insertion Articulated Tissue Engager "Finger"
(Detail of Finger-Flexing Lever Action)

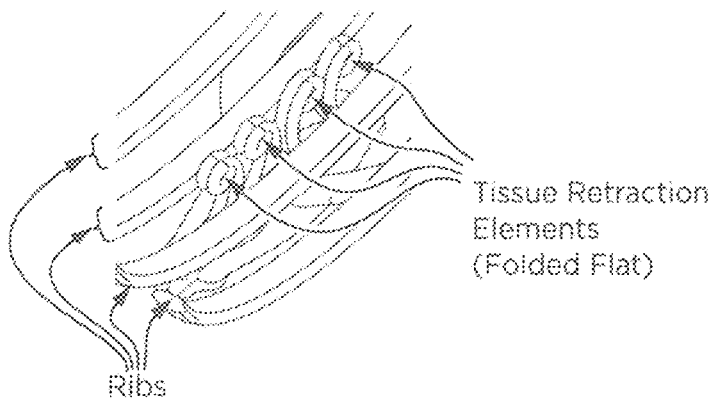
FIG. 132A  1. INSERTION STEP (view from inside chest cavity)
Tissue Retraction Elements (Folded Flat)
Ribs
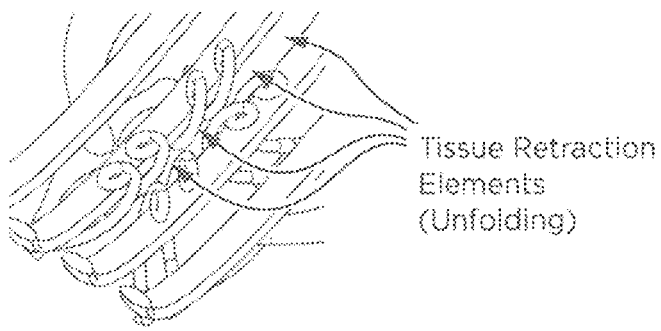
FIG. 132B  2. ENGAGING THE TISSUES
Tissue Retraction Elements (Unfolding)
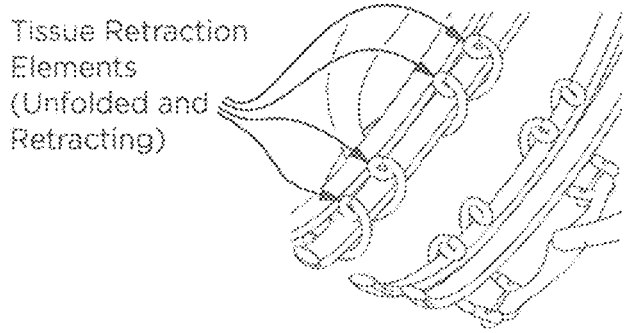
FIG. 132C  3. RETRACTING THE TISSUES
Tissue Retraction Elements (Unfolded and Retracting)

Time-Stepped Views of Swinging Safety Finger,
Showing Shape Presented to a Patient's Rib

FIG. 133A FIG. 133B FIG. 133C

PROFILE VIEW

1. Swinging Safety Finger, For Insertion
2. Swinging Safety Finger, Engaging
3. Swinging Safety Finger, For Retraction ⇐ Direction of Retraction for Profile and Top Views

FIG. 133D FIG. 133E FIG. 133F

TOP VIEW

METHODS AND DEVICES TO DECREASE TISSUE TRAUMA DURING SURGERY

PRIORITY AND RELATED APPLICATIONS

The present application is a continuation of and claims priority to U.S. patent application Ser. No. 13/111,762 entitled "METHODS AND DEVICES TO DECREASE TISSUE TRAUMA DURING SURGERY," filed on May 19, 2011, which has been published as U.S. Patent Application Publication No. 2012/0130180 A1, now abandoned, which claims priority to U.S. Provisional Patent Application No. 61/395,915, entitled "METHODS AND DEVICES TO DECREASE TISSUE TRAUMA DURING SURGERY," filed on May 19, 2010, which is incorporated herein in its entirety.

U.S. patent application Ser. No. 13/111,762 also is a continuation-in-part Application of U.S. patent application Ser. No. 12/422,584, now issued as U.S. Pat. No. 8,845,527, entitled "METHODS AND DEVICES TO DECREASE TISSUE TRAUMA DURING SURGERY," filed on Apr. 13, 2009, which is incorporated herein by reference in its entirety, and which in turn claims priority to the following provisional applications:

a. U.S. Provisional Patent Application No. 61/123,806, entitled "OSCILLATING LOADING TO MINIMIZE TISSUE TRAUMA DURING SURGICAL PROCEDURES," filed on Apr. 11, 2008, which is incorporated herein by reference in its entirety, and b. U.S. Provisional Patent Application No. 61/044,154, entitled "METHODS FOR DETECTING TISSUE TRAUMA DURING SURGICAL RETRACTION," filed on Apr. 11, 2008, which is incorporated herein by reference in its entirety, and c. U.S. Provisional Patent Application No. 61/127,575, entitled "SURGICAL RETRACTOR ARMS FOR REDUCED TISSUE TRAUMA," filed on May 14, 2008, which is incorporated herein by reference in its entirety, and d. U.S. Provisional Patent Application No. 61/127,491, entitled "APPARATUS AND METHODS FOR REDUCING MECHANICAL LOADING AND TISSUE DAMAGE DURING MEDICAL PROCEDURES," filed on May 14, 2008, which is incorporated herein by reference in its entirety, and e. U.S. Provisional Patent Application No. 61/131,752, entitled "APPARATUS AND METHODS FOR ENGAGING HARD TISSUES TO AVOID SOFT TISSUE DAMAGE DURING MEDICAL PROCEDURES," filed on Jun. 12, 2008, which is incorporated herein by reference in its entirety.

FIELD OF THE DISCLOSURE

The field of the disclosure relates to spreaders, retractors, angioplasty balloons, and retraction devices used to deform tissue during surgery or other medical procedures.

BACKGROUND

Deformation of tissues is commonly performed during surgery or other medical procedures either to achieve surgical access or to specifically alter the dimensions of one part of the anatomy. Examples of deformations of tissue for surgical access include spreading ribs during a thoracotomy, spreading a bisected sternum during a sternotomy, and separating the vertebrae of the spine for surgery on the intervertebral disk. Examples of deformation of tissues to alter the dimensions of the tissue include angioplasty to open blocked arteries, valvuloplasty to enlarge heart valves, and distraction to adjust the position of vertebrae. Such deformations are collectively referred to herein as "retraction".

Spreaders, retractors, distractors, and even angioplasty balloons (collectively called "retractors" here) can impose significant forces on the surrounding tissues during retraction. The resulting strain on these tissues, and on associated tissues such as the ligaments attaching ribs to vertebrae, can be large, leading to damage of these tissues, including the fracture of ribs and the rupture or irreversible deformation of ligaments and other fibrous tissues.

Retraction occurs in two different phases-deforming the tissue (referred to herein as the first phase or retraction) and holding the tissue at that deformation (referred to herein as the second phase of retraction). Usually both are done with the same instrument. For example, a rib spreader is used both to force the ribs apart during a thoracotomy and to hold the ribs apart during the surgical procedure. Sometimes two different instruments are used, especially if the deformation is to be permanent. For example, an angioplasty balloon is used to force open an atherosclerotic plaque, and then a stent is used to hold the artery open; or a distractor is used to separate vertebrae, and a metal plate is used to secure the vertebrae in that position. An example of two different instruments being used when the deformation is not permanent is disclosed in U.S. Pat. No. 5,201,325 by McEwen (McEwen, Auchinleck et al. 1993), therein a surgeon manually retract an incision with a disclosed retractor blade, and an automated mechanism is then used to hold the incision open. In the medical literature, both phases are frequently referred to as retraction.

Both phases of retraction traumatize tissue. Trauma from the first phase of retraction can include the rending and tearing of tissues—bones bend and break; muscles stretch beyond normal limits; ligaments and other connective tissues stretch and tear; or nerves are stretched. Trauma from the second phase of retraction can include ischemia of the tissue due to elevated tissue pressure, for example, under a retractor blade; blockage of nerves; and blockage of blood vessels causing ischemia in tissues distant from retraction.

Tissue trauma and ensuing complications resulting from retraction can be greater than the trauma resulting from the medical procedure that required the retraction. For example, thoracotomies are extremely traumatic, and can result in post-surgical pain and respiratory complications that exceed that of the thoracic procedure, such as a lung segmentectomy.

There is, therefore, need for improved methods and devices to perform one or both phases of retraction.

SUMMARY OF THE DETAILED DESCRIPTION

The embodiments disclosed herein provide retraction devices adapted to retract tissue. In one embodiment, such a device comprises at least one pair of opposed retraction members, with each retraction member being able to operably engage the tissue to be retracted. A drive mechanism is operably engaged with at least one of the retraction members in each of the at least one pair of retraction members. The drive mechanism is adapted to provide a continuous, smooth deformation of the tissue, following, for example, a parabolic distance/time curve during retraction.

In another embodiment, retraction devices that are adapted to provide a constant force during retraction of tissue. The retraction devices comprise at least one retraction member, with the at least one retraction member being able to operably engage the tissue to be retracted. A drive mechanism is operably engaged with the at least one retraction member.

In another embodiment, a retraction device includes automated control while detecting imminent fracture. In this manner, the automated control comprises measuring the retraction force and monitoring for transients in the force signal, such as a negative-going spike or an increased variance in the force signal.

In another embodiment, a retraction device includes at least one pad in contact with the margins of an incision. The pad is adapted to cool the tissue at and surrounding the margin of the incision to reduce inflammation and minimize temporary ischemia of the tissue.

In another embodiment, a retraction device includes at least one pad in contact with the margins of an incision. The pad is adapted to elute pharmacologically active compounds into the tissues at the margin of the incision to achieve beneficial outcomes, such as hemostasis or reduced inflammation.

In another embodiment, a retraction device is provided to retract tissue. In this manner, multiple tissue engagers that automatically self-balance force comprise at least one retraction member, with the at least one retraction member being able to operably engage the tissue to be retracted. A drive mechanism is operably engaged with the at least one retraction member.

In another embodiment, a retraction device is provided to retract tissue with forces aligned with the retraction. The retraction device comprises at least one pair of opposed retraction members, with each retraction member being able to operably engage the tissue to be retracted. A drive mechanism is operably engaged with at least one of the retraction members in each of the at least one pair of retraction members. At least one of the retraction members comprises an arm that can rotate around an axis perpendicular to the drive axis connecting the two retraction members, permitting the retraction members to align with respect to the retraction.

In another embodiment, a retraction device is provided to retract tissue. In this manner, the retraction member comprises a retractor arm fitted with tissue engagers that engage hard tissues while minimizing deformation of soft tissues.

In another embodiment, a retraction device to retract tissues is disclosed wherein the creep of the tissues is accommodated. The retraction device comprises at least one pair of opposed retraction members, with each retraction member being able to operably engage the tissue to be retracted. A servo-drive mechanism is operably engaged with at least one of the retraction members in each of the at least one pair of retraction members such that the retraction members are driven apart. At least one retraction member comprises a retractor arm fitted with a force measuring device that measures force on the at least one retraction member. This measured force is used to determine the deformation of the retraction member, and the servo-drive mechanism adjusts the separation of the retraction members to accommodate for creep of the tissues.

In another embodiment a thoracic retractor for performing a thoracotomy is disclosed, comprising a linear drive element having at least two arms, with at least one of them moveable along the linear drive element, and at least one self-balancing tissue engager associated with each arm. The self-balancing tissue engager comprises a first rotary joint between the arm and a first balance bar, which has additional rotary joints on each of its two ends to which second balance bars join, and each balance bar has rotary joints on each of its two ends to which join descender posts that engage a rib on one side of the incision. Opposing arms and associated tissue engagers thus engage opposing ribs on each side of an incision and retraction in opposing directions along the linear drive element spreads the ribs apart to retract the thoracic tissue.

In another embodiment, two opposing arms are each associated with a doubletree balance bar, each doubletree balance bar having two ends to which rotatably join swingletree balance bars, one swingletree balance bar on each end of the doubletree balance bar. Each swingletree balance bar has two ends to which rotatably mount a descender post each of which engages a rib. There are thus four descender posts, with forces automatically balancing through the doubletree and swingletree balance bars, that engage a rib.

In another embodiment, a tissue engager for thoracic retraction is disclosed, comprising a balancing assembly having at least one descender post descending from at least one balance bar. The descender post comprises an elongate member with a first rib-forcing surface and a hook element with a second rib-forcing surface such that a gap region is formed between the first and second rib-forcing surfaces, the gap region being concave and extending far enough in the direction of retraction to place the second rib-forcing surface away from the neurovascular bundle.

In another embodiment, the concave shape of the gap region of the descender post is further defined as a tapered hollow defined by a taper point.

In another embodiment, the taper of the descender post forms an acute angle.

In another embodiment, the tissue engager has a plurality of descender posts.

In another embodiment, the tissue engager has a plurality of balanced descender posts.

In another embodiment, a tissue engager for thoracic retraction is disclosed, comprising at least one retraction bar capable of moving along a direction of retraction and having at least one descender post descending into the incision. The descender post has an elongate member, having two ends with a first rib-forcing surface adjacent to the second end and the first end joining a balance bar at a rotatable mount, and a hook element adjoining the second end of the second end of the elongate member. The hook element has a second rib-forcing surface adjacent the hook element's second end. The first end of the slender element joins the balance bar via a rotatable joint having a rotational axis that is vertical with respect to a plane of a patient's skin allowing the descender post to rotate to extend the hook element under a rib.

In another embodiment, the descender post is substantially curved, and the first rib-forcing surface projects a distance radially out from the vertical axis, thereby defining a moment arm reaching out from the vertical axis to the first rib-forcing surface. Thus when a rib bears on the first rib-forcing surface, the descender post has a moment that would make the descender post rotate about the vertical axis.

In another embodiment, the curved descender post can rotate around the vertical axis by 90 degrees.

In another embodiment, a tissue engager possessing a balancing assembly has an elastic element that provides elastic recoil to return the balancing assembly to its original configuration after deformation by a load.

In another embodiment, the elastic element is associated with the first joint axis.

In another embodiment, the elastic element is associated with the second joint element.

In another embodiment, the elastic element is associated with the third joint element.

In another embodiment, all components of a self-balancing tissue engager are substantially encompassed by an elastic sheath.

In another embodiment, the elastic element of the tissue engager has a Young's modulus between 0.1 MPa and 60 MPa to permit retaining a preferred positioning of the elements of a self-balancing tissue engager and recovering that preferred positioning of the elements.

In another embodiment an elastic element is spatially associated with the gap region and provides a padded surface to the patient's tissues.

A method for retracting thoracic tissue, comprising retracting thoracic tissue in the direction of a linear drive element by moving along the linear drive element at least one of two arms that are oriented substantially perpendicular to the direction of retraction while self-balancing tissue engagers automatically balance the forces amongst four descending posts that are pushing on a rib.

BRIEF DESCRIPTION OF THE DRAWINGS

FIGS. 49A, 49B.1 and 49B.2 show the use of a balancing assembly in a thoracic retractor having multiple retractor blades;

FIGS. 55A through 55C show top, side, and front views, respectively, of a balance assembly used for retracting a rib, wherein hooks that descend from the balance bars engage the rib;

FIGS. 56A through 56C shows top, side, and front views, respectively, of a balance assembly used for retracting a rib, wherein hooks that descend from the balance bars engage the rib and an articulation in the balance bar permits the hooks to orient to the curvature of the rib;

FIGS. 59A through 59E shows another embodiment of a retractor having articulations in the arms, retraction hooks to engage the tissues, and cables to provide automatic force balancing on the hooks;

FIGS. 63A through 63E show another embodiment in which fenestrated bars on a fulcrum provide automatic force balancing for multiple retraction hooks;

FIG. 65A through 65C show side views of the assembly in FIG. 64.

FIGS. 66A and 66B show another embodiment in which pivots are used to provide adjustable pivot points for swingletrees;

FIG. 71 shows a more complete accounting of the forces and torques on a retractor;

FIGS. 92A through 92C show an embodiment of a tissue engaging element comprising posts placed into holes drilled into adjacent ribs;

FIGS. 98A and 98B show another embodiment of a descender post comprising a hook engaged with the retractor arm via a rotatable mount;

FIGS. 101A through 101E shows another embodiment of a descender post comprising a projection that projects laterally from the descender post and terminates in a tip having one of several configurations;

FIGS. 120A-120I show various embodiments of Tissue Retraction Elements.

FIG. 120A—A thin Tissue Retraction Element in profile view.

Figure 1A:
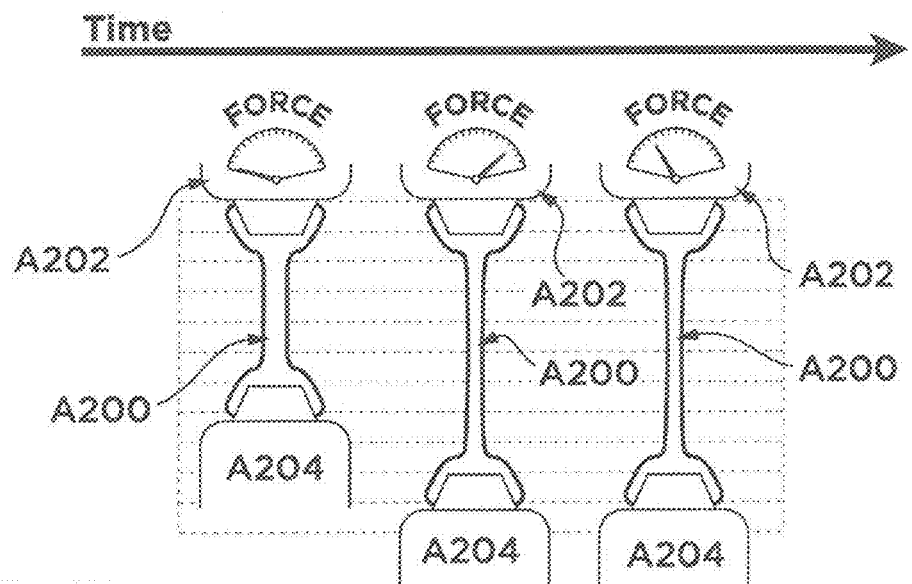
FIGS. 1A and 1B illustrate two tests of a biological sample demonstrating the biomechanical phenomena of force relaxation and creep, respectively.

FIG. 120B1—A Tissue Retraction Element with a square shape of the prior art.

Figure 2:
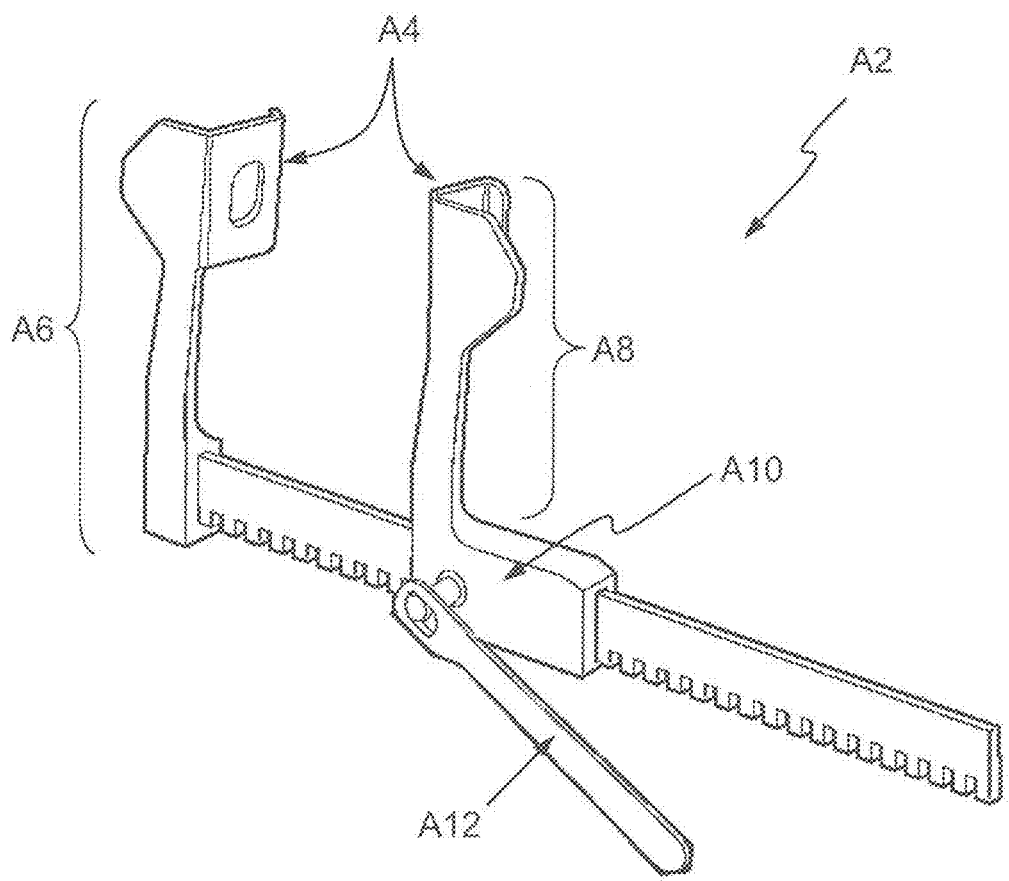
FIG. 2 is a diagram of a prior art retraction device.

FIG. 120B2—A Tissue Retraction Element with a polished surface.

FIG. 120C—Another example of a Tissue Retraction Element that is polished smooth, for example as shiny and smooth as glass, to more easily slide easily into place without friction or impediment.

FIG. 120D—A very low-friction Tissue Retraction Element.

FIG. 120E—A bagged, lubricated Tissue Retraction Element.

FIG. 120F—A Tissue Retraction Element with lubricant applied in the operating room.

FIG. 120G—A Tissue Retraction Element with water-activated lubricant coating.

FIG. 120H—A Tissue Retraction Element with an elastic sheath.

FIG. 120I—A Tissue Retraction Element with elastic joints.

Figure 121:
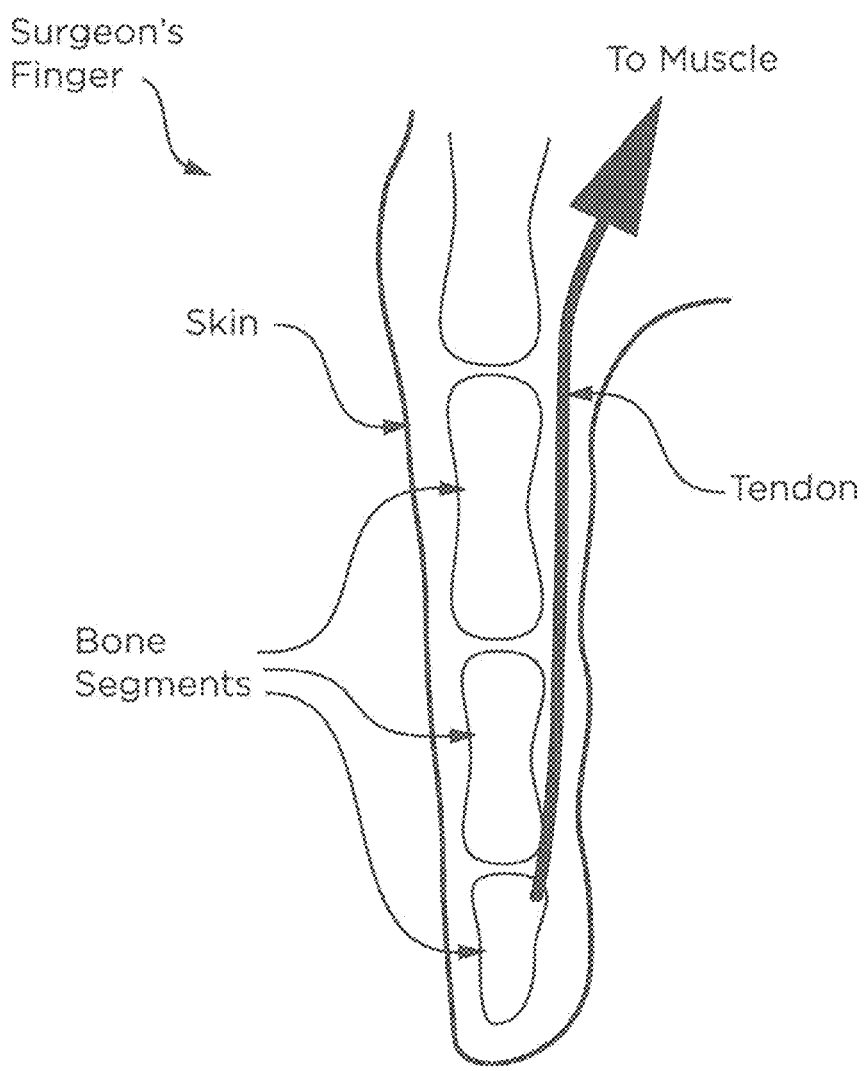

FIG. 121—A surgeon's finger, in section view.

Figure 122:
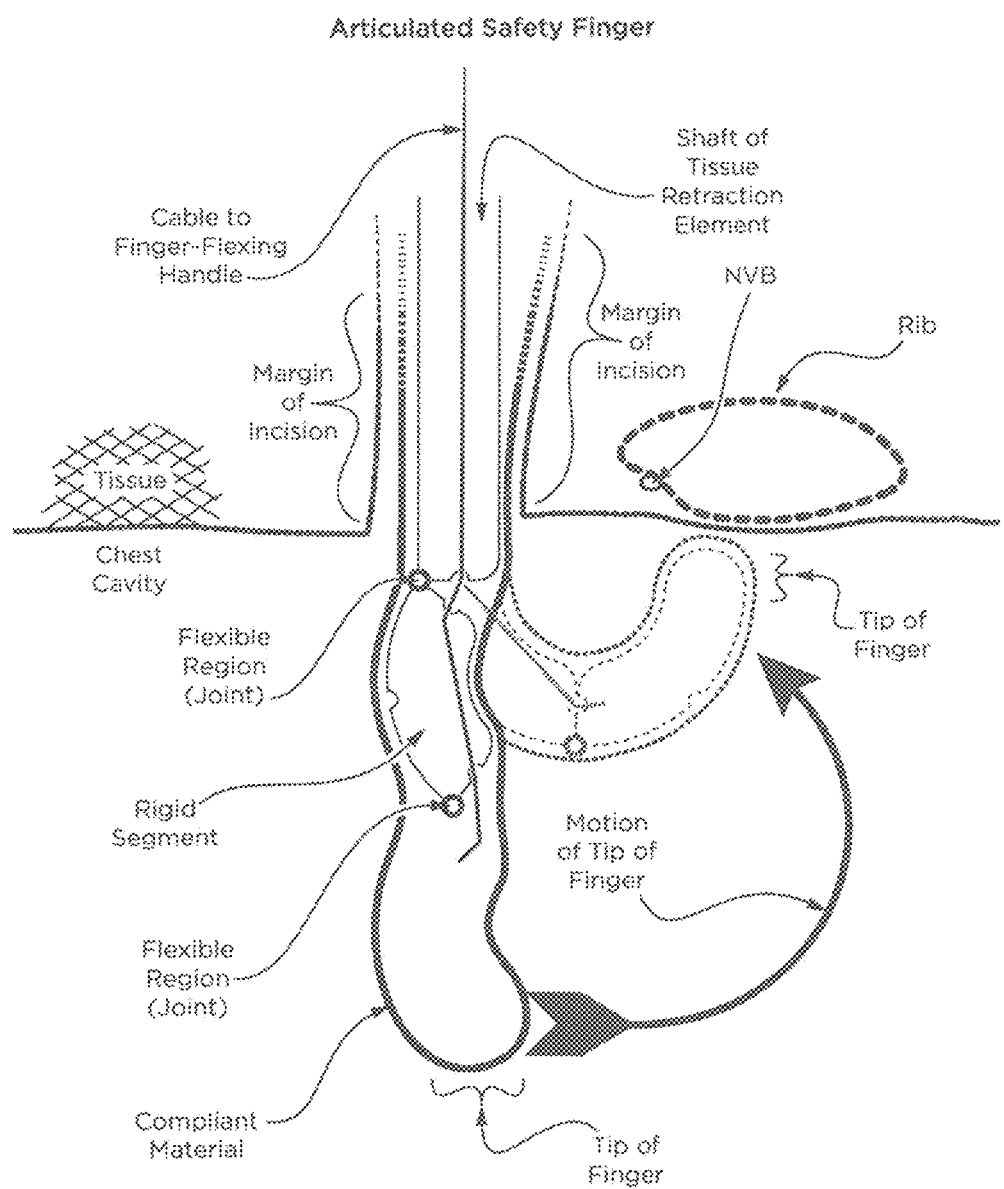

FIG. 122—An Articulated Safety Finger, in section view.

Figure 123:
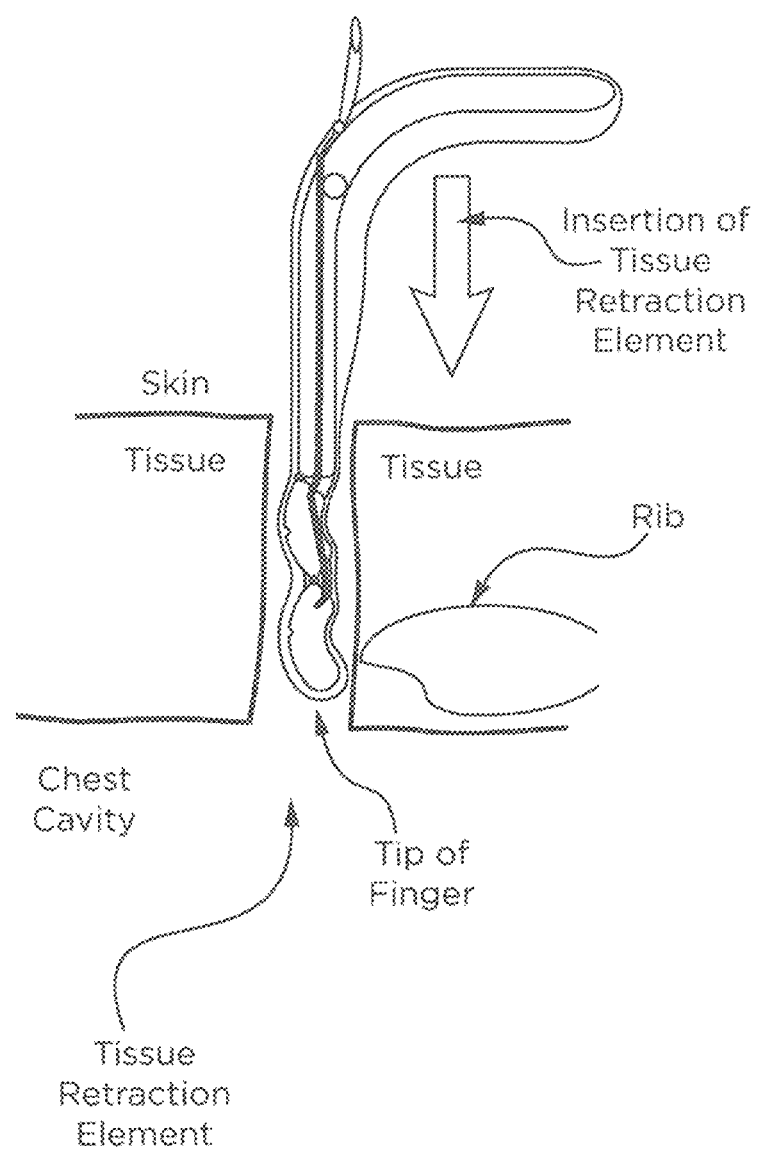

FIG. 123—An Articulated Safety Finger, straight for insertion.

Figure 124A:
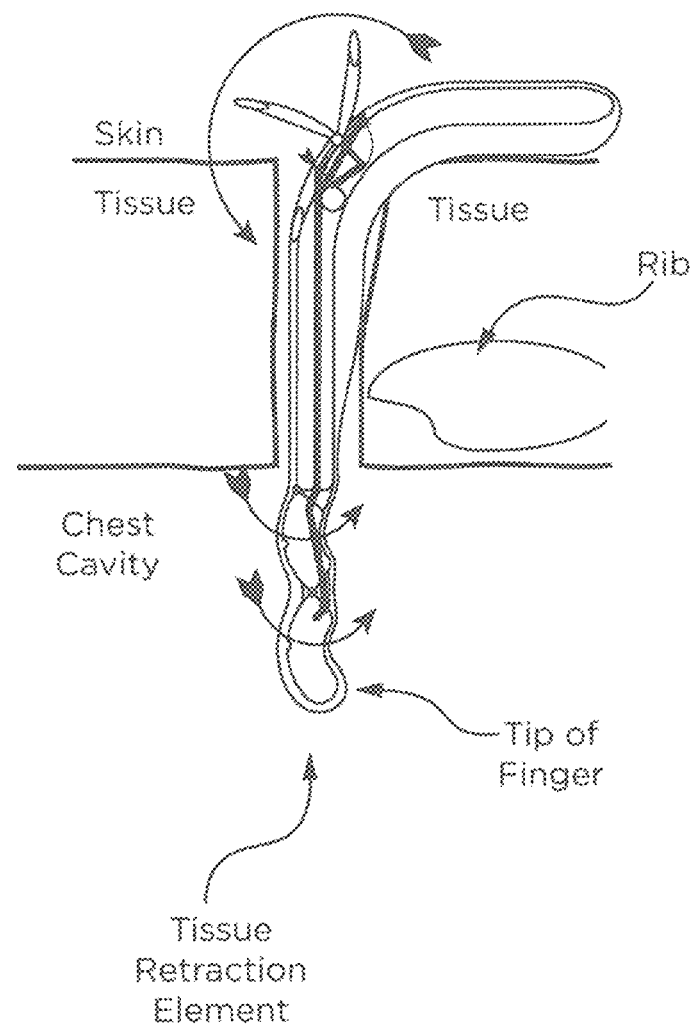

FIG. 124A—An Articulated Safety Finger, pulling on cable.

Figure 124B:
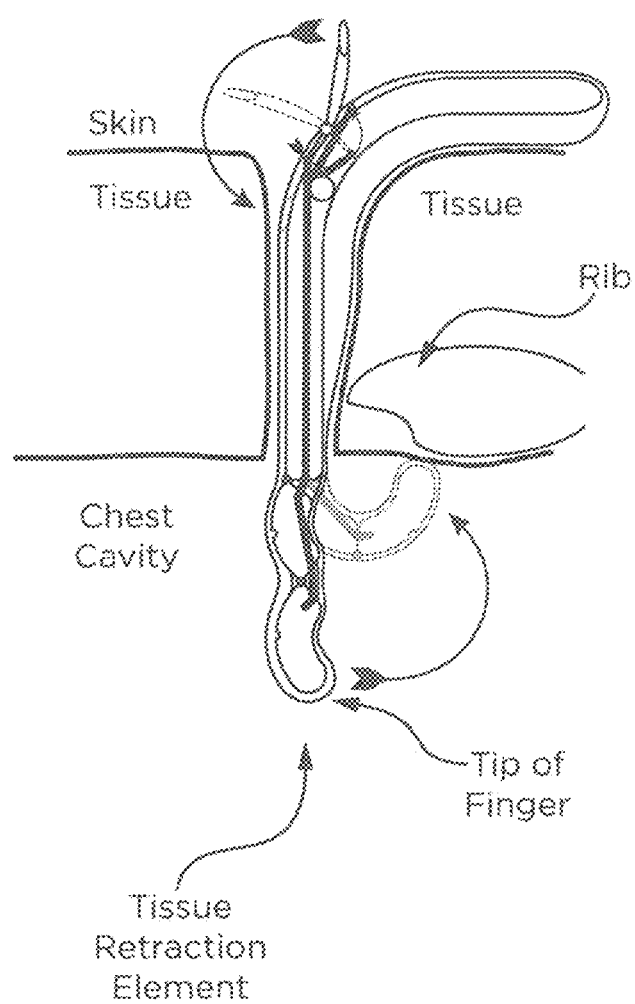

FIG. 124B—An Articulated Safety Finger, flexed.

Figure 125:
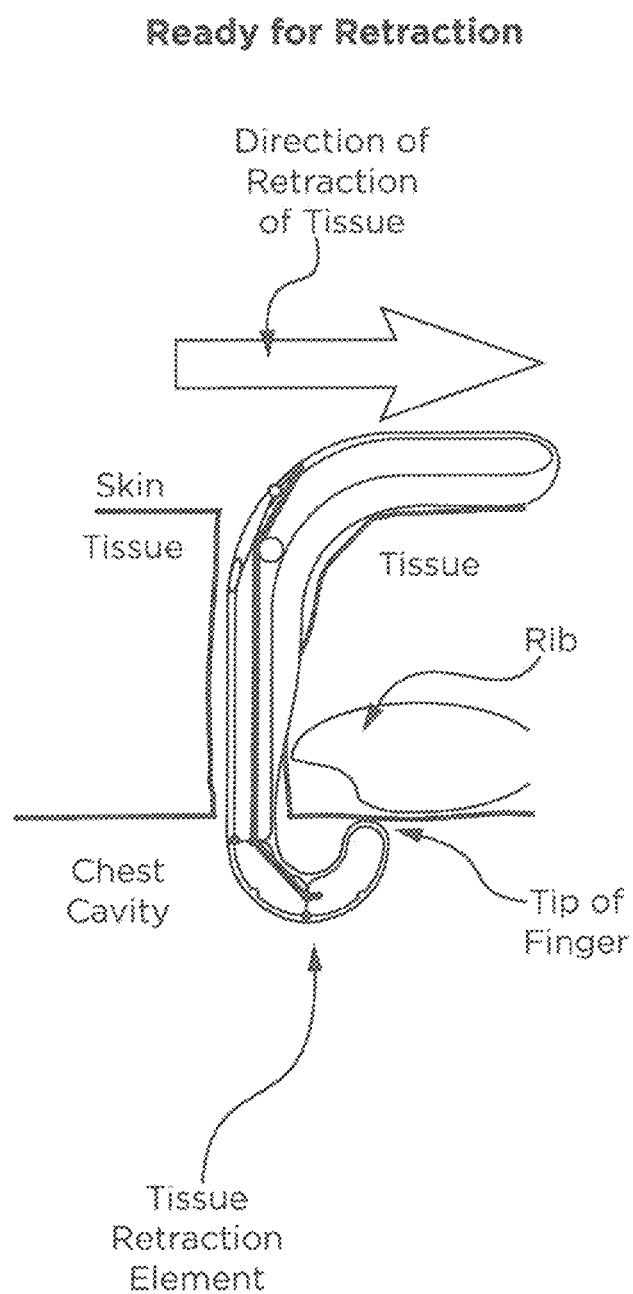

FIG. 125—Articulated Safety Finger, ready for retraction.

Figure 126C:
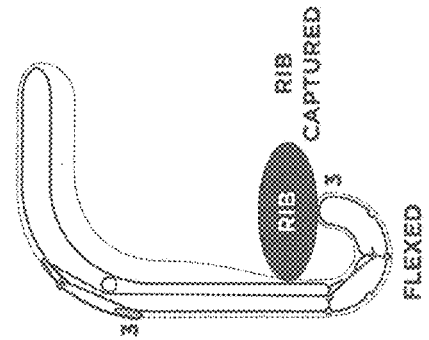
Figure 126B:
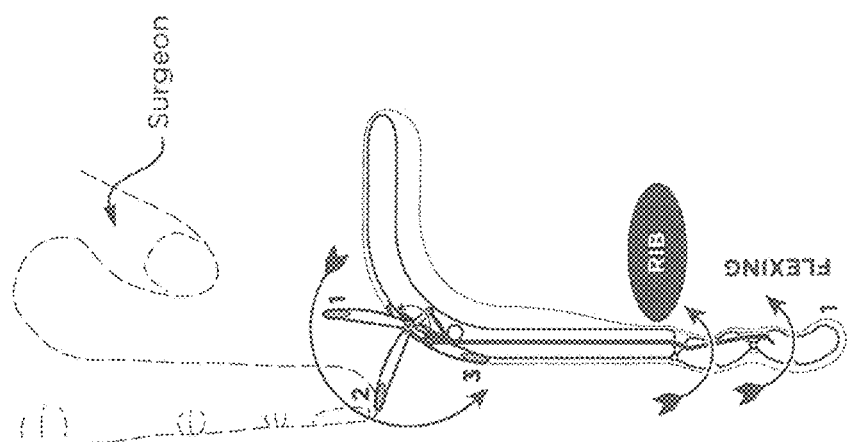
Figure 126A:
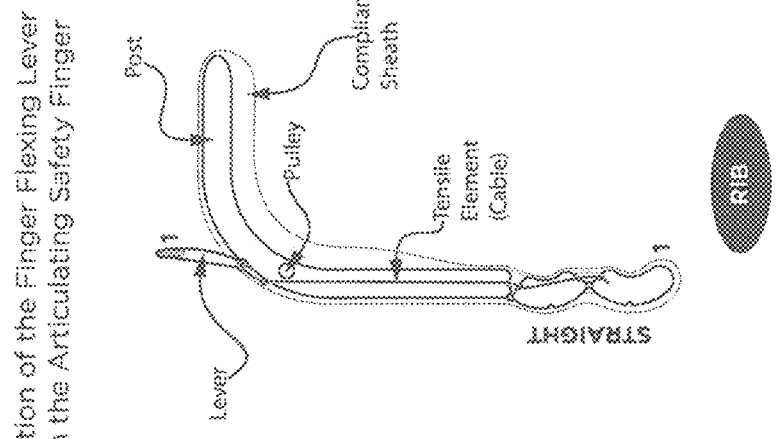

FIGS. 126A through 126C—Surgeon hand-actuating the ASF's Finger Flexing Lever.

Figure 127:
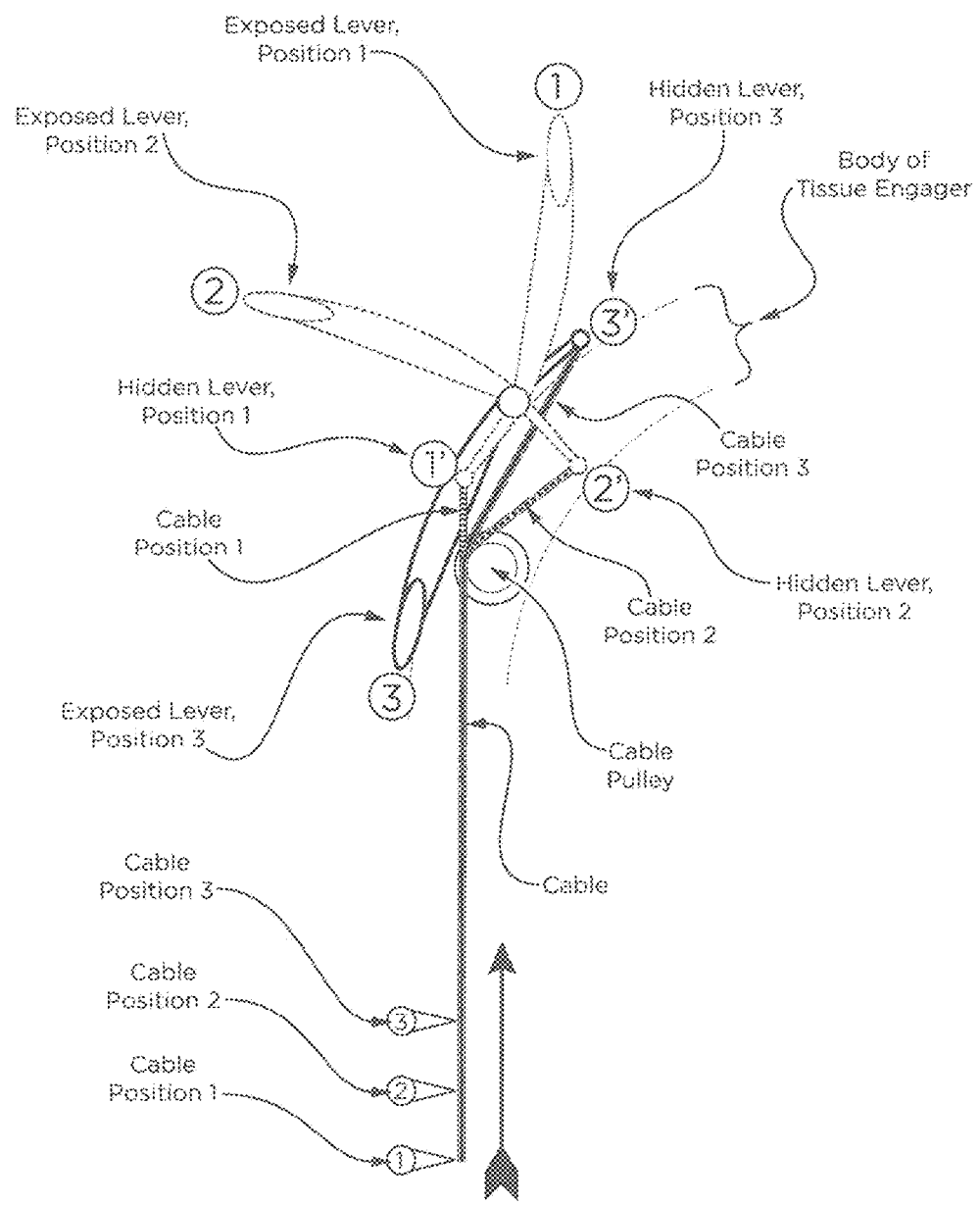

FIG. 127—Detail of the ASF's Finger Flexing Lever.

Figure 128:
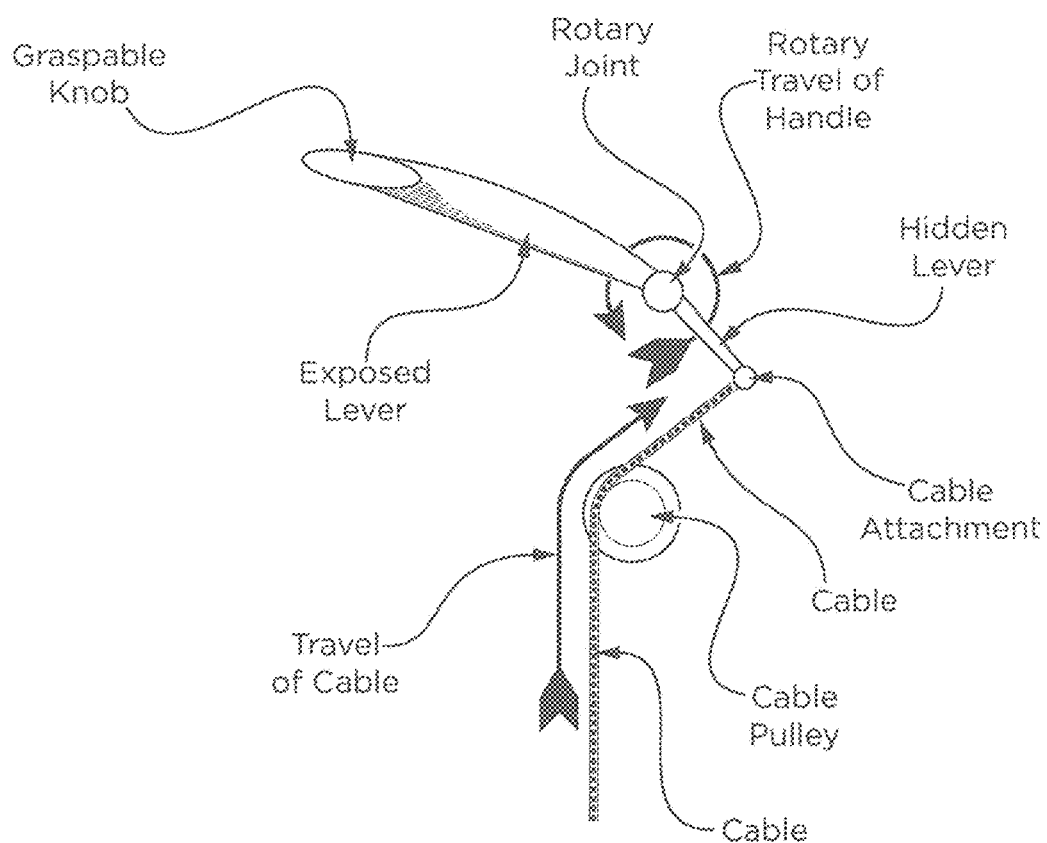

FIG. 128—Detail showing the action of the ASF's Finger Flexing Lever.

Figure 129:
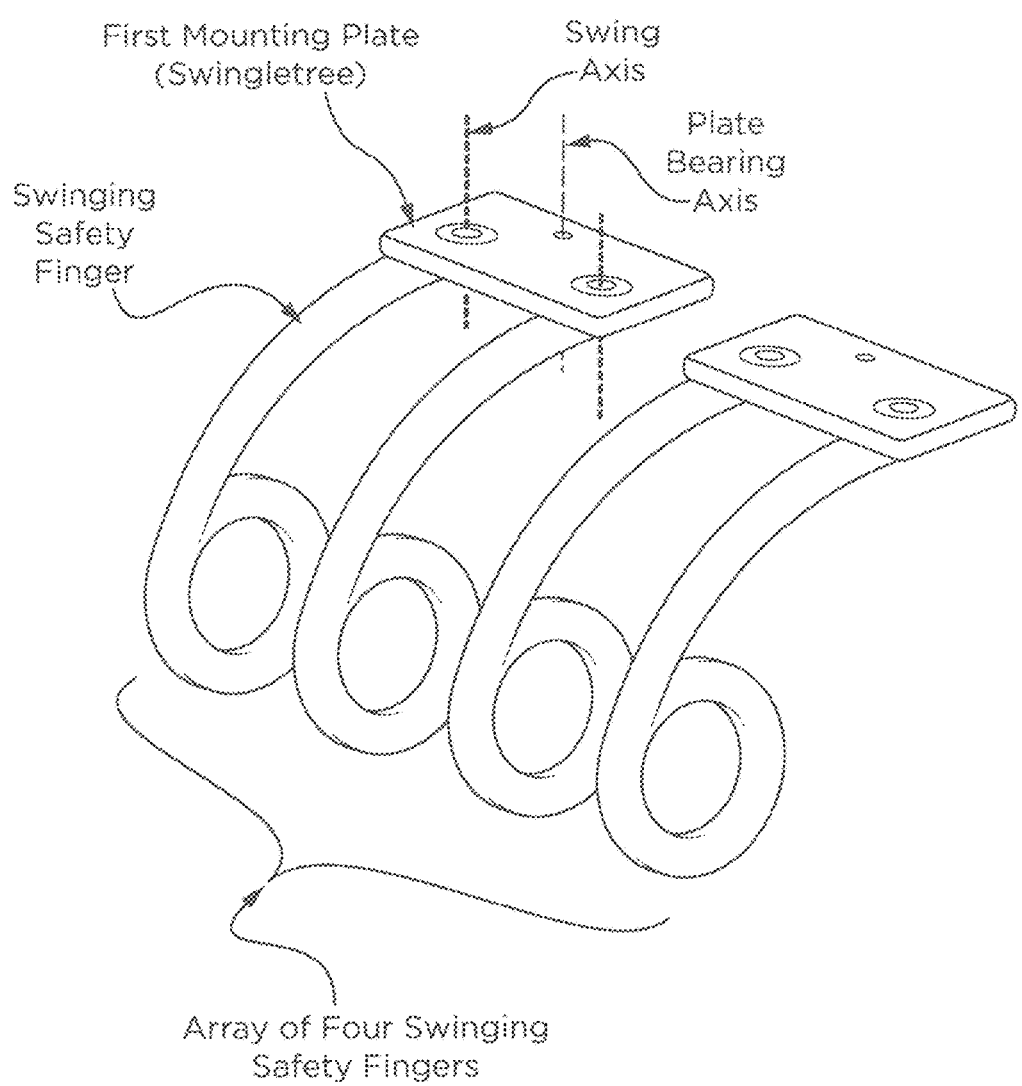

FIG. 129—Oblique view of Swinging Safety Finger TRE.

Figure 130A:
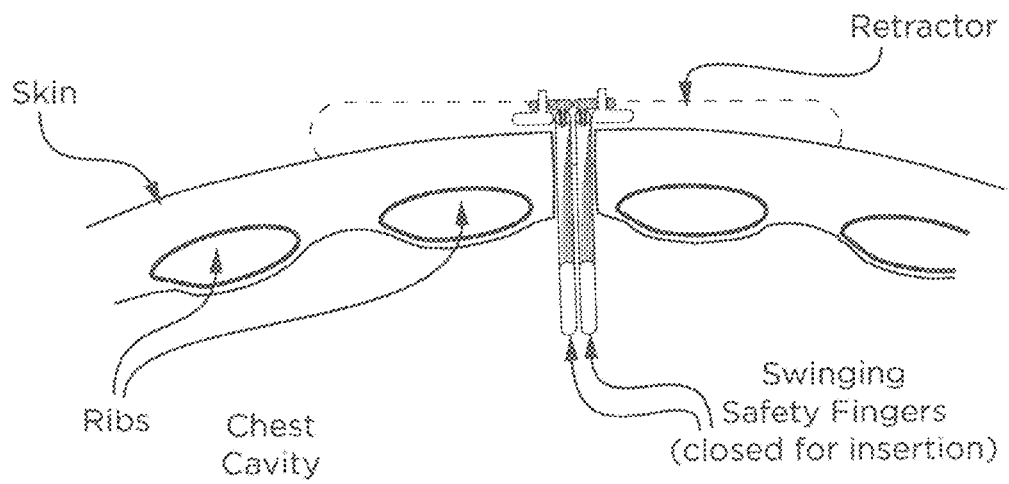

FIG. 130A—Profile view of Swinging Safety Finger closed and thin for insertion.

Figure 130B:
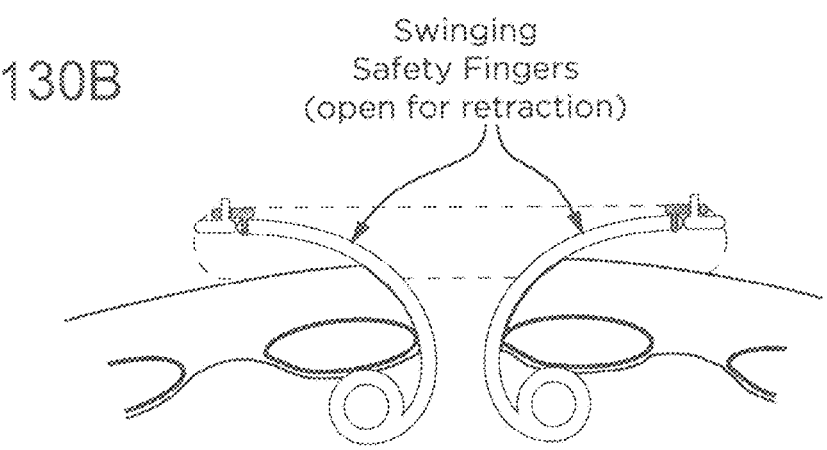

FIG. 130B—Profile view of Swinging Safety Finger opened and retracting tissue.

Figure 131:
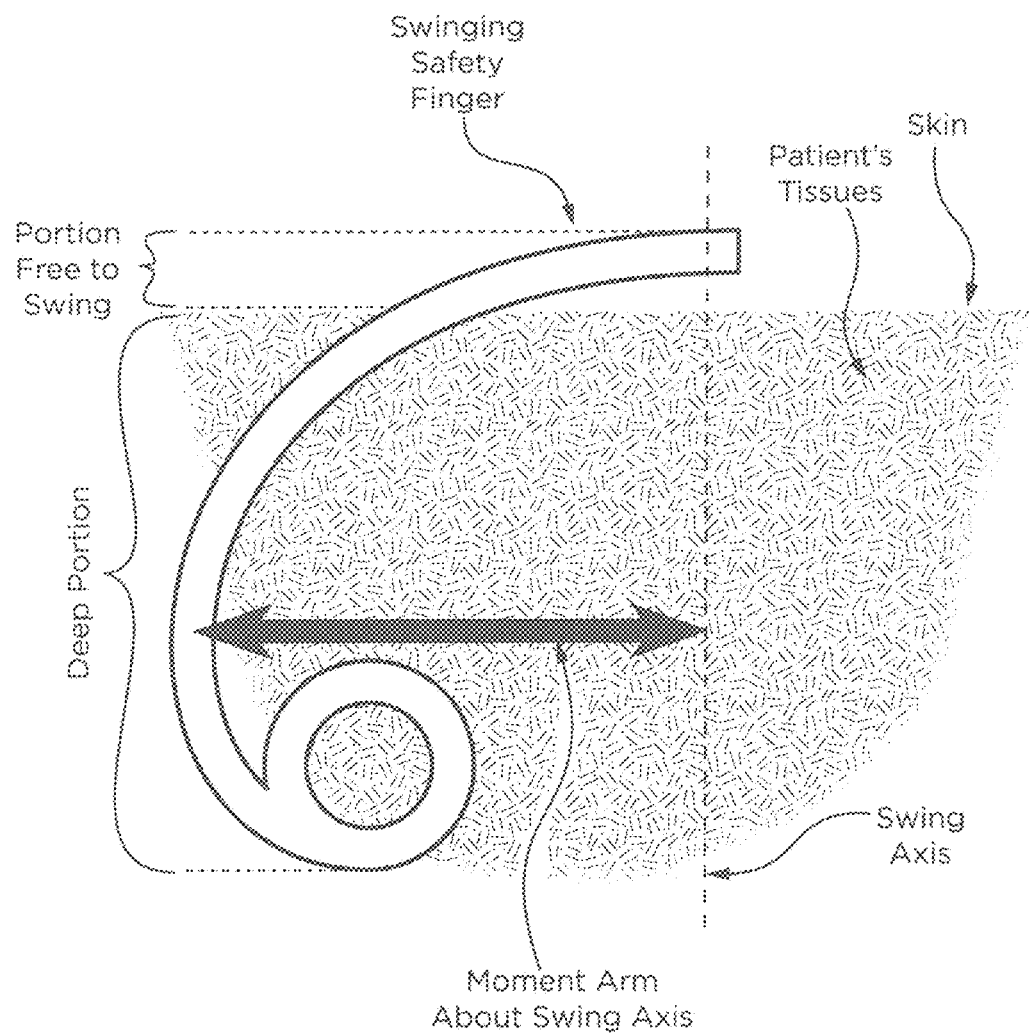

FIG. 131—Swinging Safety Finger showing off-center deep area creating moment.

FIGS. 132A through 132C—Deployment sequence of the Swinging Safety Finger.

FIGS. 133A through 133F—Time-stepped views showing gradually changing profile of SSF showing three steps viewed from the side and same three steps viewed from above.

Figure 134:
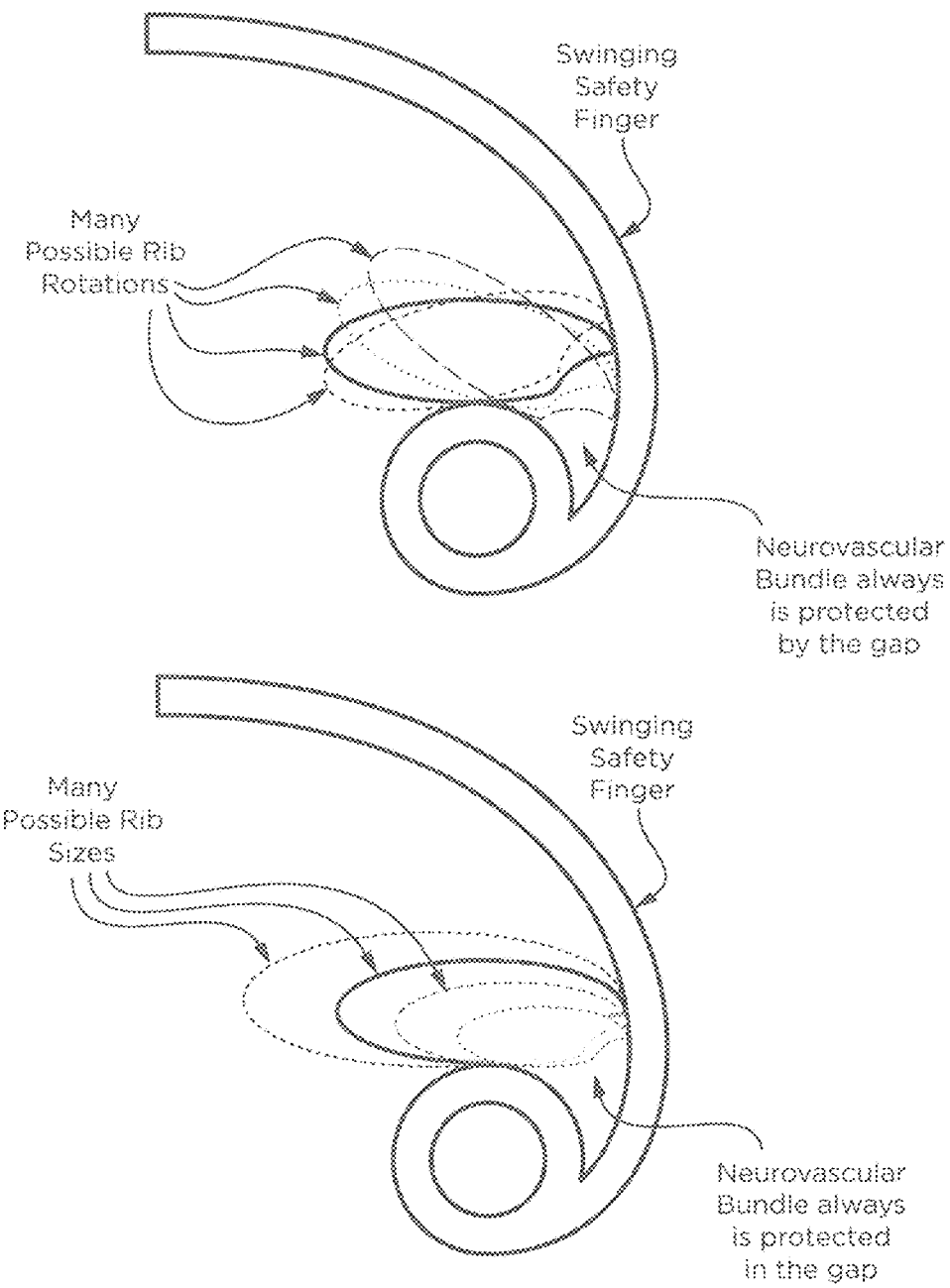

FIG. 134 shows how the gap accommodates many rib rotations and sizes to always protect the neurovascular bundle.

Figure 135:
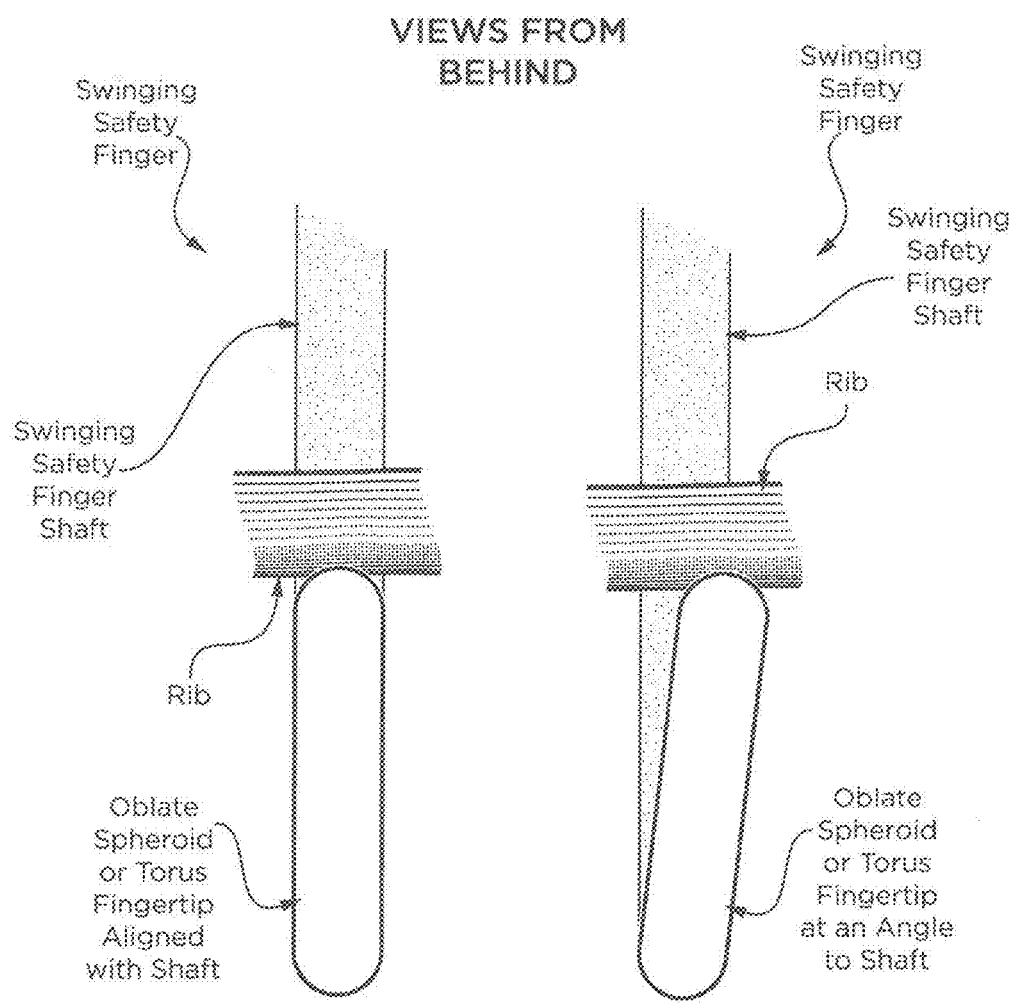

FIG. 135 shows a swinging safety finger with a rib resting on it.

Figure 136A:
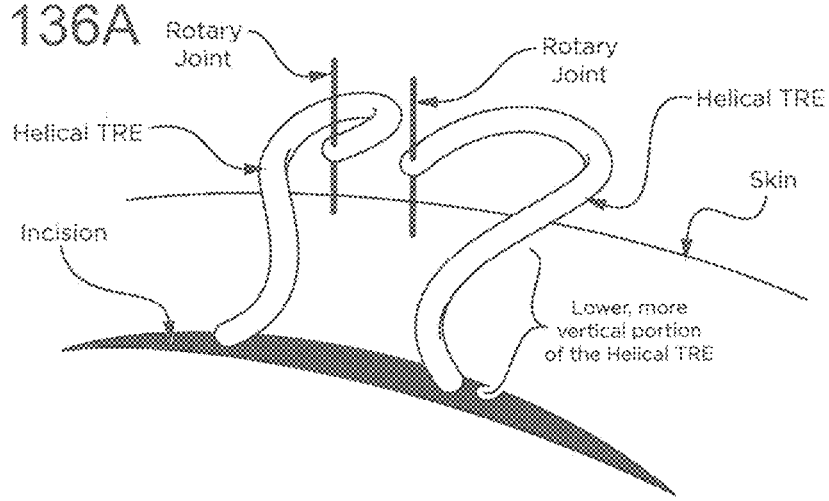
Figure 136B:
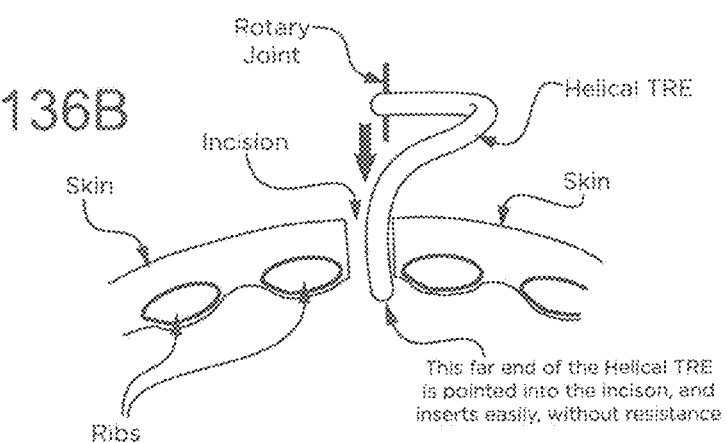
Figure 136C:
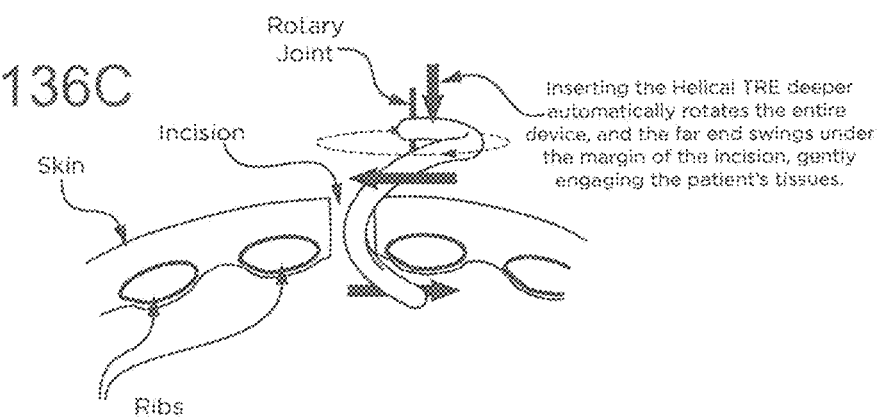

FIGS. 136A through 136C shows a helical retraction element that self-engages on insertion.

Figure 137:
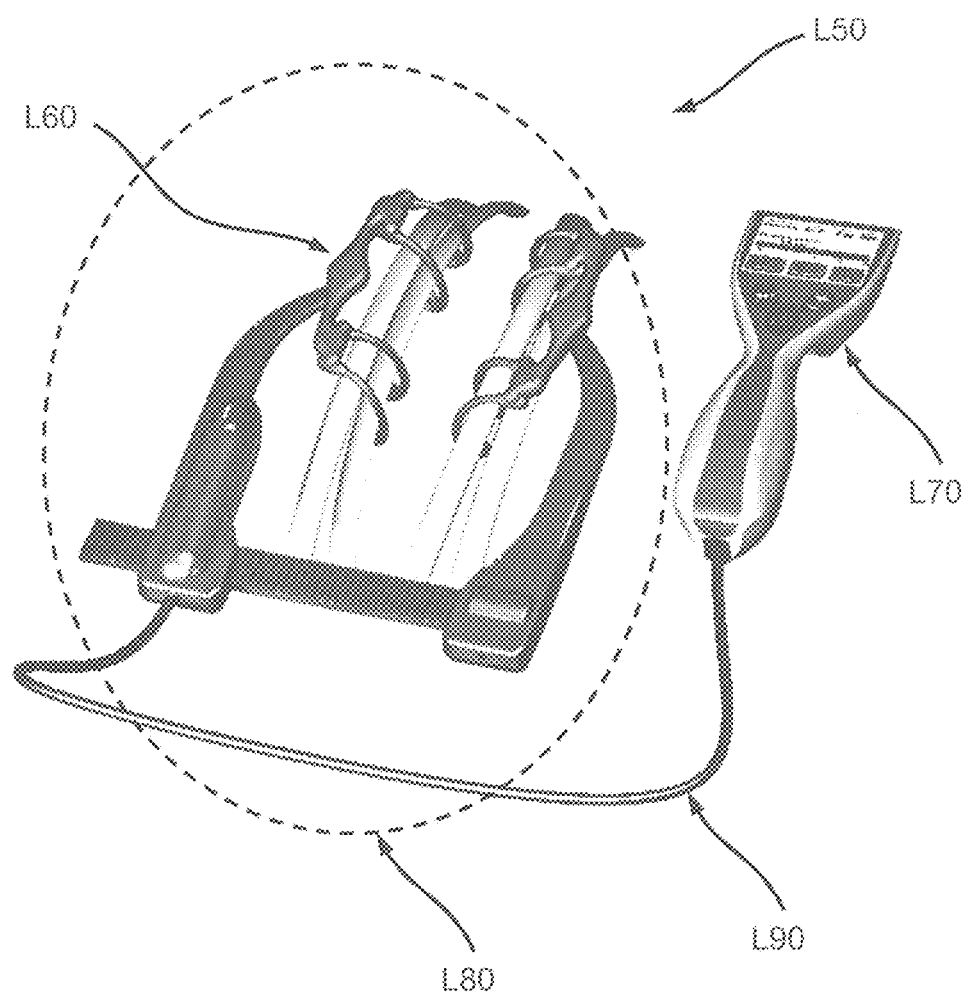

FIG. 137 shows a prototype automated retractor for thoracotomy.

Figure 138:
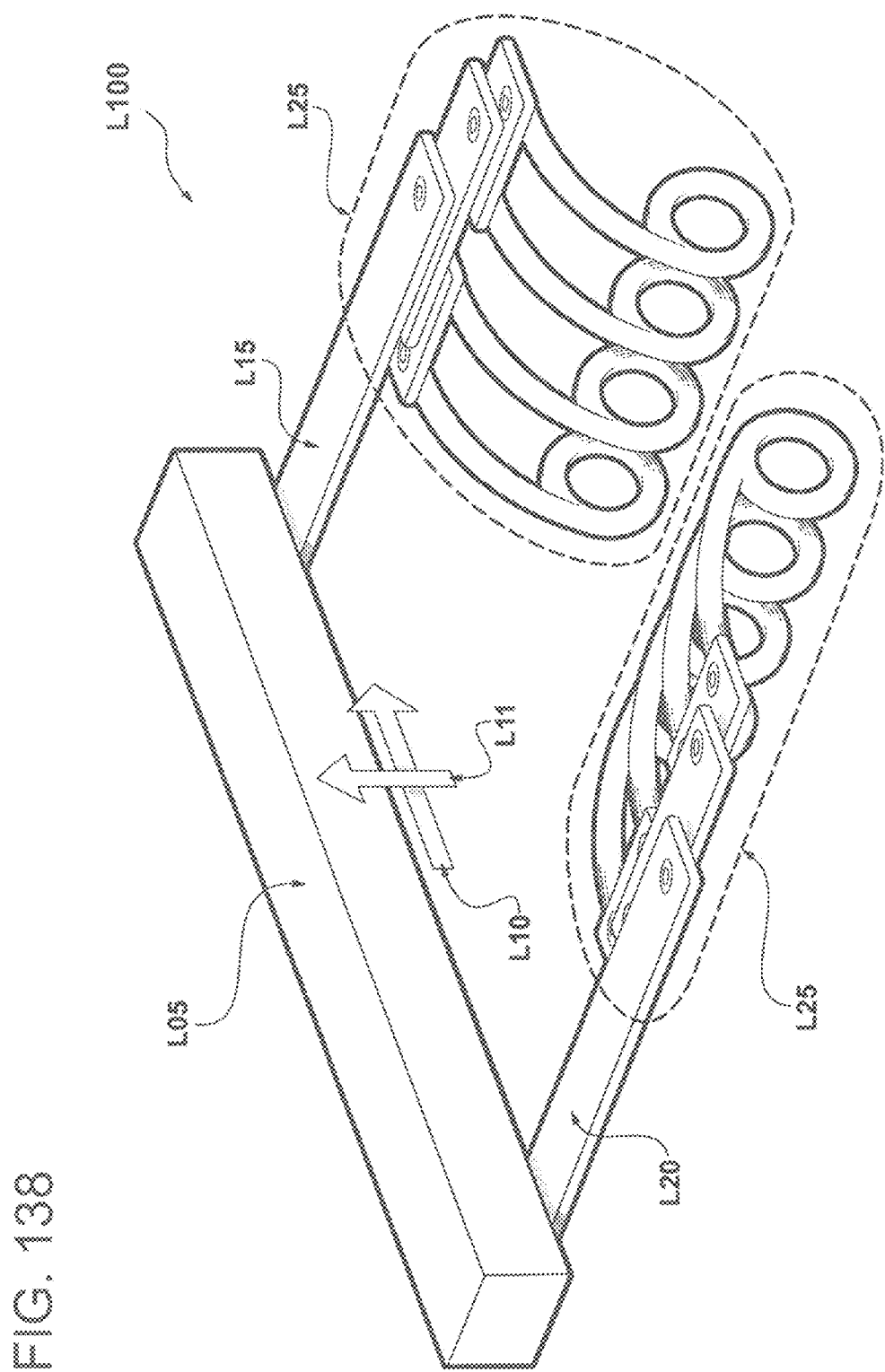

FIG. 138 shows a retractor with tissue engagers having balancing beams and descender posts to retract ribs for thoracotomy.

Figure 139:
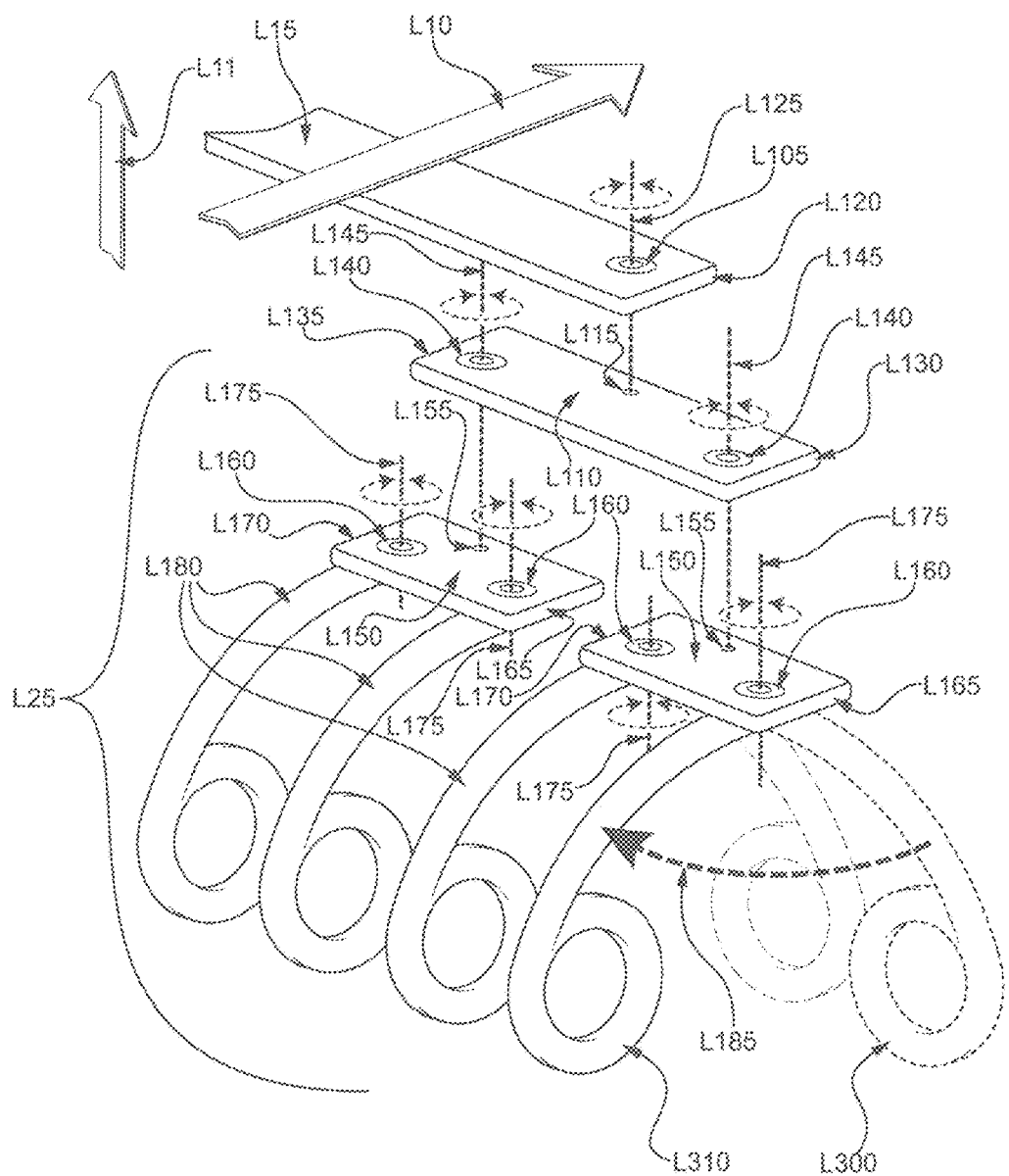

FIG. 139 shows a self-balancing tissue engager for retracting ribs.

Figure 140:
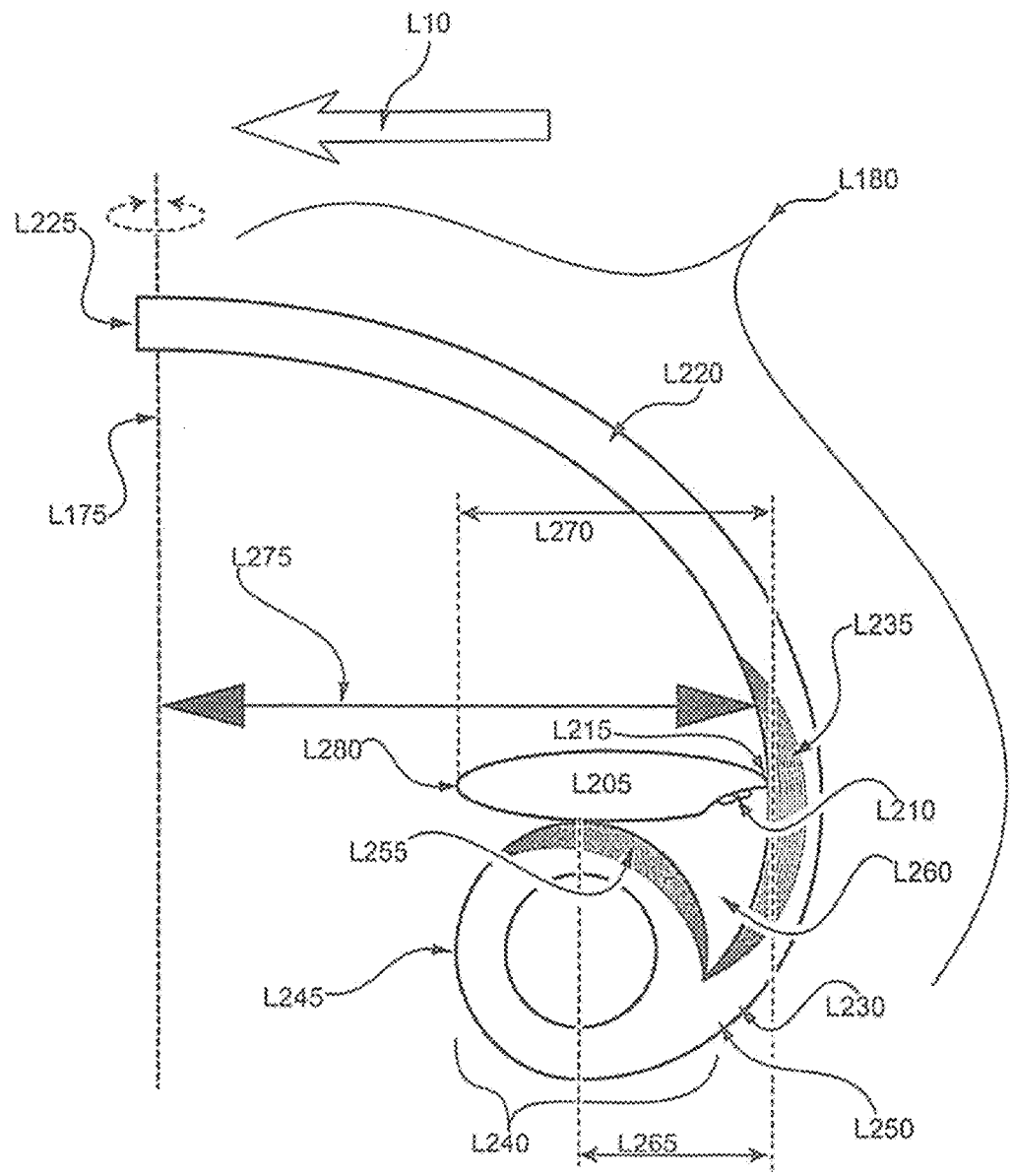

FIG. 140 shows a descender post engaging a rib for retraction.

Figure 141:
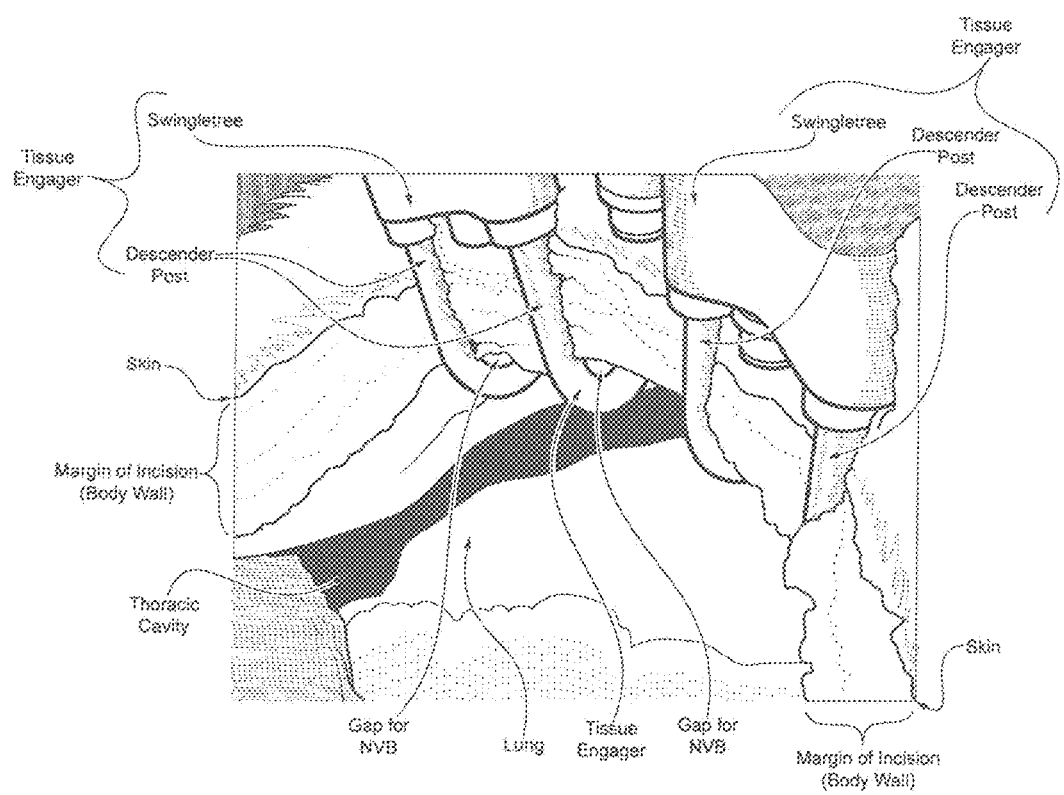

FIG. 141 shows a photograph from a thoracotomy on a pig showing the gap.

DETAILED DESCRIPTION

A. Constant Force (Creep)

Figure 1B:
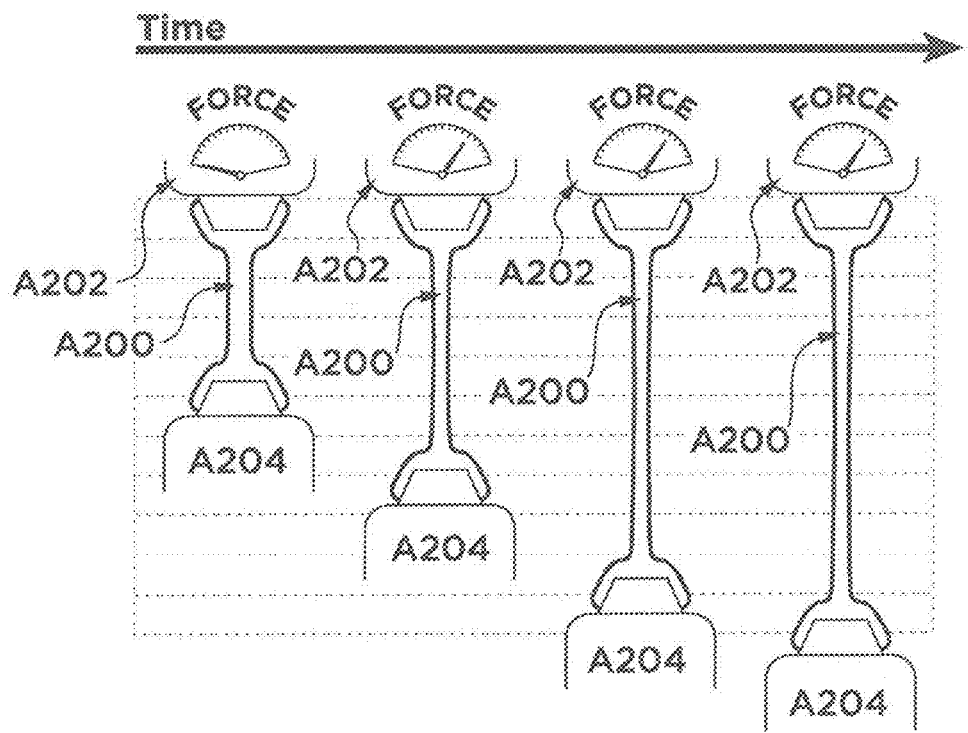

Many biological materials are viscoelastic, so they exhibit time-dependent mechanical properties (Wainwright et al., 1976, Mechanical Design in Organisms, John Wiley & Sons; Woo et al., 1999, Animal Models in Orthopaedic Research, CRC Press. pp. 175-96; Provenzano et al., 2001, Ann. Biomed. Eng. 29:908; Vanderby and Provenzano, 2003, J. Biomech. 10:1523; Yin and Elliott, 2004, J. Biomech. 37:907). To simplify this discussion, consider the force (the stress) required to stretch a sample of biological material. Consider FIG. 1A which illustrates test on a sample A200 of a biological material whereby the sample A200 is stretched by an instrument has a stationary unit A202 that measures force and a moving unit A204 that measures displacement while stretching a sample. The sample A200 is initially stretched by having the moving unit A204 move away from the stationary unit A204. The stationary unit A204 then remains at a fixed position, holding the sample A200 at constant deformation. Over time, the measured force decreases. This is an example of "force relaxation" or "stress relaxation". FIG. 1B shows a similar test on sample A200. Initially, the sample A200 is stretched; however, now moving unit A204 moves such that a constant force is applied to sample A200, and now the sample A200 stretches longer over time, a phenomenon known as "creep". Force relaxation and creep occur when retracting an incision. The deformations of the tissues around the incision are more complex than the simple stretch shown in FIGS. 1A and 1B, but the tissues, nevertheless, exhibit force relaxation and creep.

Standard practice during a sternotomy or thoracotomy is to spread the ribs slowly to a few centimeters, hold for a minute or so (allowing stress relaxation), and then slowly open over several minutes (allowing continued viscous deformation/stress relaxation) to the final opening.

The time dependent behavior of biological tissues has been specifically considered in the design of some retraction devices. U.S. Pat. No. 4,899,761 to Brown and Holmes discloses a distractor for separating vertebrae to measure spinal instability. The distractor of Brown and Holmes uses constant velocity deformation to standardize measurements of the mechanical properties of the motion segment of a spine to diagnose whether surgical intervention is necessary. Additionally, US Patent Application Publication No. 2006/0025656 to Buckner and Bolotin discloses stress relaxation as a means of reducing force during retraction.

Creep has not been considered in the design of retraction devices. However, application of a constant force ensures that (a) an unexpectedly or inappropriately large force is applied as would be the case for manual or motor driven retraction devices, and (b) viscoelastic deformation is allowed to proceed, thereby reducing the loads on anatomical elements that might rupture.

Different embodiments are disclosed, with reference to the figures, of assemblies and devices that apply a substantially constant force to one or more anatomical elements to move the anatomical elements. Not all embodiments of the invention are shown. Indeed, these inventions may be embodied in many different forms and should not be construed as limited to the embodiments set forth herein; rather, these embodiments are provided so that this disclosure satisfies applicable legal requirements.

FIG. 2 illustrates a retraction device in the prior art. Retractor A2 is a mechanical device utilizing two opposed retraction elements A6, A8. Each retraction element A6, A8 has a blade A4 that is inserted into an incision, each blade A4 engaging one side of an incision. One retraction element A8 is moveable with respect to the other retraction element A6, with motion being driven by a rack-and-pinion drive A10 that is manually driven with a drive handle A12. The retraction elements A6, A8 exert a force on the anatomical elements on either side of the incision to separate the anatomical elements, thereby opening the incision. A limitation of this device is that the force can vary dramatically with small displacements, thus an operator might exert an inappropriate force while attempting to move the retraction elements A6, A8 only a small distance.

Figure 3:
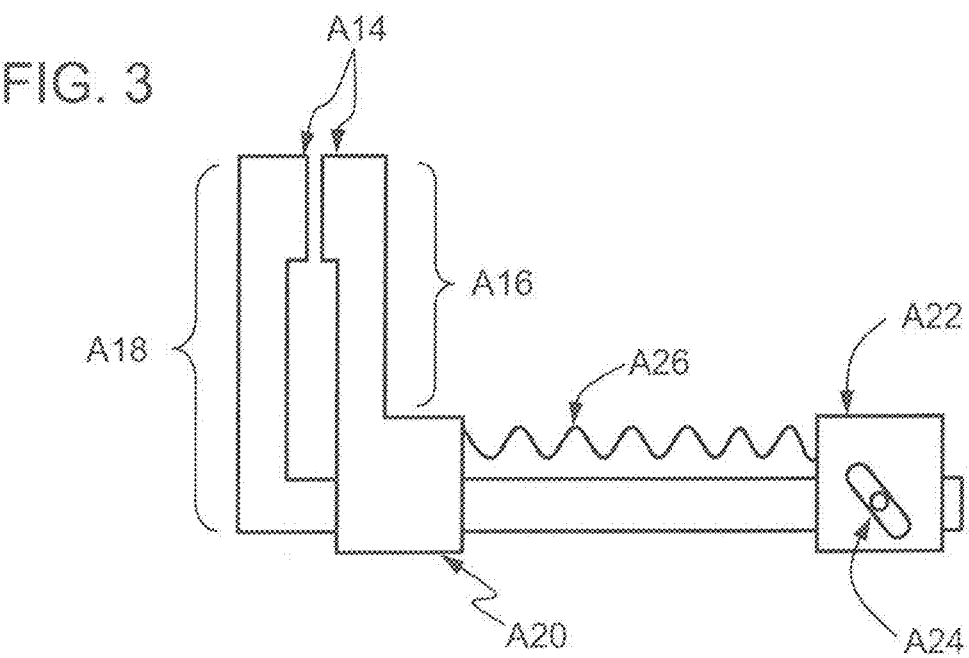
FIG. 3 is a diagram of one embodiment of a device for separating anatomical elements using a spring that exerts substantially constant force on the anatomical elements.

FIG. 3 illustrates an embodiment of the present invention which is designed to apply a constant force. It is a mechanical device utilizing two opposed retraction elements A16 and A18. Each retraction element A16, A18 has a blade A14 (similar to blade A4) that is inserted into an incision, each blade A14 engaging one side of the incision. One retraction element A16 is moveable with respect to the other retraction element A18 and is mounted on a sliding carriage A20. The sliding carriage A20 is driven by a spring A26 that exerts a substantially constant force over the range of motion such that the force exerted by the opposing retraction elements A16, A18 on the anatomical elements is substantially constant. The spring A26 is connected to a moveable anchor block A22 that allows an operator to adjust the stretch of the spring A26 and, thereby, the force exerted by the spring A26 on the anatomical element via the sliding carriage A20. The moveable anchor block A22 has a lock screw A24 to secure the position of moveable anchor block A22 after adjustment. Thus, the spring A26 serves to exert a substantially constant force, and this force cannot be accidentally exceeded by, for example, attempting to move the retraction elements A16 and A18 a small distance. Furthermore, if the spring A26 does not have a large spring constant, then the distance from the sliding carriage A20 to the moveable anchor block A22 can be sufficiently large that small errors in adjustment of this distance do not introduce large errors in the force.

Figure 4:
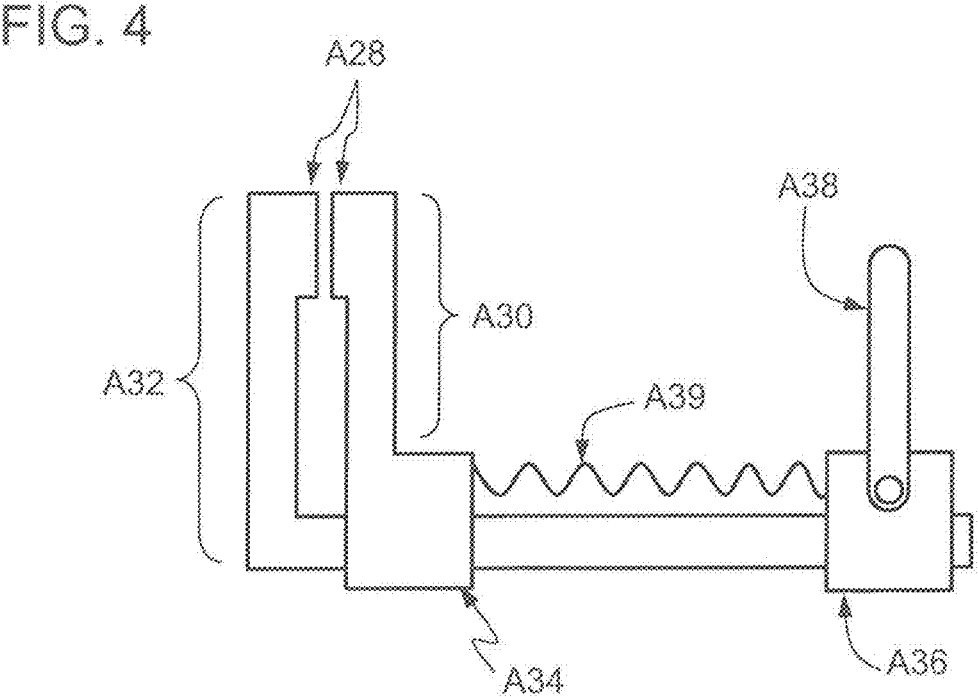
FIG. 4 is a diagram of another embodiment of a device for separating anatomical elements using a spring attached to a moveable drive block that exerts substantially constant force on the anatomical elements.

FIG. 4 illustrates another embodiment of the present invention which is designed to apply a substantially constant force that is larger than that depicted in FIG. 3. It is a mechanical device utilizing two opposed retraction elements A30, A32. Each retraction element A30, A32 has a blade A28 (similar to blade A4) that is inserted into an incision, each blade A28 engaging one side of the incision. One retraction element A30 is moveable with respect to the other A32, being mounted on a sliding carriage A34. The sliding carriage A34 is driven by a spring A39 that exerts a substantially constant force over the range of motion such that the force exerted by the opposing retraction elements A30 and A32 on the anatomical elements is substantially constant. The spring A39 is connected to a driven anchor block A36 that allows an operator to adjust the stretch of the spring A39 and, thereby, the force exerted by the spring A39 on the anatomical element via the sliding carriage A34. The driven anchor block A36 has a manual drive mechanism, such as a ratchet or a rack-and-pinion, driven by a handle A38 for manual drive and, optionally, a lock screw to secure the position of the driven anchor block A36 after adjustment.

Figure 5:
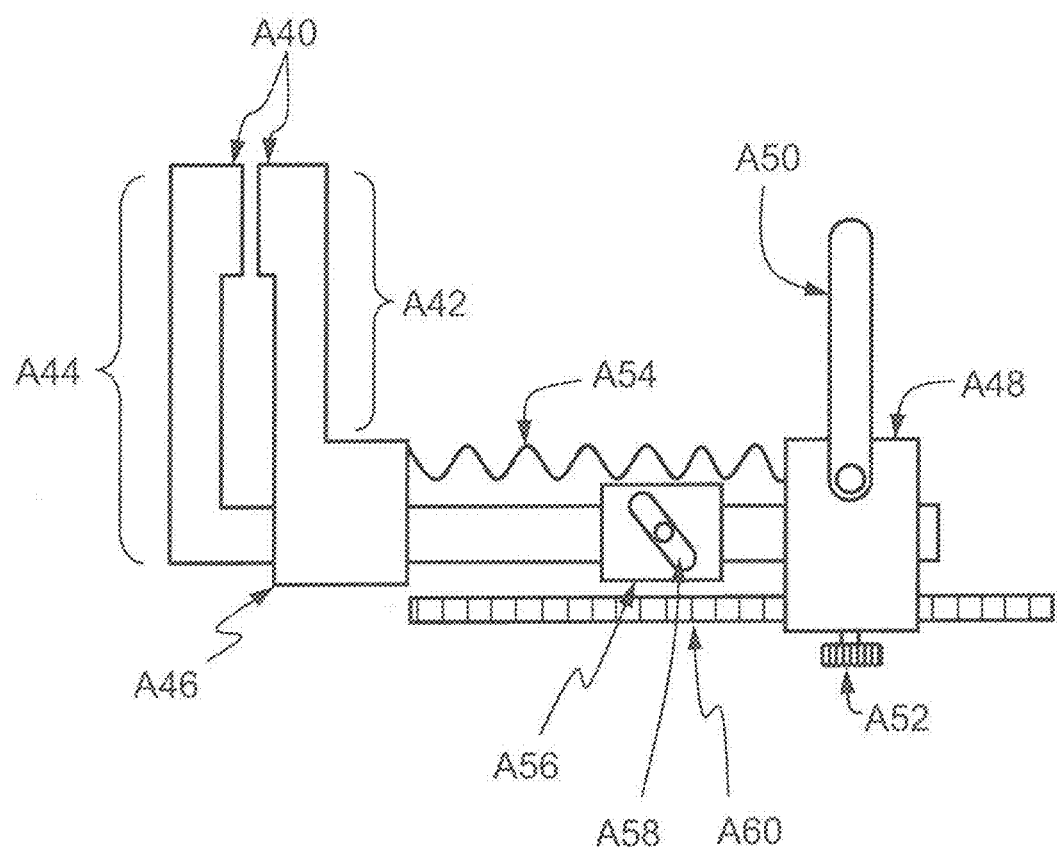
FIG. 5 is a diagram of another embodiment of a device for separating anatomical elements using a spring attached to a moveable drive block that exerts substantially constant force on the anatomical elements, wherein the device also includes an adjustable indicator that is used to adjust the force exerted by the spring and a mechanical stop to limit the range of motion of a retraction element.

FIG. 5 illustrates another embodiment of the present invention that provides an indicator of the force exerted on the tissue. It is a mechanical device utilizing two opposed retraction elements A42, A44. Each retraction element A42, A44 has a blade A40 (similar to blade A4) that is inserted into an incision, each blade A40 engaging one side of the incision. One retraction element A42 is moveable with respect to the other retraction element A44, and is mounted on a sliding carriage A46. The sliding carriage A46 is driven by a spring A54 that exerts a substantially constant force over the range of motion such that the force exerted by the opposing retraction elements A42, A44 on the anatomical elements is substantially constant. The spring A54 is connected to a driven anchor block A48 that allows an operator to adjust the stretch of the spring A54 and, thereby, the force exerted by the spring A54 on the anatomical element via the sliding carriage A46. The driven anchor block A48 has a manual drive mechanism, such as a ratchet or a rack-and-pinion drive, driven by a handle A50 for manual drive and, optionally, a lock screw to secure the position of the driven anchor block A48 after adjustment. There is also a force indicator A60 that is a graduated rod, with graduations indicating force exerted by the spring A54 for the indicated stretch, that is used to indicate where to place the driven anchor block A48 or whether the driven anchor block A48 should be moved to maintain appropriate stretch of the spring A54 to maintain a substantially constant force on the moveable retraction element A42. The position of the force indicator A60 is secured by an indicator set screw A52. There is also a mechanical stop A56 with its position secured by the stop set screw A58 such that the motion of the sliding carriage A46 cannot exceed a predetermined motion.

Figure 6:
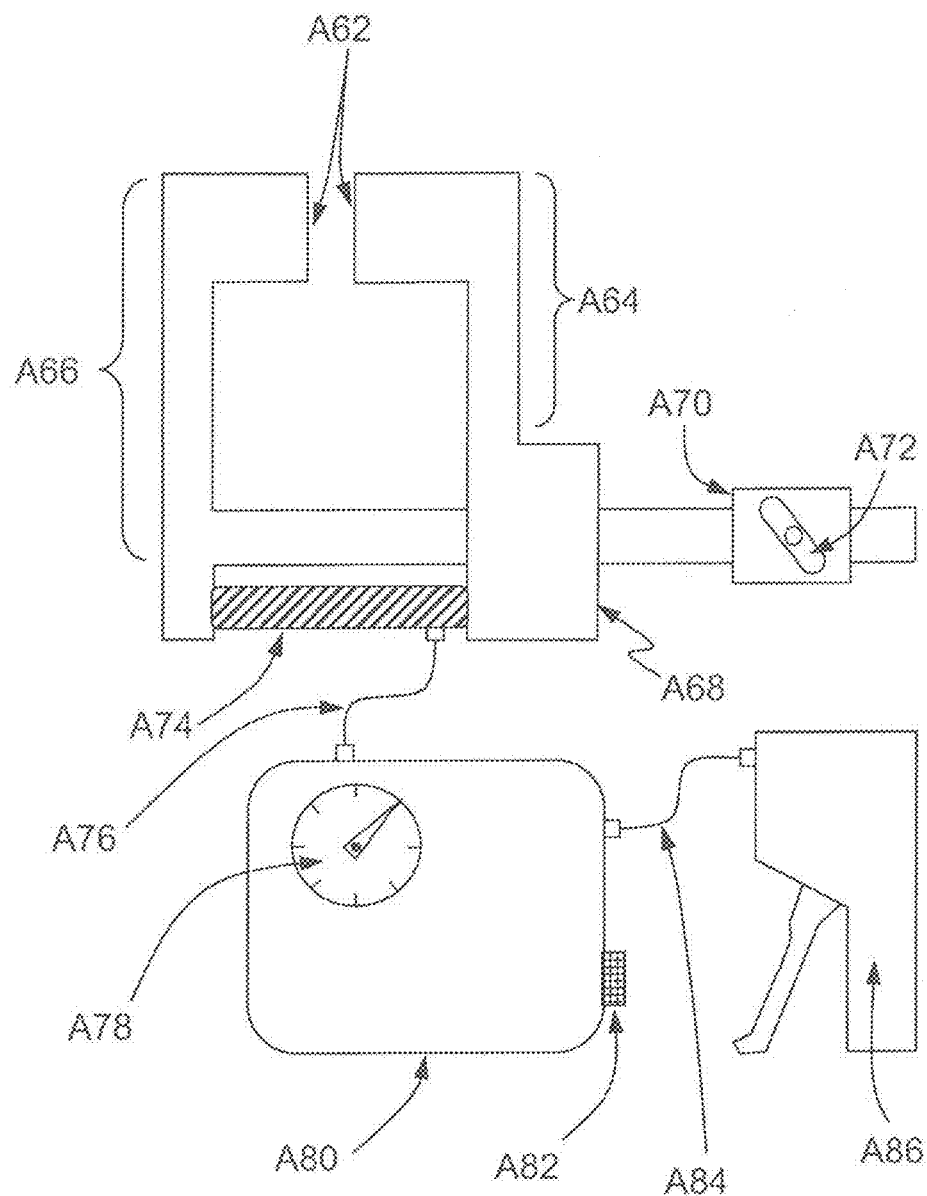
FIG. 6 is a diagram of another embodiment of a device for separating anatomical elements using a pneumatic cylinder to exert a substantially constant force, where in a pressure reservoir can be used to keep the pressure in the pneumatic cylinder substantially constant as the cylinder expands, and wherein a pump can be used to keep the pressure in the reservoir nearly constant.

FIG. 6 illustrates another embodiment of the present invention that uses a pneumatic piston to exert a substantially constant force. It is a mechanical device utilizing two opposed retraction elements A64, A66. Each retraction element A64, A66 has a blade A62 (similar to blade A4) that is inserted into an incision, each blade A62 engaging one side of the incision. One retraction element A64 is moveable with respect to the other retraction element A66, and is mounted on a sliding carriage A68. The sliding carriage A68 is driven by a pneumatic piston A74 that exerts a substantially constant force over the range of motion such that the force exerted by the opposing retraction elements A64, A66 on the anatomical elements is substantially constant. The piston A74 is connected to a pressure reservoir A80 by a pressure hose A76. The pressure reservoir A80 has sufficient volume of gas such that changes in the volume of the piston A74 as the piston A74 moves do not introduce large changes in the pressure. The pressure reservoir A80 can be fitted with a pressure gage A78 that allows an operator to observe the pressure. The pressure reservoir A80 can be connected to a pressure pump A86 that permits an operator to increase the pressure in the reservoir both to initiate the force at the piston A74 or to prevent pressure from dropping in the pressure reservoir A80 should the motion of the piston A74 be too large, causing a drop in pressure, or to allow the piston A74 to change from a first substantially constant force to a second substantially constant force. The pressure reservoir A80 also can have a bleed valve A82 that allows an operator to reduce the pressure, to release the pressure, or to move from a first substantially constant force to a second substantially constant force. Additionally, there can be a mechanical stop A70 with its position secured by a stop set screw A72 such that the motion of the sliding carriage A68 cannot exceed a predetermined motion.

Figure 7:
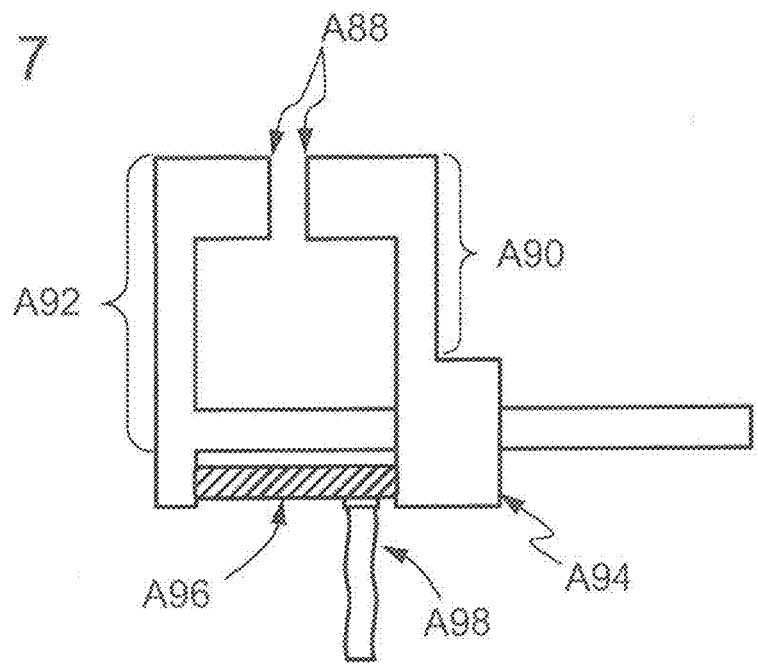
FIG. 7 is a diagram of another embodiment a device for separating anatomical elements using a motor to exert a substantially constant force, wherein the electrical current driving the motor is kept substantially constant to keep the force substantially constant.

FIG. 7 illustrates another embodiment of the present invention which utilizes a motorized drive to exert a substantially constant force. It is a mechanical device utilizing two opposed retraction elements A90, A92. Each retraction element A90, A92 has a blade A88 (similar to blade A4) that is inserted into an incision, each blade A88 engaging one side of the incision. One retraction element A90 is moveable with respect to the other retraction element A92, and is mounted on a sliding carriage A94. The sliding carriage A94 is driven by a motor A96 that exerts a substantially constant force over the range of motion such that the force exerted by the opposing retraction elements A90, A92 on the anatomical elements is substantially constant. The motor A96 is connected by an electrical cable A98 to a motor controller (not shown). The motor controller ensures that the torque generated by the motor A96 is substantially constant such that the force exerted by the opposing retraction elements A90, A92 on the anatomical elements is substantially constant.

Figure 8:
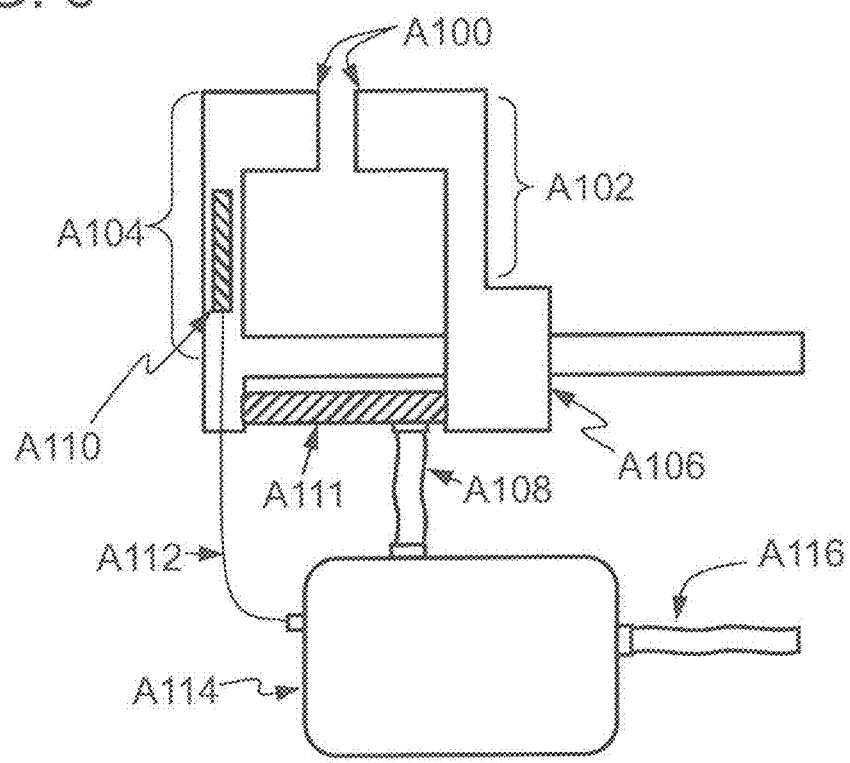
FIG. 8 is a diagram of another embodiment of a device for separating anatomical elements using a motor to exert a substantially constant force, wherein a force measuring device is used to determine the force, and a feedback loop is used to control the motor such that the force is substantially constant.

FIG. 8 illustrates another embodiment of the present invention which utilizes a feedback system to exert a substantially constant force. It is a mechanical device utilizing two opposed retraction elements A102, A104. Each retraction element A102, A104 has a blade A100 (similar to blade A4) that is inserted into an incision, each blade A100 engaging one side of the incision. One retraction element A102 is moveable with respect to the other A104 and is mounted on a sliding carriage A106. The sliding carriage A106 is driven by a motor A111 that exerts a substantially constant force over the range of motion such that the force exerted by the opposing retraction elements A102, A104 on the anatomical elements is substantially constant. The motor A111 is connected by an electrical cable A108 to a motor controller A114. A force measuring device A110 is attached to the retraction element A104 (or optionally to retraction element A102) such that the force measuring device A110 determines the force exerted by the retraction element A104 on the anatomical element. The force measuring device A110 is connected to the motor controller A114 via a signal cable A112 such that the force is transmitted as a signal to the motor controller A114. The motor controller A114 implements a feedback loop such that the force measured by the force measuring device A110 is substantially constant such that the force exerted by the opposing retraction elements A102, A104 on the anatomical elements is substantially constant. Motor controller A114 can, optionally, be connected to another device (not shown) by cable A116 to, for example, provide additional processing abilities or to provide a display of force.

Figure 9:
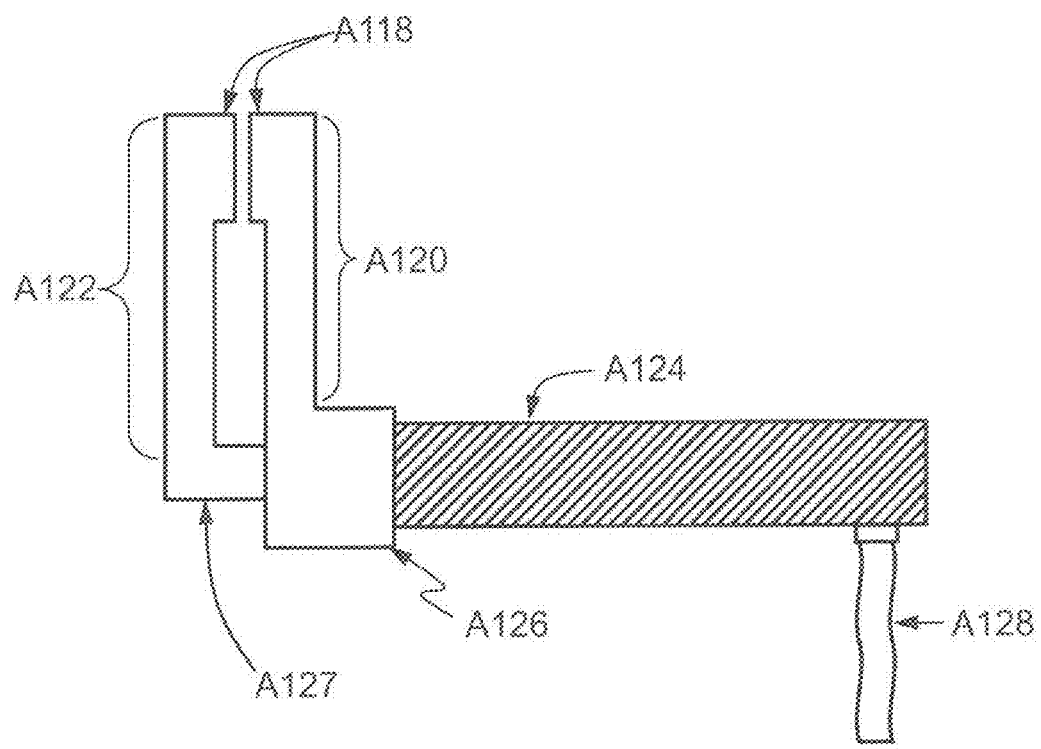
FIG. 9 is a diagram of another embodiment of a device for separating anatomical elements using a motor to exert a substantially constant force which includes an alternate means for mechanical coupling of the motor.

FIG. 9 illustrates another embodiment of the present invention that is similar to that disclosed in FIG. 7 but in which a motor A124 is mounted differently. Motor A124 is directly attached to retractor element A120 by mount A126, and retractor element A122 is directly attached to the linear drive shaft A127. This permits use of a differently configured motor, possibly with integrated motor controller (not shown) or connected by a cable A128.

Figure 10:
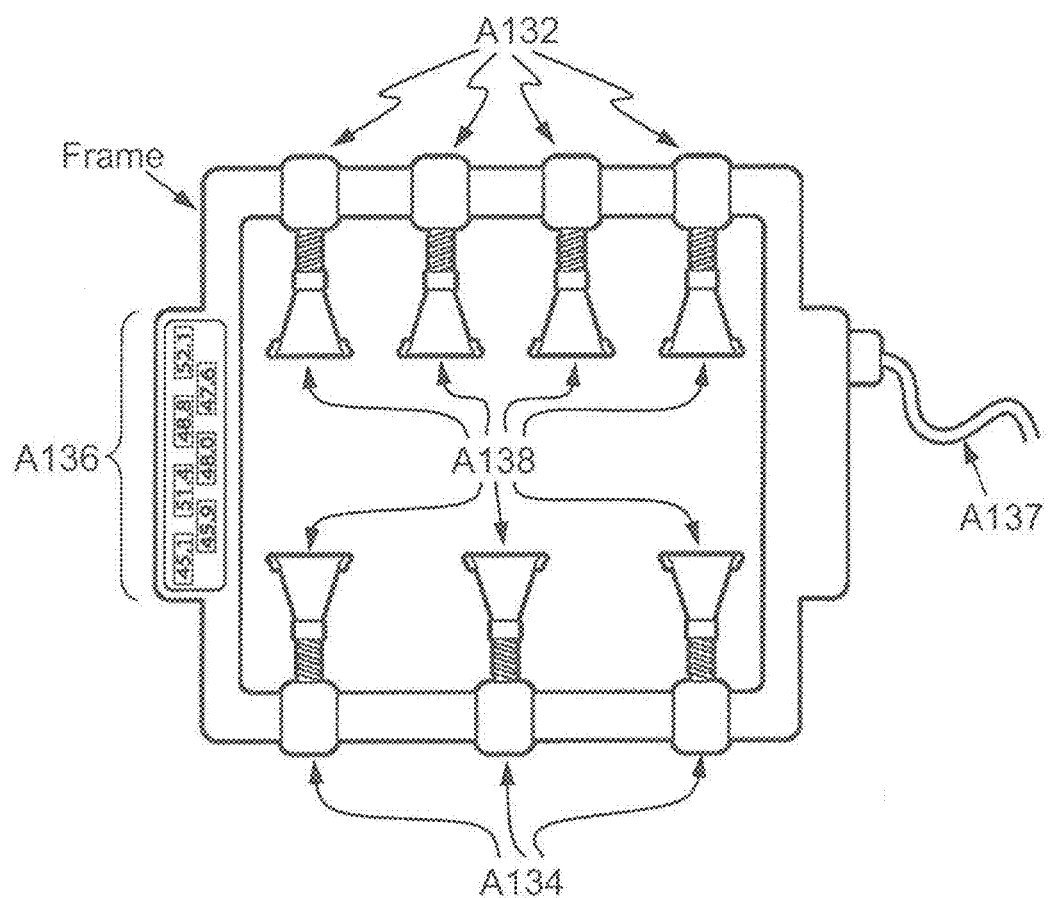
FIG. 10 is a diagram of another embodiment of a device for separating anatomical elements with an alternate configuration using more than one retraction element and also using a visual indicator of the motion of the retraction elements.

FIG. 10 illustrates another embodiment of the present invention which is a mechanical device utilizing multiple moveable retraction elements A132, A134 that are mounted on a frame A130. Each moveable retraction element A132, A134 can be independently moved. The various mechanisms described in FIGS. 3 through 9 for exerting a substantially constant force via the blades A138 (examples of blades include curved or bent blades that extend into the incision) of retraction elements can be implemented for each of these moveable retraction elements A132, A134. The mechanisms can be implemented such that the force exerted by each individual moveable retraction element A132, A134 is independent of the force exerted by any other moveable retraction element A132, A134. Optionally, position measuring devices (not shown, examples include linear potentiometers, LVDTs, optical encoders) can be placed on each moveable retraction element A132 and A134 such that an independent measure of position is determined and displayed on a visual position indicator A136 on the frame A130. Alternatively, the force exerted by blades A138 of retraction elements A132, A134 on their respective anatomical elements can be measured by a force measuring device (not shown, examples include appropriately placed strain gauges), and the forces displayed on indicators (not shown) also on the frame A130. An electrical cable A137 can be used to provide power to electrical devices on the frame A130 and to convey electrical signals from electrical devices on the frame A130 or elsewhere on the retractor to a separate motor controller (not shown) or computer (not shown).

B. Oscillating Loading

Deformation of biological materials during the first phase of retraction is usually done one-directionally—the deformation pushes anatomical elements apart (e.g., thoracotomy) or stretches arteries open (e.g., angioplasty). The direction of motion during deformation is rarely reversed and then only to correct for errors, such as to reposition a rib retractor that has slipped or to free a blood vessel that has accidentally been captured under a retractor blade.

Trauma to the displaced tissue is a common consequence of these deformations. Ribs fracture during thoracotomy, costosternal joints dislocate during sternotomy, muscles tear during retraction, and blood vessel walls rip during angioplasty. Even for those deformations used to change anatomical position or shape, damage to the tissue can be larger than desired; for example, a fibrous capsule might tear when stretching is preferred.

Many biological materials are viscoelastic, so they exhibit time-dependent mechanical properties (Wainwright, Biggs et al. 1976; Woo, Manson et al. 1999; Provenzano, Lakes et al. 2001; Vanderby and Provenzano 2003; Yin and Elliott 2004; Erdogan, Erdogan et al. 2005).

One behavior of biological complex materials that has not been considered in the design of retractors is "work" or "stress" softening. Work softening is evident during cyclic loading/unloading and is characterized as a reduction in the force at a given deformation during successive cycles, relative to the initial loading. Viscoelastic materials exhibit stress softening, but the initial stiffness recovers with rest for most non-biological viscoelastic materials (e.g. filled rubbers). For many biological materials, initial stiffness is not recovered, reflecting changes in the non-viscous components of the material, thought to arise from the irreversible dislocation of components (such as the unentanglement of tangled polymers), from plastic deformation of polymeric components, or from failure of microscopic components (such as the fracture of single molecules). The underlying phenomenology of stress softening is not well understood (Horgan, Ogden et al. 2004), especially for biological materials (Vincent 1975; Weisman, Pope et al. 1980; Fleck and Eifler 2003; Kirton, Taberner et al. 2004; Kirton, Taberner et al. 2004; Speich, Borgsmiller et al. 2005; Chaudhuri, Parekh et al. 2007; Dorfmann, Trimmer et al. 2007). Nevertheless, the generally observed phenomenon of work softening, or any change in material property when subjected to oscillating loading, can be exploited.

Thus, an alternate means of deforming tissue, relative to traditional unidirectional loading, is to cyclically load the tissue. For example, the blades of a retractor move forward and backward, or an angioplasty balloon cyclically inflates and deflates.

Oscillatory motion provides at least three benefits. First, it can "work soften" the material, decreasing the forces required to achieve a deformation. Second, oscillatory motion can be used to measure the viscoelastic parameters of the material (elastic and viscous moduli), and the results of these measurements can optionally be used to guide additional manipulations of the tissue. Third, a large number of small deformations in series can lead to small scale failure of components thus avoiding catastrophic failure of the entire structure—similar to the release of energy at a geologic fault line by many small tremors as opposed to one large earthquake.

Note that oscillation can be at different frequencies. A frequency sweep can be used to identify a harmonic. "White noise" can be used in dynamic analysis to determine multiple resonant frequencies that can arise from the composite nature of biological materials. Oscillation can be conducted at two different frequencies, either one following the other or with both frequencies superimposed, to act upon different components of the composite material comprising the tissue. For example, a lower frequency can be used to work soften a ligament and a higher frequency can be used to work soften a polymer by vibrating the molecules in the polymer. These frequencies can be fractions of a Hertz to a megaHertz. Thus, oscillations can include mechanical vibrations, acoustic vibrations, ultrasound, and any other reciprocating motion.

B.1 Reduction of the Force of Retraction & Reducing Catastrophic Failure

B.1.1 Tissue Spreaders and Retractors

Oscillatory motion of a spreader or retractor can be generated in many different ways, depending on the necessary frequency and amplitude of actuation, which when coupled with the force of retraction and the mass of the oscillating system (retractor blade and tissue) determine the power requirements for the motor or other actuator.

For the following discussion, two motions are defined:
1. the retraction motion, which is the overall, or average, motion during the first phase of retraction that is used to achieve the final deformation of the tissue; and
2. the oscillation motion, which is a motion that is superimposed on the retraction motion.

Figure 11A:
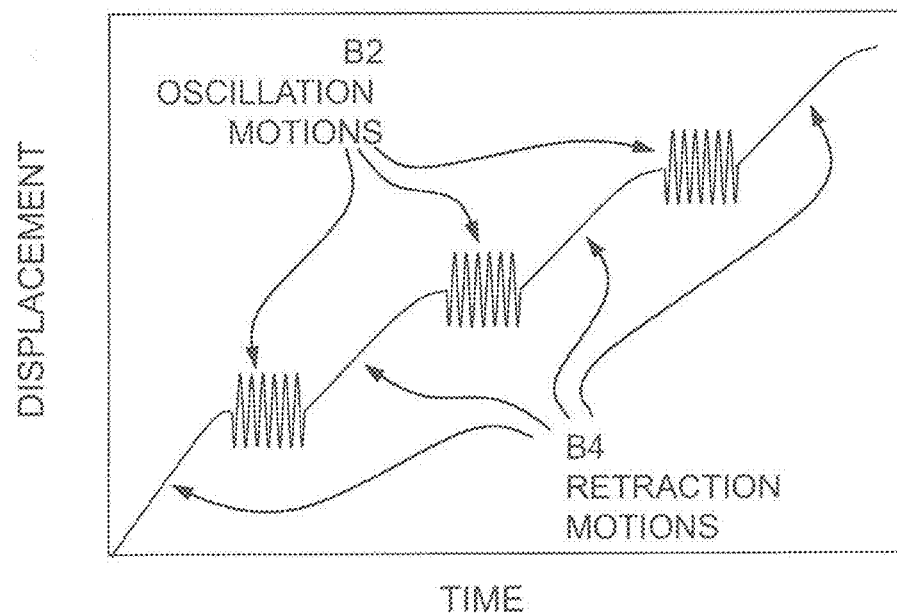
FIGS. 11A and 11B illustrate exemplary time/displacement trajectories for retraction with oscillating loading.
Figure 11B:
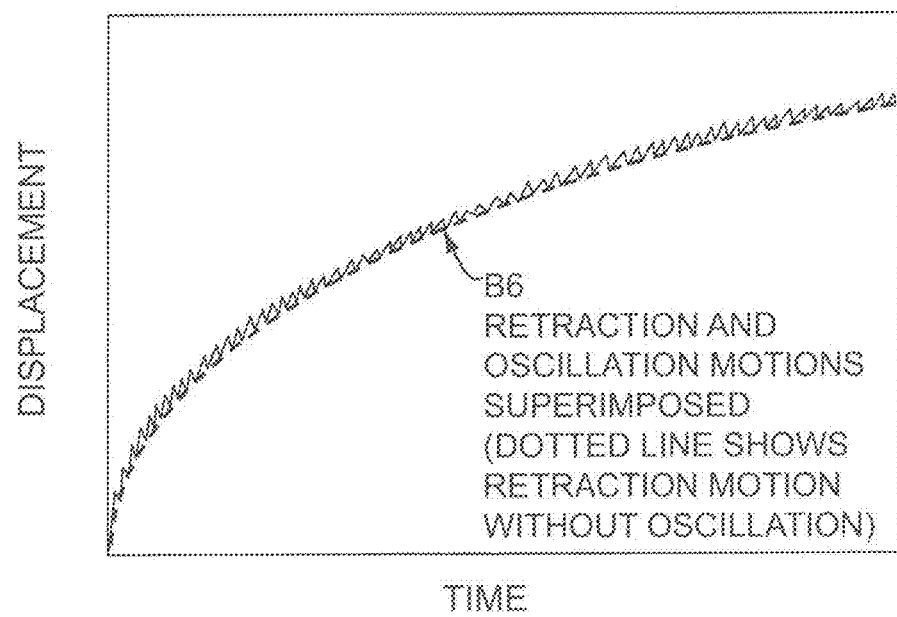

As shown in FIG. 11A, the two motions can be performed separately in time, with a retraction motion B4 proceeding to a given separation and then pausing, followed by an oscillation motion B2. Alternatively, as shown in FIG. 11B, the retraction motion B4 and the oscillation motion B2 can be superimposed in time, thus the retraction motion B6 would be a near-zero frequency component of the motion, and the oscillation motion would be the higher frequency component.

B.1.1.1 Experimental Results from Oscillating Loading of Tissues

B.1.1.1.1 an Example of a Retractor for Oscillating Motion

Figure 12:
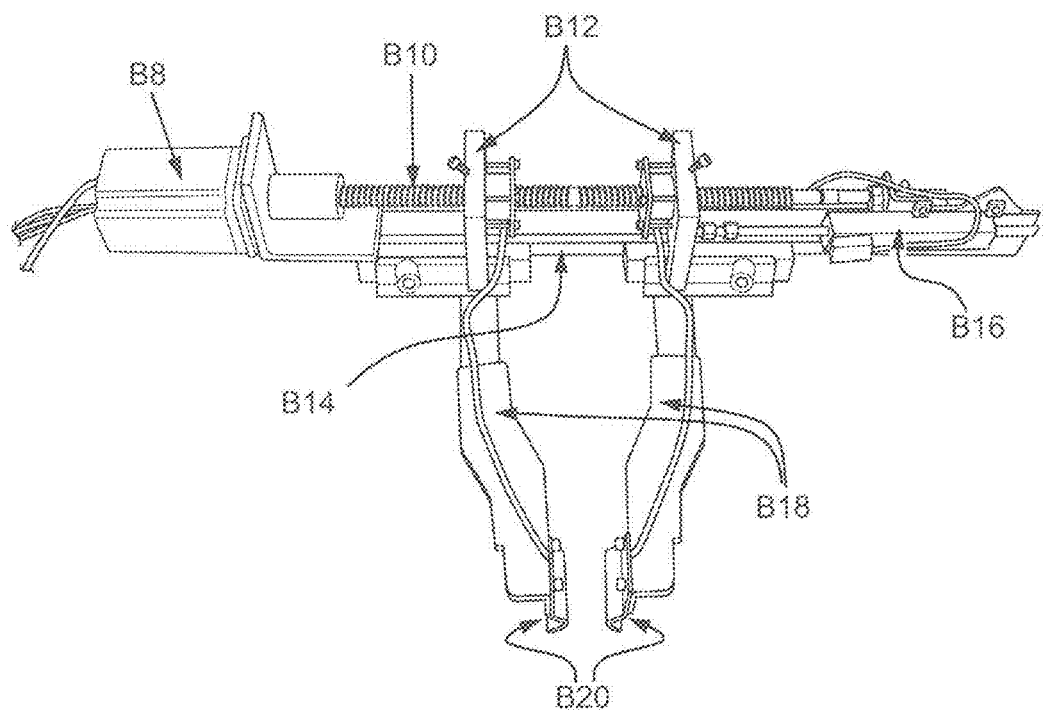
FIG. 12 illustrates a prototype motorized retractor utilizing a bi-directional lead screw and that measures force on both retractor blades and separation of the blades.

A retractor is shown in FIG. 12 that uses a bi-directional ball screw B10 (i.e., having two bearings that travel in opposite directions) that is driven by a stepper motor B8, which here is an MDrive 23Plus made by Intelligent Motion Systems, Inc. The bi-directional ball screw B10 is mounted to a rail B14 with two linear translation stages B12, which here are LWHG 25 made by IKO, such that each translation stage B12 attaches to one of the bearings of the bi-directional ball screw B10, thus when the bi-directional ball screw B10 is rotated by the motor B8, the translation stages B12 travel in opposite directions. A retractor arm B18, fabricated by hand from mild steel angle iron that was cut/bent/welded into shape, is mounted to each translation stage B12. Each retractor arm B18 has a retractor blade B20 that is fabricated by hand with mild steel.

A linear potentiometer B16, which in this case is a 5 kOhm 100 mm made by Schaevitz, is used to measure separation of the retractor blades B20. The static mount of the potentiometer B16 is affixed to the rail B14, and the piston of potentiometer B16 is affixed to one of the translation stages B12. Note that any means of measuring displacement can be used here, such as optical encoders, contact and non-contact proximity sensors, digital calipers, and the like.

The retractor blades B20 are instrumented with a full-bridge strain gauge assembly which includes two (2) gauges, which in this case are model CEA-06-125UN-350 made by Vishay Micro-Measurements, on each side of each retractor blade B20. The signal from the strain gauges is then amplified by a signal conditioner (not shown) which in this case is a Model OM-2 from 1-800-LoadCells. Note that force can be measured by any of several means, such as drive current on the motor (and other means of measuring torque on the drive mechanism), fiber optic strain gauges, optical sensors of deformation, and the like.

All signals from the potentiometer B16 and the signal conditioners/strain gauges are read by a Windows-based computer using a data acquisition card, which in this case is a National Instruments Model USB-6211 and software, such as LabVIEW made by National Instruments, with software prepared by Katya Prince of Prince Consulting.

The stepper motor B8 is controlled with IMS Terminal software, made by made by Intelligent Motion Systems, Inc. Note that a servo-motor can also be used.

The strain gauges were calibrated by hanging known weights from each blade B20 of the retractor. The linear potentiometer B16 was calibrated with a metric ruler.

B.1.1.1.2 Experiments

A series of experiments were conducted with the retractor presented in FIG. 12 using parts from pig cadavers. The parts were a "front quarter" purchased from Nahunta Pork Center (Pikeville, N.C.). A front quarter is basically a whole pig cut at the waist (forming a front half) and split down the vertebrae (forming left and right quarters); thus, each quarter had an intact rib cage (one side), spine (bisected), and shoulder. All parts had been refrigerated after slaughter, used within 24 hours of slaughter, and warmed by immersion in warm water (while wrapped in a plastic bag to prevent soaking of the tissue) to near body temperature (31° C. to 37° C.). The quarters ranged in size from 8 to 12 kg.

Thoracotomies were performed between three (3) to four (4) rib pairs on each quarter, almost always performing an incision between ribs five (5) and six (6), seven (7) and eight (8), nine (9) and ten (10), and eleven (11) and twelve (12). Thoracotomies were performed by:
  cutting the skin with a scalpel over the range of the thoracotomy;
  bisecting the muscles overlying the ribs with a scalpel;
  cutting through the intercostal tissues with a scalpel;
  pushing a finger between the ribs to make a small opening;
  inserting the closed blades of the retractor into the opening;
  positioning the retractor such that the blades sat just dorsal of the midline and its axis of opening were parallel with the midline; and
  initiating opening according to a specified algorithm via computer control of the stepper motor.

Incisions were typically 110 mm to 130 mm long, with longer incisions being performed on larger quarters.

Figure 13:
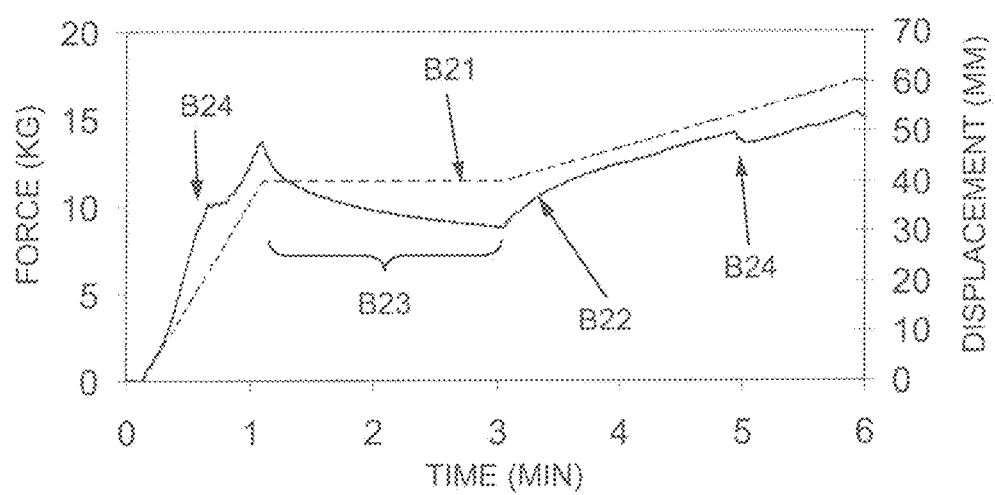
FIG. 13 illustrates a force/time trace for a thoracotomy performed with the prototype motorized retractor of FIG. 12.

Experimental retractions with the retractor shown in FIG. 13 are the first simultaneous measurements of force and displacement during thoracic retraction.

FIG. 13 shows the displacement B21 of the blades B20 (i.e., the distance between the blades B20), and force B22 on one blade B20 with respect to time for a "standard retraction", similar to that defined by Bolotin et al. (Bolotin, Buckner et al. 2007), which proceeds as follows:
  a first move, opening to 40 mm in one (1) minute (⅔ of final opening),
  pause 2 minutes for force relaxation,
  a second move, opening to 60 mm in three (3) minutes (to the final opening).

Thus, a total opening of 60 mm is reached in 6 minutes in this example. Retraction was of a fully automated—the computer controlled the motor B8, and the motor drove the blades B20 apart. Each of the two moves is constant velocity (40 mm/min for the first and 6.8 mm/min for the second). This somewhat matches the pace described by thoracic surgeons, but there is no standard clinical practice. Surgeons use a procedure defined by their training, personal experience, patient condition, and estimates of force applied at the handle of a hand-cranked retractor. Force relaxation, as described by Buckner and Bolotin (Buckner and Bolotin 2006; Bolotin, Buckner et al. 2007) is evident during a two-minute pause B23—the force required to maintain the 40 mm opening decreases with time. The points on the force B22 marked with arrows B24 mark significant tissue breaks, as evidenced by the change in the force/time slope and by audible "snaps" during the retraction.

Figure 14A:
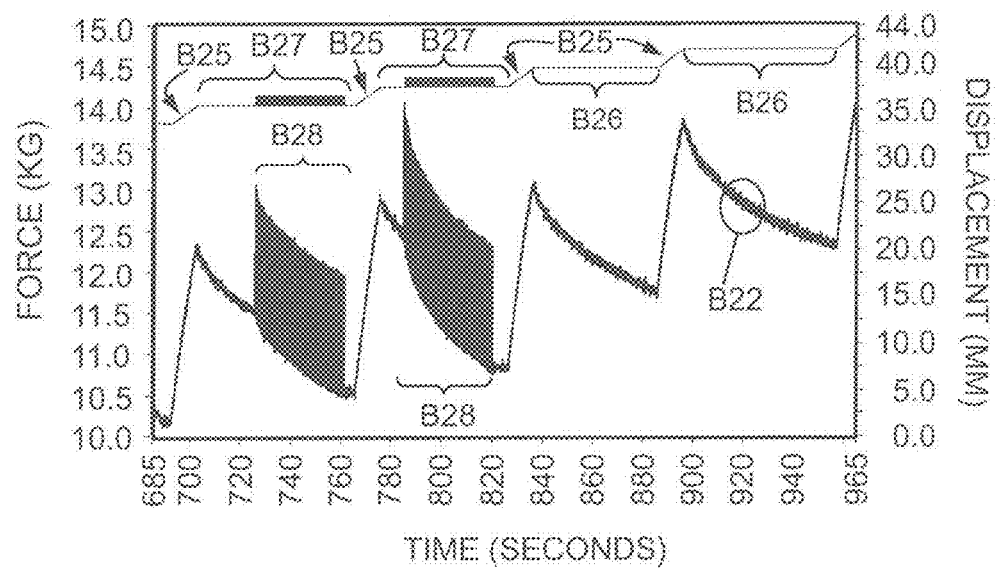
FIGS. 14A and 14B show acceleration of force relaxation during bouts of oscillating loading.

FIG. 14A shows a retraction in which the displacement B21 is shown by the upper trace, and force B22 on one blade is shown by the lower trace. There are four small retractions B25 (2 mm each over 10 seconds, velocity=0.2 mm/s) of which the second two were followed by pauses B26 of approximately 50 seconds and the first two were followed by pauses B27 of 50 seconds interrupted by oscillation motions B28. The oscillation motions B28 were 11 Hz with one (1) mm amplitude, 400 cycles, and given the high frequency of oscillation, they appear on the displacement trace as thickened regions of the trace. Force relaxation was seen for each of the four pauses B26, B27, as evidenced by the decrease in force that follows the onset of each pause. During each oscillation motion B28, the force oscillated with each cycle of opening/closing. Importantly, when the force minima are examined over successive cycles, the force dropped rapidly.

Figure 14B:
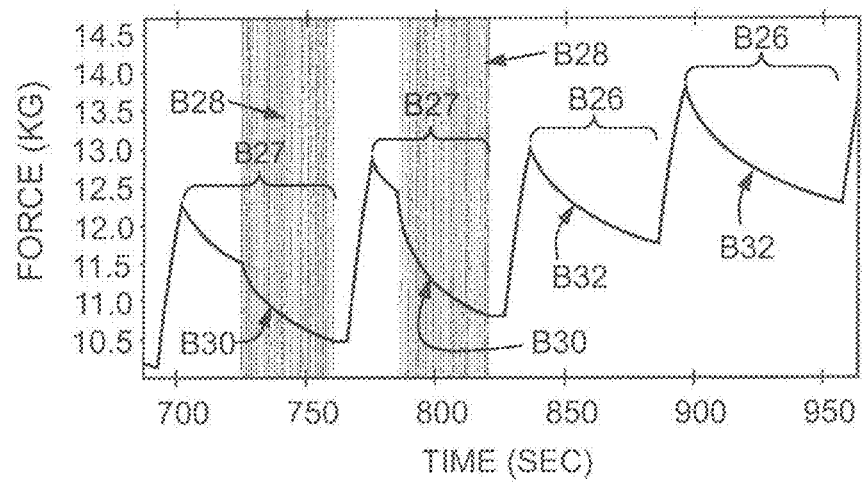

FIG. 14B shows what the force/time curve looks like when only the force minima are considered—there is an accelerated force relaxation (AFR) B30, during the oscillation motions B28, as illustrated by the grey regions in FIG. 14B. Thus, while the force declined during normal force relaxation (NFR) B32, as depicted during the two-minute pause in FIG. 13 and during the 3rd and 4th pauses B26 in FIG. 14B, the force declined much more rapidly during the AFR B30 (1st and 2nd pauses B27 of FIG. 14B) than during the NFR B32. Also, the AFR B30 had a larger magnitude when the oscillation motion B28 was initiated earlier in the pause, as evidenced when the 2nd pause/oscillation motion B28 is compared to the 1st pause/oscillation motion B28—the oscillation motion B28 started sooner in the 2nd pause oscillation and a larger AFR B30 was seen.

Figure 15:
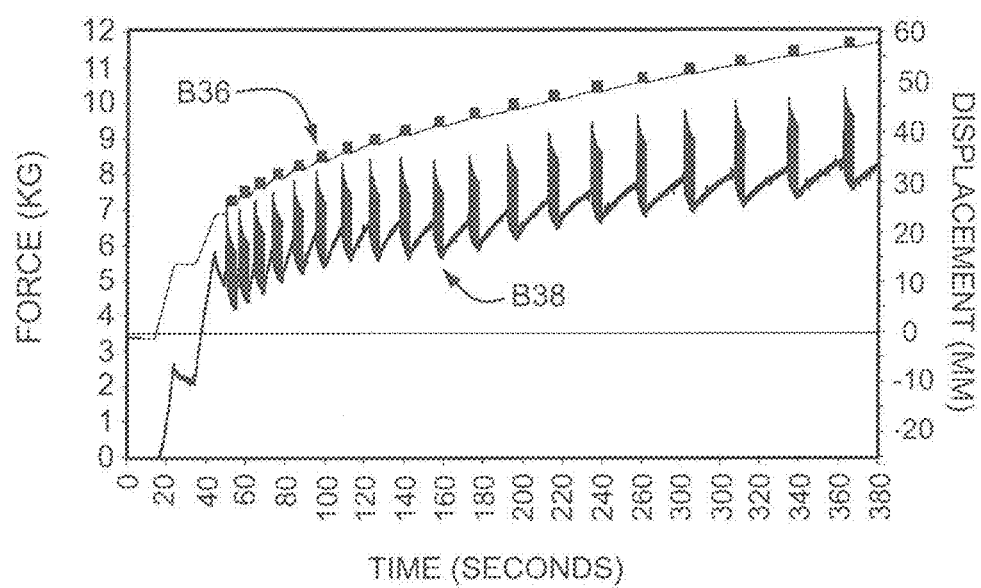
FIG. 15 shows a retraction for a thoracotomy in which oscillating loading is periodically applied.

FIG. 15 shows a retraction in which a different trajectory is followed than for a standard retraction, which is called an "oscillating retraction" for this discussion. Displacement, or separation of the blades B20, is shown by trace B36. Force on one blade B20 is shown by trace B38. During the experiment depicted in FIG. 15, the incision was opened and oscillated repeatedly. Three general features observed during oscillating retractions like this are:
1. the retraction force does not peak as high as is seen during the first opening of the standard clinical pace retraction (compare to FIG. 13);
2. the maximum force during oscillating retraction is frequently lower than the maximum force in a standard clinical pace (compare to FIG. 13); and
3. there are fewer large, obvious breaks during oscillating retractions than during standard clinical pace retractions.

The latter point is shown in FIG. 13 where breaks B24 are marked with arrows B24—the breaks appear as rapid changes in the slope of the force/time trace that are almost always accompanied by loud snaps or cracks. These events are common during standard retractions, especially in the final 20 seconds of the first, one-minute opening and during the last two minutes of the second, three-minute opening. These rapid changes in slope, accompanied by loud snaps or cracks, are almost never seen/heard during oscillating retractions. This point is especially important in light of the tissue trauma that is frequently observed during normal surgical practice—broken ribs, dislocated costo-chondral joints, and torn ligaments and tendons (Vander Salm, Cutler et al. 1982; Greenwald, Baisden et al. 1983; Baisden, Greenwald et al. 1984; Woodring, Royer et al. 1985; Bolotin, Buckner et al. 2007; Lewis 2007).

Thus, there are several advantages conferred by oscillating retractions:
1. accelerated force relaxation rapidly decreases the force required for opening;
2. the large peak in force seen during the first, one-minute opening of a standard retraction is not evident;
3. the maximum force experienced during retraction is frequently smaller during oscillating retraction; and
4. there are fewer, large tissue breaks during oscillating retraction.

All of these advantages can result in reduced tissue trauma during retraction.

B.1.1.2 Single-Actuator Retractors

Figure 16:
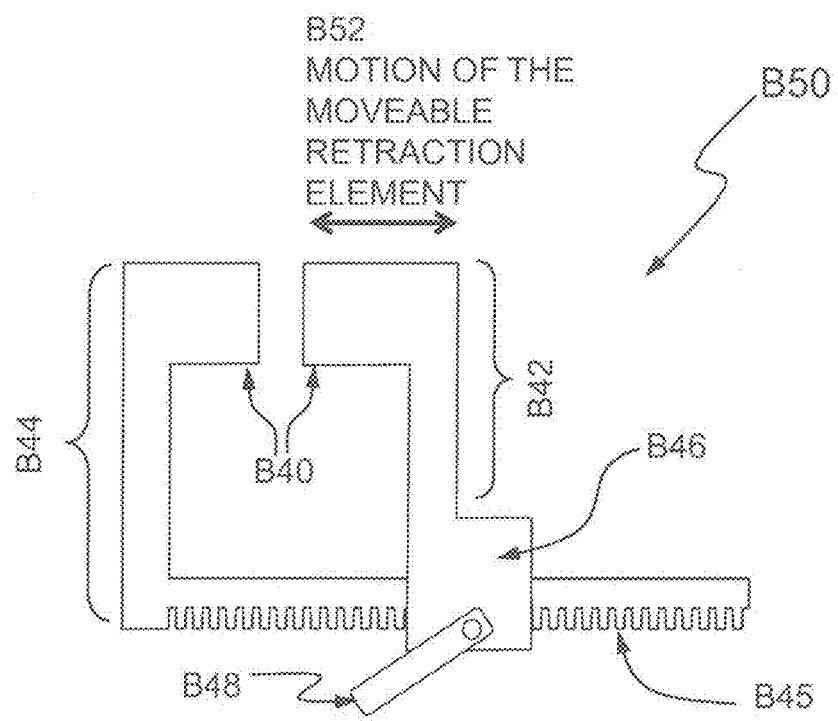
FIG. 16 shows an example of a Finochietto thoracic retractor in the prior art.

FIG. 16 shows a Finochietto retractor in the prior art (similar to retractor A2 in FIG. 2). It has a fixed retraction element B44 attached to a rack B45 of a rack-and-pinion drive B46. A moveable retraction element B42 is attached to the rack and pinion drive B46 that drives motion B52 of the moveable retraction element when manual handle B48 is rotated. Each of the retraction elements B42, B44 has a single blade B40 (similar to blade A4 in FIG. 2) that engages the tissue to be retracted.

One way to implement a retractor with both a retraction motion and an oscillation motion is to use a single actuator that drives both the retraction and the oscillation motions, such as the retractor shown in FIG. 12.

Figure 17:
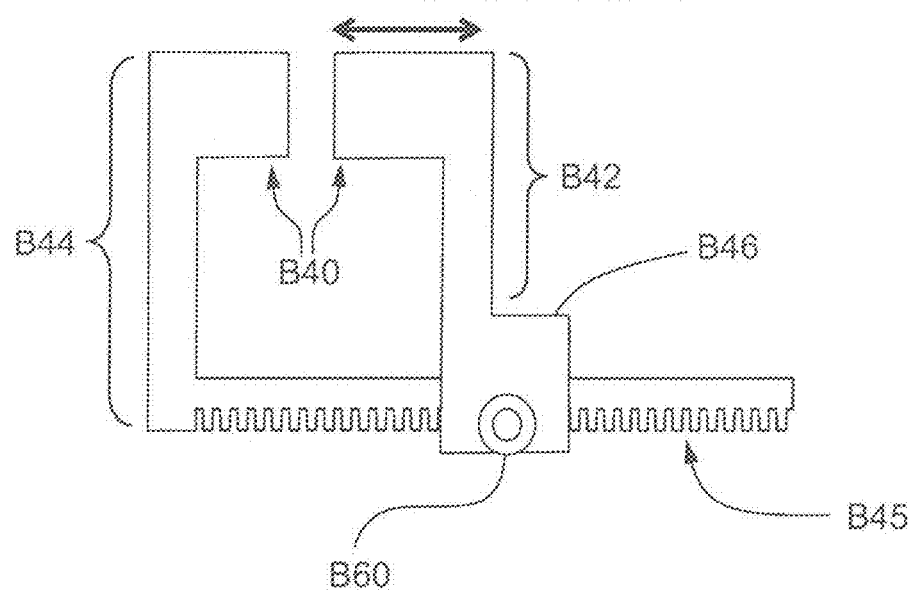
FIG. 17 shows a thoracic retractor of the prior art with a standard hand-cranked rack-and-pinion and a thoracic retractor in which the hand crank is replaced with a motor.

FIG. 17 shows another embodiment of a single actuator retractor, in which a motor B60 replaces the hand crank B48 of a typical Finochietto-style rack-and-pinion retractor. The motor B60 can be any motor appropriate for generating the desired motions B52, such as a servo-motor or a stepper motor. The instructions to the motor generate any desired motions for retraction motions as well as oscillations for oscillation motions. Thus, the retractor can perform retraction and oscillation motions that either are separated in time or are superimposed in time.

Figure 18:
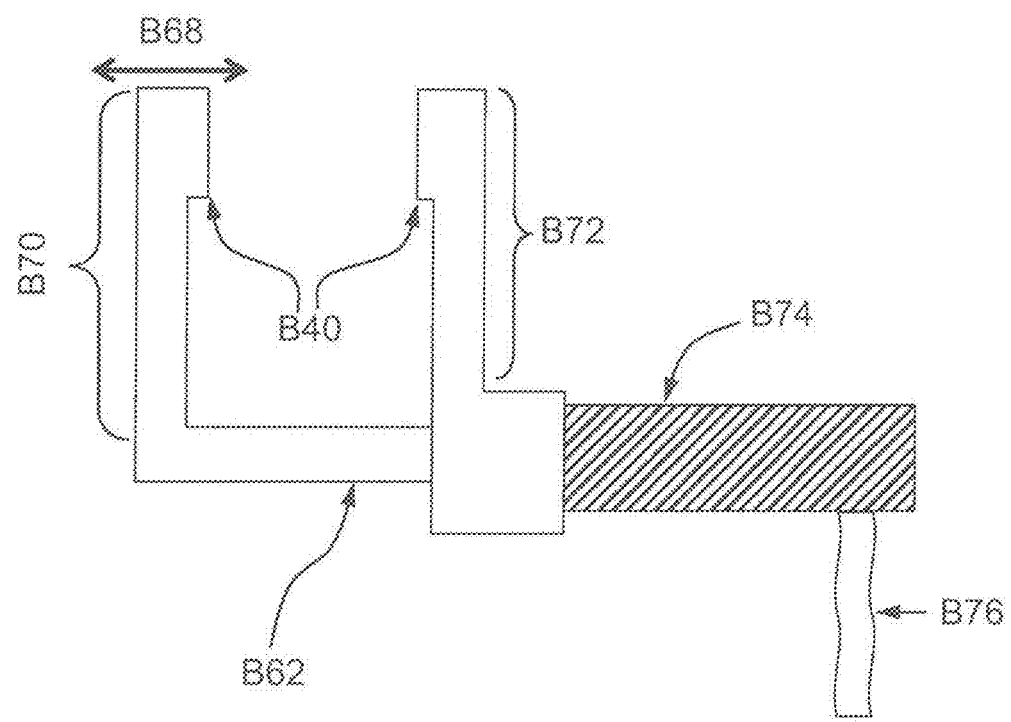
FIG. 18 shows a thoracic retractor driven by a computer controlled motor on a ball screw.

FIG. 18 shows another embodiment in which the rack-and-pinion drive B46 is replaced with a lead screw B62 turned by a motor B74, either a stepper motor or a servo-motor. The motor B74 moves the moveable retraction element B70 with respect to fixed retraction element B72 to achieve the desired motion B68. Control of the motor B74 can be either on-board with the motor B74 or off-board connected by an electrical cable B76.

Figure 19:
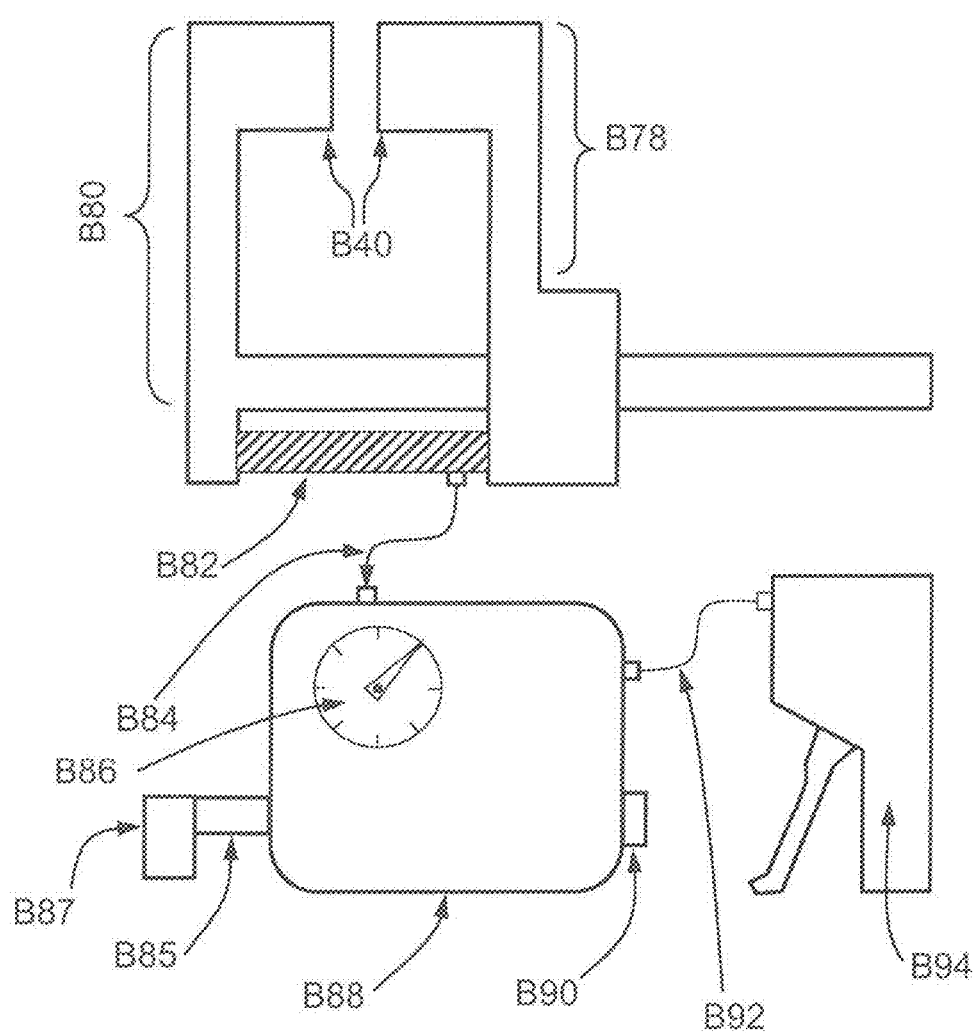
FIG. 19 shows a thoracic retractor driven by a hydraulic cylinder.

In yet another embodiment shown in FIG. 19, the rack-and-pinion drive B46 is replaced by a hydraulic cylinder B82. A pressure pump B94 is connected to a pressure reservoir B88 by a pressure hose 92, and the pressure reservoir B88 is connected to the hydraulic cylinder B82 by a pressure hose B84. Pressurization of the hydraulic fluid in the pressure pump B94 pressurizes the pressure reservoir B88 that feeds the hydraulic cylinder B82 which forces a moveable retraction element B78 and a fixed retraction element B80 apart. A pressure gauge B86 reports the pressure in the system, and a bleed valve B90 permits release of pressure. Oscillation of the pressure in the hydraulic fluid generates the oscillation motion. Oscillation can be driven by one of several means, such as a piston B85 attached to pressure reservoir B88 that is driven in and out by motor B87.

B.1.1.3 Dual-Actuator Retractors

The retraction and oscillation motions can be generated by separate actuators. For example, a first actuator drives the retraction motion, and a second actuator drives the oscillation motion. This confers several advantages:
different actuators can be matched to the different power requirements for the two different motions;
different actuators can be matched to the displacements required for the two different motions; and
different distributions of masses are permitted, e.g. removing bulky components required for the large amplitude motions of the retraction motion from the components that must be driven at higher frequency but lower amplitude for the oscillation motions.

Figure 20:
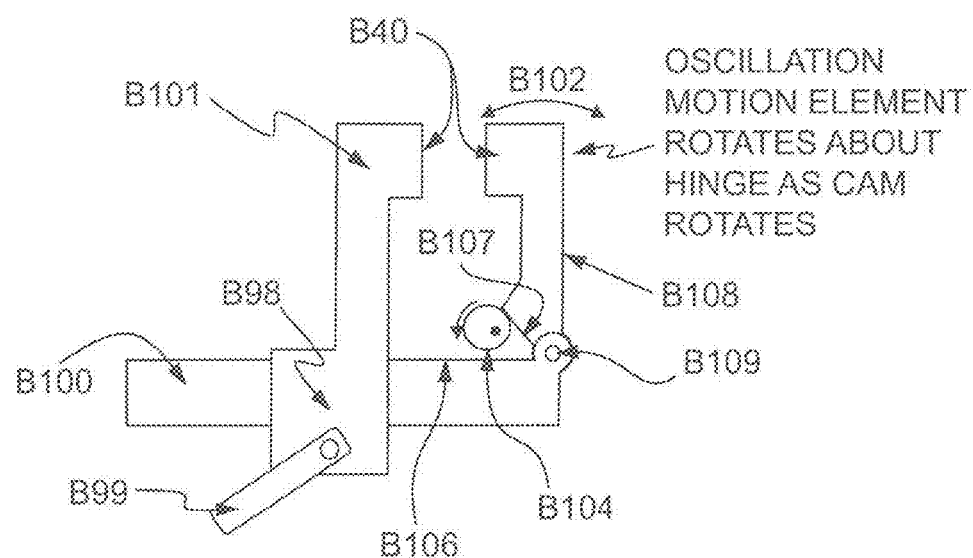
FIG. 20 shows a thoracic retractor having two actuators, a first hand-driven actuator drives apart the arms of the retractor, and a second motorized retractor that drives oscillating motion.

In one embodiment shown in FIG. 20, a retraction motion is generated by a first actuator which in this example is a rack-and-pinion drive B98 driven by hand crank B99 along a rack B100 on a conventional Finochietto-style retractor. The first actuator moves a moveable retraction element B101. The oscillation motion B102 is generated by a motor-driven acentrically mounted cam B104 that rides on two surfaces, a first surface B106 attached to the rack B100 of the retractor and a second surface B107 attached to an oscillation motion element B108 that is mounted to the rack B100 by a hinge B109. When the acentrically mounted cam B104 rotates, the oscillation motion element B108 oscillates with motion B102 with the frequency of rotation of the motor and with amplitude determined by the diameter and acentricity of the cam B104 and the lever-arm of the oscillation motion element B108.

Figure 21:
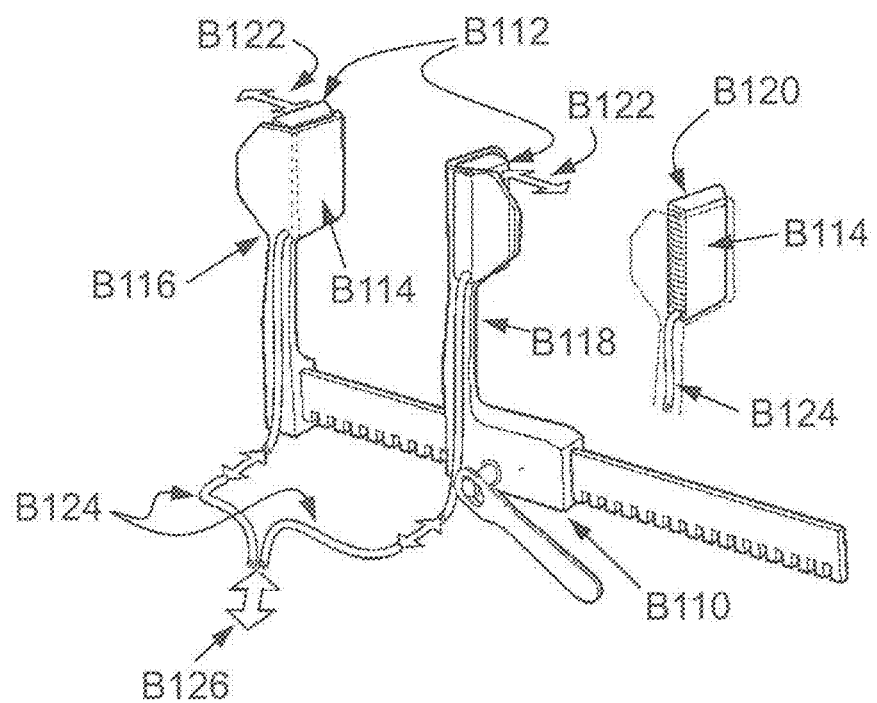
FIG. 21 illustrates a thoracic retractor having a first hand-driven actuator that drives apart the arms of the retractor and a second hydraulically driven pressure pad used to drive oscillating motion.

In another embodiment shown in FIG. 21, a hand-cranked rack-and-pinion drive B110 is used for performing the retraction motion. A second actuator B112 drives the oscillation motion. The second actuator B112 presented here is a thin hydraulic cylinder or pressure pad B120 mounted on each retractor blade B114 and is driven by a hydraulic system capable of generating the necessary pressures and volumes to drive the requisite motion. In this example, a pressure hose B124 attached to pressure pads B120 and to an external pressure source (not shown) permits cyclic oscillation of the pressure pads B120 via an oscillating flow B126 of fluid. The second actuator B112 could be any actuator that mounts to the retractor blades B114 of retraction elements B116, B118, such as a voice coil, a linear motor, a hydraulic cylinder or other actuator capable of generating the oscillation motion. A semi-transparent view of a retractor blade 114 is provided to allow a more complete view of the assembly.

Figure 22:
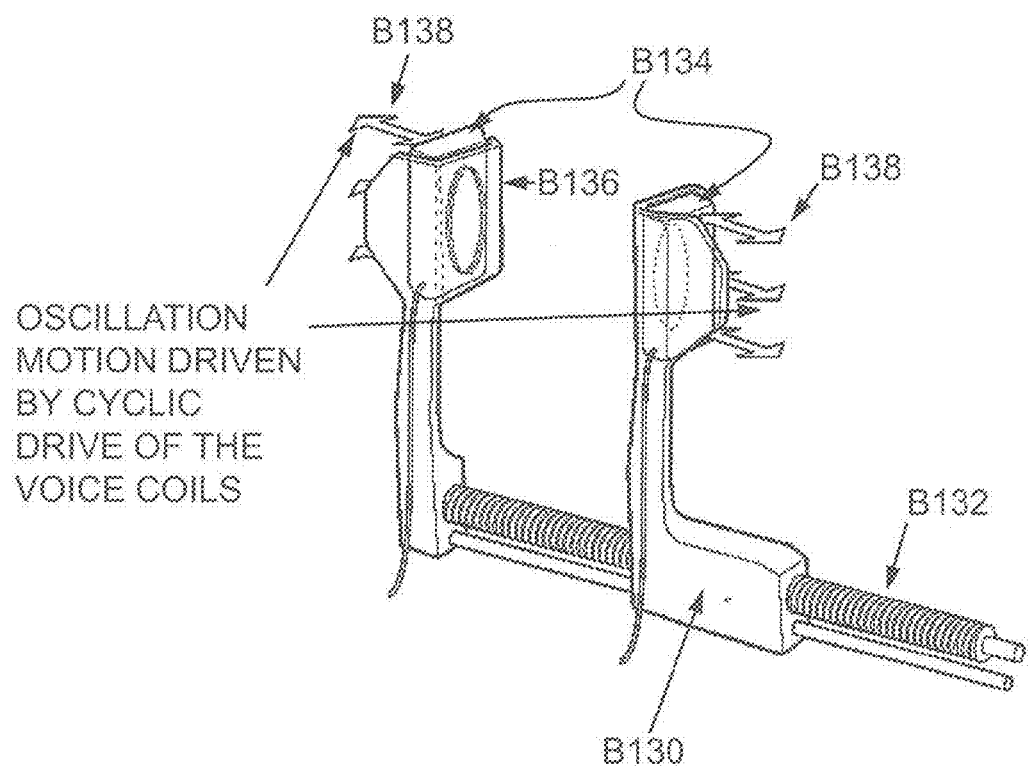
FIG. 22 shows a thoracic retractor having a first hand-driven actuator that drives apart the arms of the retractor and a second voice coil actuator used to drive oscillating motion.

In another embodiment shown in FIG. 22, a retractor has a motorized lead screw drive B130 that drives along the lead screw B132 for the retraction motion. Voice coils B134 mounted onto blades B136 of the retraction elements drive an oscillation motion B138.

B.1.1.4 Multiple-Actuator Retractors

Figure 23:
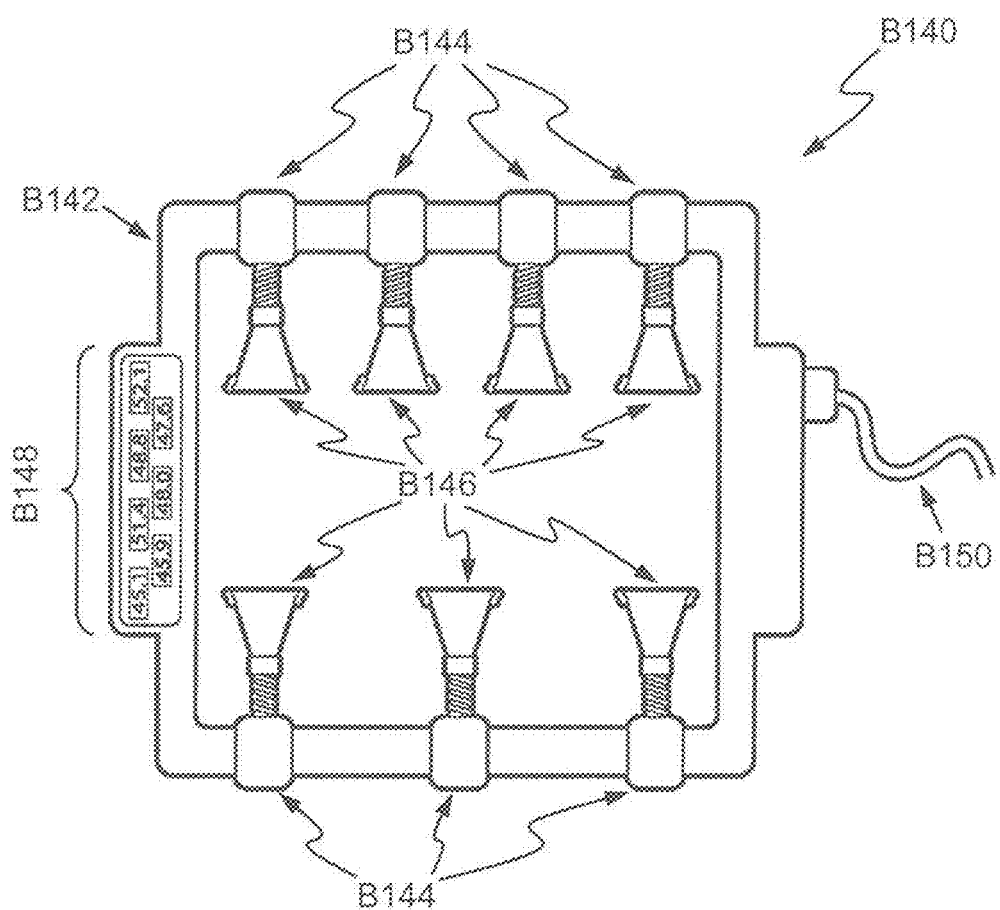
FIG. 23 shows a retractor having multiple arms and actuators that apply oscillating loads.

FIG. 23 shows an embodiment in which a retractor B140 with multiple arms and actuators can apply oscillating loads. The retractor B140 has a frame B142 to which independent actuators B144 and arms with attached blades B146 are mounted. The actuators B144 can be motors, hydraulic cylinders, or other appropriate actuators and can be actuated by one of a variety of methods, including all moving in synchrony, opposing pairs of actuators B144 or other functional groupings of actuators B144 moving in synchrony but not in synchrony with other functional groupings of actuators B144, or all actuators B144 moving independently. The actuators B144 perform both the retraction motion and the oscillation motion. The actuators B144 can be wire or cable wound onto a spool that is driven by a servo-motor or by a manually driven worm drive, with the blades B146 of the retraction elements attached to the wire or cable. Optionally, the retractor B140 can be instrumented with sensors that measure the force on the blades B146 of the retraction elements, or the displacements of the blades B146 of the retraction elements, or any other parameter relevant to the motion of the blades B146 of the retraction elements. The output from the sensors can be displayed by indicators B148 on the frame of the retractor B142 or on the monitor of a computer attached to the retractor B140 via an electrical cable B150.

Figure 24:
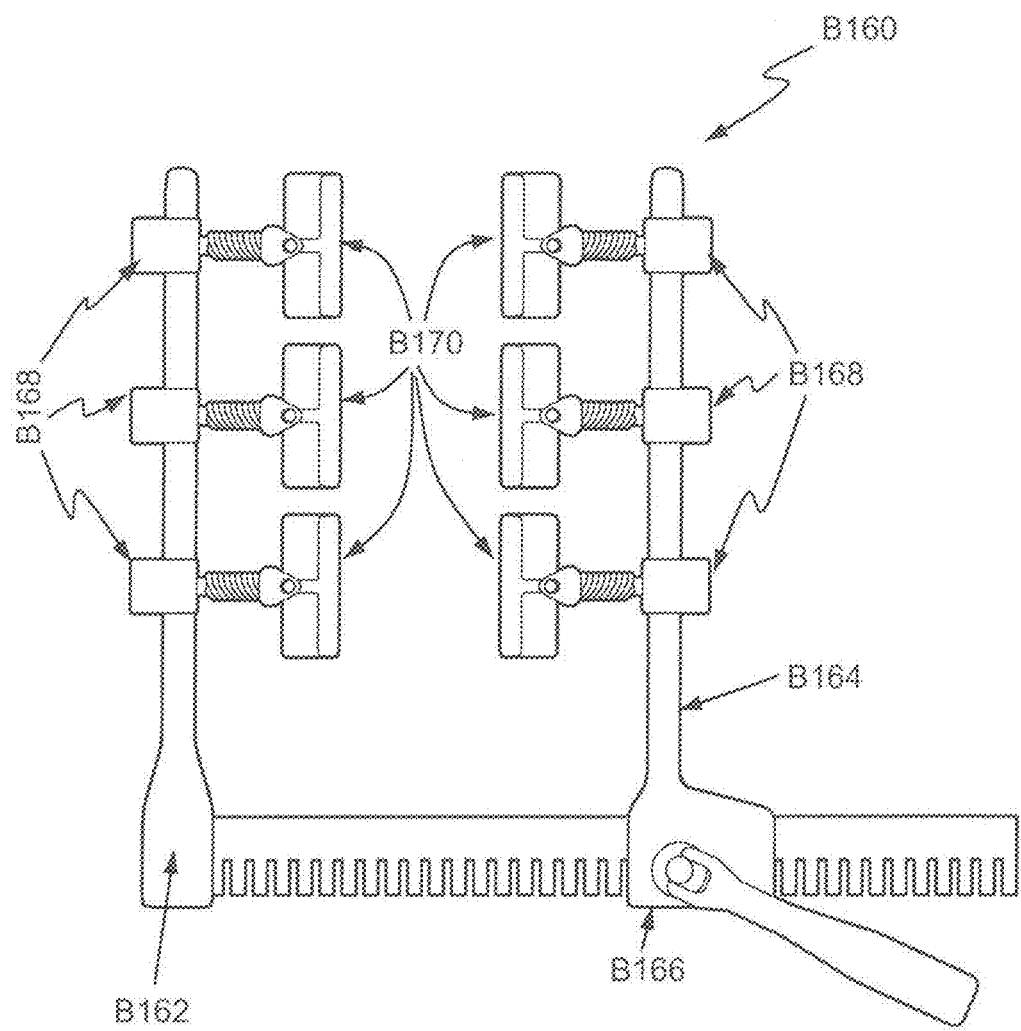
FIG. 24 shows a retractor having multiple pairs of arms and actuators, wherein one actuator separates the pairs of arms, while actuators on each arm drive oscillating motion.

FIG. 24 shows another embodiment of a retractor B160 with multiple arms and actuators. Here there is a first actuator that generates the retraction motion by separating two halves B162, B164 of the retractor frame that resembles a Finochietto-style retractor. This first actuator is a rack-and-pinion B166 driven by a hand crank, but, optionally, could be driven by a motor or other appropriate actuator. Additional actuators B168 attached to both halves B162, B164 of the retractor frame drive the oscillation motion of retractor blades B170. The additional actuators B168 can be driven by any appropriate actuator, such as a motor, a voice coil, a piezoelectric driver, or a hydraulic actuator. The additional actuators B168 can be rack-and-pinion in which the retractor blades B170 are attached to the rack. The additional actuators B168 can be wire or cable wound onto a spool that is driven by a servo-motor with the cable attaching to the blade B170 of the retraction element. Alternatively, the actuators can be linear motors.

B.1.2 Angioplasty Balloons and Stents

Another common actuator for deforming anatomical tissues is the balloon used for angioplasty with or without placement of a stent. The deflated balloon is inserted via a catheter into the blood vessel to be enlarged, and the balloon is inflated such that it presses against the walls of the blood vessel, enlarging the radius of that portion of the blood vessel. Similar methods are used in valvuloplasty, where the diameter of a heart valve is enlarged. Similar methods are used in tuboplasty to enlarge portions of the urinary tract and other surgical procedures to enlarge tubular anatomical elements, such as biliary tubes.

In the prior art, motions of the balloons are one-directional—they are simply inflated with a sterile fluid. Sometimes several balloons of increasing diameter are used to enlarge the anatomical element in increments, but each balloon is simply opened.

For angioplasty and valvuloplasty, inflation of the balloon is similar to the "retraction motion" described earlier for retractors. We present inventions to impose an "oscillation motion", as described above. To simplify the following discussion, each cycle of oscillation is divided into an "inflation phase" and a "deflation phase".

Figure 25:
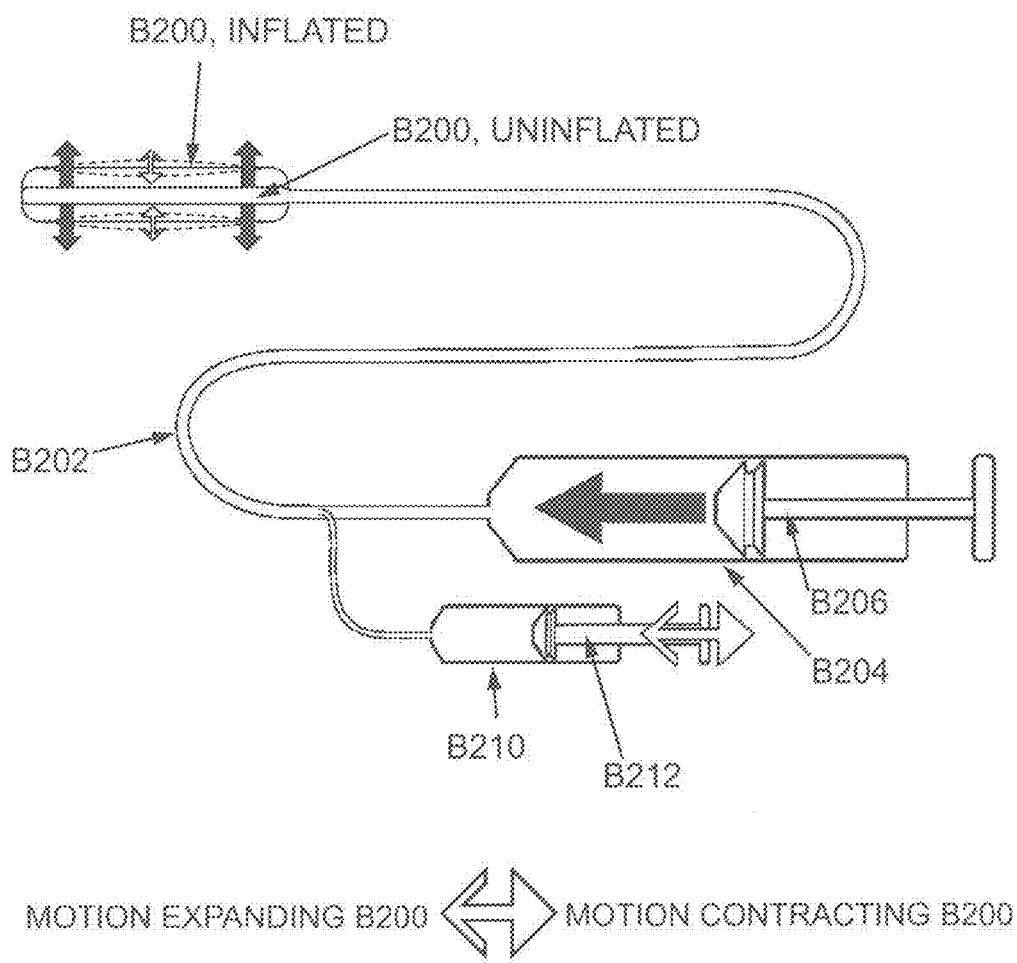
FIG. 25 shows an angioplasty system for dilating tissues with an oscillating motion.

In one embodiment depicted in FIG. 25, an angioplasty balloon B200 is inflated by a sterile fluid that passes through a catheter B202 from a first syringe B204 that is used to generate the pressure to inflate the balloon B200. The retraction motion is inflation of the balloon B200, which is driven by the plunger B206 of the first syringe B204. These retraction motions are shown in solid black, single-headed arrows. A second syringe B210 is also connected to the catheter B202. A plunger B212 of the second syringe B210 oscillates in and out, cycling a pressure that drives the oscillation motion of the balloon B200. The oscillation motion of the balloon B200, and the associated oscillating drive of the plunger B212, are shown as asymmetric, double-headed arrows with one arrow shape depicting the inflation phase and the other arrow shape depicting the deflation phase. Thus, oscillation of the pressure is achieved with a reciprocating motion of the plunger B212 such that the plunger B212 stroke length determines the amplitude of the oscillation and the plunger B212 stroke frequency determines the frequency of the oscillation motion. Motion of fluid during the deflation phase can be driven both by the combined elastic strain in the wall of the balloon B200 and in the wall of the anatomical element and by the rearward motion of the plunger B212.

Figure 26:
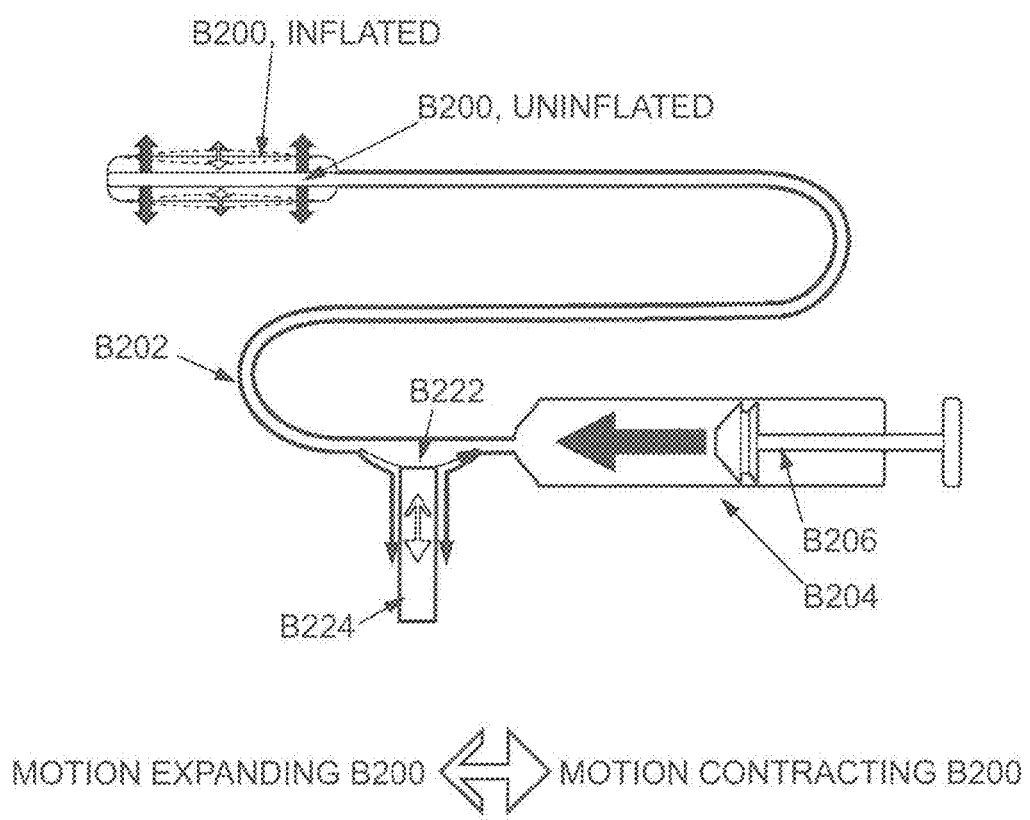
FIG. 26 shows another angioplasty system with an oscillating motion.

In another embodiment depicted in FIG. 26, motion of fluid up the catheter B202 for inflation of the balloon B200 is driven by a first syringe B204 as described for FIG. 25. The oscillation motion is driven by a piston B224 that impinges on a drive membrane B222 separating fluid from the piston B224. This separation of fluid from the piston B224 facilitates cleaning and sterilization of the moving parts for maintenance of sterility of the fluid. During the oscillation motion, the motion of fluid up the catheter B202 during the inflation phase is driven by the piston B224. Motion of fluid in the opposite direction during the deflation phase is driven by the combined elastic strain in the wall of the balloon B200 and in the wall of the anatomical element and by rearward motion of the piston B224.

One limitation of driving the inflation and deflation motions of the fluid up and down the lumen of the catheter is the resistance to fluid motion imposed by the long, narrow catheter lumen. This high resistance to fluid motion limits the frequencies and amplitudes attainable for the oscillation motion.

Figure 27A:
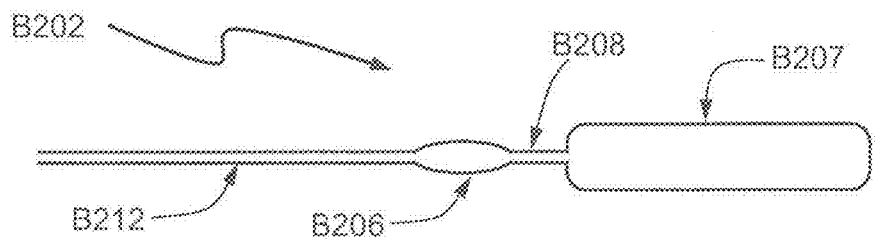
FIGS. 27A through 27C illustrates an angioplasty system with two compartments to generate oscillating motions having higher frequencies.
Figure 27B:
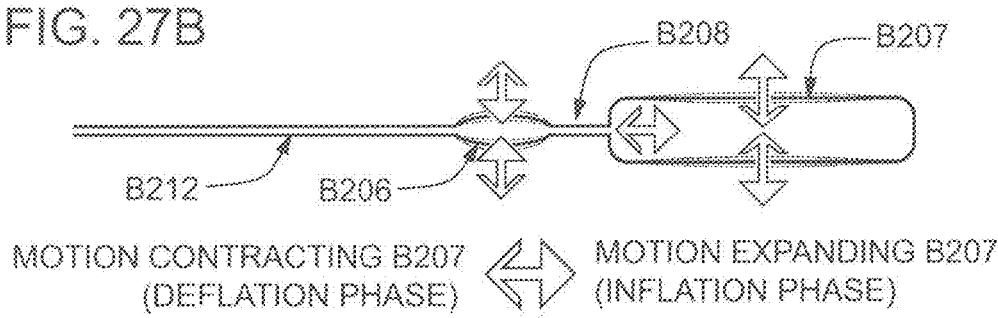
Figure 27C:
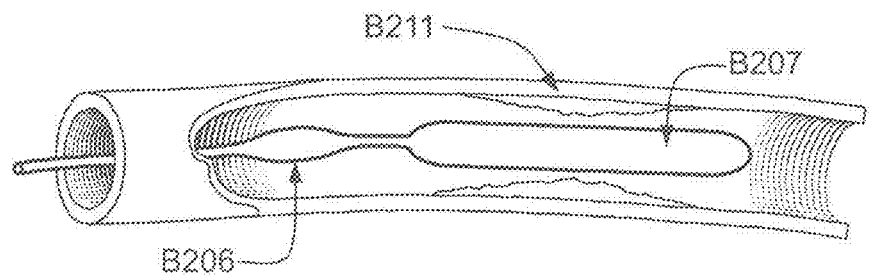

One means of eliminating the limitation is to restrict fluid motion during both phases of the oscillation motion to short distances through larger diameter connections. This is achieved in the embodiments depicted in FIGS. 27 and 28. Consider FIG. 27, the balloon has two compartments. A first larger diameter compartment B207 functions to force the anatomical element B211 open (see FIG. 27C), and a second smaller diameter compartment B206 functions as a fluid reservoir. Second compartment B206 can be placed upstream, as depicted, or downstream from the first compartment B207. Fluid flows easily between the two compartments through connecting channel B208. The retraction motion is driven, as in the prior art, by pumping fluid up the catheter B212 to inflate the first compartment B207. The oscillation motion is generated by forcing fluid back and forth from the second compartment B206 to the first compartment B207. The oscillation motion is thus driven by a second actuator, comprising the second compartment B206.

Figure 28A:
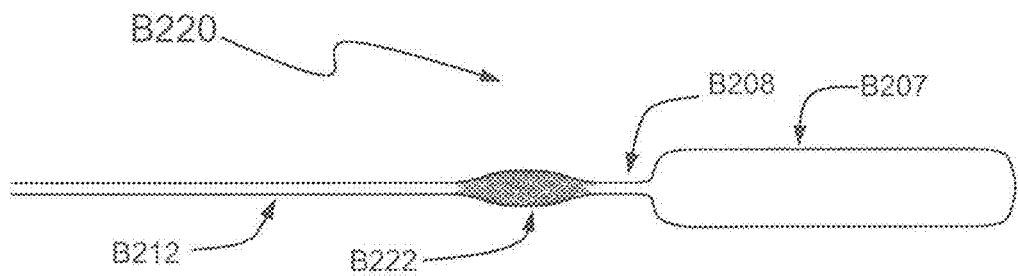
FIGS. 28A and 28B show another angioplasty system with two compartments to generate oscillating motions having higher frequencies.
Figure 28B:
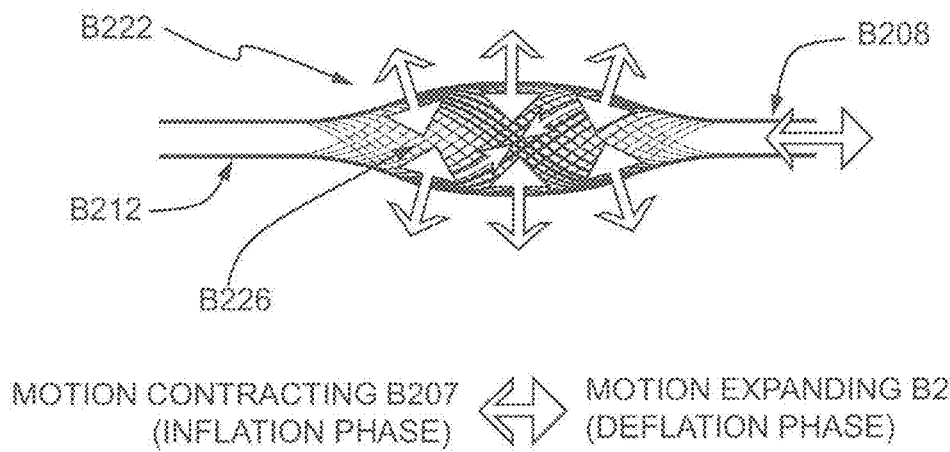

One means for driving the motions of the second compartment B206 is shown in FIG. 28A. FIG. 28B shows an enlarged view of second compartment B206. The second compartment B222 can be helically wound B226 with a wire or cable made of a shape memory material, such as Nitinol. Electrical actuation of the Nitinol decreases the diameter, and thus the volume, of the second compartment B222, forcing fluid through connecting channel B208 into the first compartment B207 to drive the inflation phase of the oscillation motion. The deflation phase is then driven by the combined elastic strain in the wall of first compartment B207 and the wall of the anatomical element. The elastic strain driving the deflation phase can also be augmented by a second helical wind (not shown) of spring material around the first balloon compartment B207.

Figure 29A:
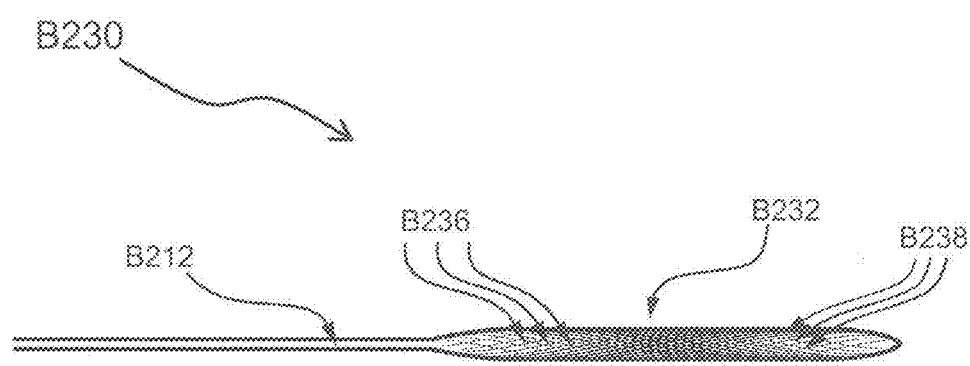
FIGS. 29A and 29B show another angioplasty system in which all components are contained in a single compartment to permit oscillating motions having higher frequencies.
Figure 29B:
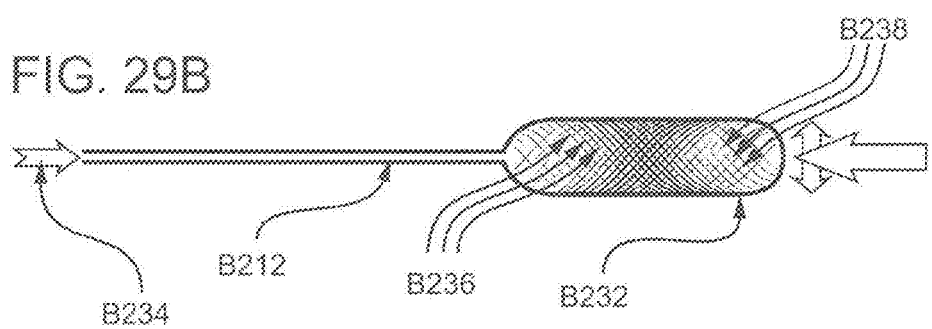

In another embodiment depicted in FIG. 29, the angioplasty balloon B230 has a single compartment B232 and is shaped as a cylinder, and the oscillation motion is generated in the walls of the compartment B232. FIG. 29A shows compartment B232 deflated, and FIG. 29B shows compartment B232 inflated. Compartment B232 is inflated by flow B234 through catheter B212, driving the retraction motion. The two phases of oscillation motion are driven by a first helical wind B236 of shape-memory material, such as Nitinol, and a second helical wind B238 of an elastic spring material. The first helical wind B236 of shape-memory material causes the cylindrical compartment B232 to decrease diameter (and elongate to maintain constant volume), thereby driving the deflation phase. The second helical wind B238 of spring material stores elastic strain energy during the deflation phase that then drives the inflation phase when electrical actuation of the first helical wind B236 ends. Similarly, the two helical winds B236, B238 can be wound such that electrical actuation of the first helical wind of shape-memory material increases the diameter of the balloon driving the inflation phase, and elastic energy storage in the second helical wind of material decreases the diameter of the balloon driving the deflation phase. Furthermore, shape memory material and elastic spring material can be included in the first helical wind B236 and in the second helical wind B238 such that actuation of one helical wind B236, B238 and then the other helical wind B236, B238 drives both phases of oscillation. Furthermore, only shape memory material can be included in the first helical wind B236 and in the second helical wind B238 such that actuation of one helical wind B236, B238 and then the other helical wind B236, B238 drives both phases of oscillation.

Figure 30A:
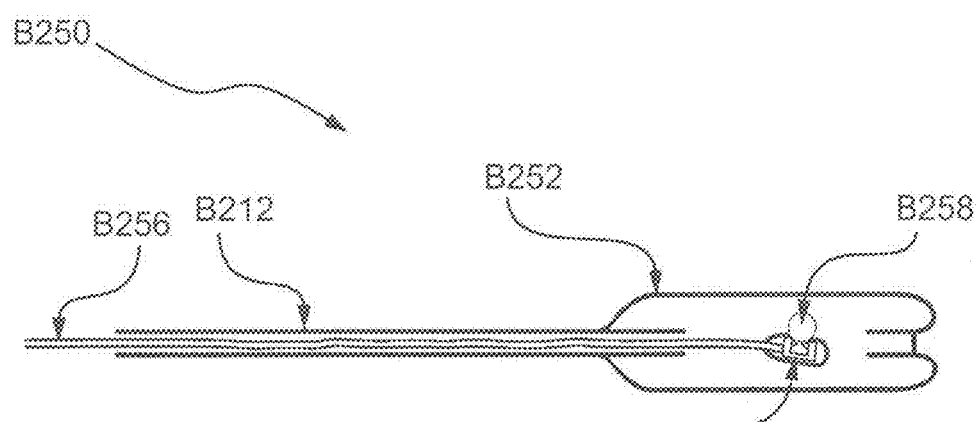
FIGS. 30A and 30B show another angioplasty system in which oscillating motions are driven by a thermally expanded bubble.

In another embodiment depicted in FIG. 30A, the angioplasty balloon B250 has a single compartment B252 and the oscillation motion is driven by a bubble generated inside the compartment B252. The retraction motion is driven by inflation of the compartment B252 by fluid motion up the lumen of the catheter B212. The oscillation motion is driven by a small electrical heater B254 mounted onto a wire B256 inside catheter B212 underlying the compartment B252 such that a bubble B258 of water vapor is formed, driving the inflation phase of the oscillation motion. Heat dissipation to the surrounding fluid and tissue causes the vapor bubble B258 to collapse, driving the deflation phase of the oscillation motion. Similarly, electrolytic bubble generation of a bubble B258 inside the compartment B252 could drive the oscillation motion.

Figure 30B:
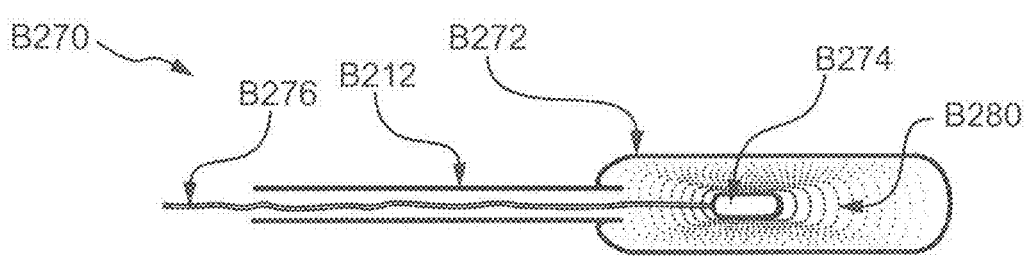

In another embodiment depicted in FIG. 30B, high frequency of oscillation is generated by a piezoelement. Angioplasty balloon B270 has a single compartment B272 and the oscillation motion is driven by a piezo-vibrator B274 mounted on a wire B276 inside the compartment B272. The retraction motion is driven by inflation of the compartment B272 by fluid motion up the lumen of the catheter B212. The oscillation motion is driven by actuation of piezo-vibrator B274 which emits high-frequency pressure waves B280 which transmit as high-frequency, low-amplitude oscillations of the wall of compartment B272.

B.2 Measurement of Tissue Properties

Oscillating deformation of a tissue with simultaneous measurement of selected parameters (e.g., force, displacement) can yield important information about the tissue's material properties and physiological state.

Leveque et al. (Leveque, Rasseneur et al. 1981) disclose oscillating loading for measurement of the Young's modulus and the internal damping factor of a viscoelastic material, including excised biological tissues, by oscillating loading. Long et al. (Long 1992; Long, Pabst et al. 1997) disclose measurement of the dynamic bending stiffness and damping coefficients of isolated intervertebral joints that are loaded by oscillating bending.

There are two disclosures for measuring the mechanical properties of an intact biological tissue:

1. Brown and Holmes (Brown and Holmes 1990) disclose a method for measuring the mechanical properties of intact tissues, and they disclose only constant velocity deformation as a means for standardizing measurements for spinal instability; and
2. Huszar (Huszar 1984) discloses a modified version of the technique of Leveque et al. (Leveque, Rasseneur et al. 1981) to make a measuring device that applies a force on the uterine cervix to measure the modulus of extensibility of the tissue in situ; the purpose is to assess the status of the cervix during obstetric procedures, especially for pregnancy, and Huszar also suggests use for ear or skin.

Measurements on intact tissues, as opposed to excised tissues, limits direct applicability of the above techniques disclosed for measuring mechanical properties by oscillating loading. This is due to the unknown dimensions of the intact tissues, unknown mass and connectivity to surrounding tissues, etc. However, modifications we disclose permit the collection of information relevant to the mechanics and physiology of the tissue being retracted or dilated. Importantly, these modifications can provide information relevant to the processes of retraction or dilation.

Figure 31:
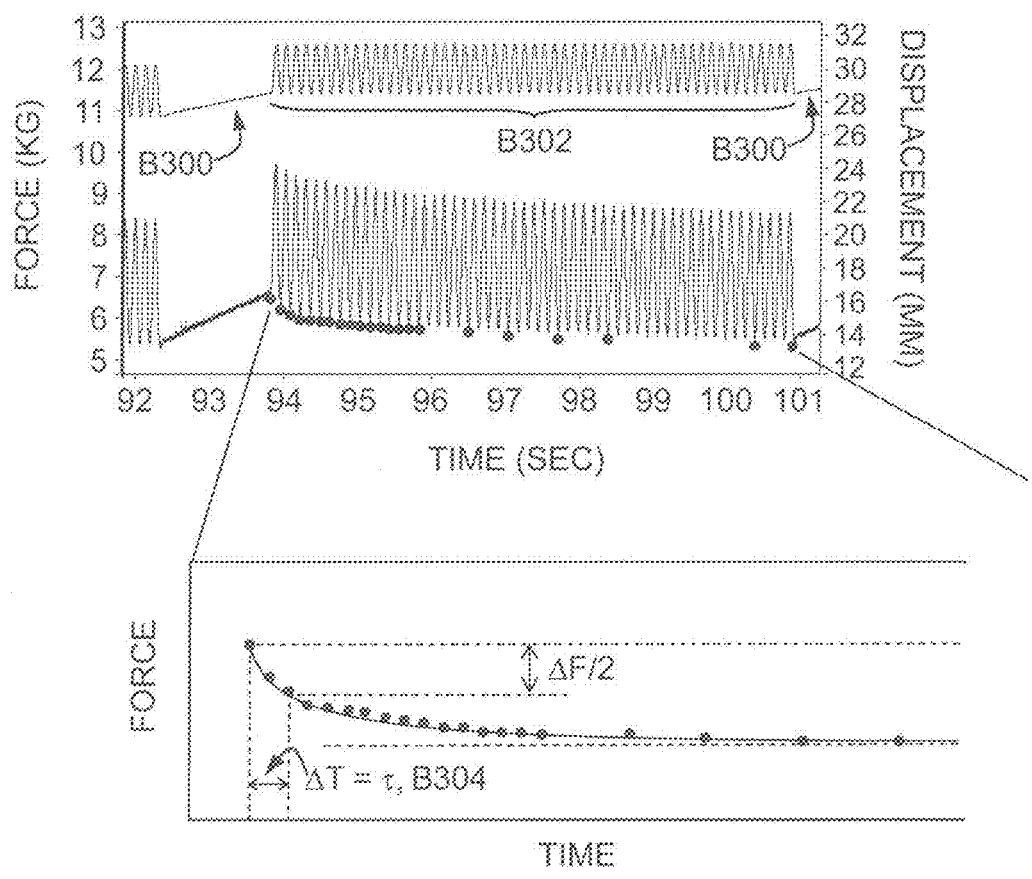
FIG. 31 illustrates how the time constant can be determined for force relaxation.

In one embodiment, as disclosed in Section B.1.1.1 and shown in FIG. 12, simultaneous measurement of force and displacement during oscillating loading permit measurement of effective stiffness (the slope of force/distance of displacement) and of viscous losses (area bound by hysteresis of the force/displacement curve seen during one cycle of loading/unloading). Furthermore, accelerated force relaxation AFR can be measured as disclosed in Section B.1.1.1.2 and shown in FIG. 31 to determine when to end an oscillation period. As shown in FIG. 31, a time constant t for accelerated force relaxation AFR can be determined by fitting a decay curve to the minimum force points for each oscillation, and cyclic loading can then be terminated when a fraction of the time constant has expired. For example, when retracting a tissue, the following sequence of steps can be followed:

(1) a retraction motion B300 is performed;
(2) retraction is paused;
(3) an oscillation motion B302 is performed with measurement of force and real-time calculation of the time constant t, B304 of the force relaxation as shown in FIG. 31; such that when a time equal to the time constant t, B304 has elapsed;
(4) oscillation motion B302 ceases; and
(5) retraction motion B300 resumes.

This algorithm can be used to optimize the reduction of force during a retraction (maximum force decrease in the smallest amount of time). Similarly, the oscillation can be stopped when some fraction or multiple of the time constant is achieved. Conversely, the force decrease can be monitored, and the oscillation motion terminated when the force has declined by a specified amount or percentage of the starting force.

Figure 32:
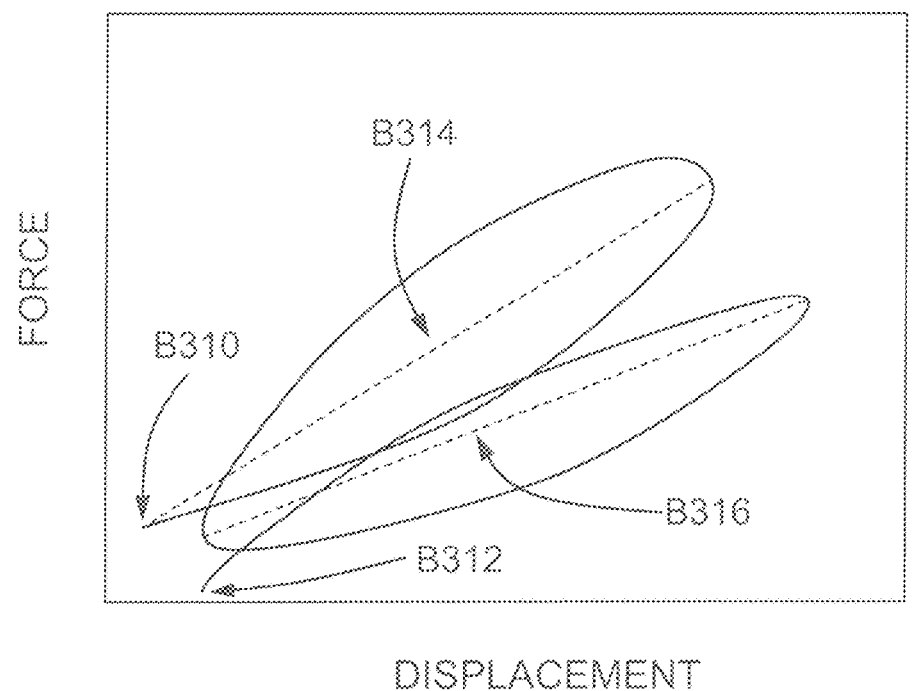
FIG. 32 illustrates how effective stiffness can be compared for sequential cycles of an oscillating loading.

In another embodiment shown in FIG. 32, decline in effective stiffness of a tissue can be measured arising from oscillating loading via phenomena such as work softening. Effective stiffness (force/displacement, dF/dx where F is force and x is distance) decreases in a tissue that displays work softening. Measurement of force and distance during repeated cycles of loading/unloading permit comparison of stiffness during each successive loading (or unloading). Thus, as shown in FIG. 32, which shows two (2) cycles of loading, the force displacement trace begins at B310 and ends at B312. As an example, the effective stiffness of the material during the first cycle of loading is estimated as the slope of the line B314, drawn between the limits of minimum and maximum displacement for that cycle, and, again, during the second cycle as the slope of the line B316. The decrease in slope from line B314 to line B316 is then used as an estimate of the degree of work softening. Comparisons of effective stiffness can be made repeatedly, in real time, during oscillating loading. The embodiment of a retractor described in Section B.1.1.1 would serve for such measurements. Another embodiment would be an angioplasty balloon in which pressure and volume in the balloon are measured during oscillating loading, such that volume is used as an estimate of displacement and pressure is used as an estimate of force. Pressure can be measured with any appropriate pressure gauge. If loading is at a low frequency, then measurement anywhere in the fluidic system would suffice because pressure gradients that drive flow into the balloon would be small. If loading is at higher frequencies, the measurements can be made inside the balloon with several methods including miniaturized pressure sensors (membrane deflection, capacitance based, etc.) Volume can be measured by measuring the displacement of fluid in the balloon by means such as piston displacement, or with a mass flow sensor placed along the channel to the balloon. The diameter of the balloon can also be used to directly determine deformation of the anatomical part or to estimate the volume of the balloon. The diameter of the balloon can be measured acoustically or optically via reflection of radiation off the wall of the balloon.

Viscous losses during deformation of the tissue can be estimated by any of several methods, including: measuring the phase lag between force and displacement, measuring the area bound by the hysteresis curve during one cycle of loading/unloading, or measuring the difference in work performed by the motor during loading and unloading.

The resonant frequency of the materials may be measured by oscillating at different frequencies as disclosed by Leveque et al. (Leveque, Rasseneur et al. 1981), by identifying the frequency at which the force required for deformation is smallest, by identifying the frequency at which viscous loss is smallest, or by other methods known in the fields of mechanics and biomechanics.

Many methods of testing by oscillation require testing at multiple frequencies of oscillation. This can be accomplished by testing at multiple discrete frequencies, testing via a frequency sweep, or testing with "white noise".

B.3 Tissue Deformation Via Oscillating Loading, Tissue Measurement, and Feedback Information obtained by measurements such as those disclosed in Section B.2 can be used to make decisions about how best to perform a tissue deformation by either oscillating loading (e.g., an oscillation motion) or normal one-directional loading (e.g., a retraction motion).

In one embodiment, force and displacement are measured by a retractor. Alternating retraction motion and oscillation motion are used. A retractor similar to that in Section B.1.1.1.1 and shown if FIG. 12 can be used. The first phase of retraction proceeds as follows:

(1) The retraction motion starts, during which the distance is measured, and the retraction motion is stopped when a fraction of the desired opening is reached, e.g. 10% or 30%;
(2) Oscillation motion is then imposed to determine the frequency that results in the smallest time constant t for accelerated force relaxation (AFR).
(3) Oscillation motion is then continued for a duration of 1.5τ and then stopped; and
(4) Retraction motion is resumed.

This cycle is repeated, possibly with different opening extents (e.g. another 10% of desired opening or another 20% of desired opening) until the desired opening is obtained.

In another embodiment, the stiffness of the material is used to determine when an oscillation motion begins. Force (F) and distance (x) are measured by the retractor, and stiffness is measured in real-time as dF/dx. Alternating retraction motion and oscillation motion are used as described in the preceding paragraph. Retraction proceeds as follows:
(1) Retraction begins with a retraction motion, and stiffness is measured throughout motion. When stiffness starts to decrease, indicating the material properties of the tissue are changing, retraction motion stops;
(2) Oscillation motion commences with an amplitude of approximately 2 mm and a frequency of approximately 5 to 10 Hz, or with an amplitude of approximately 4 to 8 mm and a frequency of approximately 0.5 to 2 Hz;
(3) Oscillation occurs for approximately 10 to 50 cycles to alter the material properties of the tissue such that stresses in the tissue are relieved and large-scale tissue components don't break; and
(4) retraction motion is resumed.

Other frequencies and amplitudes can be used, and frequency and amplitude can be adjusted for the tissue to be retracted, with bone, for example, being oscillated at a frequency of kHz and an amplitude of micrometers. The oscillation motion can be any combination of frequency and amplitude that achieves appropriate modification of the tissue being retracted.

In another embodiment, retraction and oscillation motions are superimposed. Retraction follows a pre-determined trajectory (e.g., a trajectory in which the retractor blades move apart quickly at first but increasingly slowly as retraction proceeds such that the desired opening is achieved in a proscribed time, such as that shown in FIG. 11B). Force and distance are measured. Oscillation serves both to accelerate force relaxation, which now occurs concomitantly with continuous deformation, and to permit repeated stiffness measurements, as shown in FIG. 32) to regulate the velocity of the retraction motion about the predefined trajectory (e.g., if stiffness is too high, then the velocity of the retraction motion slows, or if the stiffness is too low, then the retraction motion accelerates).

In another embodiment, pressure in the tissue is measured by a catheter sensor, such as the miniaturized sensors from Scisense, Inc. of London, ON, Canada and ADInstruments of Colorado Springs, Colo., USA. One or more pressure sensors are placed into the tissue near the retractor blades, such that the pressure sensors sense internal tissue pressure and how internal tissue pressure rises during retraction. Alternating retraction and oscillation motions are used. Retraction motion starts and proceeds until tissue pressure reaches a threshold (e.g., a level that indicates that perfusion of the tissue has stopped). Retraction motion is halted and oscillation motion is started. Oscillation motion is used for accelerated force relaxation until the pressure drops below the threshold. Retraction motion is resumed, and the process repeated until the desired opening is achieved.

C. Detecting Tissue Trauma During Retraction

Figure 33:
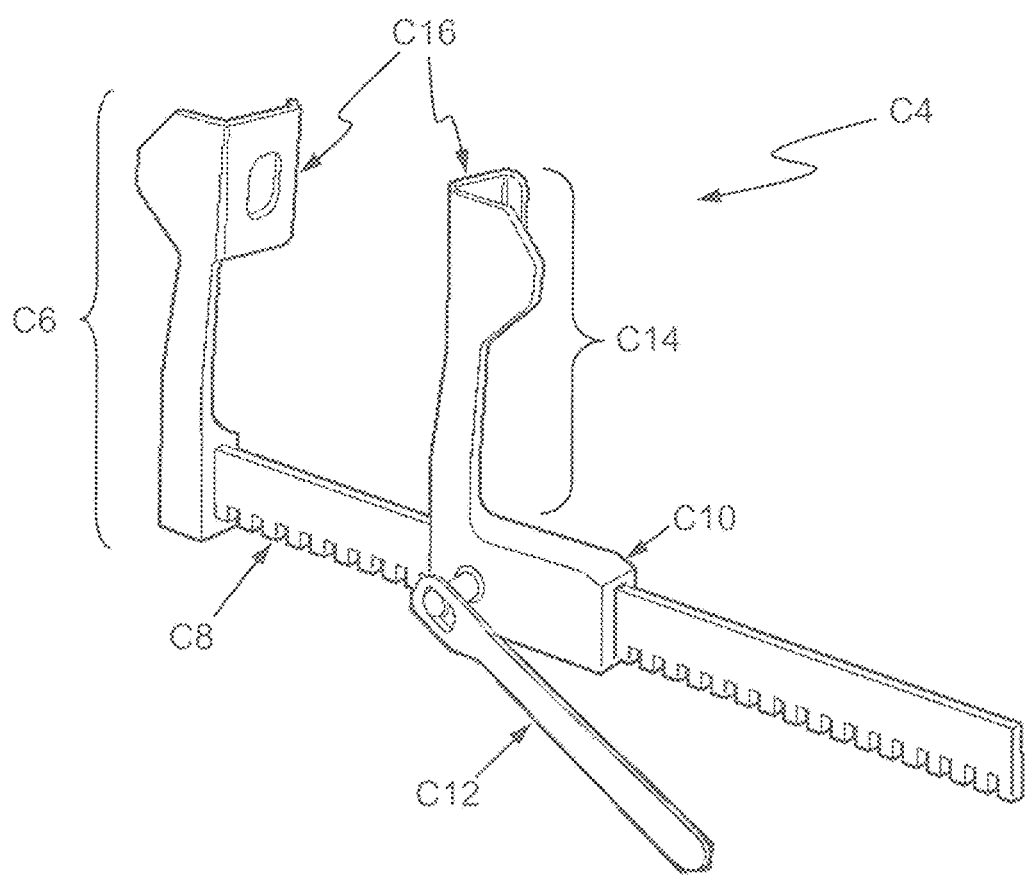
FIG. 33 depicts an example retractors in the prior art.

FIG. 33 presents an example of a Finochietto-style retractor C4 in the prior art. The retractor C4 has a fixed retraction element C6 attached to one end of a rack C8 of a rack-and-pinion drive C10 driven by a manual drive handle C12. A moveable retraction element C14 is attached to the rack-and-pinion drive C10 and moves along the rack C8. Each of the retraction elements C6, C14 has a single blade C16 that engages the tissue to be retracted.

A retractor C4, such as that shown in FIG. 33, can be instrumented to measure several parameters during retraction. For example, the blades C16 of the retractor C4 can be fitted with force sensors (such as strain gauges or a load cell), and the separation of the blades C16 can be measured by fitting a displacement sensor onto the retraction elements C6, C14 (such as a linear potentiometer or an optical encoder). The output from these sensors can be fed into a display (such as a digital numeric display or a bank of light emitting diodes LEDs) for direct readout, or the signal can be fed into an analog-to-digital converter and read by a computer for subsequent calculations and display. Multiple sensors measuring a parameter (for example, a plurality of load cells and/or accelerometers indicating forces and/or accelerations acting on a corresponding plurality of retractor blades) can provide a map in two dimensions (2D), three dimensions (3D), or four dimensions (4D, with time) of the forces and moments acting on the system consisting of the body of the patient and the retractor C4.

Figure 34:
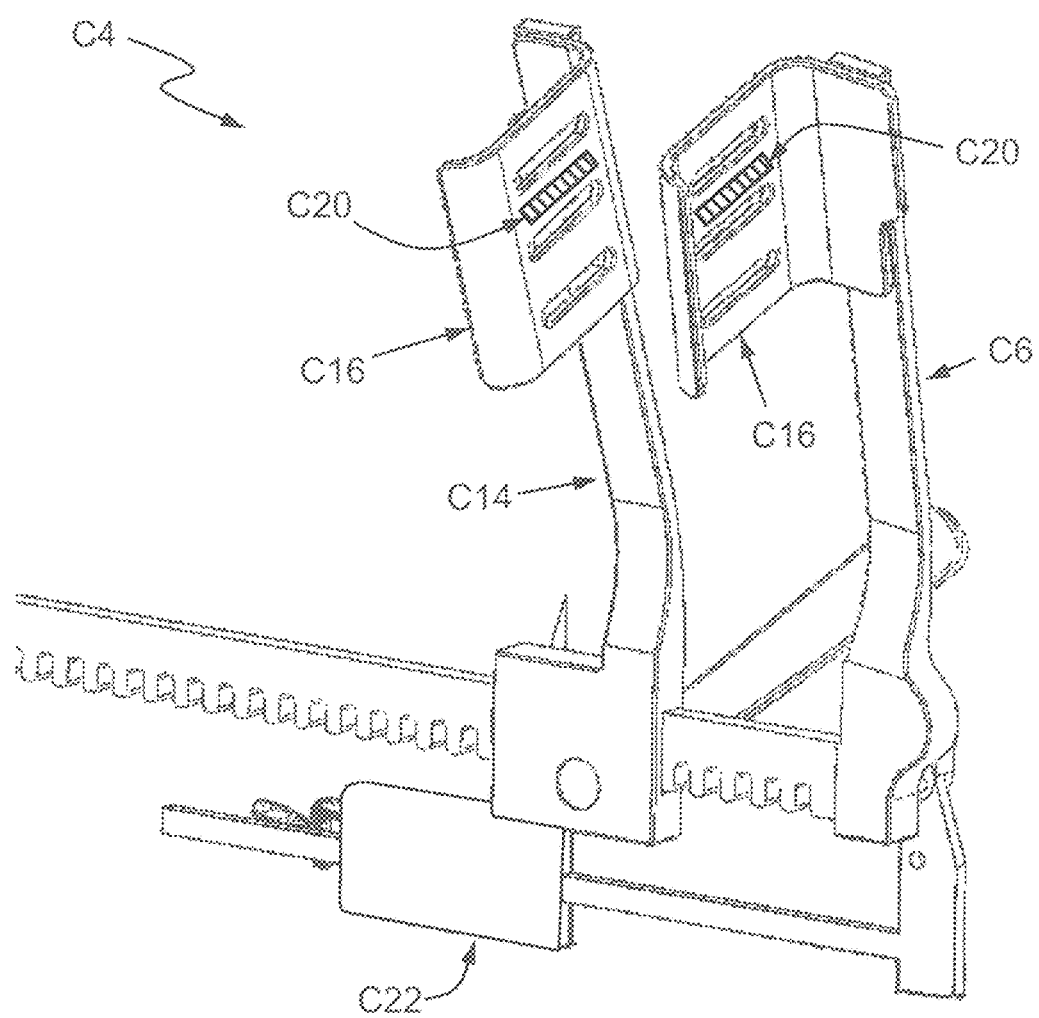
FIG. 34 illustrates the retractor of FIG. 33 fitted with a set of calipers for measuring the separation of retraction elements and with strain gauges for measuring the forces on each of the blades of the retraction elements.

FIG. 34 depicts the retractor C4 showing how it might be fitted with a set of calipers C22 for measuring the separation of the retraction elements C6, C14. Additionally, strain gauges C20 can be placed on each of the two blades C16 of the retraction elements C6, C14 ("retractor blades") to measure forces on the retractor blades C16.

Figure 35:
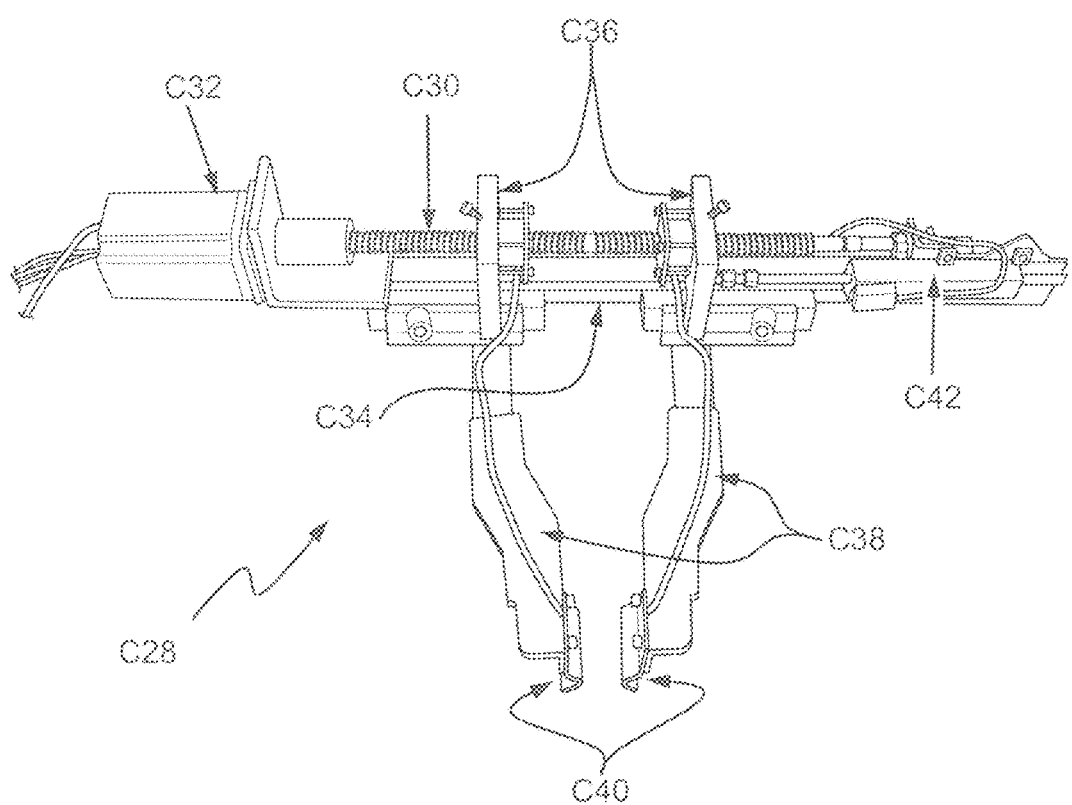
FIG. 35 shows a prototype retractor having a motorized drive, a linear potentiometer for measuring the separation of the retraction elements, and strain gauges for measuring the forces on each of the blades of the retraction elements.

FIG. 35 shows a retractor C28 that uses a bi-directional ball screw C30 (i.e., having two followers that travel in opposite directions) that is driven by a stepper motor C32 which in this case is a MDrive 23Plus from Intelligent Motion Systems, Inc. The bi-directional ball screw C30 is mounted to a rail C34 with two linear translation stages C36 which in this case is the IKO LWHG 25 from IKO, Inc. such that each translation stage C36 attaches to one of the bearings on bi-directional ball screw C30, thus when bi-directional ball screw C30 is rotated by the stepper motor C32, the translation stages C36 travel in opposite directions. A retractor arm C38 fabricated by hand from mild steel angle iron that was cut/bent/welded into shape, is mounted to each translation stage C36. Each retractor arm C38 has a retractor blade C40 fabricated by hand with mild steel.

A linear potentiometer C42 which in this case is a 5 kOhm, 100 mm linear potentiometer from Schaevitz is used to measure separation of the retractor blades C40. The static mount of the potentiometer C42 is affixed to the rail C34, and the piston of the potentiometer C42 is affixed to one of the translation stages C36. Note that any means of measuring displacement could be used here, such as optical encoders, contact and non-contact proximity sensors, digital calipers, and the like.

The retractor blades C40 are instrumented with a full-bridge strain gauge assembly (not shown) which includes two (2) gauges, which in this case are model CEA-06-125UN-350 from Vishay Micro-Measurements, Inc., on each side of the blade. The signal from the strain gauges is the amplified by a signal conditioner (not shown) which in this case was model OM-2 from 1-800-LoadCells. Note that force could be measured by any of several means, such as drive current on the motor (and other means of measuring torque on the drive mechanism), fiber optic strain gauges, optical sensors of deformation, and the like.

All signals from the linear potentiometer C42 and the signal conditioners/strain gauges are read by a Windows-based computer using a data acquisition card, which in this case is a model USB-6211 from National Instruments, and software, which in this case is LabVIEW from National Instruments, Inc. using a custom program prepared by Katya Prince of Prince Consulting. The stepper motor C32 is controlled with IMS Terminal software from Intelligent Motion Systems, Inc. Note that a servo-motor could also be used. The strain gauges were calibrated by hanging known weights from the retractor blades C40 of the retractor C28. The linear potentiometer C42 was calibrated with a metric ruler.

A series of experiments were conducted with the prototype retractor C28 described above using parts from pig cadavers. The parts were a "front quarter" purchased from Nahunta Pork Center (Pikeville, N.C.). A front quarter is basically a whole pig cut at the waist (forming a front half) and split down the vertebrae (forming left and right quarters); thus, each quarter had an intact rib cage (one side), spine (bisected), sternum (bisected), and shoulder. All parts had been refrigerated after slaughter, used within 24 hours of slaughter, and warmed by immersion in warm water (while wrapped in a plastic bag to prevent soaking of the tissue) to near body temperature (31° C. to 37° C.). The quarters ranged in size from 8 to 12 kg.

We performed thoracotomies between 3-4 rib pairs on each quarter, almost always performing an incision between ribs 5-6, 7-8, 9-10, and 11-12. Thoracotomies were performed by:

cutting the skin with a scalpel over the range of the thoracotomy, and in a direction parallel to the ribs,
bisecting the muscles overlying the ribs with a scalpel,
cutting through the intercostal tissues with a scalpel,
pushing a finger between the ribs to make a small opening,
inserting the closed blades of the retractor into the opening,
positioning the retractor such that the blades sat approximately halfway between the spine and the sternum and the retractor's axis of opening was approximately parallel with the spine,
initiating opening according to a specified algorithm via computer control of the stepper motor.

Incisions were typically 110 mm to 130 mm long, with longer incisions being performed on larger quarters.

Figure 36:
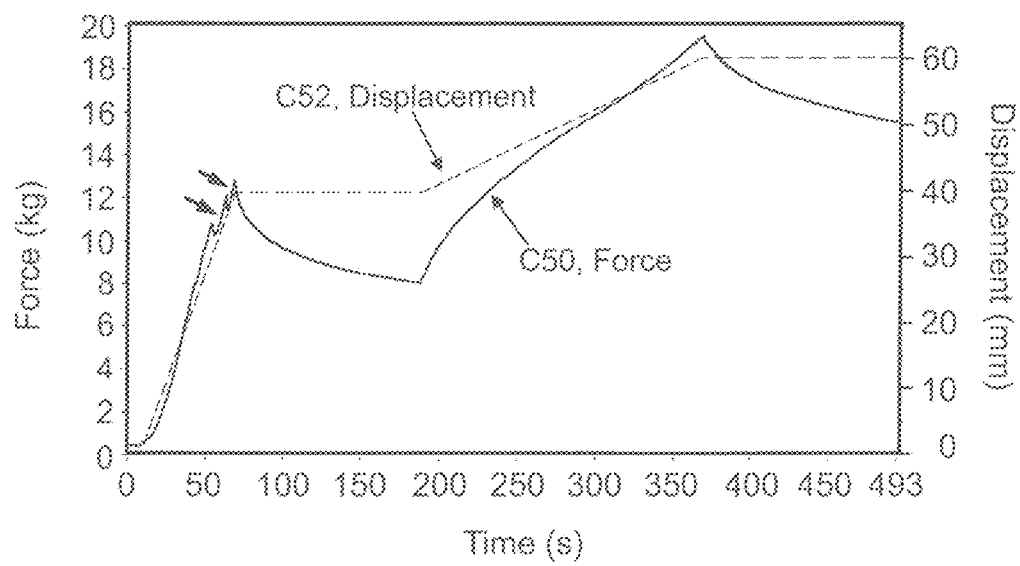
FIG. 36 shows force and displacement with respect to time for a retraction during an experimental thoracotomy on a pig carcass.

FIG. 36 shows data from the retractor C38, with force C50 and displacement C52 (distance measured by the linear potentiometer C42) plotted with respect to time for a "standard retraction", similar to that defined by Bolotin et al. (US Patent Application Publication Number 2006/0025656 and 2007, J. Thorac. Cardiovasc. Surg. 133:949), which proceeds as follows:

open to 40 mm in one (1) minute (⅔ of final opening);
pause two (2) minutes for force relaxation; and
open to 60 mm in three (3) minutes (i.e., to the final opening).

Thus, a total opening of 60 mm is reached in 6 minutes. Each of the two moves is constant velocity (40 mm/min for the first and 6.8 mm/min for the second). These moves were controlled by a computer program executed in a computer with the IMS Terminal software. Thus, unlike Buckner and Bolotin et al. (US Patent Application Publication Number 2006/0025656 and 2007, J. Thorac. Cardiovasc. Surg. 133: 949) the velocity of the retraction motions was precisely controlled. This somewhat matches the pace described to us by other thoracic surgeons, but there is no standard clinical practice. Surgeons use a procedure defined by their training, personal experience, patient condition, and sense-of-touch (i.e., non-quantitative) estimates of force applied at the handle of a hand-cranked retractor. Furthermore, surgeons have no velocity control, other than hand-eye coordination. Importantly, the self-locking Finochietto-style rack-and-pinion drive C10 engages and advances in rather abrupt half-step turns of the handle C10, producing a non-linear relationship between rotation and motion of the retractor blades C16, making control of velocity and force difficult.

Figure 37:
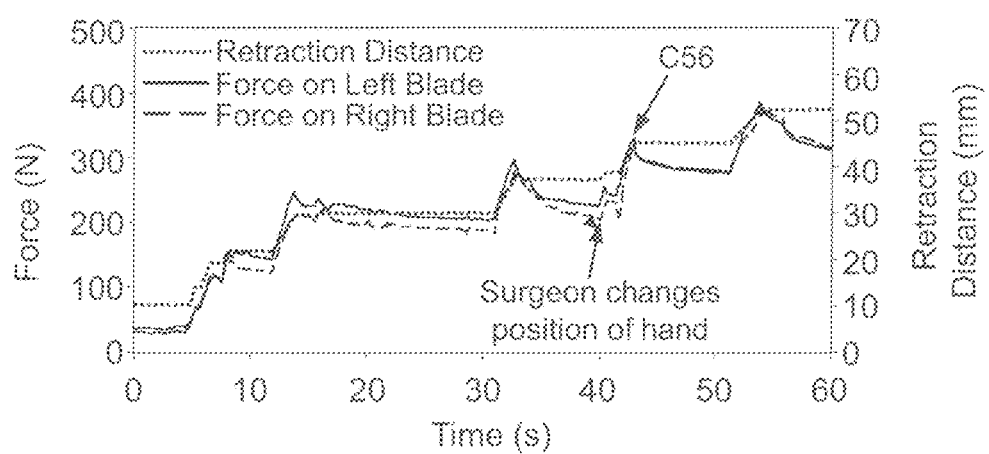
FIG. 37 shows force and displacement with respect to time for a retraction during an experiment thoracotomy on a pig using a Finochietto-style retractor.

FIG. 37 shows the displacement and force on both arms for a Finochietto retractor instrumented like the retractor shown in FIG. 34, except that a linear potentiometer is used to measure displacement, instead of the caliper shown in FIG. 34. These measurements are from a thoracotomy performed on an anesthetized pig (female, 50 kg weight, procedures similar to those in FIG. 36 except that opening was to 52 mm in one minute without a long pause in retraction). The force and displacement traces in FIG. 37 are not smooth. Both traces show the step-by-step increases generated by the ½-rotations of the crank. Furthermore, even small adjustments or other motions of the crank resulted in large deflections in the force trace. For example, when the surgeon simply adjusted the position of his hand on the crank at 42 s, an approximately 30 N change in force is seen in the force trace for both retractor blades. During this retraction, a rib broke. Importantly, the point on the trace where the rib broke could not be identified in any of the traces. The point C56 on the trace where the rib broke was identified by careful analysis of a time-correlated video recording of the procedure in which the break could be heard as a "crack". Thus, it is not possible from these force or displacement traces to detect that a rib is about to break. Nor is it possible to determine if a rib breaks.

Returning to FIG. 36, the force of the motorized retraction rises rapidly over the first minute of retraction (opening to 40 mm). Force relaxation, as described in Buckner and Bolotin et al. (US2006/0025656 and 2007, J. Thorac. Cardiovasc. Surg. 133:949), and also illustrated in FIG. 1, is evident during the two-minute pause—the force required to maintain the 40 mm opening decreases with time. Force again rises when retraction is resumed at 3 minutes, rising at a time-varying rate, but the increase in force is smooth up until 60 mm retraction is achieved.

No significant tissue breaks occurred during the retraction shown in FIG. 36. Two small breaks are evident over the first 50-60 s interval, as evidenced by small downward deflections in the force trace (marked by arrows). The absence of significant breaks is unusual. Most retractions of this type resulted in large tissue breaks, as seen in FIGS. 38A-38C and 40A-40B (discussed below).

Figure 38A:
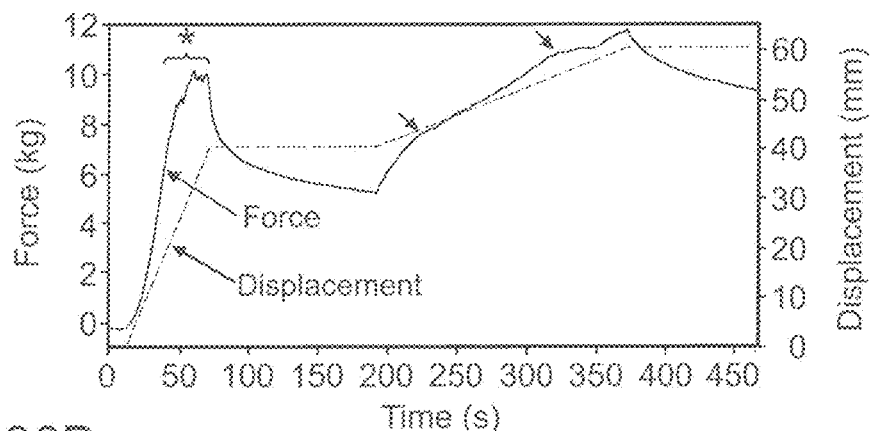
FIGS. 38A through 38C shows force and displacement with respect to time for a second retraction during another experimental thoracotomy on a pig carcass, wherein a larger break and two smaller breaks occurred during this retraction and two force events and a slope event preceded the larger break.
Figure 38B:
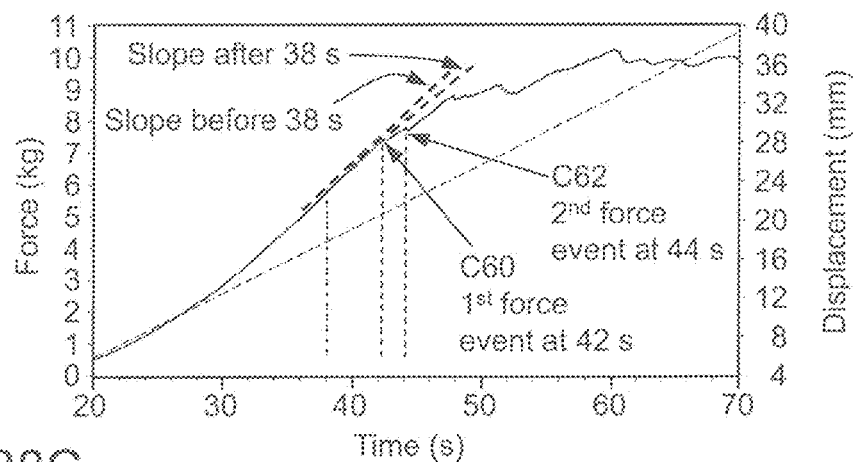
Figure 38C:
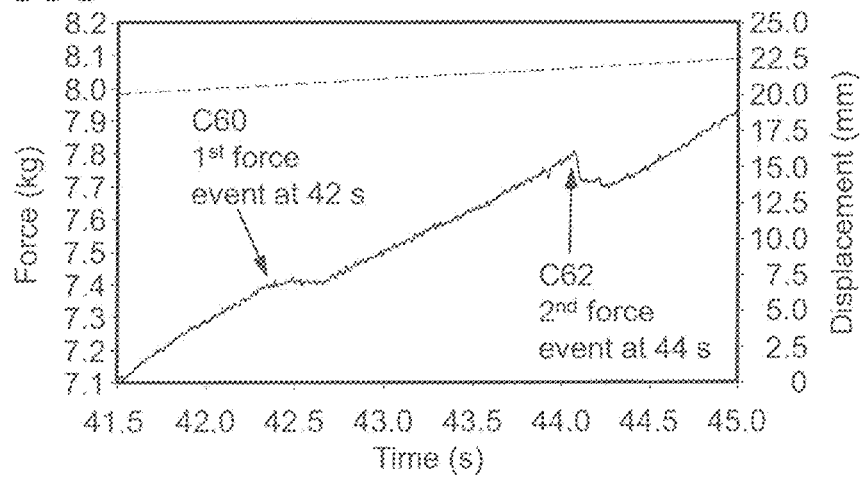

FIG. 38A shows data from another retraction, using the same motorized standard retraction as in FIG. 36. A large break is seen—a break that spanned several seconds (46-70 s on the graph, marked with an asterisk) and ended only with the start of the pause period. There are also several smaller breaks (marked with arrows), also evident as significant drops in the slope of the force plot. FIG. 38B shows an expanded view of the data from 20 to 70 s, showing the large break. There are two types of events that precede this large break. The first type of event is a decrease in the slope of the curve beginning at 38 s (illustrated by the two dashed lines—termed a "slope event"). The second type of event is a small break seen as a drop C60 in force at 42 s, marked with an arrow in FIG. 38B (termed a "force event"). Note that there is a second force event C62 at 44 s. FIG. 38C shows the interval from 41.5 to 45 seconds on an expanded scale; the two force events, the first force event C60 at 42 s and the second force event C62 at 44 s, are clearly visible.

Figure 39:
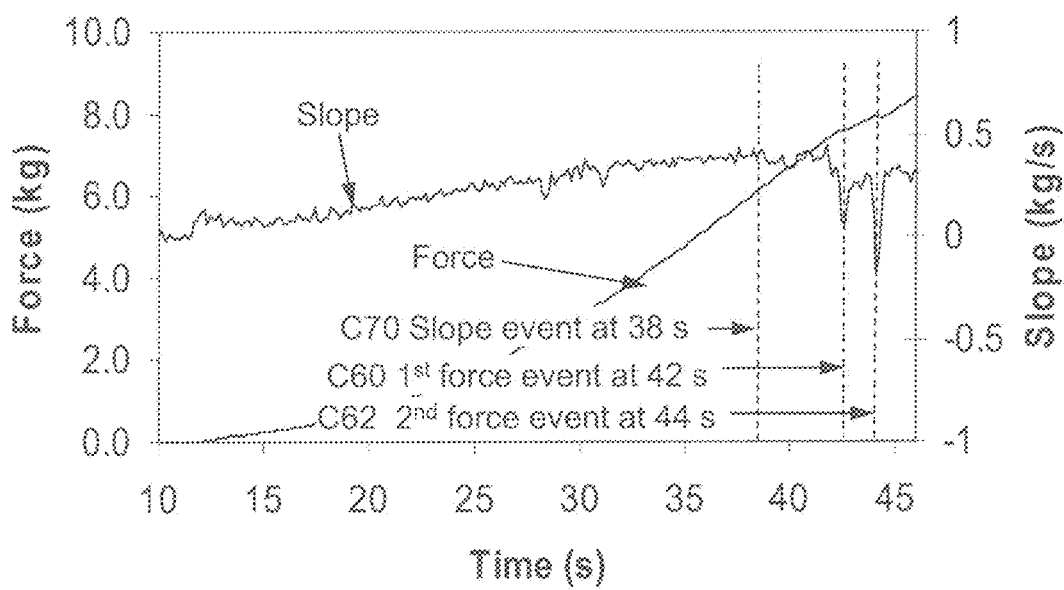
FIG. 39 shows the force and the slope of the force in an expanded view of the retraction in FIGS. 38A-38C. This shows how examination of the slope provides a clearer signal of the slope and force events.

The two types of events, slope events and force events, preceding the large break are better seen in FIG. 39 which plots both the force (kg) and the slope of the force (kg/s) for the interval of 10 to 46 s in the retraction shown in FIG. 38. A slope event C70 beginning at 38 s is more visible, and the two small breaks are now much more prominent as negative-going peaks marking the first force event C60 and the second force event C62.

Figure 40A:
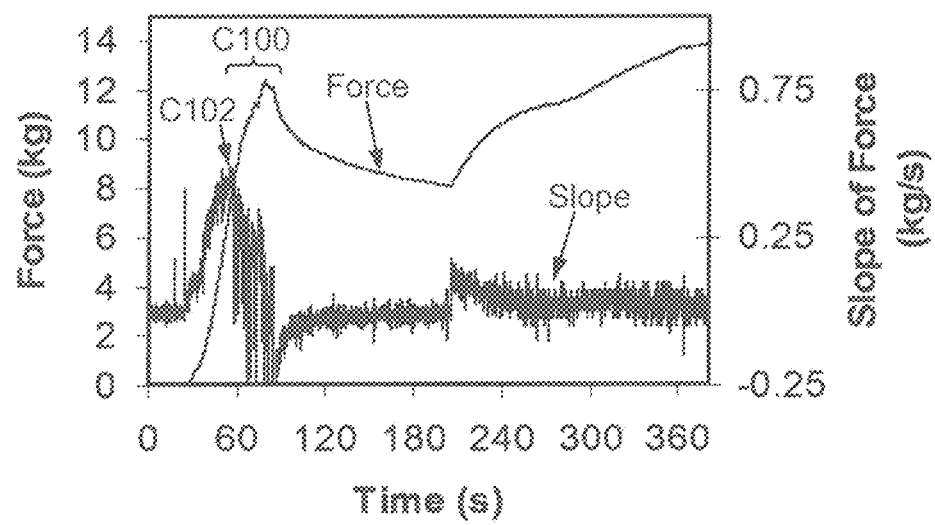
FIGS. 40A and 40B illustrate the force and the slope of the force over time for a third retraction during another experimental thoracotomy on a pig carcass.
Figure 40B:
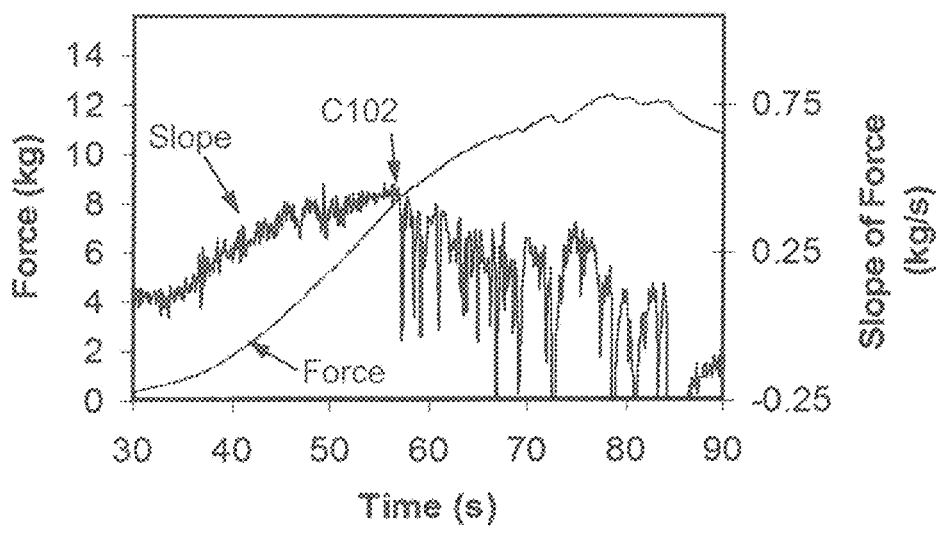

FIGS. 40A and 40B present another example of a standard retraction—FIG. 40A presents data from the entire retraction, and FIG. 40B presents a magnified view of one minute of data from 30 s to 90 s. In this retraction, there is, again, a large break C100 at the end of the first 1-minute of retraction, beginning at about 72 s. Several small force events occur (e.g., at 57 s, 59 s, 61 s and others), but preceding these is a slope event C102 beginning at 57 s. This drop in slope C102 is more obvious than the slope event C70 seen in the retraction shown in FIGS. 38 and 39. The slope event C102 in FIG. 40 is evident in the force trace, but is more easily seen in the slope trace. Another common feature is evident here—both the force trace and the slope trace become noisier; their variance increases. This provides third and fourth indicators of an imminent break—termed a "force variance event" and a "slope variance event".

All four of these events, (a) a force event, (b) a slope event, (c) a force variance event, and (d) a slope variance event are frequently seen preceding a large break and can be used as indicators that a large break is about to occur.

Figure 41A:
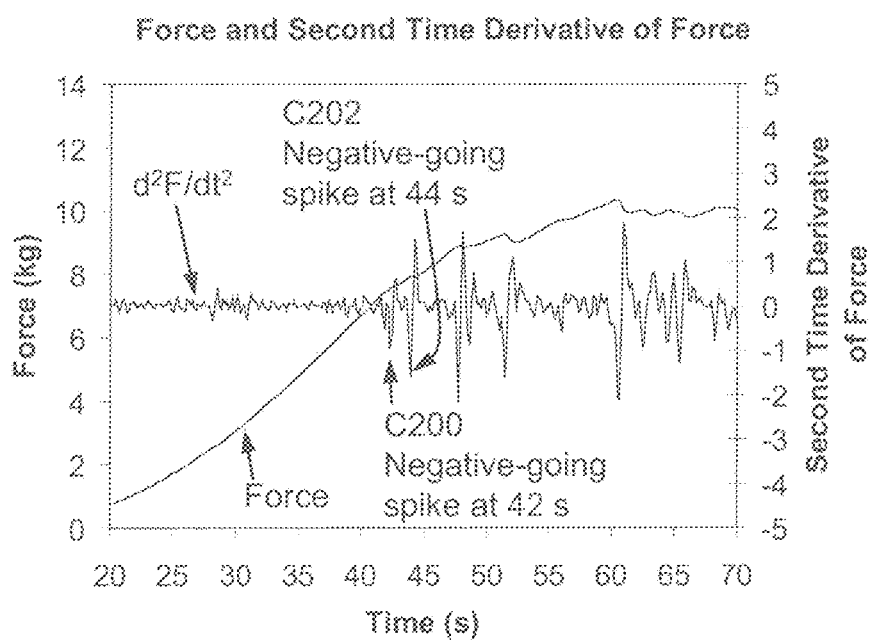
FIGS. 41A and 41B illustrate the force and a second time derivative of the force (d2F/dt2) for two experimental retractions.
Figure 41B:
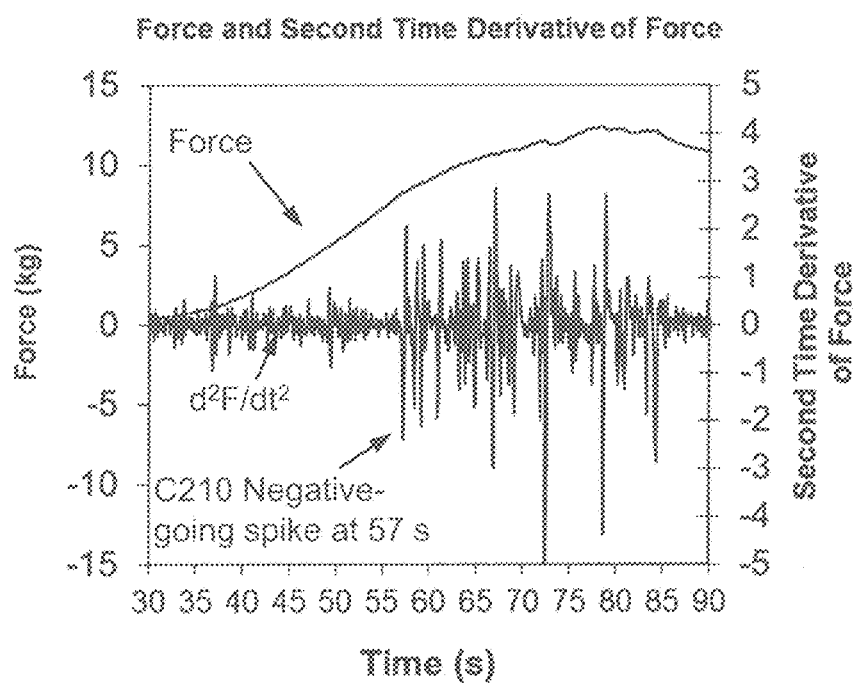

Note that higher order time derivatives of the force trace (e.g., d2F/dt2, etc) also present information relevant to imminent breaks and can make a distinction from baseline simpler because the signal stays near zero. FIGS. 41A and 41B show the second time derivative, $d^2F/dt^2$, of the force for the retractions presented in FIGS. 38, 39, and 40. (FIG. 41Aa presents the retraction from FIGS. 38 and 39, and FIG. 41B presents the retraction from FIG. 40.) In FIG. 41A, the force event C60 at 42 s and the force event C62 at 44 s are now clearly resolved as negative-going spikes C200 and C202. In FIG. 41B, the slope event at 57 s is now clearly resolved as a large, negative-going spike C210. Thus, the second time derivative of the force provides both (a) a flat baseline over much of the retraction and (b) a negative-going spike at force and slope events providing a clear signal indicating the onset of the variance. Detection of the spike can be accomplished by comparison of substantially instantaneous values of d2F/dt2 versus a time-averaged value of d2F/dt2, with the ratio of instantaneous/time-averaged values of d2F/dt2 exceeding a predefined threshold, or by comparison of instantaneous values of d2F/dt2 with variance of d2F/dt2 measured over a preceding time interval, such as the ratio of the instantaneous value of d2F/dt2 with the sum of squares of d2F/dt2 over the preceding 20 s or over the preceding 4 s. There are many such detection algorithms well-established in the art of signal processing that can be used to detect a negative-going spike in d2F/dt2.

Implementation of these indicators within automated control systems in medical devices would permit both (a) the presentation of indicators to the physician, permitting the physician to take corrective action before a break occurs, and (b) automated operation whereby the device contains appropriate mechanisms to implement corrective action. Software executed by microprocessors can perform appropriate signal processing (e.g., Butterworth filter, Fourier analysis, etc.) of signals from sensors to improve signal-to-noise, and this software can also perform automatic event detection with automatic response. For example, an automated system can initiate a pause in the first phase of retraction if a negative-going spike in $d^2F/dt^2$ is detected, or an automated system can initiate an oscillating motion in the first phase of retraction if a negative-going spike in d2F/dt2 is detected.

Importantly, detection of these events requires a stable force-time trace. This requires a means of regulating the velocity of retraction to ensure that it maintains a commanded velocity free of substantial variations in velocity; for example, the retraction velocity remains constant during measurement, or the trajectory of motion during the first phase of retraction follows a substantially parabolic profile, retracting more quickly at first and increasingly slower as retraction approaches a desired opening of the surgical incision or a desired dilation of the artery. This can be accomplished with a retraction system with manual actuation permitting very smooth motion, such as a hydraulic actuator or a fine pitched lead screw. Preferably, retraction is performed by a motor-driven retractor such that velocity can be maintained at predetermined rates by internal control, such as by an open-loop system with a stepper motor that is capable of generating sufficient torque as to not be impeded by retraction forces or by a closed-loop system with a servo-motor. Closed loop control of velocity in a hydraulically-actuated system is also possible. The velocity of retraction can be constant, but this is not necessary. For example, a smoothly time-varying velocity can be used.

Figure 42:
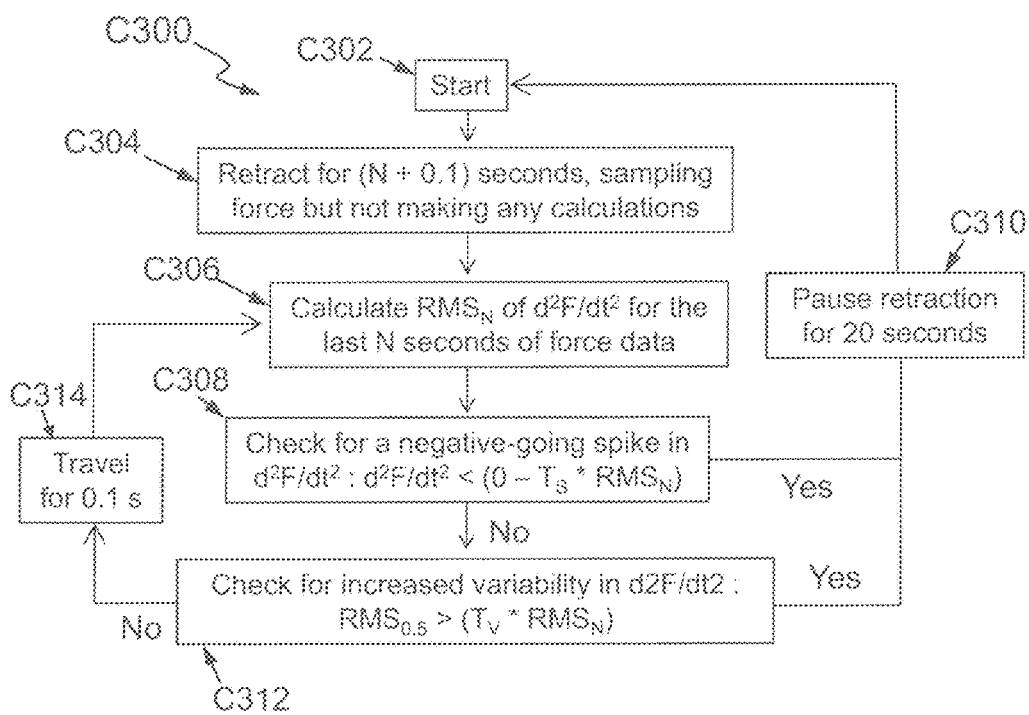
FIG. 42 shows an algorithm for detecting an imminent tissue fracture and pausing retraction in response.

FIG. 42 depicts an example of an algorithm C300 for detecting imminent tissue trauma. The algorithm C300 can be used for any retraction profile (displacement over time) with any device that measures force. The algorithm C300 searches for both a negative-going spike in the force trace and for an increased variability ("noisier") force trace. The user inputs two thresholds, $T_S$ for detecting the negative-going spike and $T_V$ for detecting increased variance. The thresholds $T_S$ and $T_V$ allow the user to set the sensitivity of the algorithm C300. For example, a surgeon might choose to use a more sensitive setting for a patient expected to have fragile bones. Variability in the force signal is calculated as the root-mean-square (RMS) of the force trace, as shown in FIG. 42. Execution of the algorithm C300 starts (block C302) at the initiation of retraction. Retraction proceeds for N+0.1 seconds (block C304), with force sampled at a rate equal to or greater than 10 Hz. The algorithm C300 then calculates RMS of $d^2F/dt^2$ over the last N seconds (block C306), skipping the first 0.1 second to avoid transients from the start of retraction (e.g., motor stiction, etc.). The algorithm C300 first looks for a negative going spike in $d^2F/dt^2$ by comparing the last measurement to the RMS over the last N seconds ($RMS_N$) multiplied by the threshold $T_S$ input by the user ($d^2F/dt^2 < (0-TS*RMS_N)$) (block 308). If the force is more negative than this parameter, then a 20 s pause in retraction (block C310) is triggered permitting force relaxation in the tissues, and the algorithm C300 returns to the start (block C302). If $d^2F/dt^2$ is not more negative than this parameter, then the algorithm C300 checks for increased variability in $d^2F/dt^2$ by comparing the RMS over the past 0.5 seconds ($RMS_{0.5}$) to the RMS over the past N seconds ($RMS_N$) multiplied by the threshold $T_V$ (block C312). If $RMS_{0.5}$ is greater then a 20 second pause (block C310) in retraction is triggered permitting force relaxation in the tissues, and the algorithm C300 returns to the start (block C302). If $RMS_{0.5}$ is not greater then retraction proceeds for another 0.1 second (block C314) and checks again (block 306). Thus, force is checked for a negative-going spike in $d^2F/dt^2$ and for increased variability in $d^2F/dt^2$ every 0.1 seconds. The force trace can be checked more or less frequently. Other sampling frequencies can be used. The 0.1 second added to N in block C304 can be any other time interval sufficient to avoid transients in the force trace on starting the motor or around any other event deemed spurious to detecting tissue trauma. The event triggered by the detection algorithm (a 20 second pause in this case) can be any event that is appropriate to the detected signal. For example, retraction can pause with continued measurement of force and then retraction can resume after the slope of the force trace becomes shallow, indicating that force relaxation has approached a limit. Another example is to initiate an oscillation of the retractor to accelerate force relaxation, or to pause for a first period and then to oscillate for a second period.

There is a fifth event for predicting imminent large breaks in tissue during retraction. Breaks are audible. Snaps and pops ("audible events") are heard throughout a retraction. Big breaks are louder. The large break at 46-70 s in FIG. 38B was actually a series of repeated fractures of the tissue. This was audible as a rapid series of loud audible events. Thus, the audible events of tissues breaking can be used as an indicator of tissue trauma, and audible events, including less loud events, can be used as indicators that a larger traumatic event is about to occur. Also, the qualities of an acoustic signal (e.g., the frequency of occurrence of audible events) can be used as an indicator of impending trauma. In the preceding example, the frequency of occurrence of acoustic events becomes higher as trauma increases.

Figure 43:
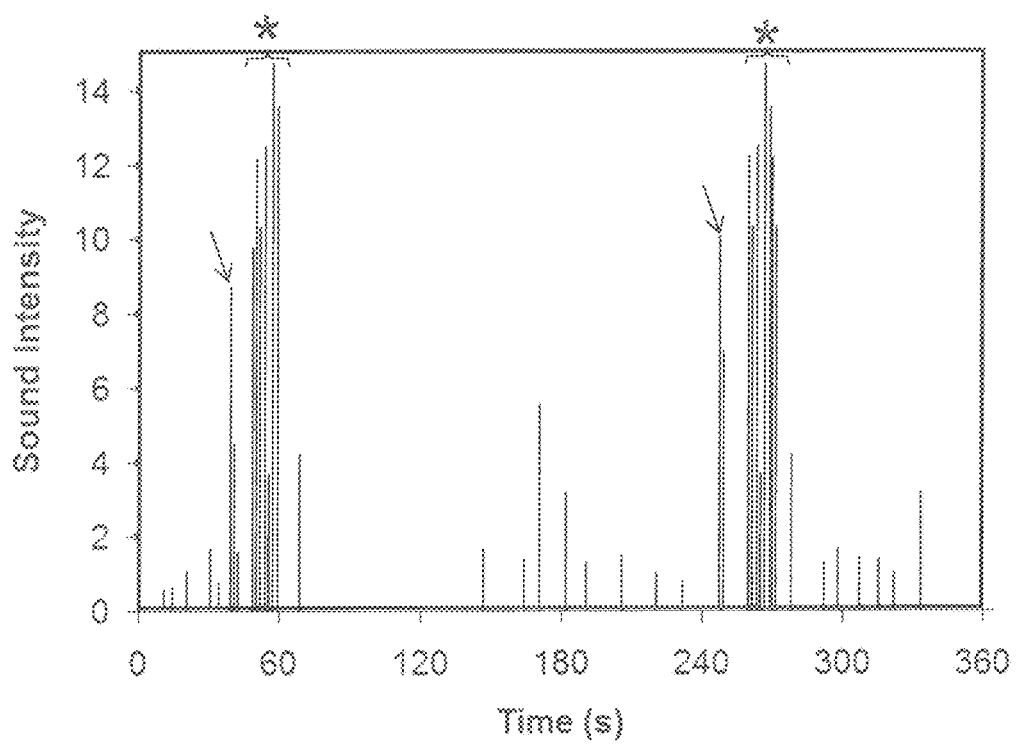
FIG. 43 shows how acoustic events during retraction can occur over time during a retraction and how they can be used as predictors of tissue fracture.

FIG. 43 depicts how such a trace would look—two breaks occur, one at about 55 s and another at about 255 s (marked with an asterisk). These are preceded by audible events (marked by arrows). These audible events might be distinguished from background noise by sound intensity, spectral composition, or both. In another example, the acoustic frequency (i.e., the pitch) of each acoustic event might change; for example, the pitch of earlier events might be higher than the pitch of later events as the tissue approaches a large fracture.

Sound measurement can be performed by microphones or other sound sensors placed in the air near the incision; on the retraction device, such as with a contact microphone; or on the patient's body, for example, with a contact microphone embedded in a gel beneath an adhesive pad, in which the gel matches the acoustic conduction of the body. If the sound measuring device is placed on the patient's body, then multiple sound measuring devices placed at distinct locations can be used to detect the position of the fracture either by relative intensity of the sound or by detecting time-of-arrival for triangulation of the location of the fracture or the propagation of a locus of damage.

Acceleration can serve as a sixth event indicator. When a large ligament snaps during retraction, the entire retractor suddenly shakes, as will all or a portion the body of that patient (depending on the magnitude of the tissue trauma event). With a smooth retraction, even smaller sounds can be "felt" with fingertips that lightly touch the retractor. Accelerometers are ideally suited to measure these motions. Accelerometers mounted on elements such as the body of the retractor, on the retractor blades, and/or on the body of the patient would provide an indication of the motions of any, some, or all of these elements. Acceleration is thus indicative of any number of a range of events occurring within (or to) a patient's tissues, including incipient tissue trauma. In this way, acceleration can serve prognostic goals. Acceleration can also provide feedback, to track the behavior of the device itself.

An accelerometer typically measures acceleration along a single axis. Accelerations acting directly along this axis produce the strongest signal, while accelerations acting exactly perpendicularly to that axis may produce little or no signal at all. In an actual patient's body, with complex tissues and force transmission paths, one may encounter the situation where one cannot expect an accelerometer associated with that body to ever register a zero output. One might mount one or more accelerometers to a surgical instrument (for example, the body of a retractor), to a portion of a surgical instrument (for example, one, two or a plurality of a retractor's blades), and/or to a patient's body. With its axis oriented at a carefully chosen angle with respect to the local axis of retraction, a given accelerometer can provide indications of not only an early warning of impending tissue trauma, but also a local direction of interest with respect to those accelerations, and a complex time series of accelerations associated with specific tissue types or tissue behaviors. As with the acoustic event detection above, one can use accelerometers to detect (a) acceleration events, (b) acceleration slope events, (c) acceleration variance events, and (d) acceleration slope variance events.

Attaching multiple accelerometers at multiple locations and/or angles can provide a picture, or map, in 2D, 3D, or 4D (with time) of the forces and moments acting on the system consisting of the body of the patient and the retractor. This picture can enable a surgeon (or the corrective software) to know which tissue type (or which of many tissue elements) might be involved, and/or when and where tissue trauma will occur before the onset of major damage. As one example, accelerations parallel to the surface of a given retractor blade might indicate the incipient failure of fibrous connective tissue (e.g., fascia or periosteum) oriented in that direction, while accelerations perpendicular to the surface of that retractor blade might indicate the incipient failure of the rib that that retractor blade is moving. As for corrective actions, in that example one might try to prevent snapping connective tissue by initiating oscillating loading, whereas one might instead respond to prevent rib breakage by pausing the retraction.

Furthermore, accelerometers might also provide independent confirmation of how well the actual behavior of a motorized instrument (such as a retractor) is conforming to the commanded behavior (whether controlled by the surgeon, the software, or some combination of the two). This could serve as an on-the-fly diagnostic to permit active self-correction and self-calibration. Accommodation and re-modulation can correct performance variances should they occur, further increasing confidence in the safe operation of the device.

A further aspect of self-operational feedback features (e.g., for acceleration) is that the device could adapt to the different operating styles of surgeons, for example by enabling detection of the operator's instrument handling patterns. For example, an accelerometer mounted to the retractor can be used to detect motions of the retractor arising when a surgeon inadvertently touches the retractor (e.g., when inspecting the incision) or purposefully handles the retractor (e.g., to adjust the position of the retractor). Such inadvertent touches or purposeful handling of the retractor can create transients in the signals that resemble imminent trauma. Signals from the accelerometer can be used to discriminate transients in the force and/or sound traces arising from the surgeon's actions.

Using any of these events for detecting an imminent tissue fracture or other damage, it is possible for a surgeon or an automated system to take corrective steps to prevent the tissue fracture. For example, upon detection of an event, retraction can be paused, permitting force relaxation, or retraction can switch from constant velocity retraction to an oscillating loading to use work softening of the tissue (or related phenomena arising from oscillating loading) to either induce an accelerated force relaxation or to create many small tissue fractures that relieve the stress in the tissue and prevent fracture of a major tissue component.

It is important to recognize that the techniques described here for detecting imminent tissue trauma by measuring force and sound, coupled with detection of transients, can be used without prior knowledge of a particular patient's physiology or pathology—the signals are unique to tissue trauma, but independent of a patient's unique characteristics. Thus, tissue trauma can be detected whether a patient is old or young, large or small, osteoporotic or normal. There is no requirement for determination of a threshold force to try to avoid tissue trauma, nor is there any need for databases of patients' characteristics and related force-distance measurements for adjusting retraction to unique patient parameters.

There are any number of other tissue trauma early warning event indicators. The aforementioned examples are only intended to teach the principle of early detection, not limit the embodiments of sensing modality to force, sound, and acceleration.

F. Self-Balancing Retractor Blades

Figure 44:
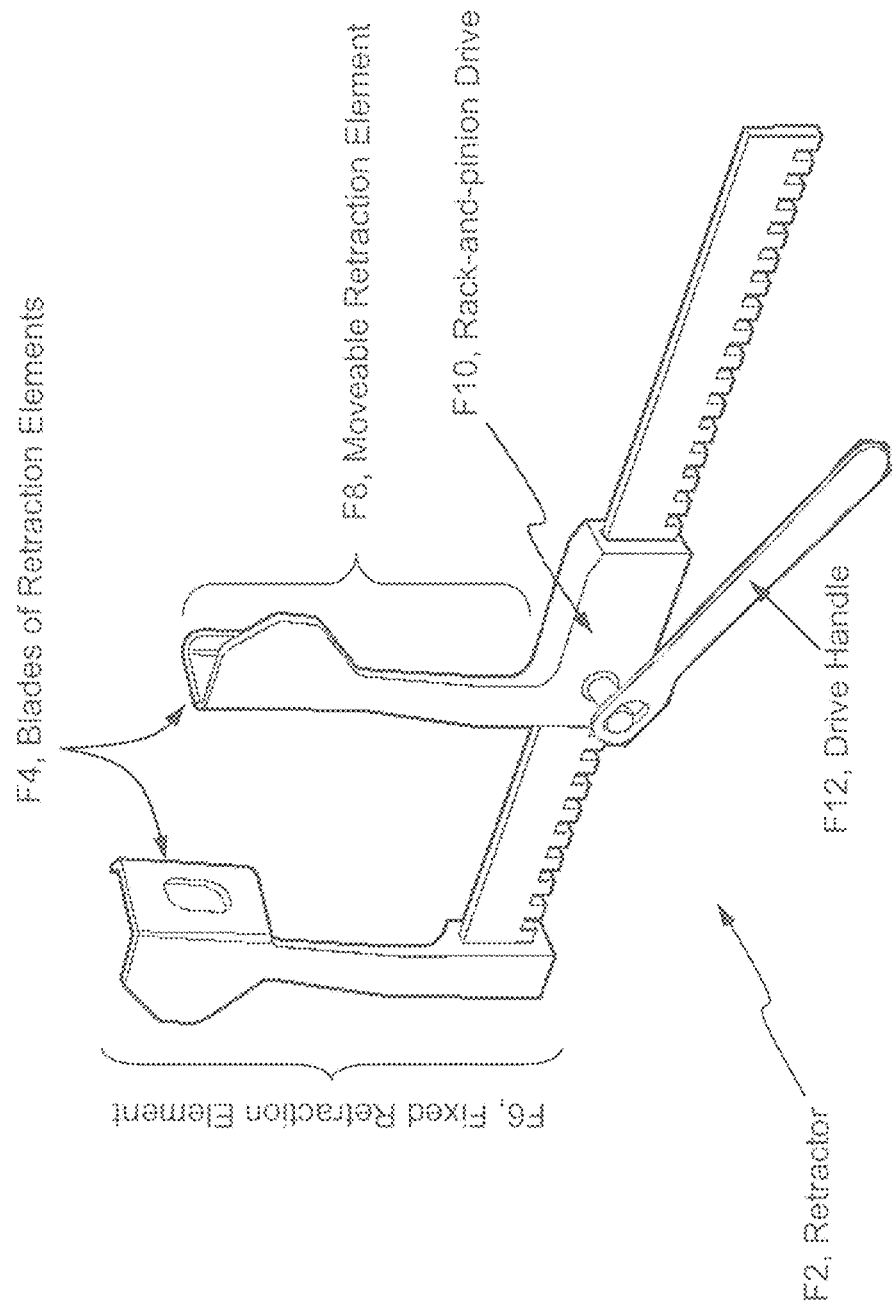
FIG. 44 shows an example of a Finochietto thoracic retractor in the prior art.

FIG. 44 presents an example of a Finochietto-style retractor F2 in the prior art. It has a fixed retraction element F6 attached to rack of a rack-and-pinion drive F10 that is manually driven by rotation of the drive handle F12. A moveable retraction element F8 is attached to the drive of the rack-and-pinion drive F10. Each of the retraction elements F6, F8 has a single retractor blade F4 that engages the tissue to be retracted.

The forces under the retractor blades F4 can be large. Furthermore, an edge of a retractor blade F4 can become a point-load if the retractor blade F4 is not well-seated or if the retractor blade F4 contacts a curved surface, such as a rib. If a retractor blade F4 becomes a point load, then the stress in the tissue at the point of loading can become extreme. Broken ribs are common using these types of devices.

Figure 45B:
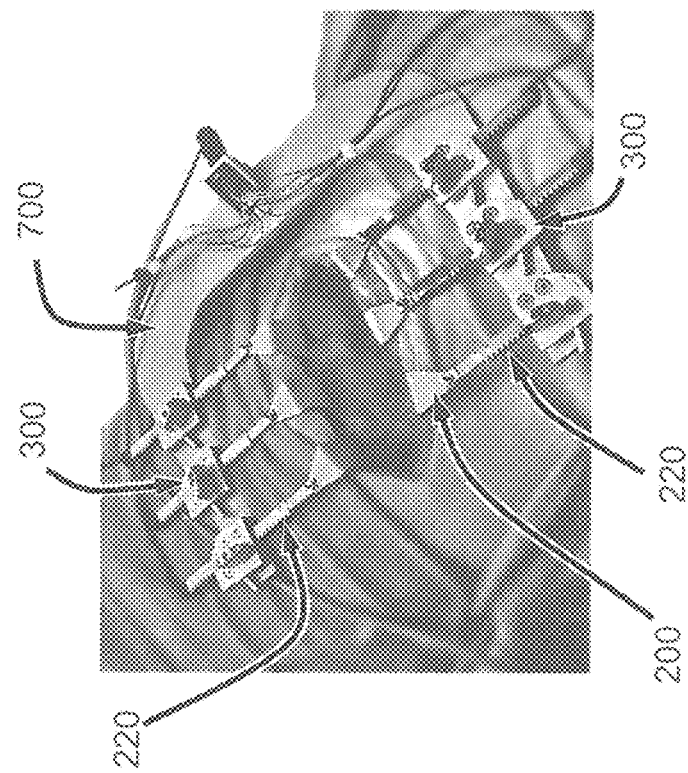
FIGS. 45A and 45B show an experimental thoracic retractor in the prior art.
Figure 45A:
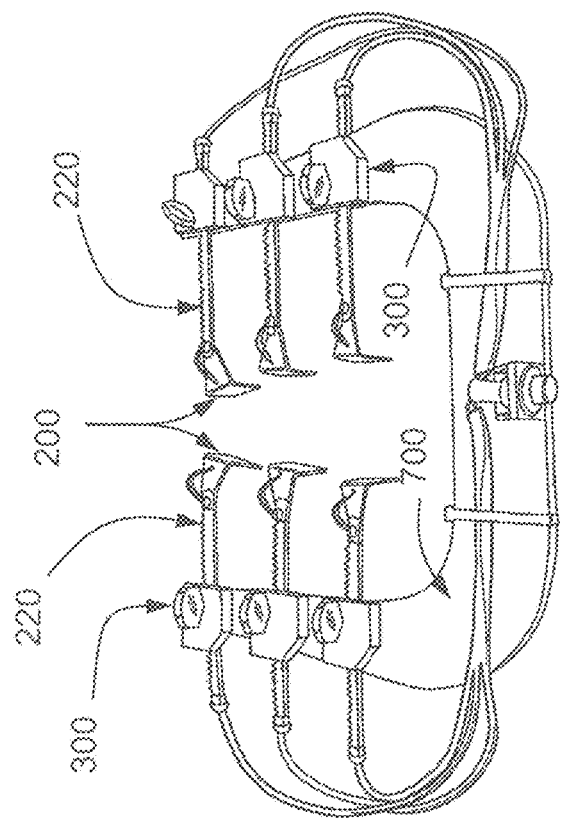

Such maladjustments of a blade can be reduced if several blades are used to engage the edge of an incision. FIG. 45 shows a retractor 300 in the prior art from the lab of Greg Buckner (Buckner and Bolotin 2006; Bolotin, Buckner et al. 2007). This retractor has six retractor blades 200 attached to a common frame 700. Each retractor blade 200 has an intermediate member 220 that connects the retractor blade 200 to an actuator 300. Thus, each retractor blade 200 has its own actuator 300. FIG. 45A is a diagram of the retractor 300. FIG. 45B is a photograph of the retractor 300 being used in a thoracotomy in a sheep, demonstrating how the retractor blades 200 engage the margins of the incision. The use of multiple retractor blades 200 along the margin of the incision distributes the retraction forces, reducing the force on any single retractor blade 200. However, the load on any single retractor blade 200 is determined by how hard it pulls on the incision as set by the actuator 300 of that particular retractor blade 200. Adjusting the forces to be equivalent to one another, or to have any other desired distribution of forces, requires individual adjustment of all the actuators 300 which must be made by an operator (which would be slow and irregular) or by an automated system combining force measurement, motorized actuators, and a control system (which might be expensive).

Figure 46:
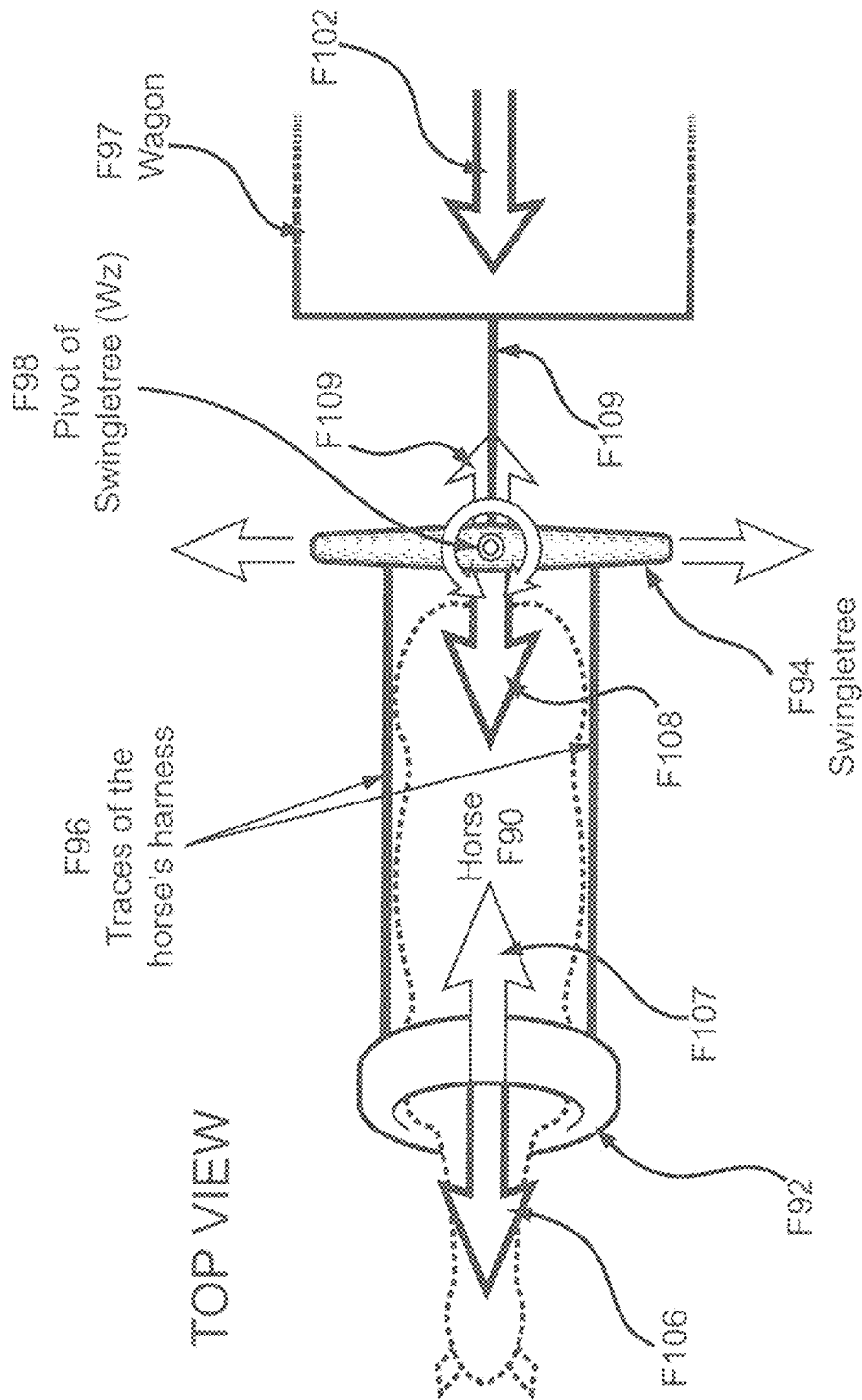
FIG. 46 show the orientations and motions of a swingletree and the forces on the swingletree.

Discussion of the next section requires review of a piece of very old prior art, related to the harnesses of draught horses that pull wagons. A "swingletree" is a pivoted, suspended crossbar to which the two traces of a horse's harness are attached when it pulls a wagon. FIG. 46 shows a top view of a swingletree F94 attached to wagon F97 by first harness component F104. Swingletree F94 attaches to harness component F104 at pivot F98. Two traces F96 of the harness extend from swingletree F94 to the collar F92 against which horse F90 pulls, exerting force F106 met by reaction force F107 and creating force F108 on the pivot F98 and force F102 on the wagon F97. If due to uneven motion of the horse, the force on traces F96 become unbalanced, then the moment about pivot F98 causes swingletree F94 to rotate until the forces on the traces F96 become balanced.

Figure 47:
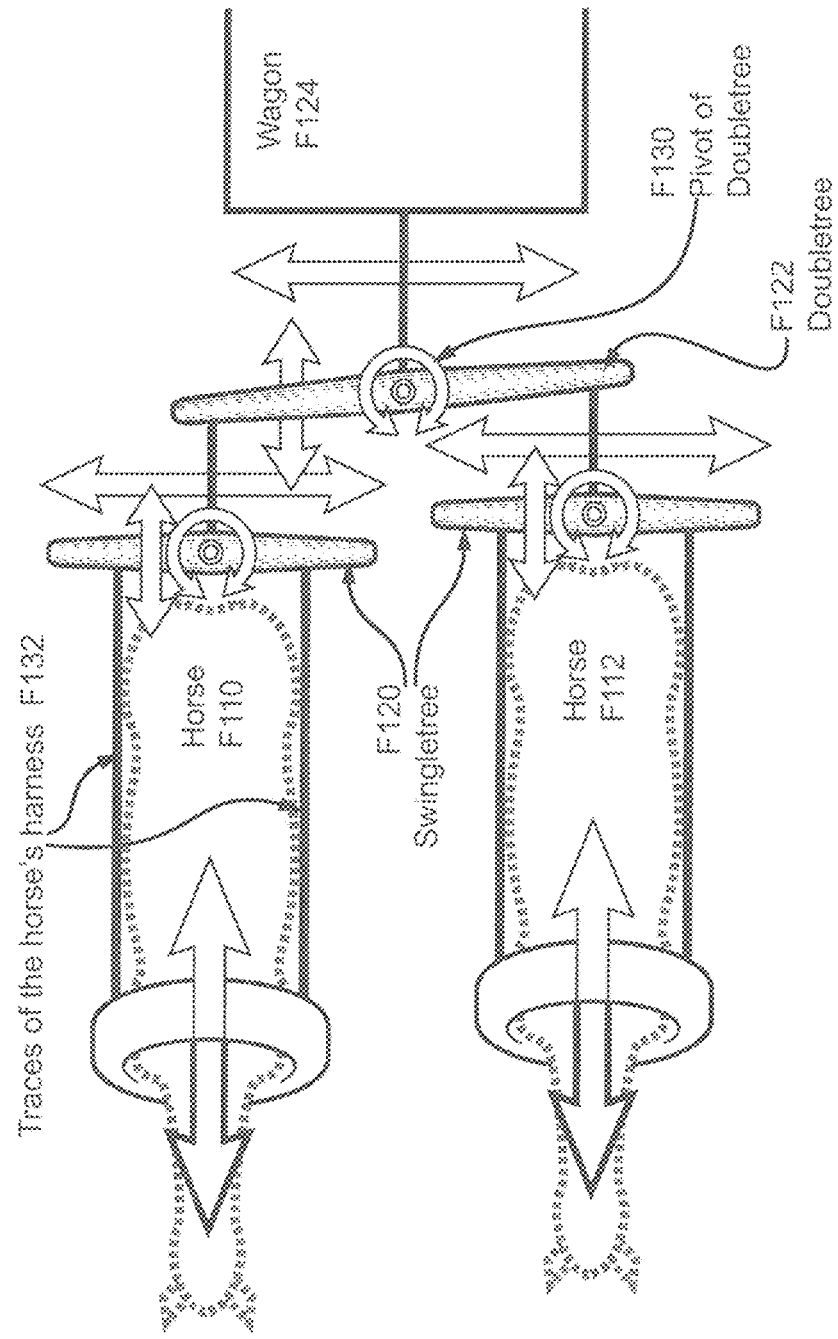
FIG. 47 shows the orientations and motions of a doubletree and the forces on the doubletree.

Every horse F90 attached to a wagon F97 pulls against a swingletree F94. When more than one horse pulls a wagon, multiple swingletrees are tiered, as shown in FIG. 47. Two horses F110 and F112 pull a wagon F124. Each horse F110 and F112 pulls on its own (child) swingletree F120, and the two swingletrees F120 are attached to a third (parent) swingletree F122 that is also known as a "doubletree". The entire structure connecting the swingletrees F120 and F122 is a tensile one, and rotation of swingletrees F120 and F122 balances the forces on each swingletree. Ultimately, the pivot F130 ensures that only a tensile force is applied to wagon F124, and rotation of the swingletrees F120 and F122 isolates all unbalanced forces from wagon F124.

Figure 48B:
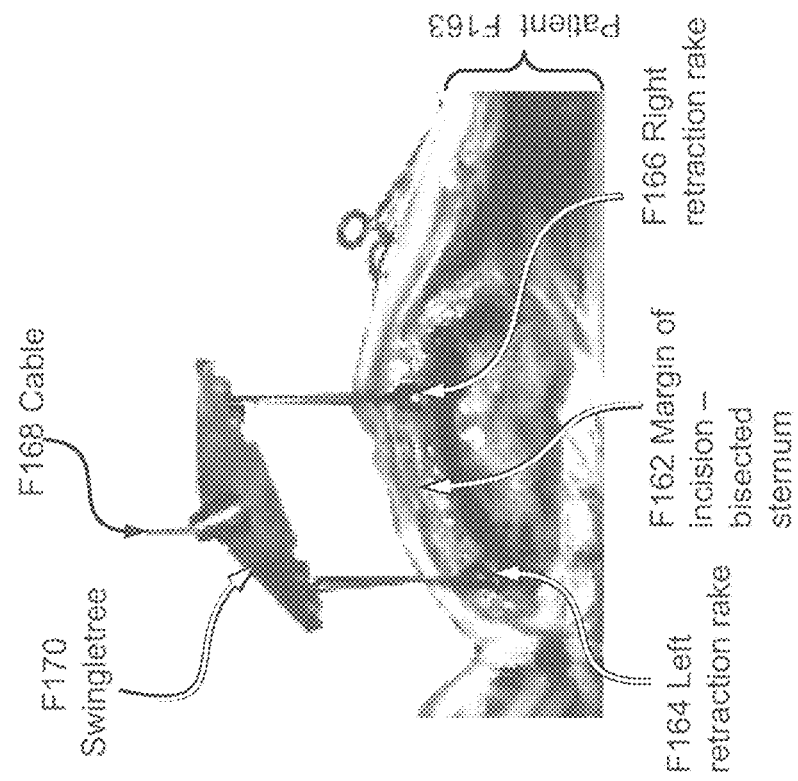
FIGS. 48A and 48B show an example of the prior art in which a derrick-like arm suspends a swingletree over an incision.
Figure 48A:
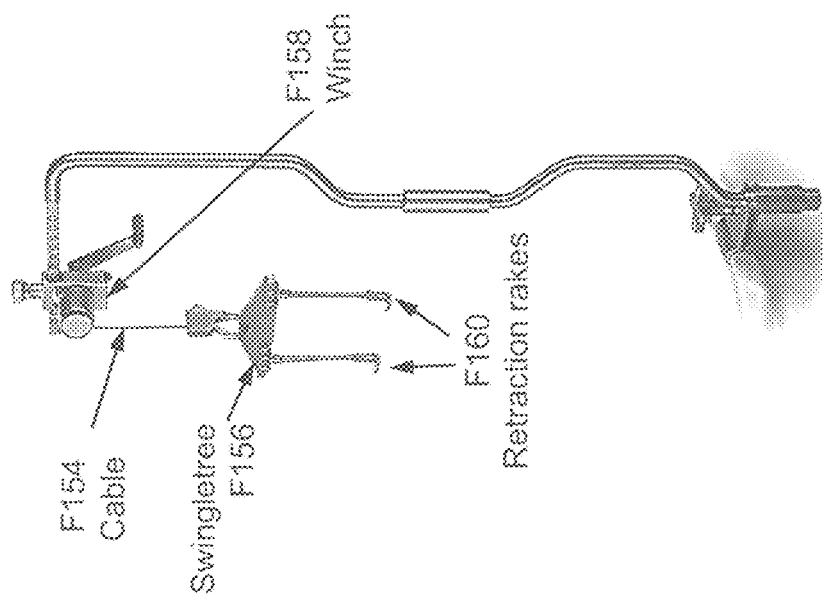

FIGS. 48A and 48B show another retractor F150 in the prior art. This is the Skyhook from Rultract (www.rultract-.net, U.S. Pat. No. 4,622,955). The retractor F150 is a hoist, suspended above a patient F163, with two retraction rakes F160, F164, F166 that engage a bisected sternum F162 at two locations, and the retraction rakes F160, F164, F166 attach to the opposite ends of a swingletree F156, F170. A cable F154, F168 attaches to the mid-point of the swingletree F156, F170, and the swingletree F156, F170 is free to pivot about this attachment. As seen in FIG. 48B, when the winch F158 pulls the swingletree F156, F170 upward, if one of the retraction rakes, such as F164, engages the margin of the incision F162 first, then that retraction rake F164 is pulled downward, which pulls the opposite retraction rake F166 upward until both rakes F164 and F166 engage the margin of the incision F162, where the swingletree F170 has rotated with the right retraction rake F166 raised above the left retraction rake F164. Force exerted by the cable F168, through the swingletree F170, and then through the retraction rakes F164 and F166 pulls the bisected sternum F162 upward to provide surgical access for the surgeon. The swingletree F170 here ensures that the forces on the two retractor rakes F164 and F166 remain equal—if the force on one retraction rake, for example retraction rake F164, is larger, then the other retraction rake F166 is pulled upward until the forces on the two retraction rakes F164 and F166 are balanced. More specifically, the swingletree F160, F170 rotates whenever the moment about the pivoting attachment to the cable F154, F168 become unbalanced. This occurs automatically. One drawback of the retractor F150 is that it requires a large derrick-like arm F152 that is bolted to an operating table F153 that suspends the winch F158 over the patient F163, or some similar superstructure over the operating table F153. Such structures can obstruct the surgical field, making access difficult from some angles, and present the risk of dropping the requisite fasteners into the patient's open chest cavity.

A means for automatically adjusting the force exerted by each retractor element without the large, table-mounted hardware of the retractor F150 and with fewer actuators than the device of FIGS. 45A & 45B is desirable.

Figure 49A:
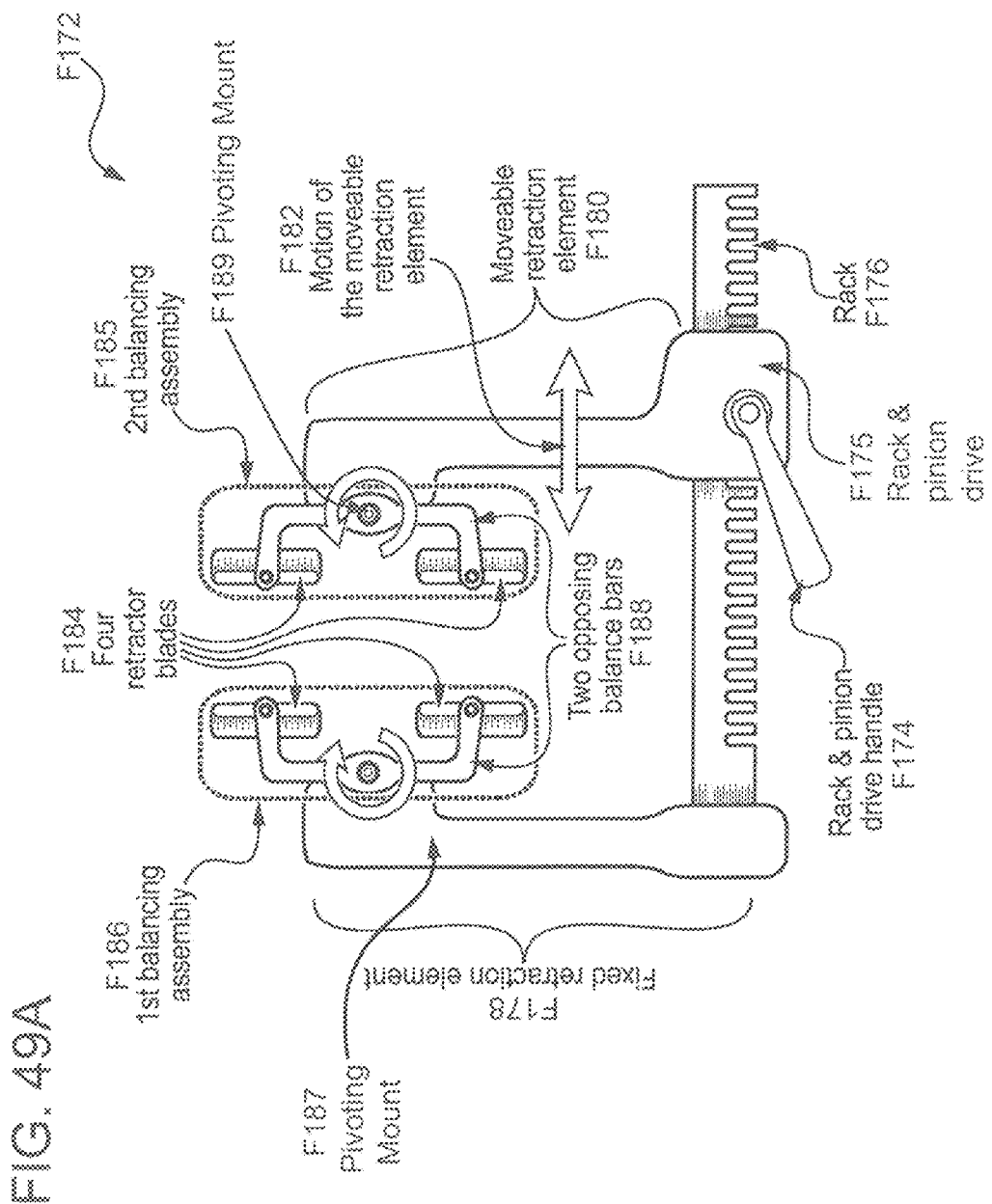

FIGS. 49A and 49B illustrate one embodiment that balances the forces on multiple retractor blades without table-mounted hardware and with fewer actuators. This is a retractor F172 that uses a mechanical system for balancing forces on the opposing arms of a Finochietto-style retractor in the prior art (see FIG. 44). Four retractor blades F184 engage the margins F202 of the incision to be retracted and create a surgical aperture F200. Retraction is manually driven by rotation of the drive handle F174 acting on rack-and-pinion drive F175 which moves along rack F176. There is a pair of blades F184 (also labeled F196 and F198 in view F190 in FIGS. 49B.1 and 49B.2, respectively) on each retraction element F178 and F180 of the retractor F172. A first balancing assembly F186 is comprised of two retractor blades F184 in each pair which are attached to a balance bar F188, and the first balancing assembly F186 on the fixed retraction element F178 opposes a second balancing assembly F185 on the moveable retraction element F180. Each balance bar F188 is attached to its respective retraction element F178 or F180 by a pivoting mount F187 or F189 so that the balance bar F188 is able to rotate in the plane of the page in FIG. 49A, but rotation of the balancing bar F188 in the two planes perpendicular to the plane of FIG. 49A is not permitted. Prohibition of rotation in those other two planes permits the use of rigid mounts to retractor blades, retraction hooks, or retractor rakes. In FIG. 49B.1, a balance bar F193 will rotate F195 about a pivot point F194, and within the plane of the page, to balance forces F204 and F206 on the two retractor blades F196 and F198 attached to the balance bar F193, and will stop rotating F195 when the two forces F204 and F206 are balanced. Additionally, should the two forces F204 and F206 again become unbalanced as retraction F212 proceeds, the balance bar F193 will, again, automatically rotate F195 the retractor blades F196 and F198 to balance the forces F204 and F206 on the blades F196 and F198. In FIG. 49B.2 depicts a subsequent state of view F190 showing a balanced state for a pair of forces F208 and F210 during retraction F214, such that F208 and F210 have equalized due to the accommodation via rotation F218 of balance bar F216 about pivot point F217.

Figure 50C:
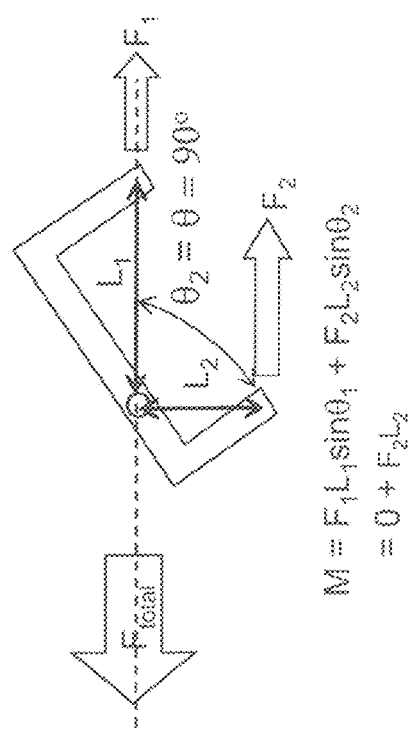
FIGS. 50A through 50C show how a balancing assembly can be adjusted to provide any ratio of forces on multiple retractor blades.
Figure 50A:
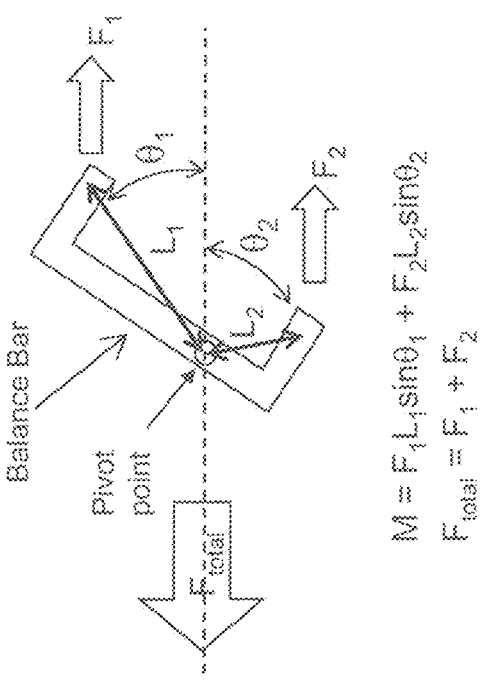
Figure 50B:
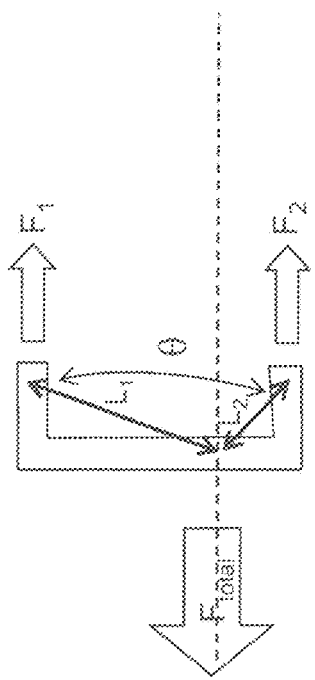

Referring now to FIGS. 50A through 50C, FIG. 50A shows how a balance bar F226, F236 and F246 can be adjusted such that the balance bar F226, F236 or F246 maintains an approximately constant ratio of forces F232, F242, F252 versus F234, F244, F 254 between two retractor blades (not shown) located at the ends of the balance bar F226, F236 or F246. As shown in FIG. 50A balance bar F226 rotates, not due to an imbalance of the forces F232 and F234 on the retractor blades, but due to an imbalance of moment M F227 about the pivot point F228. Thus, if the length L1 of a first side of balance bar F226 is longer than the length L2 of a second side of balance bar F226, then the force $F_1$ F232 on that first side will be smaller than the force $F_2$ F234 on the second side when the moment M F227 is zero. Any ratio of forces can thus be accommodated. Additionally, the geometry of the balance bar F226 determines a "righting moment", a moment that returns the position of the balance bar F226 to neutral when displaced from neutral, and thereby makes the balance bar F226 "self righting." As shown in FIG. 50B, the righting moment is determined by the angle θ (θ=θ$_1$+θ$_2$) formed by lines $L_1$ and $L_2$ and by the length of lines $L_1$ and $L_2$. For example, the moment generated by $F_2 L_2 \sin θ_2$ is maximal when $L_2$ is a long as possible and θ$_2$ equals 90°, and the moment generated by $F_1 L_1 \sin θ_1$ is minimal when θ$_1$ equals 0° regardless of the length of $L_1$; therefore, the balance bar F236 will be maximally self-aligning when θ equals 90° (see FIG. 50C). However, if a 90° rotation is not anticipated when the balance bar is used, then θ=180°−2θ$_e$ (θ$_e$=the maximum angle of rotation in use) provides the largest righting moment.

Figure 51:
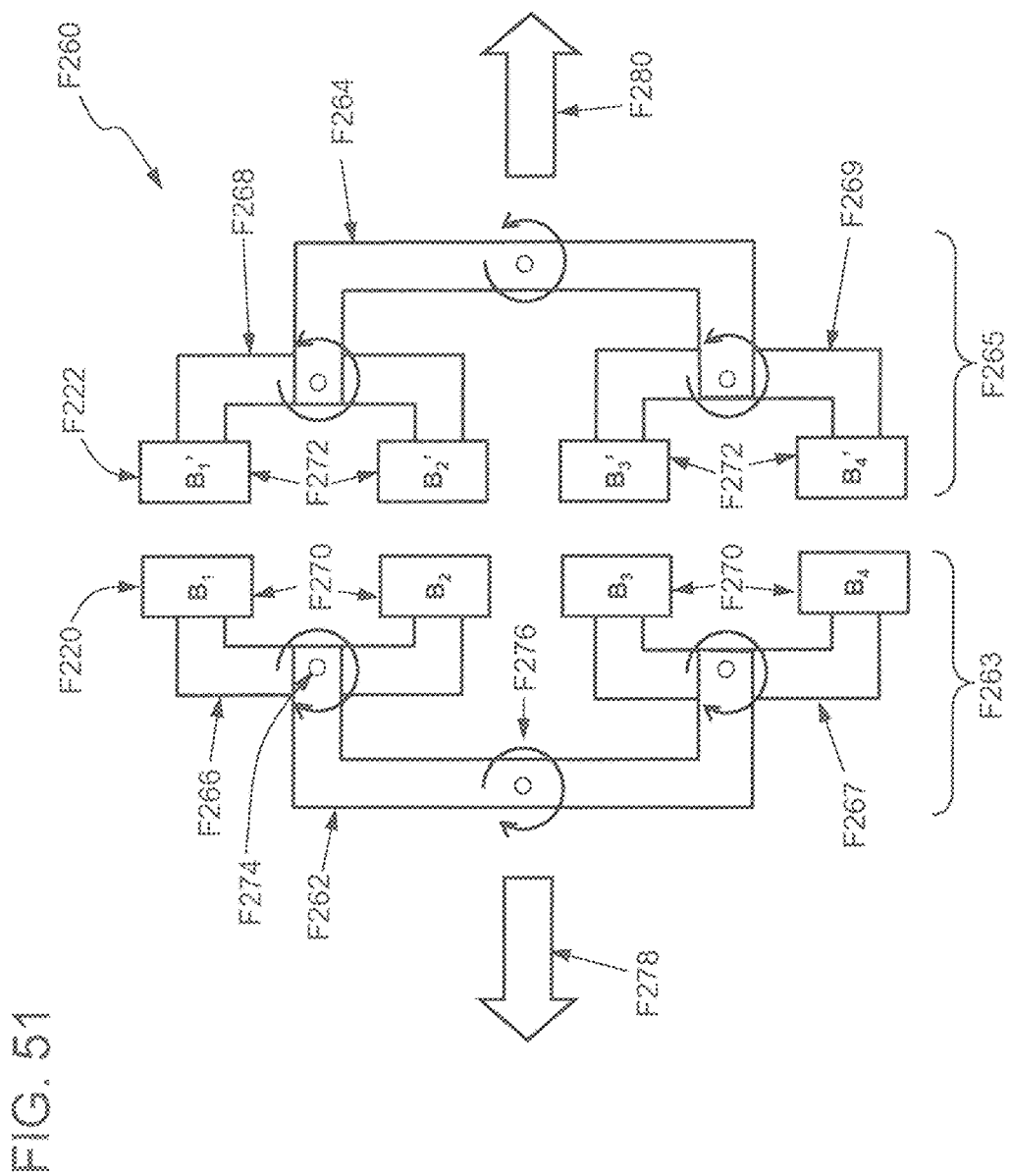
FIG. 51 shows a balancing assembly having multiple tiers of balance bars.

As shown in FIG. 51, more than two retractor blades F270, shown as F270 $B_1$, F270 $B_2$, F270 $B_3$ and F270 $B_4$, located on a retraction element F263, to be retracted in the direction F278, and another four retractor blades, shown as F272 $B_1$', F272 $B_2$', F272 $B_3$', and F272 $B_4$', located on the retraction element F265 and to be retracted in the opposite direction F280 can be placed onto each retraction element F263, 265 of a retractor F260. This is accomplished by tiering balance bars F262, F266 and F267 onto which retraction blades F270 $B_1$ to $B_4$ are mounted and also tiering balance bars F264, F268 and F269 onto which retraction blades F272 $B_1$' to $B_4$' are mounted. Multiple tiers of balance bars are possible.

Figure 52:
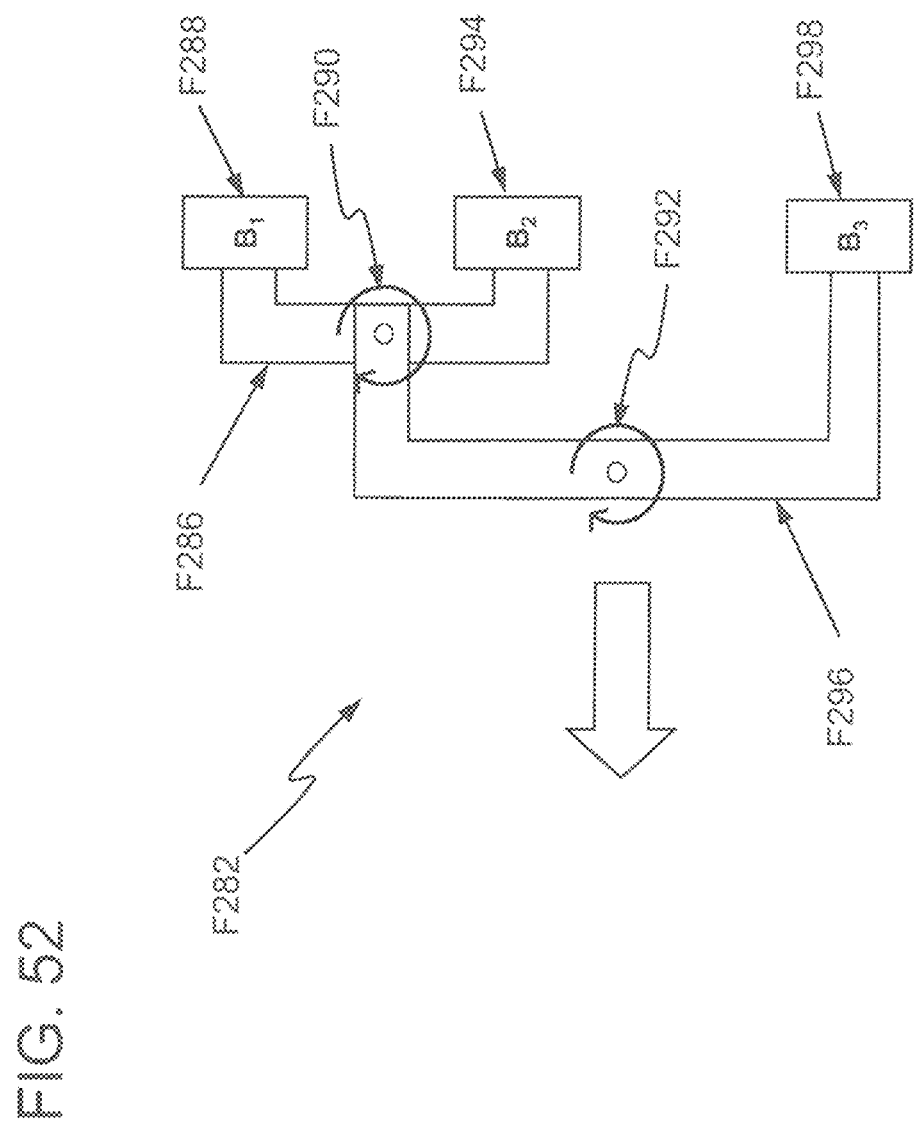
FIG. 52 shows a balancing assembly having a number of blades that is not a multiple of 2.

FIG. 52 shows how retractor blade numbers that are not multiples of 2 can be arranged so that the forces and moments still balance one another. As shown in FIG. 52 the force (not shown) generated by a retraction F300 on a blade F298 $B_3$ equals the combined forces (not shown) on two more blades F288 $B_1$ and F294 $B_2$. Similarly to that shown in FIG. 51, multiple tiers of balance bars are possible, including those creating uneven numbers of retractor blades. Again, all balance bar elements will stop rotating when the moments about their respective pivot points equalize.

Figure 53:
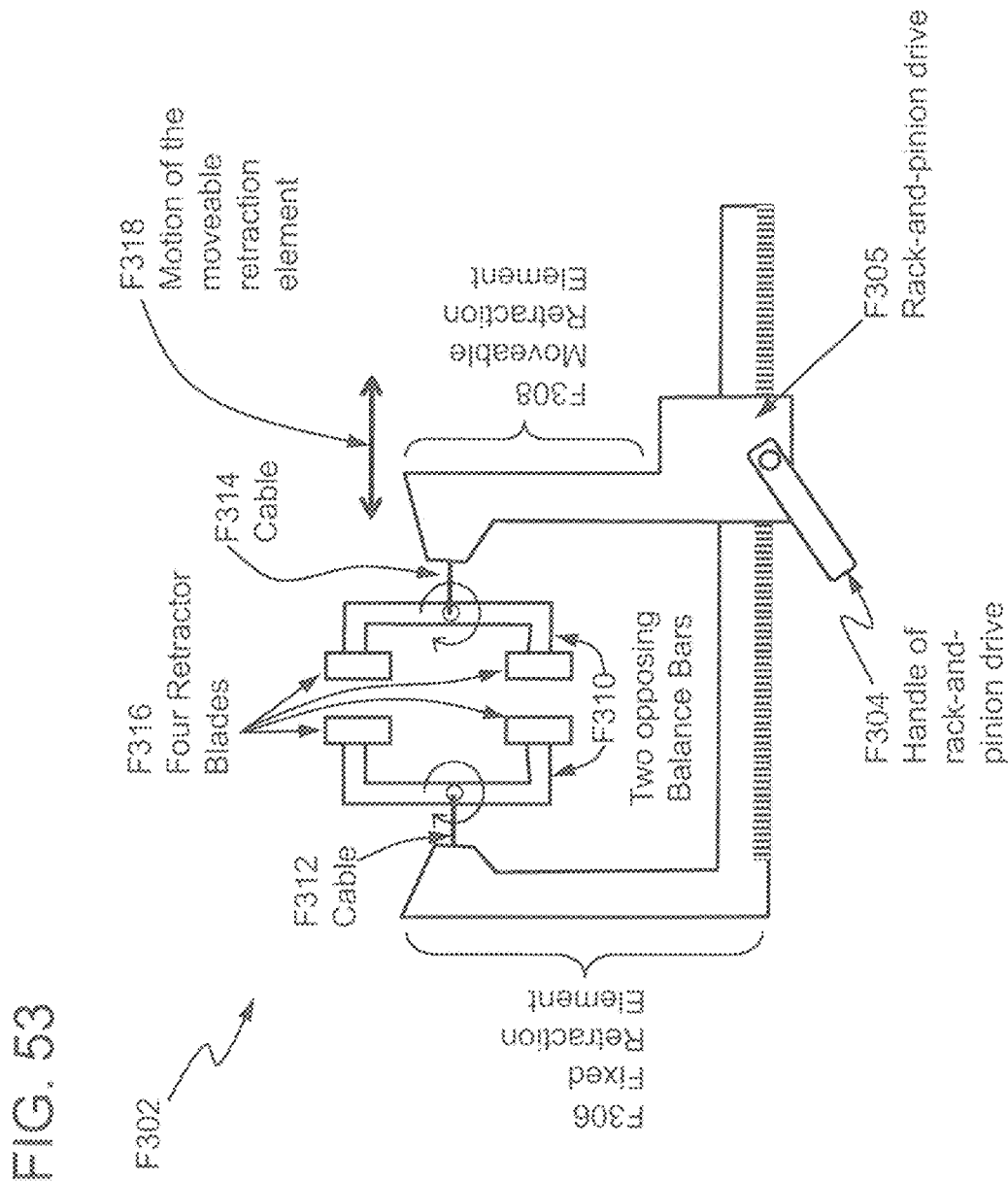
FIG. 53 shows a retractor having a cable that permits a balance bar to rotate.
Figure 54:
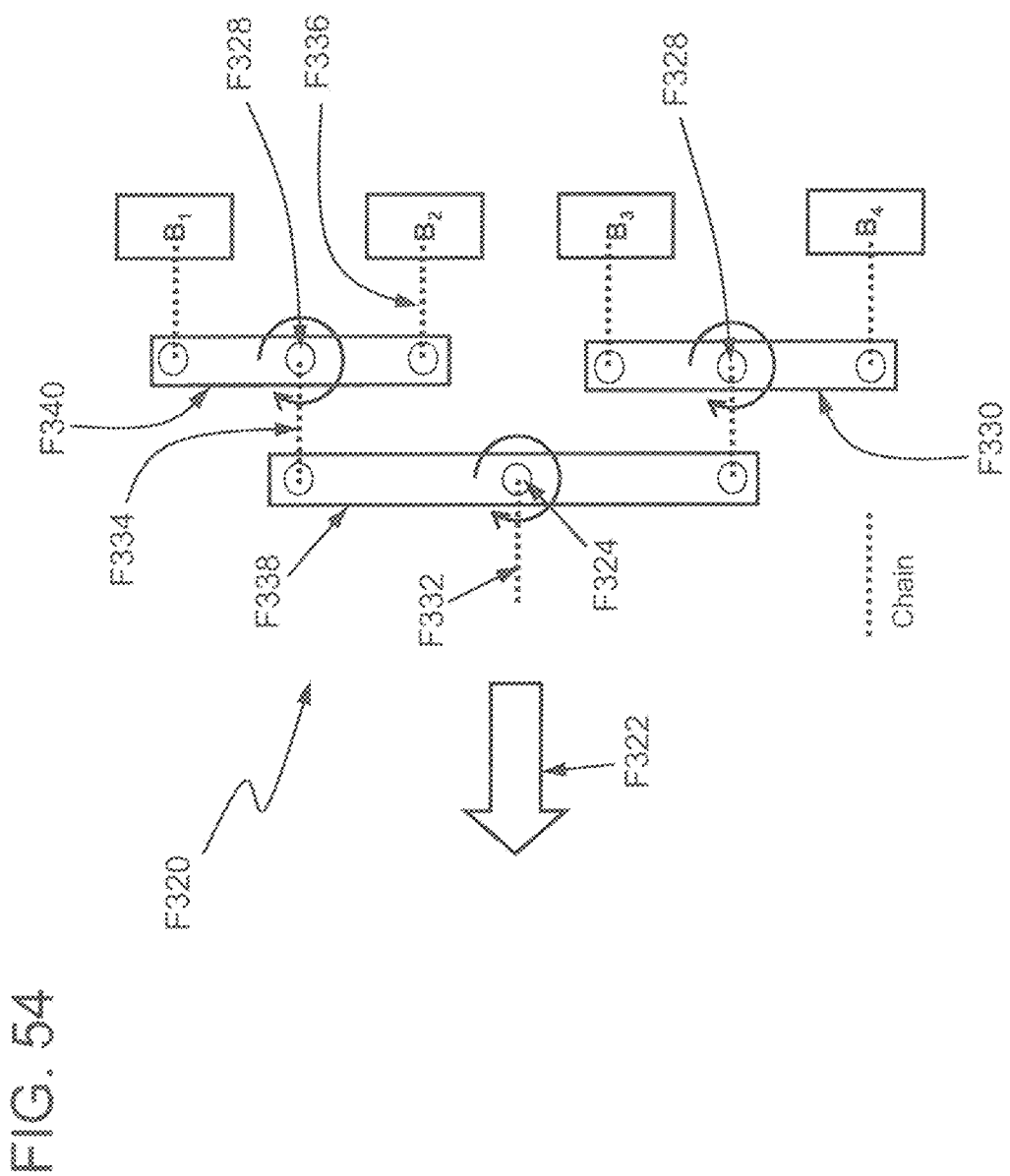
FIG. 54 shows a balancing assembly having multiple tiers, with each tier free to rotate.

Blades can be mounted to balance bars such that they are fixed or pivoting. As shown in FIGS. 53 and 54, balance bars can in some instances also be mounted by a tensile element such as a cable, chain, or wire, permitting rotation out of the plane of the page in FIGS. 53 and 54, similar to a swingletree. FIG. 53 shows in more detail a retractor F302 with retraction elements F306 and F308, a rack-and-pinion drive F305 with a drive handle F304, and four retractor blades F316 associated with two opposing balance bars F310. The balance bars F310 are connected to the retraction elements F306 and F308 by tensile elements, cables F312 and F314. Cables F312 and F314 permit easy, generous reorientation of the retractor blades F316 to forces and accommodation of moments by the balance bars F310 while still transmitting the forces arising out of the motion F318 of the movable retraction element F308. FIG. 54 shows how multiple balance bars F338, F330, F340 can be tiered (similar to FIG. 51) by the use of chains F332, F334, and F336 attached by pivoting joint F324 on balance bar F338 and pivoting joints F328 on balance bars F330 and F340.

FIGS. 55A through 55C show a top view, a side view, and a front view, respectively, of another embodiment in which an entire retractor element F348 is able to rotate around the axis of retraction F351; additionally, the retractor blades F362 are shaped like hooks that engage a rib F364 to avoid damage to a neurovascular bundle (not shown), as described more fully in Section H. In FIG. 55A, the base element F350 of the retractor element F348 is attached by a rotational joint F352 that allows the entire retractor element F349 to rotate out of the plane of the page in the top view (FIG. 55A) and within the plane of the page in the front view (FIG. 55C). Thus, rotational joint F352 permits the base element F350 of the retraction element F349 to rotate within a plane perpendicular to the axis of retraction. Base element F350 attaches to a first balance bar F354 by rotatable joint F358, and first balance bar F354 attaches to second balance bars F356 by rotatable joints F358. Two (2) hook-shaped retractor blades F364 descend from each second balance bar F356. Rotational joints 352, or their equivalents, can be placed at every rotatable joint F358 providing tremendous freedom of movement for the balance bars F354 and F356 and the hook-shaped retractor blades F362.

FIGS. 56A through 56C show a top view, a side view, and a front view, respectively, of an embodiment similar to that shown in FIGS. 55A through 55C, but an articulation F400 has been added to balance bar F354 allowing it to bend to conform the balance bar F354 to a patient's rib F364 that curves in the plane perpendicular to the plane of the page as seen in the top view (FIG. 56A). Again, note that a cable, chain, or wire, as depicted in FIG. 54, could also permit rotation of the type shown at rotational joint F352.

Figure 57:
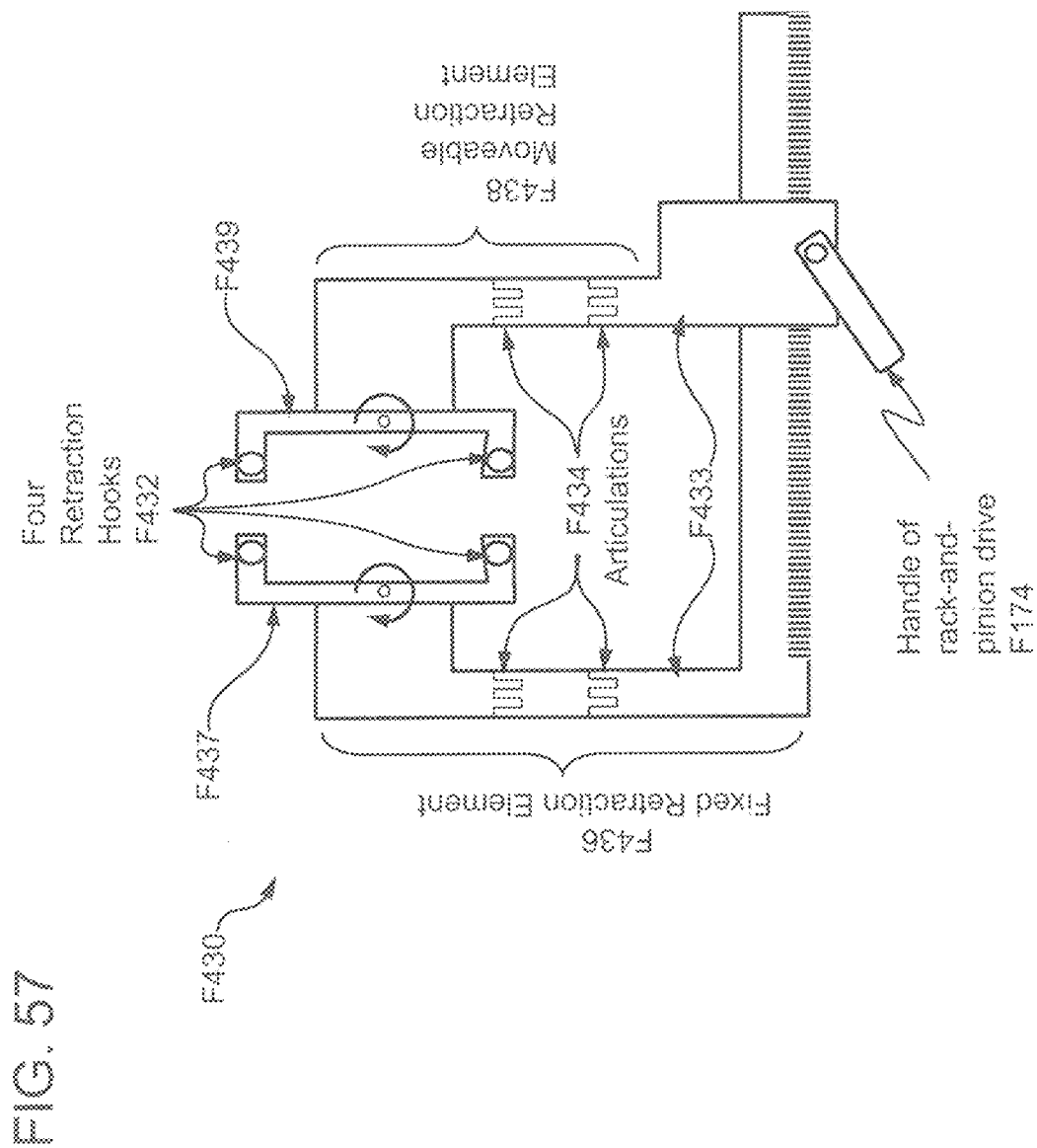
FIG. 57 shows a thoracic retractor with a balancing assembly, wherein the arms of the retractor has articulations.

FIG. 57 shows a Finochietto-style retractor F430, similar to retractor F172 shown in FIGS. 49A through 49B, with an opposing pair of swingletrees F437 and F439. Retraction elements F436 and F438 have retractor arms F433 with articulations F434 that allow the retractor arms F433 to conform to the curve of a patient's body. These articulations F434 could be passive, starting out with the retractor arms F433 straight and then conforming to the body when encountering the body, or the articulations F434 could be preset by the surgeon and rigidly fixed in a patient-body conformal shape beforehand, or they could be self-controlled via sensor feedback. The articulations F434 might be formed as hinges, with two discrete sections interdigitating as shown in the FIG. 57, or the articulations F434 might be formed as elastomeric regions that bend smoothly from one section of a retraction element to another. Another embodiment might possess retraction elements F436, F438 which are continuously, smoothly flexible (along their length) in one plane, while rigid in the others.

Figure 58:
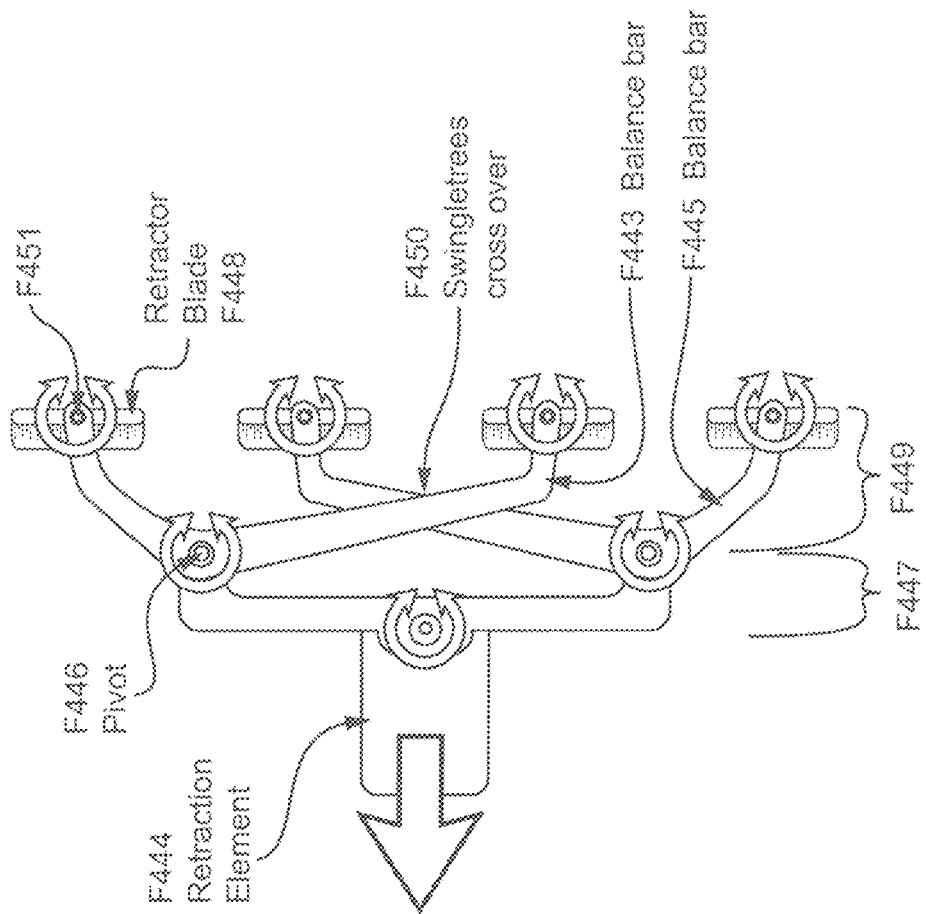
FIG. 58 shows a balancing assembly in which balance bars overlap.

FIG. 58 shows another embodiment of a retraction element F442 that permits more complex force distribution. Balance bars F443 and F445 form a second (child) tier F449 to a first (parent) tier F447, connecting at rotatable joint F446. Each balance bar F443, F448 has two retraction blades F448 attached by rotatable mounts F451. Balance bars F443 and F445 are overlapped at F450, presenting opportunities for generating a broader range of moment arms to distribute the pattern of forces along the margin of the incision. A broad range of overlap, bar length, and pivot position is possible; preferred embodiments arrange bar lengths, amount of overlap, and pivot positions so that all moments equalize, but this need not be the case. Surgical situations may arise such that a clinician wishes to apply forces irregularly, for example if one is forced to simultaneously retract both exposed bone and soft muscle or adipose tissue in the same incision, or for example if a surgeon wishes to create a surgical aperture with purposefully nonparallel incision margins. Note also that besides varying the foregoing items in a surgical instrument design, the number of hierarchical levels is not restricted. It may be advantageous to provide many 'child' levels of balance bars below the 'parent' level, forming a balance bar cascade of arbitrary fineness, for example to ensure that dozens of tiny retraction hooks engage a patient's tissues, providing for nearly continuous support across the tissue face. Combining all four design variables permits the design of retractors of arbitrary complexity that apply appropriate arrangements of forces in useful directions to a variety of tissues and anatomical structures without incurring tissue trauma.

FIGS. 59A through 59E show another embodiment of a retraction element that achieves automatic balancing of loads. Rather than using a swingletree, this retractor uses a cable F466 to transmit loads between retractor blades, posts, or hooks F468 that are mounted onto retraction arm units F462 by a rotational mount F460 formed by pin F470 which attaches retraction hook F468 to retraction arm unit F462. FIG. 59A shows a side view showing one retraction hook F468 attached to a retraction arm unit F462 by a rotatable mount F460. The retraction hook F468 engages a rib F456, directly against that bone, such as in a thoracotomy. The cable F466 attaches to the retraction hook F468 by passing through a hole F480 in the shaft F469 of the retraction hook F468. FIG. 59B shows a front view, with three retraction hooks F468 attaching to the retraction arm unit F462. The retraction arm unit F462 has two articulations F474, permitting the retractor arm units F462 to independently align to the curvature of the rib. Optionally, the retractor arms can be solid, without articulations F474. Referring to FIG. 59B, the cable F466 attaches at one end to a retraction element F462 and then courses through the holes F480 in the retraction hook shafts F469 and over pins F464 in the retraction arm units F462; finally, cable F466 attaches at its other end to a capstan F478 used to adjust the tension of the cable F466, and thereby adjust the magnitude of the swinging of the retraction hooks F468. FIG. 59C shows a top view, illustrating how the cable F466 travels from an attachment F482 at one end, then zig-zags left to right, back and forth as it passes from holes F480 in the shafts F469 of the retraction hooks F468 to pins F464 inside recessed holes in the retraction arm units and finally to a capstan F478. Thus, as illustrated in FIG. 59D, when a first retraction hook F468 is pushed (by the tissues at the margin of the incision) toward the left, it tensions the cable F466, which then pulls a neighboring retraction hook (F468') to the right. This repositioning of the retraction hooks F468 and F468' will continue until the force on both retraction hooks equalizes. Again, changes in the position of the through hole F480 in the shaft of the retraction hook F468 and F468' will control the ratio of forces between those retraction hooks. FIG. 59E shows how the articulations F474 between retraction arm units F462 permit the retraction arm units F462 to conform to the curvature of the patient's body.

Figure 60A:
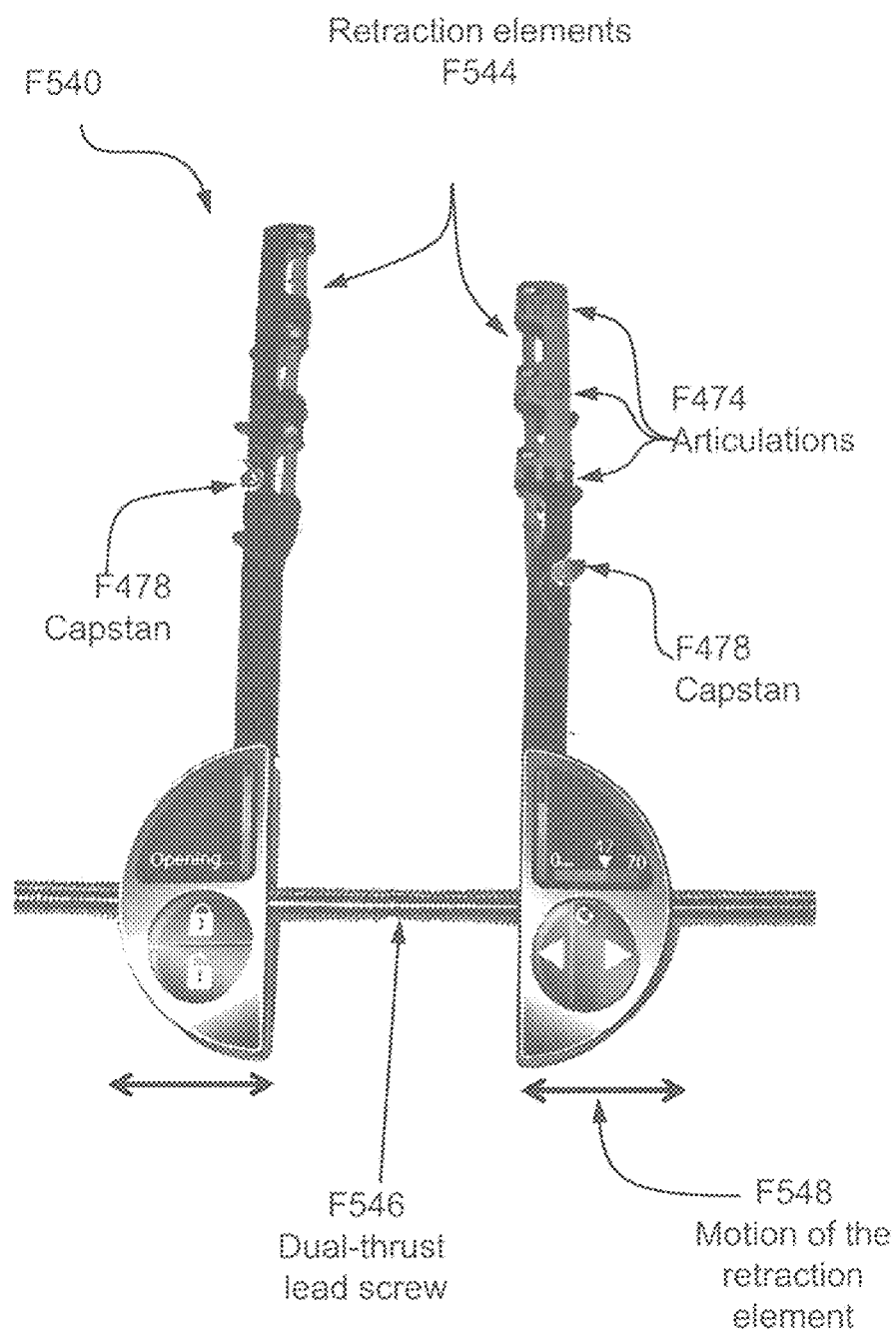
FIGS. 60A and 60B show the embodiment depicted in FIGS. 59A through 59E, but as part of a retractor driven on a dual-thrust lead screw.
Figure 60B:
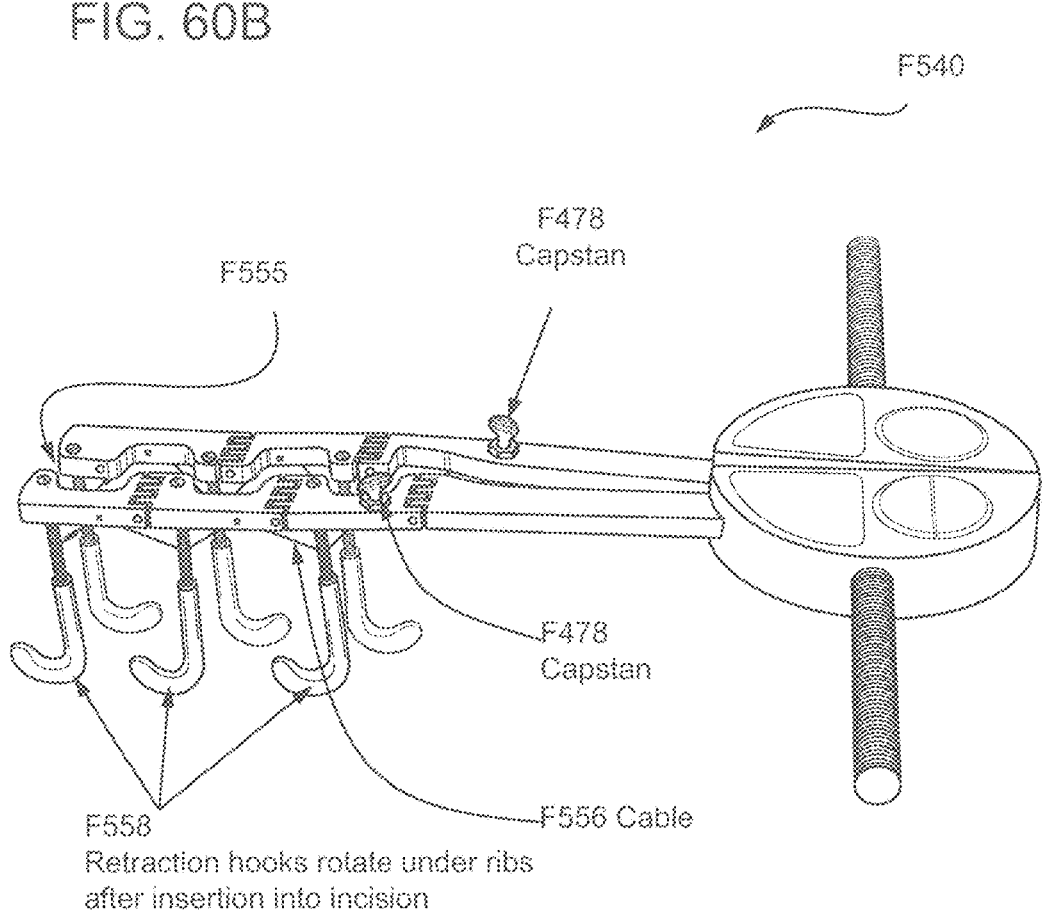

FIGS. 60A and 60B show a physical model of a retractor F540 of the type described in FIG. 59A through 59E. FIG. 60A shows a top view of the retractor F540, and FIG. 60B shows an oblique side view of the retractor F540, showing the retraction hooks F558 (similar to F468) and cables F556 (similar to F466). Paired retraction elements F544 are attached to and ride along a dual-thrust lead screw F546. Rotation of the dual-thrust lead screw F546 with respect to the retraction elements F544 causes the retraction elements F544 to move F548 apart for retraction or back together for closure. The retraction elements F544 have articulations F552, like articulations F464 in FIGS. 59A-59E. Retraction hooks F558 are attached to the retraction elements F544 in the same manner as described in FIG. 59. The retraction hooks F558 are rotatable about their long axes, such that prior to insertion into an incision to create a surgical aperture, a surgeon can first align the hook-shaped tips of the retraction hooks F558 all pointing parallel to the direction of the incision (and so parallel to the margins of the incision, making that part of the retractor F540 that actually descends into the patient as thin as possible) for easy insertion into the incision and then, secondarily, the surgeon can rotate the retraction hooks F558 such that the hook shapes swing out and under the ribs adjacent to the retraction elements F544 (on the left and right side, respectively) to engage the ribs for retraction. Margins F555 of the two retraction elements F544 can be shaped such that the retraction hooks F558 on one retraction element F544 interdigitate with the retraction hooks F558 of the opposing retraction element F544, decreasing the separation of the axes of the retraction hooks F558 to zero when they are inserted into the incision. FIG. F60B shows the retraction hooks F558 aligned in this instance parallel to the direction of the incision; the retraction elements F544 here have been somewhat differentially rotated about the dual-thrust lead screw F546 to make it clear how the shape of the margin F555 of the retraction elements F544 can be sinuous, permitting the interdigitation of the left and right retraction elements F544.

Figure 61:
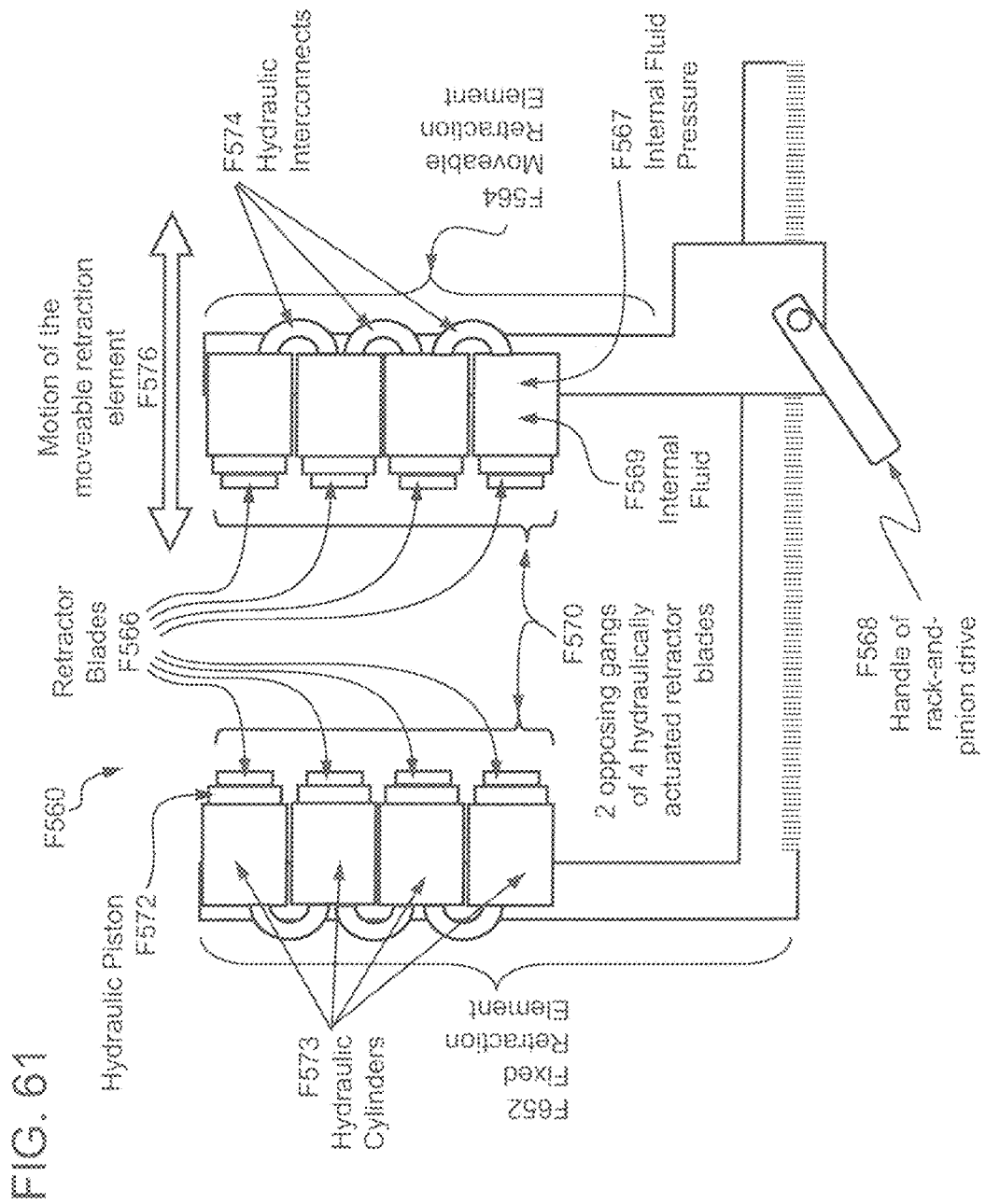
FIG. 61 shows another embodiment of a retractor using hydraulic cylinders to provide automatic force balancing on multiple retractor blades.

FIG. 61 shows another embodiment of a retractor F560 that achieves automatic balancing of loads. Multiple retractor blades F566 are mounted onto hydraulic cylinders F573 having pistons F572 that move in response to pressure F567 in the hydraulic cylinder F573, and the hydraulic cylinders F573 are fluidically F569 connected by hydraulic interconnects F574 and arrayed in opposing gangs 570 of hydraulic cylinders F573. The gangs F570 of hydraulic cylinders F573 are positioned on a fixed retraction element F562 and a moveable retraction element F564 of a Finochietto-style retractor driven by a handle F568. When, for example during retraction, the tissue resistance force on an arbitrary first retractor blade F566 draws out the first retractor blade F566 such that the first hydraulic piston F572 to which that the first retractor blade F566 is attached is also pulled a portion of the length of hydraulic piston F572 out of the first hydraulic cylinder F573, then the pressure F567 inside the first hydraulic cylinder F573 decreases. This decrease in pressure F567, communicated to the other hydraulic cylinders F573 via the hydraulic interconnects F574, causes internal fluid F569 to flow into this first hydraulic cylinder F573 from the other hydraulic cylinders F573. Flow of the internal fluid F569 out of the other hydraulic cylinders F573 decreases their internal pressures F567 consequently pulling the other hydraulic pistons F572 inward, so causing the other retractor blades F566 attached to the other hydraulic pistons F572 to move F576 in a direction opposite that of the first retractor blade F566. As with the embodiments above, the ratios of forces between all the retractor blades F566 can be designed to be any ratio desired, for example by the use of hydraulic cylinders F573 with different radii. In another embodiment, the hydraulic cylinders F573 can be a single hollow fluid-filled housing with four pistons (or other number of pistons) emitting from the housing, with the housing acting as a fluidic plenum keeping all four pistons in hydraulic communication. The hydraulic fluid in these systems can be oil, sterile water, sterile saline, or a gas, such as air. Air further provides compressibility which acts like a "spring" in such a system, enabling compliance appropriate when loading tissues, for example.

Figure 62:
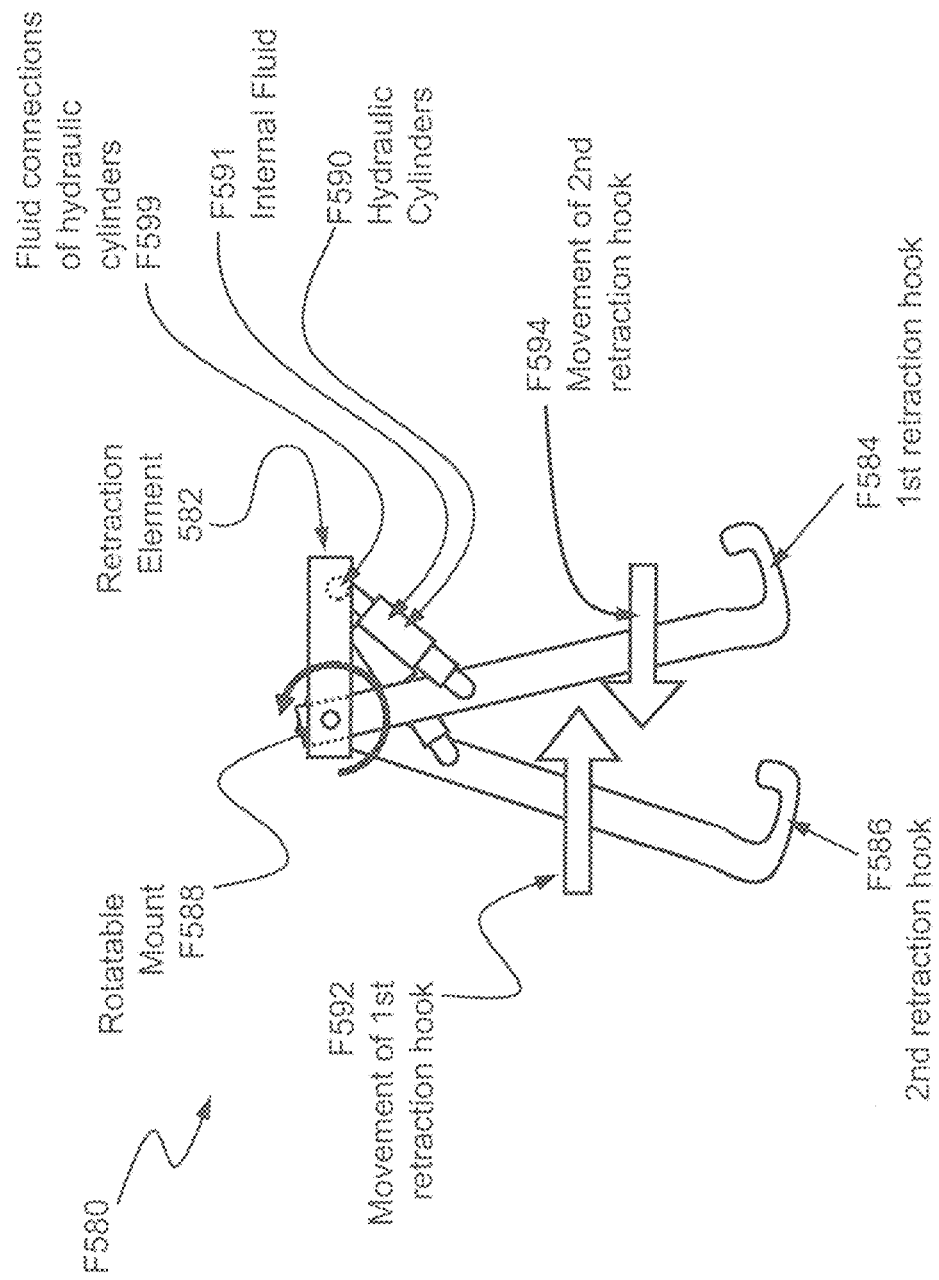
FIG. 62 shows another embodiment in which hydraulic cylinders provide automatic force balancing for multiple retraction hooks.

FIG. 62 shows another embodiment of a retractor F580 that achieves automatic balancing of loads with hydraulics. Similar to the cabled device depicted in FIGS. 59A through 59E, retraction hooks F584 and F586 are attached to retraction elements F582 by rotatable mounts F588; however, now the cables are replaced by a series of hydraulic cylinders F590 that compress or elongate (i.e., change total length) as the retraction hooks F584 and F586 rotate about the rotatable mount F588. The hydraulic cylinders F590 are fluidically connected at fluidic connection F599, so as one hydraulic cylinder F590 is elongated, for example, it pulls hydraulic fluid F591 from the other hydraulic cylinders F590, causing them to shorten. Thus, as shown in FIG. 62, as a first retraction hook F584 is pushed to the left (movement F594), causing this first retraction hook F584 to rotate clockwise about the rotatable mount F588, the hydraulic cylinder F590 of retraction hook F584 elongates, making the other hydraulic cylinders F590 (such as that associated with the second retraction hook F586) shorten, thereby rotating second retraction hook F586 counter-clockwise about the rotatable joint F588, making second retraction hook F586 move to the right (movement F592). Alternatively, the hydraulic elements F590 and F599 can be arranged to be compressed under load instead of pulled, driving fluid F591 out of the hydraulic cylinder F590 of the first (engaging) retraction hook F584 and into the hydraulic cylinder F590 of the second (reacting) retraction hook F586.

Figure 63A:
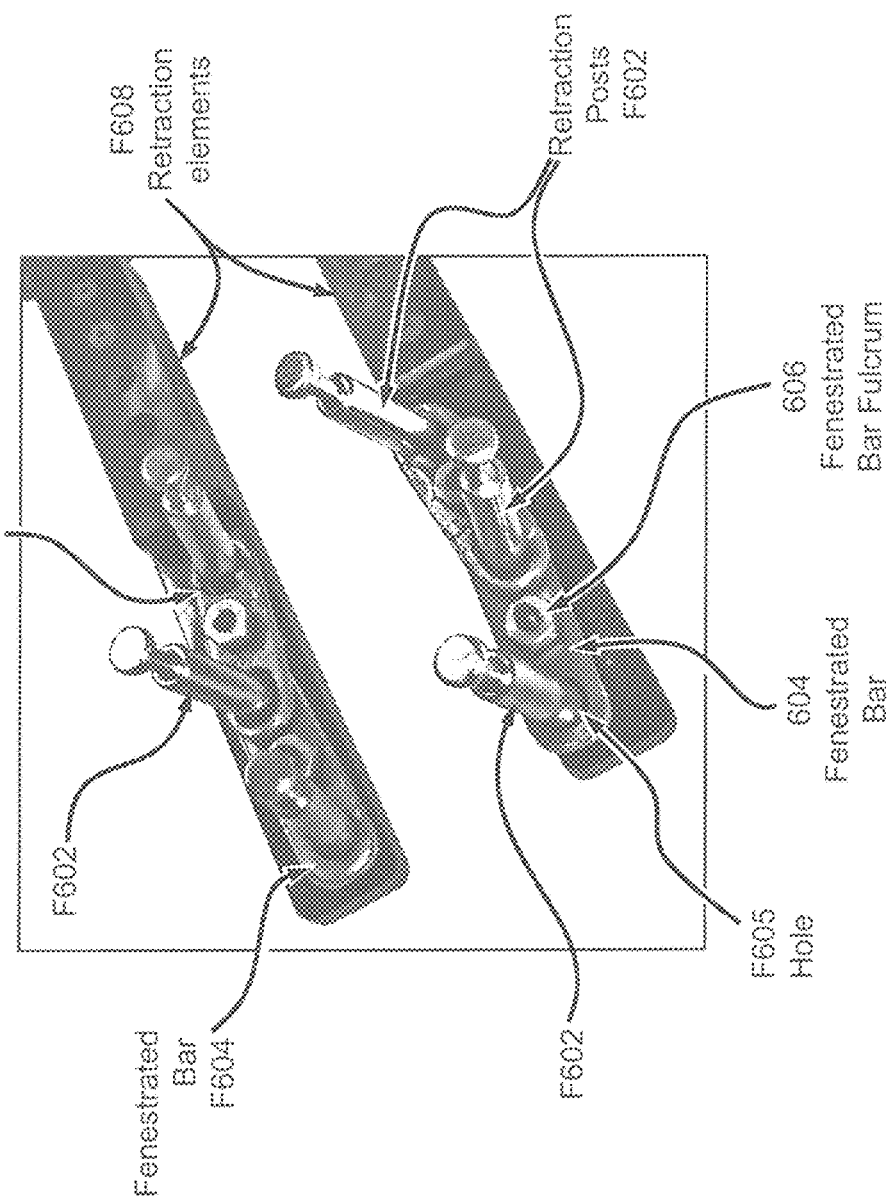
Figure 63C:
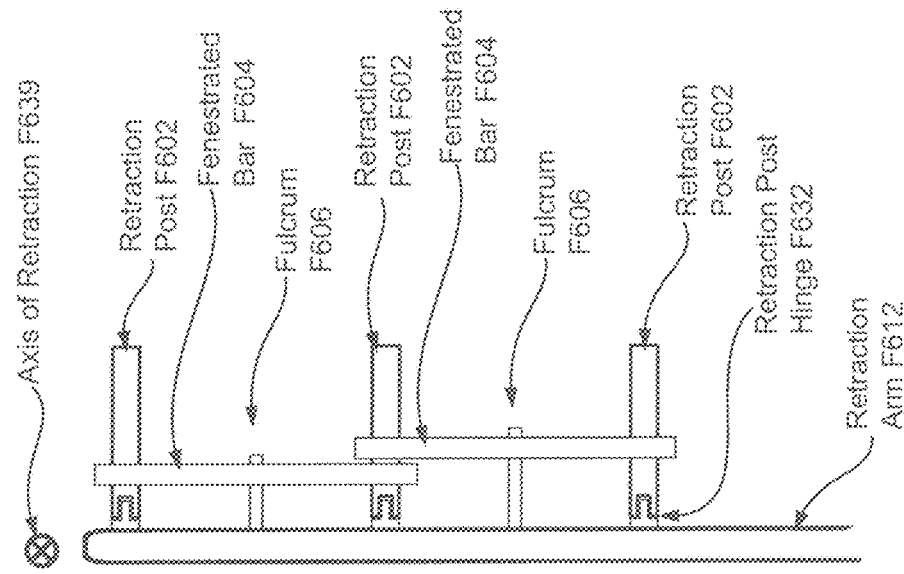
Figure 63B:
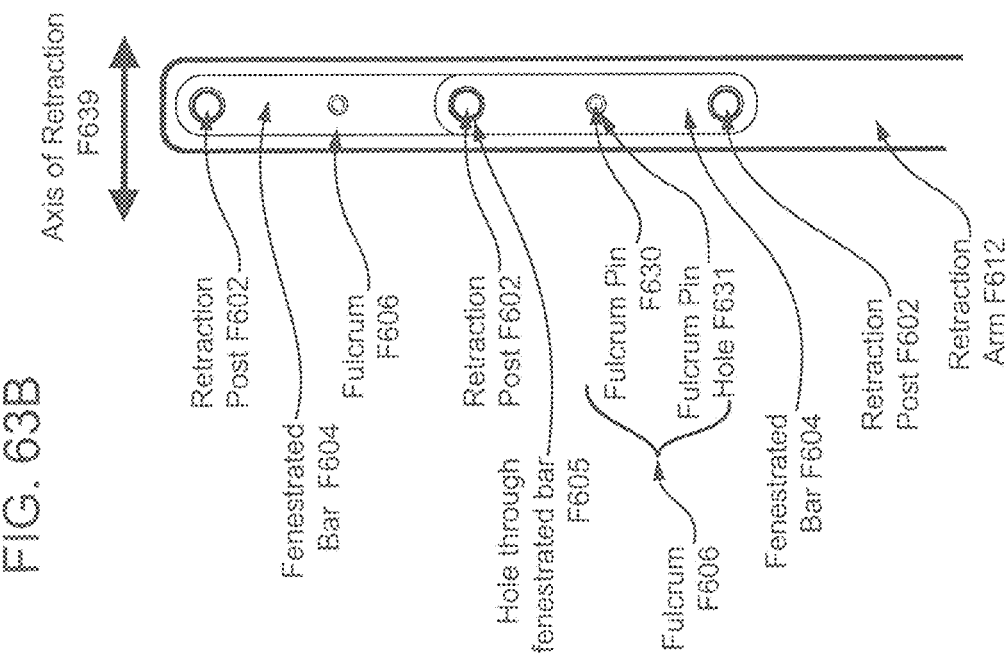
Figure 63E:
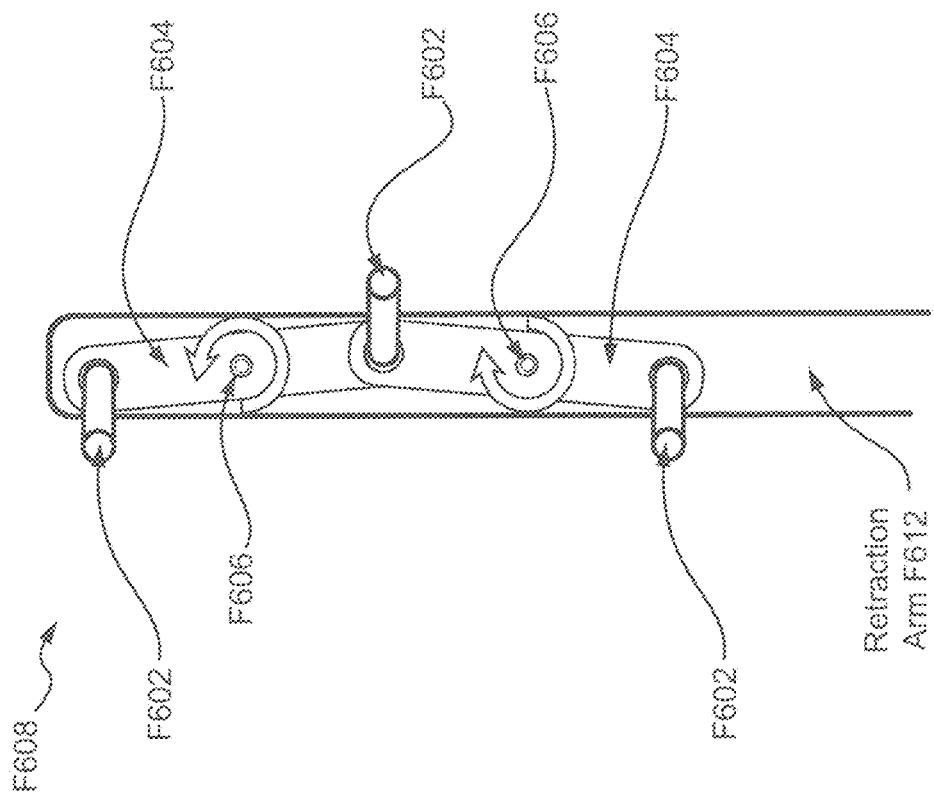

FIGS. 63A through 63E show another embodiment or a retraction element F608 with retraction posts F602 that compensate for one another's motion via retrograde action. Fenestrated bars F604 link retraction posts F602, and motion of one retraction post F602 causes the other retraction posts F602 to adjust via a mechanical linkage through fenestrated bars F604. FIG. 63A shows a model with the fenestrated bars F604 mounted on a fulcrum F606 and the retraction posts F602 passing through the fenestrated bars F604 via holes F605, with the counteracting offsets of the retraction posts F602 being evident. FIG. 63B shows a top view and FIG. 63C shows a side view of a retraction element F608. Each fenestrated bar F604 in this example possesses two holes F605 through which pass two retraction posts F602. Each fenestrated bar F604 then further possesses one more hole F631 admitting a fulcrum pin F630, forming the fulcrum F606 upon which and about which the fenestrated bar F604 is free to rotate. The fenestrated bar F604 resides in this example close to the base of the retraction arm F612, to which each retraction post F602 is connected via a hinge F632 which allows each retraction post F602 to swing back and forth along the axis of retraction F639. FIG. 63D shows the action for one retraction element F608. Consider the middle retraction post F602 and its two fenestrated bars F602. As a the middle retraction post F602 gets pushed backwards by the impinging tissue, the middle retraction post F602 moves backwards, and this motion is transmitted as a moment by both fenestrated bars F604 around the fulcrum F606 to the top and bottom retraction posts F602, pushing that the top and bottom retraction post F602 forward to meet the oncoming tissue. As with some of the other embodiments disclosed above, the motion of the retraction posts F602 ceases when the moments equalize. FIG. 63E shows the counter motion of that shown in FIG. 63D. This embodiment possesses two fenestrated bars F604 that together link the motions (and so the countermotions) of three retraction posts F602. Note that one may design the fenestrated bar system with an arbitrary number n of fenestrated bars linking n+1 retraction posts. Note also that one may combine fenestrated bars of arbitrary lengths and proportions so creating useful variations of motion of the retraction posts without departing from the intent of the present invention.

FIGS. 64 through 66B show still another embodiment of a retraction element of the current invention, this time providing swingletrees with the ability to automatically, dynamically and continuously adjust the position of their pivots to accommodate changing loads. In all FIGS. 64 through 66B the direction of retraction would be "up" towards the top of the page, and the patient's tissues would thus react by pulling "down" towards the bottom of the page. The retractor blades shown in FIGS. 64 through 66B thus engage an incision along the bottom of the page.

Figure 64:
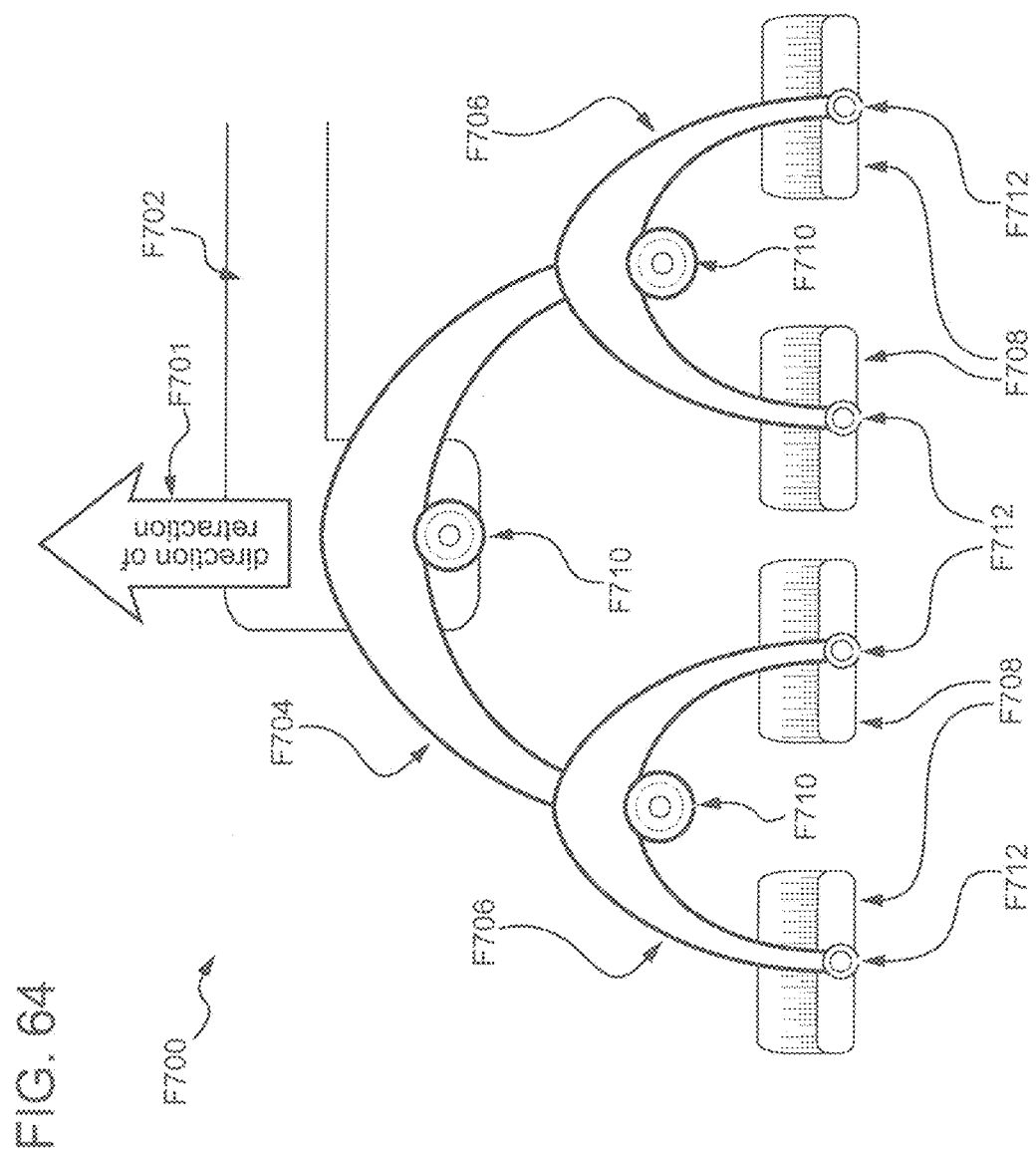
FIG. 64 show another embodiment in which pivots are used to provide adjustable pivot points for swingletrees.

FIG. 64 A shows retraction element F700 having a rectractor arm F702 that is used to pull up in the direction of retraction F701 F722. A two-tiered assembly of swingletrees, comprised of first swingletree F704 ("parent swingletree") and second swingletrees F706 ("child swingletree") hold four (4) retractor blades F708. First singletree F704 attaches to retractor arm F702 via pivot F710, here shown as a sheave. Second swingletrees F706 attach to first swingletree F704 also via pivot F710, here shown as a sheave. Retractor arms F708 attach to second swingletrees F706 via a pivot point F712, here shown as a rotating mount formed by a pin and a bushing. Swingletrees F704 and F706 still pivot within the plane of the page about a pivot F710 that acts as a fulcrum, shown here as a freely rotating sheave.

Figure 65B:
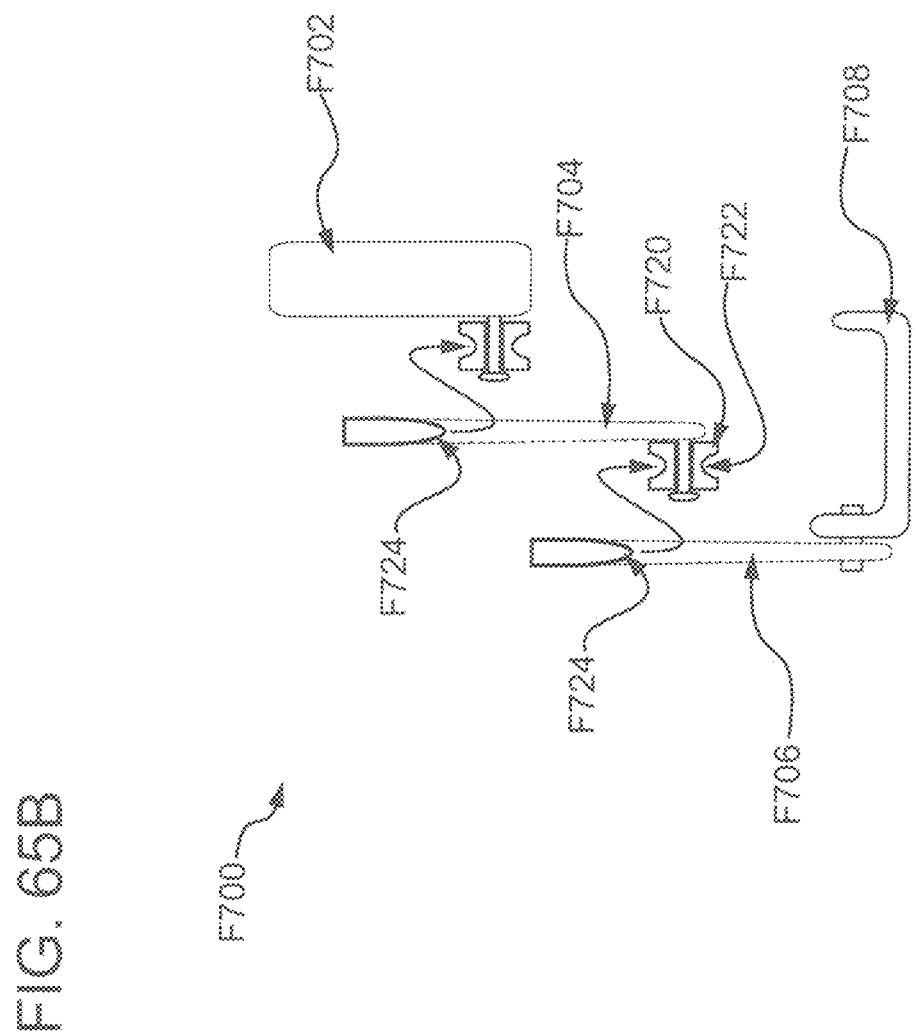

FIGS. 65A through 65C show side views of two different embodiments of retraction element F700. FIGS. 65A and 65B show side views of the retraction assembly F700 shown in FIG. 64. FIG. 65C shows another embodiment of retractor assembly F700 that captures first swingletree F704 and second swingletree F706 such that the assembly is held together. The sheave F720 at pivot F710 can be a bearing-mounted roller. As shown in FIG. 65B, the sheave F720 includes a provision (such as a groove F722 or channel around its rim) for cupping, nestling, or riding along and otherwise retaining its association with that edge F724 of each swingletree F704, F706 that is closest to the incision. The first and second swingletrees F704 and F706, respectively, includes a provision so that it mates with the sheave F720. As shown in FIG. 25B, the lower edge F724 of swingletrees F704, F706 can be convexly radiused and otherwise shaped to accept the concavely shaped groove F722 of the sheave F720. Given this arrangement, the lower edge F724 of swingletrees F704, F706 ride in the groove F722 of the sheave F720, such that the loading by the patient's tissues retraction actually seats the swingletrees F704, F706 more securely in the sheave F720.

FIG. 25C shows another embodiment of the retractor assembly F700, here labeled as retractor assembly F730. To avoid swingletrees F704,F706 disengaging from sheaves F722, first swingletree F704 is mated with another swingletee F732, creating a stacked assembly with two sheaves F722 connected to each other by a pin F732 through retractor arm F702. First swingletrees F704, F732 are thus captured by retractor arm F702, and second swingletree F706 is thus captured by doubled first swingletrees F704, F732. Another means of capturing each swingletree F704, F706 is to have sheave F720 ride in a restrictive slot formed within the child swingletree bar, instead of riding along the lower edge of the swingletree.

A "child" swingletree (e.g., second swingletree F706) can serve as the "parent" of other swingletrees (in this case, F676 and F677) lower down in the hierarchy, creating as many levels as desired. Properly sized and assembled, such a network of swingletrees automatically assures so that no excess or imbalance of forces can remain. In this way, any excess force applied against the tissue of the patient is reduced.

One problem with retractor blades and the like is their tendency to apply not only forces directly against the tissue of the patient, but to shear along (or roughly parallel to) the raw surface of the incision. As a retraction proceeds, the relative motion or loading of the retractor blades may induce sliding along the edge of the margin of the incision (or an attempt by one or more retraction elements to do so), shearing the tissue in that plane (or tearing it outright).

Figure 66A:
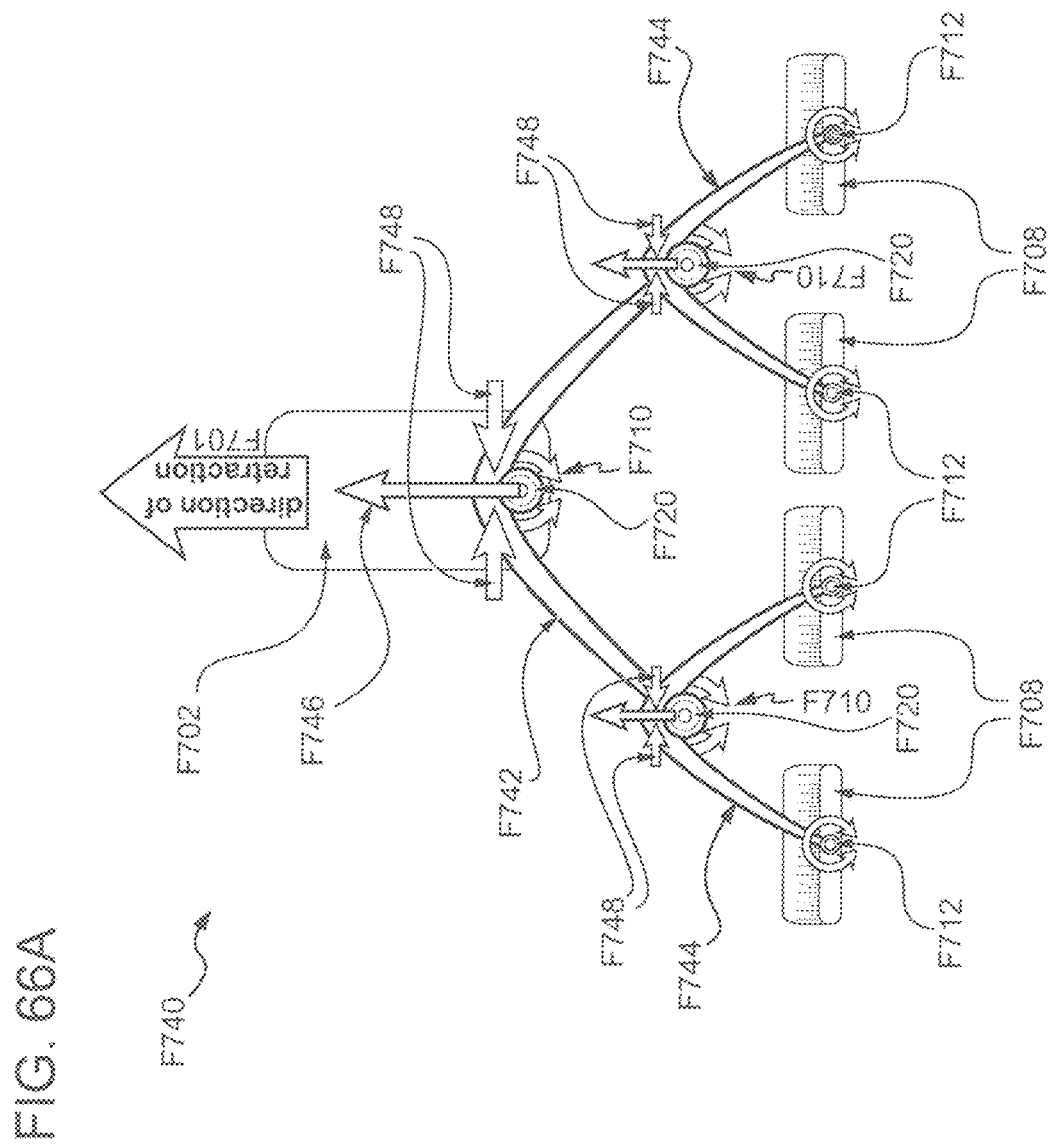

FIGS. 66A and 66B show another embodiment that uses distributed curvature of the freely riding swingletrees to limit this shearing motion of the retractor blades. FIG. 66A shows a retraction assembly F740 having swingletrees with tightly curved arms that make retraction assembly F740 more prone to shearing of the retractor blades, and FIG. 66B shows a retraction assembly F760 having swingletrees with more gently curved arms that that make retraction assembly F760 less prone to shearing of the retractor blades. The local curvature of the swingletree surface (riding in the parent sheave) influences the magnitude of the shear applied by rectractor blades F712 along the surface of the incision (i.e., the behavior of the swingletree hierarchy is a function of the curvature of the swingletrees comprising it). Consider FIG. 66A, swingletrees F742 and F744 are shaped with a substantially high curvature near the center of the swingletree, and lower curvature near their tips; thus, sheaves F720 experience strong centering forces F748 and remain more tightly centered under load, behaving much (but not all) of the time as if the pivots F710 formed by sheaves F720 were simply drilled through the bodies of the swingletrees. Under this circumstance shear is more likely to develop along the surface of the incision. Consider now FIG. 66B with swingletrees F762, F764 shaped with a much gentler distribution of curvature along the swingletree bar, then the centering forces F768 are smaller. Shear is instead relieved as the pivots F710 of the swingletrees F762, F764 can more easily shift laterally to suit owing to the smaller centering forces F768. Ideally, shear applied to the margin of the incision is minimal and the pivots F710 supporting a given swingletree F762, F764 remain substantially near the center of its respective swingletree F762, F764, thereby allowing the swingletree to rotate about the axis of the pivot F710, and within the plane of the page, to accommodate irregular loading as before. The gently curved swingletrees F762, F764 thus permit simultaneous accommodation of rotation and sliding, thereby eliminating both excessive forces and shear.

Note that the intersection between the parent sheave and the child swingletree can be formed of two smooth surfaces, or it could be formed like a rack-and-pinion, where the parent sheave is a toothed like a pinion gear and the mating lower surface of the child swingletree bar is a toothed rack. Given this, one could further arrange for the active sensing and actuator control of the sheave rotation such that the position of the child is influenced by the active rotation (or clutching) of the sheave. This example admits active modulation of the play of forces and moments through a swingletree cascade. In some instances it may prove advantageous to apply shear on purpose, or to imbalance the forces applied to the patient's tissues, according to the needs of the surgeon.

G. Reducing Inappropriate Forces

G.1 Forces Exerted by Retractors on Tissues

Figure 67:
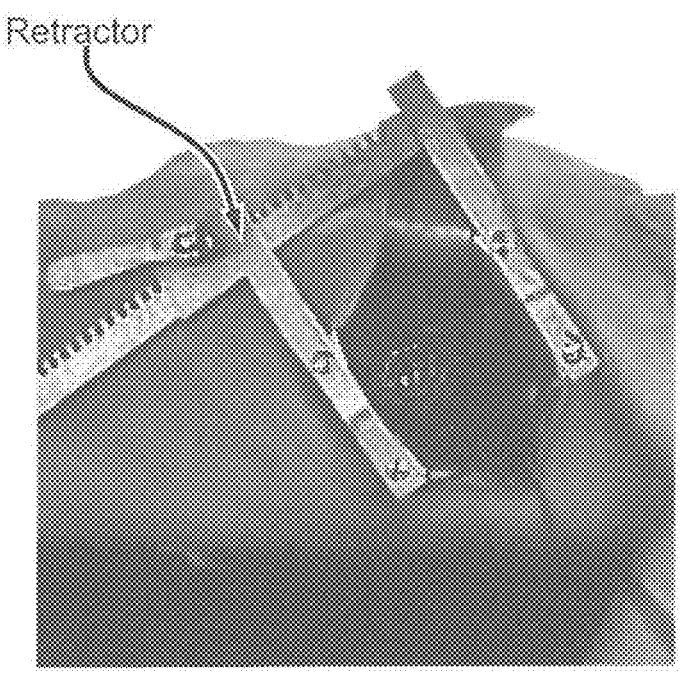
FIG. 67 shows an example of a thoracic retractor in the prior art used in a thoracotomy.
Figure 68A:
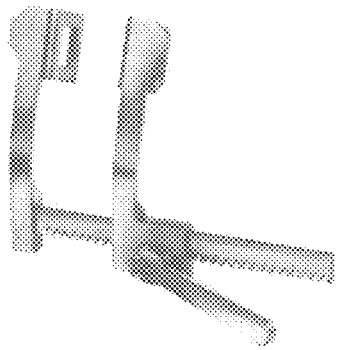
FIGS. 68A and 68B show examples of retractors in the prior art.
Figure 68B:
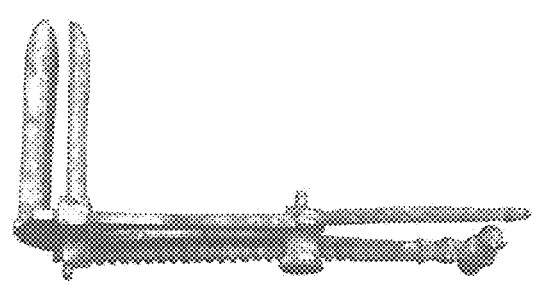

When a surgeon performs a thoracotomy, she must deform a patient's body wall to move the apposed ribs aside far enough to permit her hands to access the thoracic cavity (see FIG. 67). Current medical practice dictates that a surgeon (1) makes an incision between and parallel to two apposed, adjacent ribs; (2) simultaneously inserts the opposing blades of a rib spreader, or "retractor", into the incision; and (3) turns the crank to force open the opposing blades, and the ribs, creating a hole. The hole or surgical "aperture" is typically about 10 centimeters across, and can range from 5 cm to 20 cm. Modern retractors are essentially rigid metal devices sporting hand-cranked jack elements. Today's spreaders, such as Finochietto-style retractors (see FIGS. 2 and 68A) are typically rack-and-pinion devices that, while constructed of polished stainless steel, operate on simple mechanical principles similar to those of 2,000-year-old bronze medical instruments found in ancient Greece (a vaginal speculum, see FIG. 68B), that is, a hand-cranked jack driving projecting blades. The retractor shown in FIGS. 2 and 68A are widely used; this retractor uses a lockable rack-and-pinion crank, as first disclosed by Finochietto in 1936 and published in 1941 (Bonfils-Roberts 1972). The principle remains the same as the ancient ones: equip a frame, otherwise rigid in all directions and along all axes, with the ability to expand along a single axis to simply overpower the tissues to force access to the inside of the patient's body. Thus, referring now to FIG. 69, the force required for opening is considered to be simply opposing forces $F_1$ G8 and $F_2$ G10, applied at two points $P_1$ G12 and $P_2$ G14 lying on a single line of action. The only accommodations for more complex forces provided by the prior art are curved retractor blades, providing for example, non-point loading such as on a Cooley retractor G16 (FIG. 70A), and swiveling retractor blades such as on older retractors that are no longer used (e.g. the retractors of Sauerbruch G18 (FIG. 70B), De Quervain G20 (FIG. 70C), and Meyer G22 (FIG. 70D). Archeological museums and current medical supply catalogs visibly demonstrate that this one-dimensional thinking has underlain retraction device design for millennia.

Retractors work—they do force open bodies, but their design does not take into account the complex loading regime imposed on (and, in reaction, by) the patient's body. The result is that today's patient's tissues are bearing substantial loads that are not directly related to, or required for, opening; therefore, these retractors are causing unnecessary tissue trauma.

Figure 69:
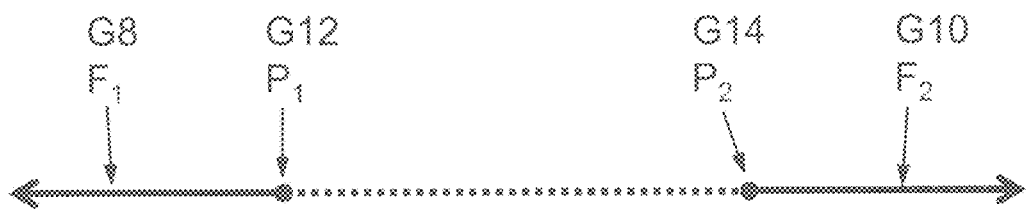
FIG. 69 diagrams the forces thought to act on the opposing blades of a retractor.
Figure 70A:
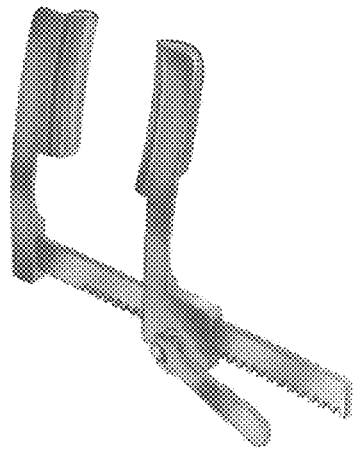
FIGS. 70A through 70D show additional examples of the prior art in which curved blades or swiveling joints permit accommodation to forces of retraction.
Figure 70B:
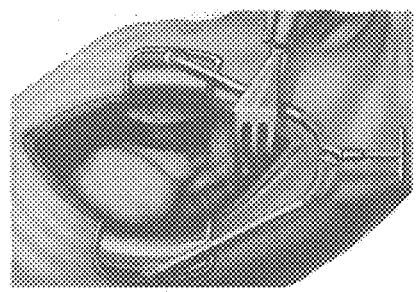
Figure 70C:
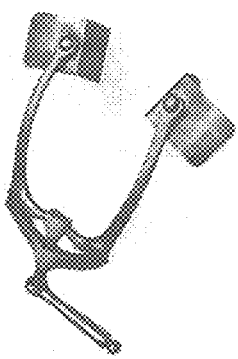
Figure 70D:
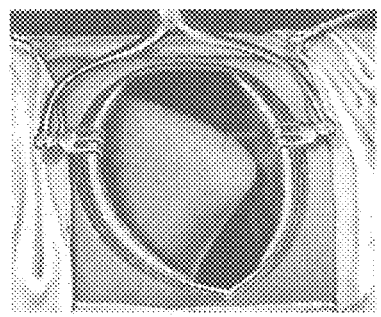
Figure 72:
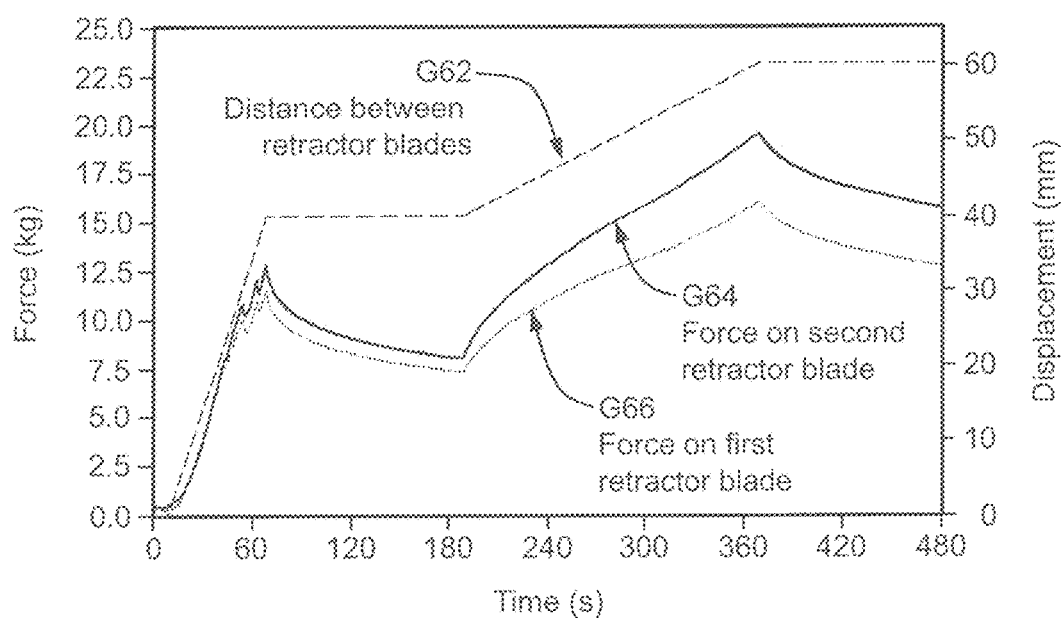
FIG. 72 shows data from an experimental thoracotomy showing that the force is not equal on two opposing blades of a retractor.

The inventors have measured forces during thoracotomy and observed for the first time that the actual forces of retraction are not the simple, one-dimensional case depicted in FIG. 69. It can now be appreciated that a complex set of forces and torques interact on the retractor, and thus on the patient's tissues. There are two lines of evidence for this claim. First, the force on a retractor (see FIG. 71, discussed below) is usually sufficient to lift the body of the retractor off the patient's body, such as in FIG. 67. Second, our measurements reveal that the forces acting on opposing retractor arms are not the same. FIG. 72 shows our new data that were collected with the retractor shown in FIG. 12, which is fitted with a computer-controlled stepper motor B8 to provide smooth motion and with a linear potentiometer B16 to measure the distance of separation of the retractor blades B20 and with strain gauges on the retractor blades B20 to measure the forces on each of the two retractor blades B20. This retractor was used to perform thoracotomies on the carcass of a pig. In the retraction shown in FIG. 72, retraction occurred over 6 minutes, starting at 10 seconds, with a two-minute pause in retraction from 70 seconds to 190 seconds. The difference in the forces G64, G66 measured on the two retractor blades is maximal at the end of retraction (at time=480 seconds, 19.5 kg versus 16.0 kg, a difference of about 20%). These force measurements demonstrate that retractors in the real world do not behave like perfect force diagrams out of a physics book as shown in FIG. 69, with two endpoints of zero extent (and equal force) connected by a one-dimensional line.

Applying pure tension or compression with today's retractors seems impossible. In light of the observations and measurements presented in FIGS. 71 and 72, it is difficult to imagine that one could ever see equal forces acting on the two blades of a conventional retractor placed inside a real patient.

Why is this so? Refer to FIG. 71. First, retractors such as retractor G24 possess significant mass that is distributed unevenly, and they have blades G33 and G31 with non-zero dimensions and corners. Second, the patient's body is a sculpturally and structurally complex composite of heterogeneous biomaterials. Every structure inside a patient (example e.g., ribs G26 and G28) is anisotropic and almost nothing behaves linearly. When the blades G31 and G33 of the retractor G24 engage the two sides of an incision, the body forcefully opposes motion of the blades G31 and G33. The patient's tissues (e.g., ribs G26 and G28) grew and developed alongside each other and the forces they generate tend to restore their apposed relationships. While the retractor G24 drives its retractor blades G31, G33 apart in a straight line, such as displacement G32 and G30, the there are numerous forces G36, G38, G40, G42, G52 G56 and G58 and torques G27, G34, G44, G46, G48, G50, G54 and G60 acting on the retractor blades G31 and G32 that arise from the deformations of the heterogeneous, three-dimensionally complex tissues surrounding the incision. Consequently, these forces are similarly three-dimensional and complex.

In the act of forcing open a living body with a conventional retractor G24, first one corner of one of the inserted retractor blades G31 will strike some part of a rib G26 and settle onto that rib G26 and the intervening muscle tissue in an irregular fashion. Once that happens, and since the retractor G24 is a rigid object, the retractor G24 will react to the first contact, shifting position, until the other retractor blade G33 encounters and settles somewhere onto its own opposing rib G28 and muscle. The retractor G24 then reacts and shifts again, with the blades G31, G33 sliding along and shearing muscle against bone, back and forth in concert, as the surgeon applies torque to the retractor handle G35 (and so the entire retractor) as the patient's body forcefully opposes motion of the retractor blades G31, G33. All the while, the patient's body deforms unevenly under the loads imposed by the retractor G24. The structures of the patient's body are deforming, which affects re-seating of the retractor blades G31, G33, which affects the deformation of the body, and so forth. All elements are shifting at once, but not evenly (i.e., not rectilinearly). The retractor G24 is essentially a rigid object; at any time, there is little or no provision for the complex mechanical behaviors that are the hallmark of living tissue. Because of this, and crucially, the retractor blades G31 and G33 apply uneven forces to the body throughout spreading, and the forces are uneven when the surgeon achieves the required opening.

The apparent intention of the designers of conventional retractors was to apply large forces along a single line of action (the "retraction axis"). However, they do not accomplish this because they do not consider the response of the patient's body. The forces on the retractor are those imposed by the reaction of the patient's body to the displacement of its tissues, and the patient's body does not respond along a single line of action—it generates complex, three-dimensional forces in response to deformation. Furthermore, these forces change as deformation proceeds while the retractor remains in contact with the patient's body tissues. The retractor, in return, opposes these forces by moving (e.g. lifting off of the patient's body) or by accumulating stresses in the retractor. Consequently, the patient's tissues bear substantial stresses beyond those required for opening, leading to tissue trauma (e.g., broken ribs) that, otherwise, should be avoidable.

Clearly, minimizing undue stresses during a thoracotomy or other surgical procedure would be beneficial to the patient, reducing tissue trauma to the barest minimum required to generate an adequate surgical aperture. This can be accomplished by (a) generating force along a line of action to retract the tissues to achieve a desired surgical opening (the "retraction axis"), (b) accommodating motions (e.g. translations and rotations) of the retraction axis such that there is minimal opposing force from the retractor to these motions, and (c) accommodating motions (e.g. translations and rotations) of the retractor blades, and of the underlying tissues, that are not parallel to the retraction axis such that these non-parallel motions occur with minimal opposing force from the retractor. To this end, the retractor should also be as lightweight as is practicable. Thus, the retraction axis is free to move in space and there is minimal force opposing motions not on the retraction axis.

This can be accomplished by a lightweight retractor that is free to move, or its parts are free to move, as the patient's body exerts forces that are not along the retraction axis. Such a retractor, thus, automatically aligns itself (e.g., its blades) such that the retraction axis is always oriented along a direction that achieves the desired surgical opening while reducing the magnitudes of all forces.

Disclosed herein are apparatus and methods for automatically minimizing the imposed deformation forces applied to the patient to the minimum required for surgical access. With the various embodiments of the present invention one can readily apply forces sufficient to deform the patient's tissues in the manner appropriate for medical procedures while minimizing forces arising from or leading to undesired deformations of the patient's tissues.

G.2 Swing Blade Retractor—Dual-Thrust Lead Screws

Figure 73:
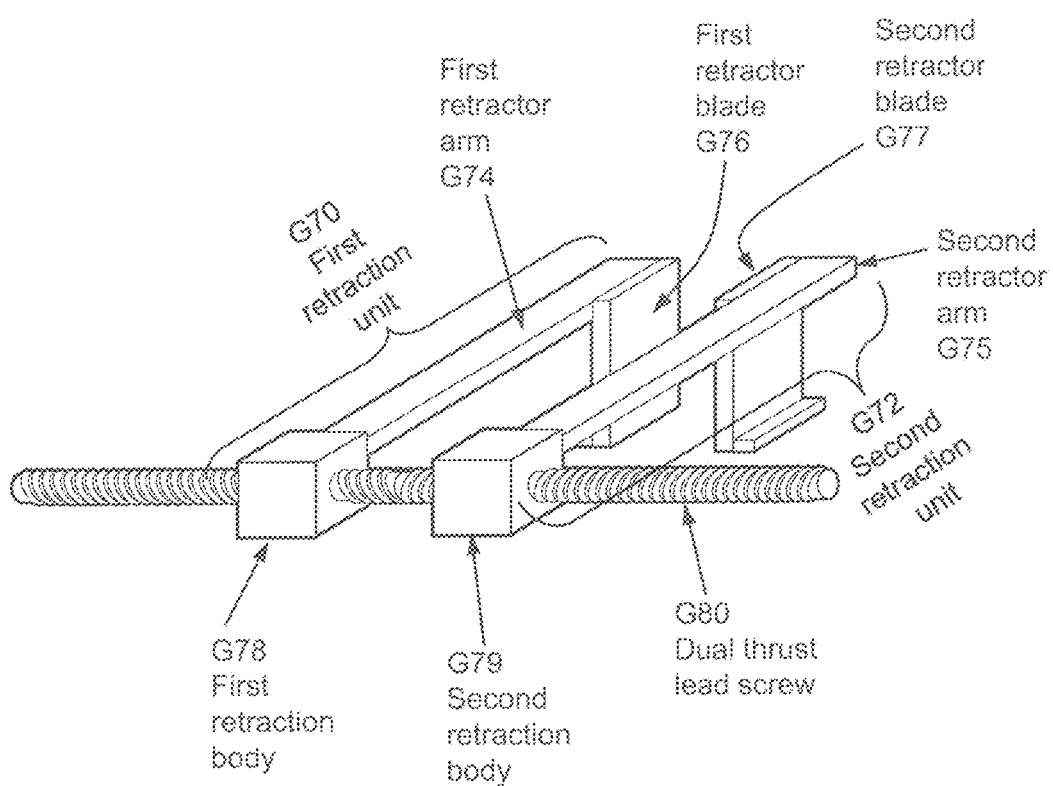
FIG. 73 shows an embodiment in which the retraction units are driven by a dual-thrust lead screw.

FIG. 73 shows one embodiment of a retractor G68 that possesses a new degree of freedom of motion, allowing the retractor blades G76 to automatically realign to reduce forces that are not parallel to the retraction axis. Retractor G68 is functionally divided into three units: a dual-thrust lead screw G80, a first retraction unit G70, and a second retraction unit G72. Collectively, retractor G68 is referred to as a "Swing Blade Retractor". The dual-thrust lead screw G80 is a lead screw having at least left-hand threads on one end and right-hand threads on the other end (such as those offered by the Universal Thread Grinding Company, Fairfield, Conn.).

Each retraction unit G70, G72 is comprised of a retraction body G78, G79 having hollow 'female' threads that engage the outside surface of the dual-thrust lead screw G80, a retractor arm G74, G75, and a retractor blade G76, G77. The retraction bodies G78, G79 have either a left-hand thread or a right-hand thread with which to follow the travel of the threads on the outside of the dual-thrust lead screw G80. When the dual-thrust lead screw G80 is rotated, the dual-thrust lead screw's threads (which are engaged with the threads in the retraction bodies G78, G79) force the two retraction units G70, G72 to move away from each other to displace the (now formerly) apposed tissues. Rotation of the dual-thrust lead screw G80 about its long axis can be accomplished by any of several means, including a hand crank mounted to one end of the dual-thrust lead screw G80, a motor mounted to one end, a hand crank attached to a gear inside one retraction body unit G78, or a motor attached to a gear inside one body unit (or both). The gears might be helical gears, crown gears, friction drives, or other means permitting a retractor body to simultaneously drive dual-thrust lead screw G80 rotation and follow the motions of the threads on the outside of the lead screw.

Note that a dual-thrust lead screw G80 could be made to have an arbitrary number of regions of both left- and right-handed threads, with arbitrary pitches (and so advance ratios), such that a plurality of retraction units G70 could be made to move all at once on a single lead screw G80, at different speeds and directions relative to one another. For example, one might wish to engage more than two ribs at once, say, four or six, and move them all in concert to distribute deformations and loading, and to prevent crushing of soft tissues between sequential sets of ribs.

While away from the body of the patient and not locked together, each of the Swing Blade Retractor's G68 retraction units G70 and G72 is able to swing freely about the long axis of the dual-thrust lead screw G80. Note that rotation of both retraction units G70, G72 about the long axis of the dual-thrust lead screw G80 is constrained when the Swing Blade Retractor G68 is placed against the patient's body or if the retractor blades G76 and G77 are engaged with the tissues. The result of this constraint is that when the dual-thrust lead screw G80 rotates, while both retractor blades G76 and G77 are against or inside the patient's body, both retraction units G70 and G72 move apart, opening the incision to create the surgical aperture. Furthermore, if a crank or motor is placed inside one retraction body G78 or G79 of only one retraction unit G70 or G72, respectively, then both retraction units G70 and G72 still move apart under rotation of the dual-thrust lead screw G80. The retraction units G70 and G72 will come back together when the dual-thrust lead screw's G80 direction of rotation about its own long axis is reversed. Thus, a motor or crank in one retraction body G78 of one retraction unit G70 can be used to rotate the dual-thrust lead screw G80 and, thereby, drive both retraction units G70 and G72 apart.

Figure 74:
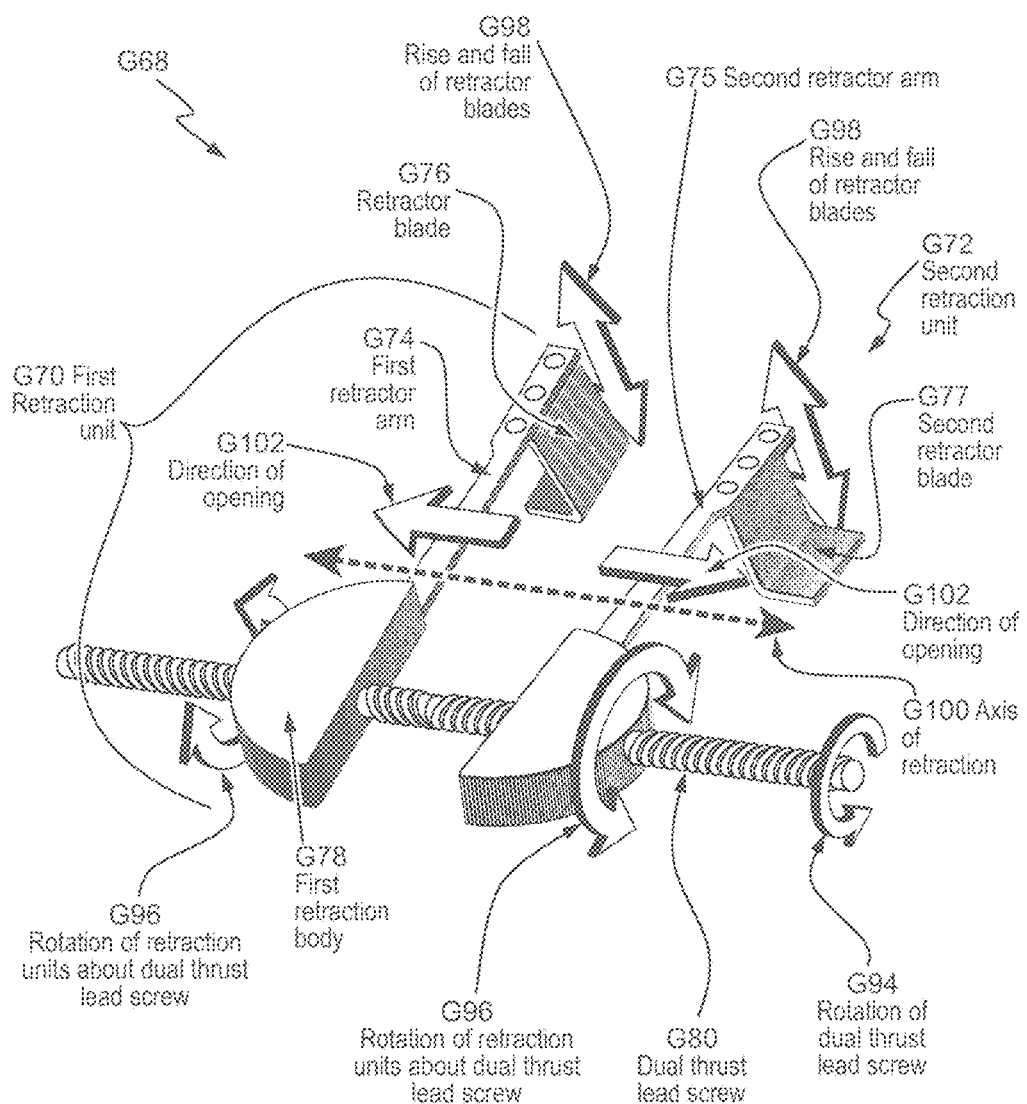
FIG. 74 shows another embodiment in which the retraction units are driven by a dual-thrust lead screw, demonstrating rotational freedom of the arms.

FIG. 74 depicts how a Swing Blade Retractor G68 has an additional degree of freedom, relative to a conventional retractor, such as those shown in FIGS. 67, 68A, 68B, and 70A through 70C. For the Swing Blade Retractor G68, retraction units G78, G79 are mounted to the dual-thrust lead screw G80 only by the threads in each retraction body G78, G79, so the retraction units G78, G79 are free to rotate about the long axis of the dual-thrust lead screw G80. The retractor blades G76, G77 are, thus, able to rise and fall in a direction G98 approximately perpendicular to the axis of retraction G100 and perpendicular to the surface of the body of the patient (i.e., in and out of the incision). In contrast, the arms of a conventional retractor are always constrained to move towards or away with respect to one another within that single axis of retraction; any tendency of the retractor blades to move in any other direction is strongly resisted by the substantial structure of the retractor. Importantly, any tendency of the body wall in contact with the retractor blades to move in some direction other than the axis of retraction is also resisted by a conventional retractor, and, subsequently, substantial stresses can form in the body's tissues that are unrelated to the force required to obtain the surgical opening. In other words, the minimum amount of force and/or trauma to open the body wall might require a curved path, or a slightly shifting path, as opposed to a unidirectional, rectilinear path.

An additional advantage of a Swing Blade Retractor is that it can assist insertion of the retractor blades into the incision during preparation for retraction. When inserting the retractor blades of the prior art into an incision through a patient's body wall, the surgeon is forced, by the rigidity of the retractor frame, to jam both retractor blades in at once. This is a problem because this cannot be done until the surgeon first uses her fingers to pry open the incision to be wide enough to be able to fit in both blades, which may themselves have wide edges. However, for the Swing Blade Retractor G68, because the two retraction units G70, G72 swing freely and independently, each retractor blade can be inserted one at a time as desired, allowing a surgeon to begin with a smaller opening.

Another advantage of the Swing Blade Retractor G68 is that the hollow threads of the retraction bodies G78, G79 can be formed of more than one piece. For example, the hollow threads can be made of two halves, each a semi-circle in section, that are brought together inside the retraction body G78, G79 to enclose, embrace and engage the threads of the dual-thrust lead screw G80. This enables another improvement over the rack-and-pinion retractors, which must be laboriously cranked back all the way shut to be removed, in that one or both of the Swing Blade Retractor's G68 retractor bodies G78, G79 can be instantly removed from the dual-thrust lead screw G80 by disengaging the two-piece hollow threads. For example the two-piece hollow threads can separate such that the dual-thrust lead screw G80 can pass through a gap made by the separation. The means of thread disengagement might be a button, lever, motor or flap that when closed retains and stabilizes the threaded halves around the dual-thrust lead screw G80. This enables the surgeon to rapidly lift one or both retraction bodies G78, G79 away to clear the surgical field in an emergency, facilitating removing the entire retractor G68. Similarly, the hollow threads, rather than being composed of two halves that fully or almost fully wrap the dual-thrust lead screw G80, can engage only one side of the dual-thrust lead screw G80, wrapping only ⅛th, for example, of the circumference of the dual-thrust lead screw G80. This facilitates disengagement of the threads from the dual-thrust lead screw G80—the threads need only be lifted away from the dual-thrust lead screw G80 to permit free motion of the retraction unit G70, G72 along the length of the dual-thrust lead screw G80.

The advancement of the retraction bodies G78, G79 usually proceeds from the rotation of the dual-thrust lead screw G80 about the dual-thrust lead screw's G80 long axis. The rotation of the dual-thrust lead screw G80 can be the result of a source of torque such as a hand crank, a motor, or the like. The source of torque can be external to the retraction body G78, G79. In one embodiment, the source of torque is located inside one retraction body G78 or G79. In this case, the retraction body G78 or G79 thus possesses its normal capability to be driven along the dual-thrust lead screw G80 while simultaneously being the agent that drives the rotation of the dual-thrust lead screw G80 about its own long axis. For example, one may modify the dual-thrust lead screw G80 by further providing rotation means co-located with the threads along the shaft so that the retraction body G78 or G79 may engage both the threads for advancement and the rotation means for rotation. One example of rotation means would be splines cut along the length of the shaft. The threads of the dual-thrust lead screw G80 and splines (not shown) can co-exist on the same driveshaft, are not mutually exclusive, and can be engaged by separate mechanisms housed within the retraction body G78 or G79. The hollow threads disclosed above can provide the engagement for advancement upon rotation of the dual-thrust lead screw G80, while a toothed ring drive (not shown) surrounding the lead screw but engaging only the splines provides the rotation. The hollow threads "see" only the threads of the dual-thrust lead screw G80 while the toothed ring "sees" only the splines, i.e., the surface gaps forming the splines do not present occlusions to the threaded follower and the surface gaps forming the threads do not present occlusions to the toothed ring drive. This form of the dual-thrust lead screw G80, called a splined dual-thrust lead screw, can be made by first cutting, machining, or rolling helical threads into a plain metal rod or cylinder, and then cutting splines in the same cylinder. Other means are possible, but the intent is to provide in one device (and even in one component of the device) simultaneous dual-thrust lead screw G80 thread following and lead screw rotation.

Another benefit of the Swing Blade Retractor G68 design is that it is self-aligning. For stability's sake, the Swing Blade Retractor G68 exploits the tendency of the edges of the patient's body wall to re-appose once separated. When a surgeon retracts the body wall, the apposed or touching edges of the incision now move apart. The body's mechanical reaction is to re-appose the edges of the incision, i.e., the distance between the edges of the incision "tries" to return to zero. Crucially, this re-apposition occurs in three dimensions. No matter the initial orientation of the retractor blades G76, G77, they cannot swing apart once engaged with the patient's body wall; thus, the natural forces at work in the patient's body automatically align the retractor blades G76, G77 (and indeed, the entire axis of retraction G100) to exactly that angle in three dimensions that minimizes the distance between the retractor blades G76, G77, and so, the force required for retraction.

G.3 Swing Blade Retractor—Roller Drives

Figure 75:
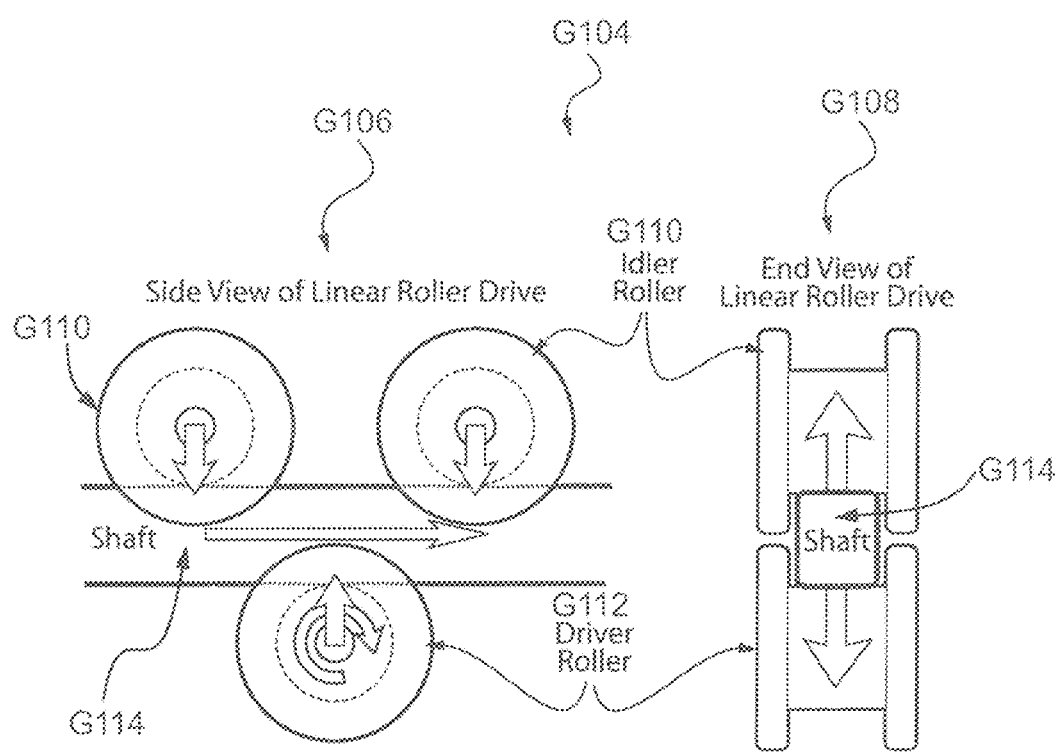
FIG. 75 shows side and end views, respectively, of an embodiment of a retractor drive mechanism comprising a roller drive with a shaft having rectangular cross-section.

FIG. 75 shows another means G104 for driving retraction units in a retractor. Rather than using a dual-thrust lead screw, a roller drive G106 is used. A roller drive combines thrust and rotation, like a dual-thrust lead screw, but can be more efficient, and it offers the ability to variably adjust the pitch of drive. Roller drive G106 has three or more rollers G110 engaging a shaft G114 with at least one of the rollers, a driver roller G112, coupled to a torque source, such as a motor or a hand crank, and with the other rollers G110 acting as idler rollers which passively roll along the shaft G114. The rollers G110 and G112 can have collars that help guide the rollers G110 and G112 along the shaft G114, ensuring that the rollers G110 and G112 remain engaged with the shaft G114. The shaft G114 can be substantially rectangular in cross section, as in FIG. 75, or shaft G114 can have any other cross-sectional shape matched to the rollers G110 and G112. The rollers G110 and G112 are forced against the shaft G114 such that friction between the driver roller G112 and the shaft G114 causes the driver roller G112 to impel the shaft G114 when the driver roller G112 rotates under the action of its torque source. Note that motion is relative, so the roller drive G112 can move along a stationary shaft G114, or a shaft G114 can be pushed by a stationary roller drive G112. The rollers G110 and G112 can be fitted with appropriate bearings to permit substantial force pushing the rollers G110 and G112 against the shaft G114 to generate substantial friction between the shaft G114 and the driver roller G112. The rollers G110 and G112 can be forced against the shaft G114 either by precise manufacture of the mounts holding the rollers G110 and G112, or the rollers G110 and G112 can be pressed into position by, for example, a cam that variably moves the rollers G110 and G112 away from the shaft G114, releasing the shaft, or presses rollers G110 and G112 against the shaft G114 to hold or drive the shaft G114.

Figure 76:
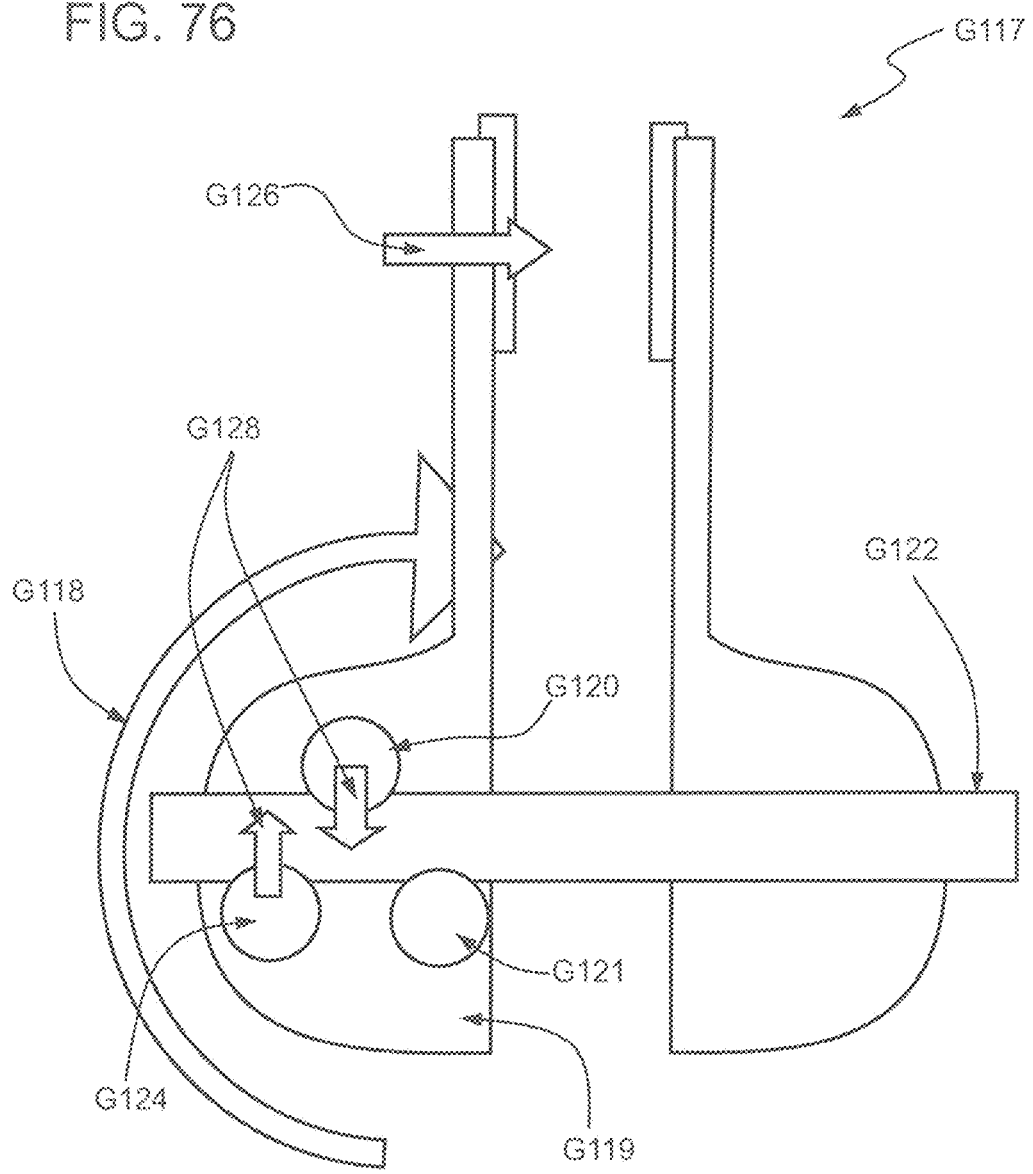
FIG. 76 shows how torques on the arms of a retractor increases forces on the drive rollers of a roller drive.

FIG. 76 shows how a roller drive G106 can be used in a retractor G116. Retraction unit G117 has a roller drive comprised of a first idler roller G120, a second idler roller G121, and a drive roller G124. Idler rollers G120, G121 and drive roller G124 engage shaft G122, and torque on drive roller G124 drives retraction against the retraction force G126 from the tissues. This configuration of idler rollers G120, G121 and drive roller G124 provides several advantages. First, retraction force G126 results in a torque G118 on retraction unit G117 that then applies a force G128 on the drive roller G124 and the first idler roller G120 that increases drive friction for drive roller G124, thereby improving engagement between the driver roller G124 and the shaft G122. Second, the shaft G124 is smooth, decreasing chances for snagging items in the surgical field. Fourth, the rollers G120, G121, and G124 and shaft G122 are easier to manufacture precisely, decreasing cost.

Figure 77:
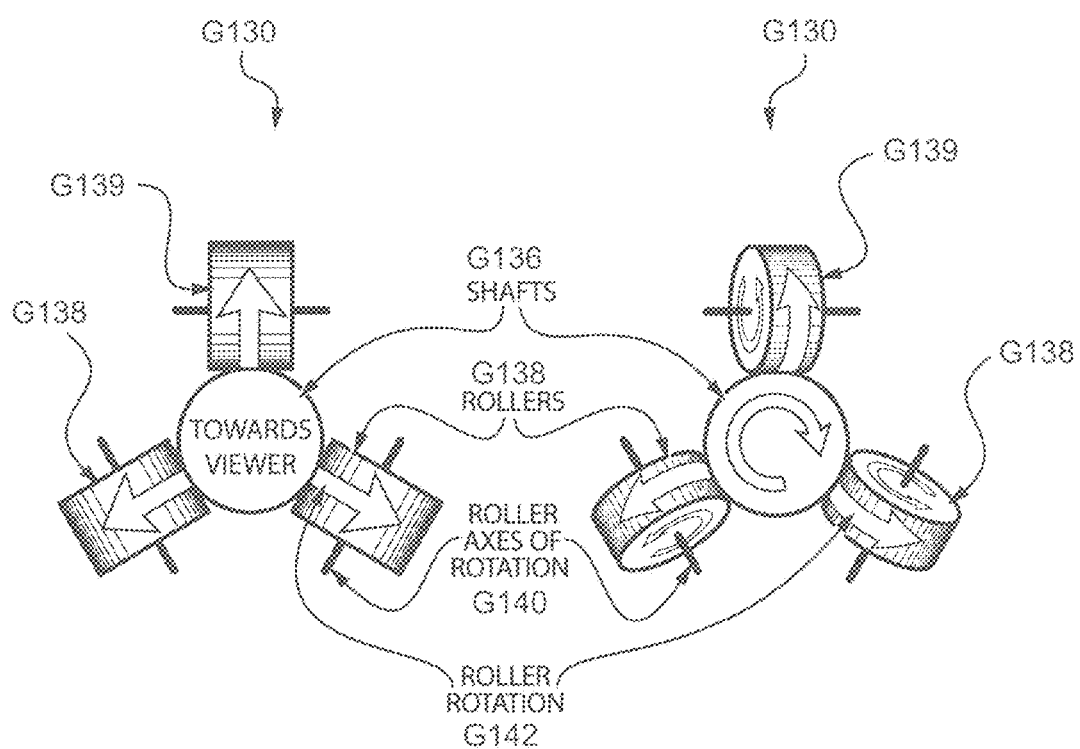
FIG. 77 shows a roller drive with a circular shaft and how alignment of the rollers with respect to the circular shaft drives rotation and translation of the shaft.

FIG. 77 shows another embodiment of a roller drive G130. The idler rollers G138 and drive roller G139 do not have collars as in FIGS. 75 and 76; rather, the idler rollers G138 and are circular cylinders. In FIG. 77, the shaft G136 is circular in cross-section. The rollers G138 have an axis of rotation G140 defining the orientation of rotation G142 of the rollers G138. On the left-hand side of FIG. 77, the rollers G138 and shaft G136 are configured such that the roller axes of rotation G140 are all perpendicular to the long axis of the shaft G136; thus, when the driver roller is actuated, the shaft moves out of the page plane (see rotation-indicating arrows). On the right-hand side of FIG. 77, the roller axes of rotation G140 are aligned oblique to the long axis of the shaft G136; thus, when the driver roller G139 is actuated, the shaft G136 moves helically out of the page plane. In other words, the motion of the shaft G136 imparted by the rollers G138 and G139 has two components, one that translates the shaft G136 out of the page plane and one that rotates the shaft G136 around the long axis of the shaft G136.

Figure 78:
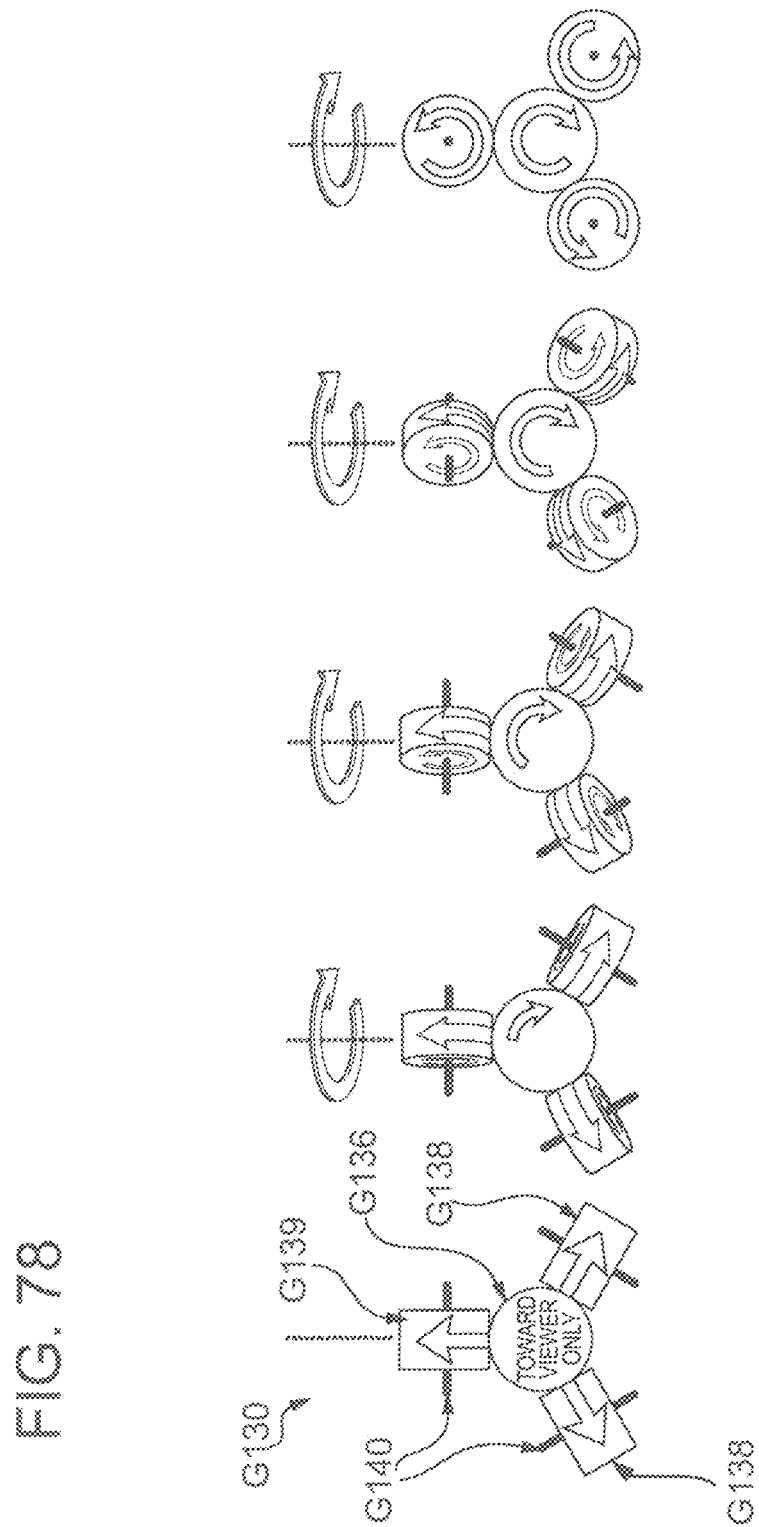
FIG. 78 illustrates multiple views of a roller drive with a circular shaft depicting how varying the alignment of the rollers with respect to the circular shaft provides variable control of shaft rotation and translation.

FIG. 78 shows that the relative degree of each motion of the shaft (translation and rotation) is determined by the angle between the roller axis of rotation G140 and the long axis of the shaft G136. The angle between the roller axis of rotation G140 and the long axis of the shaft G136 is shown to vary from left to right in FIG. 78. On the left-hand of FIG. 78, the roller axis of rotation G140 is perpendicular to the long axis of the shaft G136 resulting in translation of the shaft directly out of the page towards the viewer (without rotation). On the right-hand of FIG. 78 roller axes of rotation G140 are perpendicular to the long axis of the shaft G136, resulting in rotation of the shaft G136 within the plane of the page (without translation) when the rollers' axes of rotation G140 are parallel to the long axis of the shaft G136, and the shaft G136 cannot be moved through the rollers G139, G140 regardless of whether rollers G139, G140 are turning, i.e., the shaft G136 is locked, thus this embodiment of the retractor G130 is self-retaining. At all other angles between the roller axis of rotation G140 and the long axis of the shaft G136, rotation of the rollers G139, G140 results in a combination of rotation and translation of shaft G136.

Note in FIG. 78 that varying the angle between the rollers' axes of rotation G140 and the long axis of the shaft G136 effectively varies how the driver roller's G139 power is spent—when the roller axis of rotation G140 is perpendicular to the long axis of the shaft G136, all of the power of driver roller G139 is spent translating the shaft G136, and when the roller axis of rotation G140 is parallel to the long axis of the shaft G36, all of the power of driver roller G139 is spent rotating the shaft G136 in place. In motions in which one motion (translation or rotation) of the shaft G136 is strongly opposed and the other motion is not, then varying the angle between the roller axes of rotation G140 and the long axis of the shaft G136 effectively gears the roller driver G130, allowing the roller driver's axis of rotation G140 to be adjusted such that the power of the roller driver G139 is sufficient to generate the desired force and motion. For example, the roller axes of rotation G140 can initially be parallel to the long axis of the shaft G136 when the torque source of the driver roller G139 starts rotating the driver roller G139. This causes the shaft G136 to rotate without translation. While the driver roller G139 continues rolling, the angle of the roller axes of rotation G140 can be continuously changed such that the shaft G136 slowly starts translating. The angle of the roller axes of rotation G140 can, thus, be adjusted to place more of the power of the driver roller G139 into translating the shaft G136. Note that controlling the angle between the rollers' axes of rotation G140 and the long axis of the shaft G136 can also be used to control the velocity of translation of the shaft G136.

Figure 79:
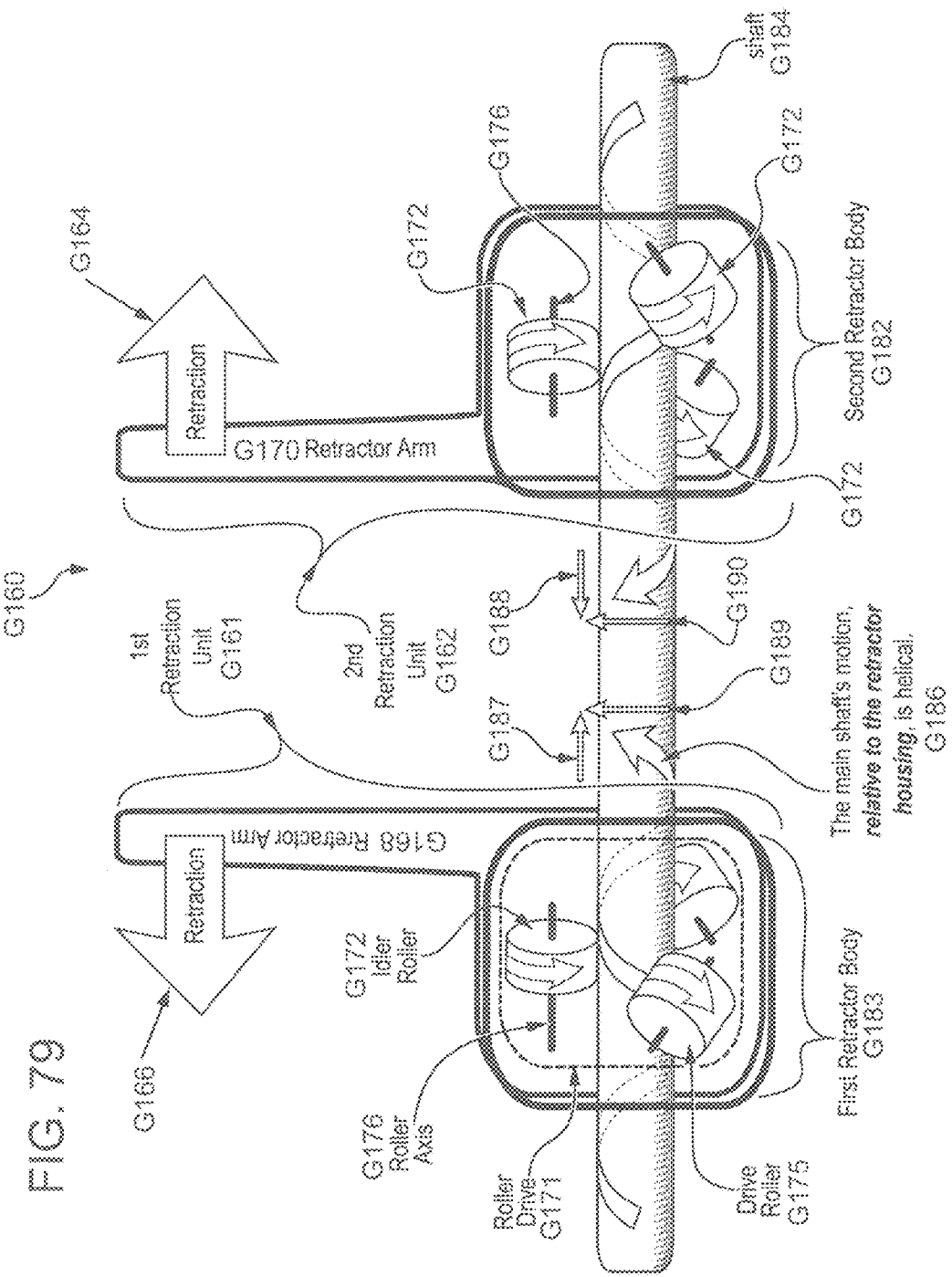
FIG. 79 shows another embodiment of a retractor using a roller drive with a circular shaft.

FIG. 79 shows one embodiment that uses roller drives in a retractor G160. Retractor G160 has two opposed retraction units a first retraction unit G161 and a second retraction unit G162, each comprised of a retractor arm G168 and G170, respectively, and a retractor body G183 and G182, respectively, mounted on shaft G184. Consider first retraction unit G161: retractor body G183 houses a roller drive G171 comprised of two idler rollers G172 and a drive roller G175, each oriented with its roller axis G176 of rotation oblique to the long axis of the shaft G184. The second retraction body G182 contains a set of three idler rollers G172, each oriented with its roller axis of rotation G176 oblique to the long axis of the shaft G184. Both retraction units G161 and G162 are, thus, driven by the one drive roller G175 in the first retraction body G183. The angle between the rollers' axes of rotation G176 in the first retraction body G183 and the long axis of the shaft G184 determines the motion G186 of the shaft G184 relative to the retractor body G183. The motion G186 of the shaft G184 can be broken into its two components of rotation G189 and translation G187 relative to first retractor body G183 and rotation G190 and translation G188 relative to second retractor body G182. The second retraction body G182 does not drive the shaft G184; rather, the rotation of the shaft G184 drives the translation G188 of the second retraction body G182 and, thus, the second retraction unit G162. Engagement of the retractor arms G168 and G170 with the patient's tissues prevents rotation of the second retraction unit G162 about the long axis of the shaft G184, so the angle between the rollers' axes of rotation G176 in the second retraction body G182 determines the translation rate G188. Thus, the driver roller G175 in the first retraction body G183 drives apart both retraction units G161 and G162 with a relative velocity of G187 plus G188, thereby providing retraction G164, G165.

Note that the angle between the rollers' axes of rotation G176 and the shaft G184 in the first retraction body G183 need not match the angle in the second retraction body G182. The angle can be such that the first retraction body G183 generates only rotation of the shaft G184, and the angle in the second retraction body G182 can be such that the second retraction unit G162 moves away from the first retraction unit, or any other range of combinations. Infinitely fine and smooth control of the rate of retraction by the rate of rotation of the driver roller (e.g. by a motor that actuates it) is thereby achieved by varying the angle between the rollers' axes of rotation G176 and the shaft G184 in the first retraction body G183, and also by varying the angle between the rollers' axes of rotation G176 and the shaft G184 in the second retraction body G182. A mechanism that variably changes the angle between the rollers' axes of rotation G176 and the shaft G184 in either or both retraction body G182, G183 can thus be used to control both the rate of retraction and the magnitude of the thrust (retraction force).

G.4 Dovetails

Figure 80:
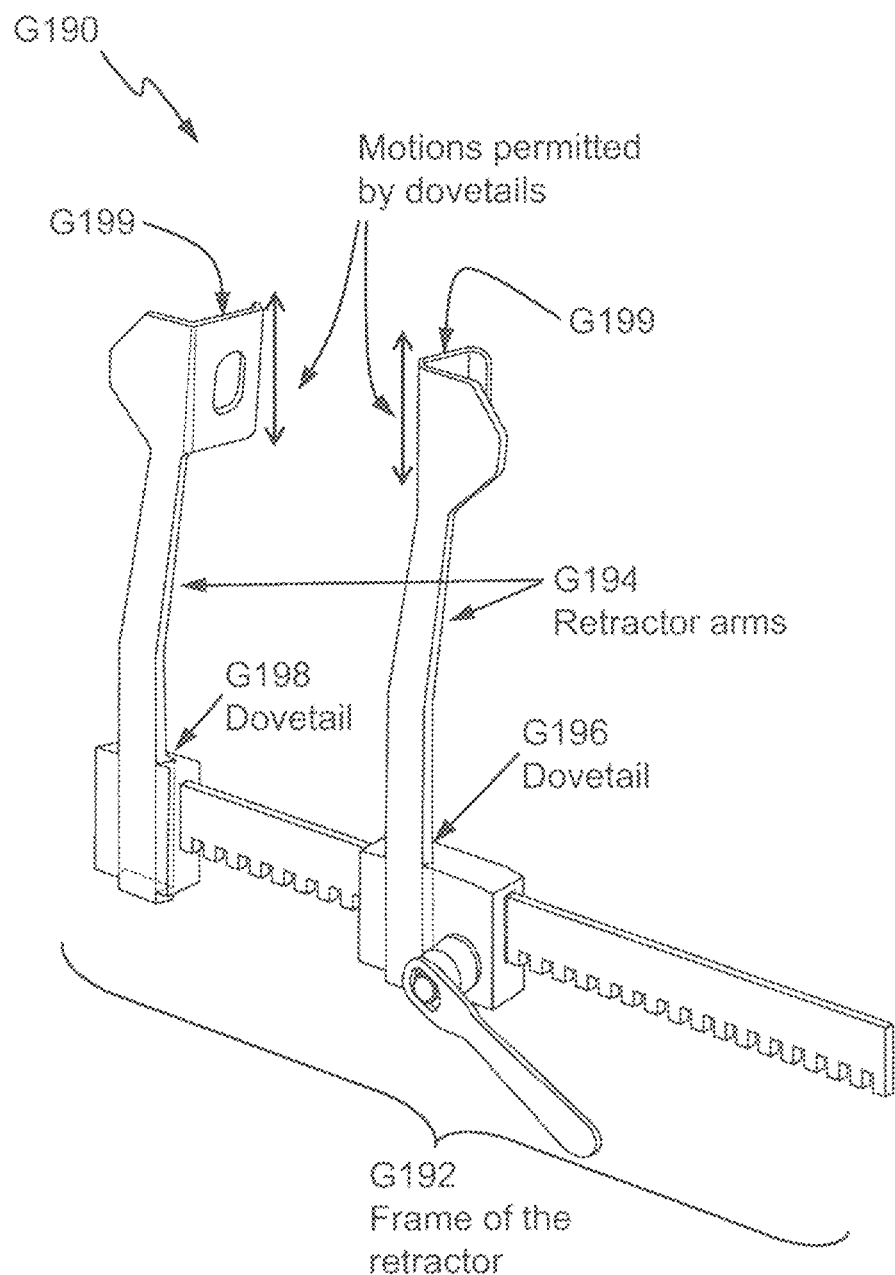
FIG. 80 shows another embodiment of a retractor having dovetail joints to permit additional motions of the retractor arms.

Another embodiment of a retractor G190 is shown in FIG. 80. Retractor G190 uses an alternative means for providing additional degrees of freedom of motion to the retractor arms G194. The two arms G194 of retractor G190 are mounted to the frame G192 of the retractor G190 via dovetail slides G196 and G198, the axes of which are perpendicular to the axis of the motion of the retractor blades (i.e., the axis of retraction). Each retractor arm G194 is thus free to slide out and back, i.e., perpendicular to the axis (or direction) of retraction. Much of the forgoing concerning the features and benefits of the Swing Blade Retractors G68 and G160 and applies here, except that the accommodating motions G200 of the retractor blades G199 enabled by the dovetails G196, G198 can be perpendicular to that of the Swing Blade Retractors G68 and G160. Additionally, the motions G200 are directly translational as opposed to rotational, as was the case for the Swing Blade Retractors G68 and G160, and the two may be combined as desired to increase a retractor's ability to accommodate the patient's reconfiguring tissues.

Figure 81:
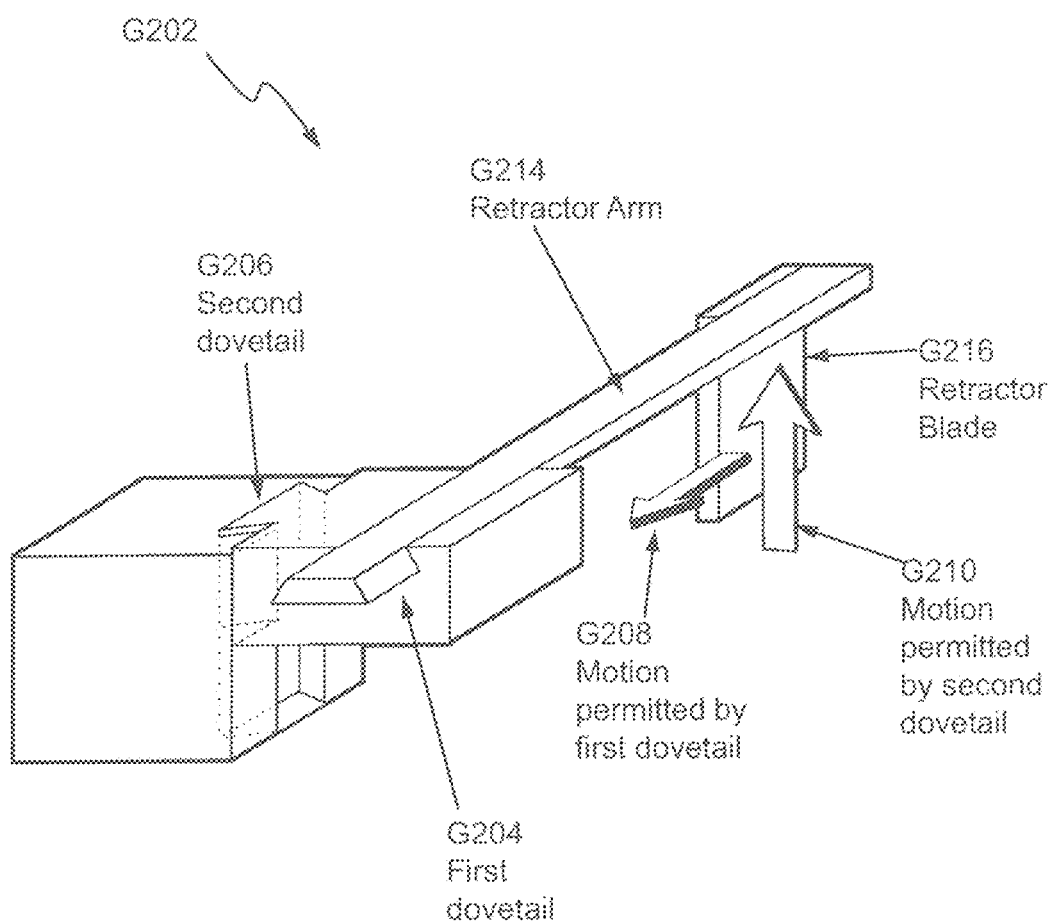
FIG. 81 shows another embodiment of a retractor arm having two dovetail joints to permit additional motions of the retractor arms.

FIG. 81 shows another retractor G202 that is fitted with two dovetail slides. First dovetail G204 permits motion G208 of retractor arm G214 and retractor blade G216, matching the motion G200 of dovetails G196, G198 in FIG. 80. Second dovetail G206 permits motion G210 of retractor arm G214 in a direction at right angles to the first dovetail G204, with both motions G208 and G210 being perpendicular to the axis of retraction. This means that this retractor can accommodate both a rise and fall of the body wall and a relative sliding of the edges of the incision parallel to the incision and within the plane of the skin of the patient, while still delivering retraction forces to the patient's body wall. This design still achieves stability and force minimization (now in 2 axes) by exploiting the tendency of the patient's body wall to re-appose.

G.5 Parallelograms

Figure 82A:
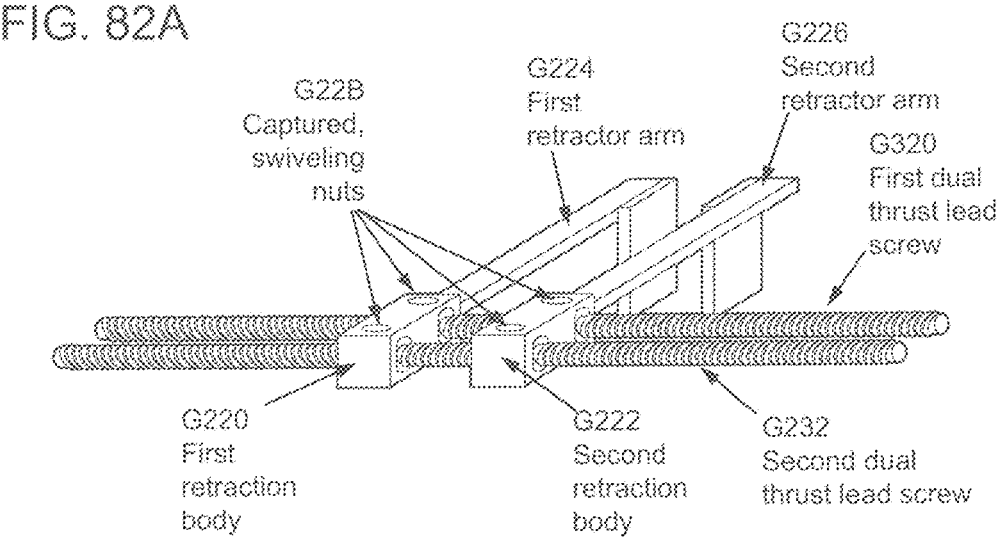
FIGS. 82A and 82B show another embodiment of a retractor having two dual-thrust lead screws permitting an additional degree of freedom of motion.
Figure 82B:
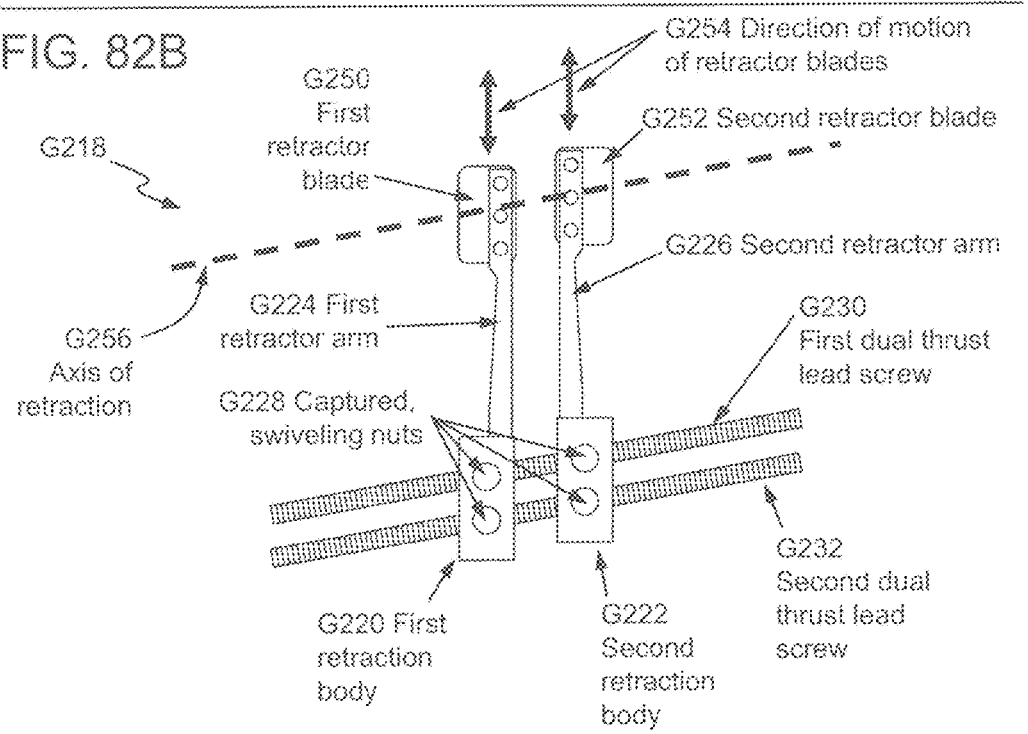

In yet another embodiment of a retractor G218 shown in FIGS. 82A and 82B, another mechanism is disclosed for providing an additional degree of freedom to the retractor arms G224, G226. Retractor G218 is comprised of two parallel dual-thrust lead screws G230 and G232 held by captured swiveling nuts G228 in a first retraction body G220 and a second retraction body G222. Each retraction body G220, G222 bears a retractor arm G224, G226, and a retractor blade G250, G252. Captured, swiveling nuts G228 are similar to those found in a Jorgenson clamp used for woodwork, such as those offered by Woodworker's Supply of Albuquerque, N. Mex. These captured, swiveling nuts G228 allow movement G254 of the retractor blades G250, G252 in a direction approximately perpendicular to the axis of retraction G256 (see FIG. 82*b*).

G.6 Tension Straps

Figure 83:
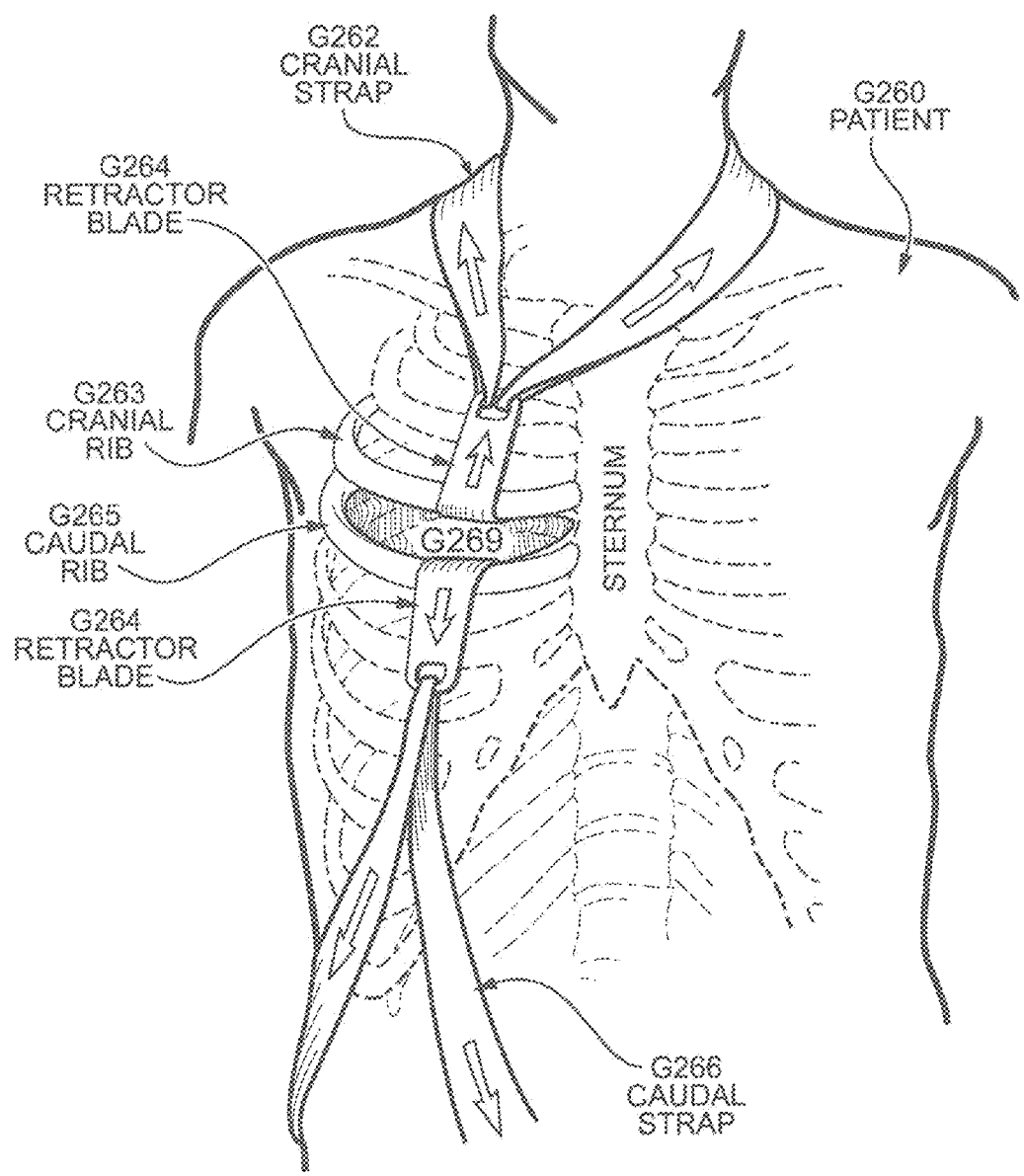
FIG. 83 shows another embodiment of a retractor for thoracotomy comprising retractor blades pulled by straps attached to a patient.

Another embodiment is shown in FIG. 83, which shows a different retractor configuration we call a "tension strap retractor" G258 that automatically aligns to the forces on the retractor blades G264. Tension straps include mechanisms integral to the strap that are capable of generating the force for retraction. Here, the retractor G258 takes the form of two or more thin straps, cranial strap G262 and caudal strap G266, that wrap around, and maybe behind, a portion of the body of the patient G260. Cranial strap G262 and caudal strap G266 are connected to retractor blades G264 which are inserted into the incision G269 to pull on the cranial rib G263 and caudal rib G265. The cranial strap G262 can be held in position by wrapping around a portion of the patient's G260 body, such as around the neck and/or shoulder. The caudal strap G266 can be held in position by wrapping around a portion of the patient's G260 body, such as around one leg. Alternatively, the straps G262 and G266 might anchor on the dermis of the patient G260 or on a bedframe. In this embodiment, retractor G258 self-aligns with the natural resistance of the body wall. Tension strap retractor G258 operates in tension, as opposed to a traditional compression- and bending-resisting frame. One benefit of a tension strap retractor G258 is that the volume of material required to withstand the retraction forces in tension is a small fraction of the volume of material required to withstand similar forces in, say, bending. Given this, a tension strap retractor can be very lightweight, further reducing unnecessary loading of the patient's tissues.

Figure 84:
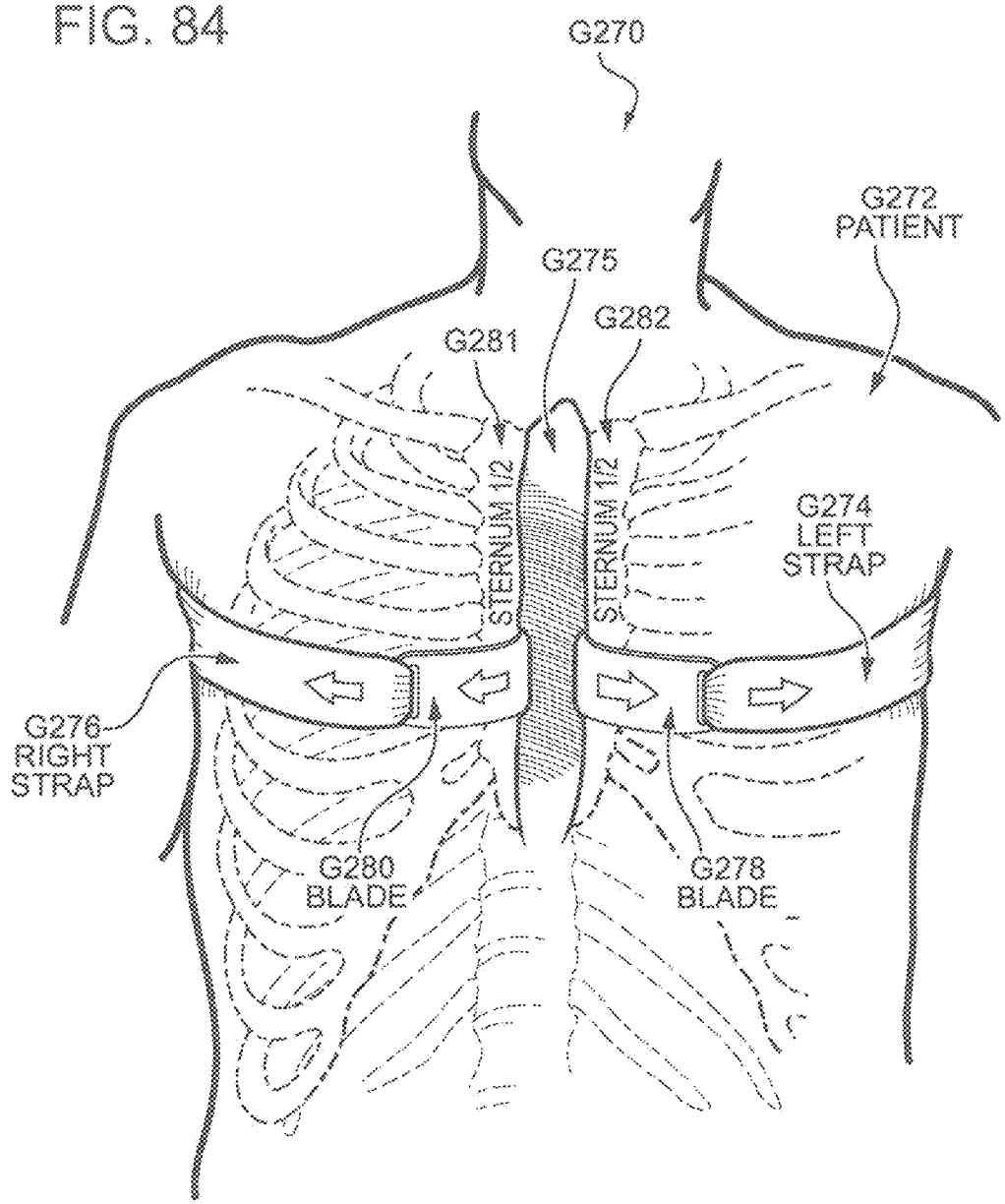
FIG. 84 shows another embodiment of a retractor for sternotomy comprising retractor blades pulled by two ends of a strap that wraps around a patient.
Figure 85:
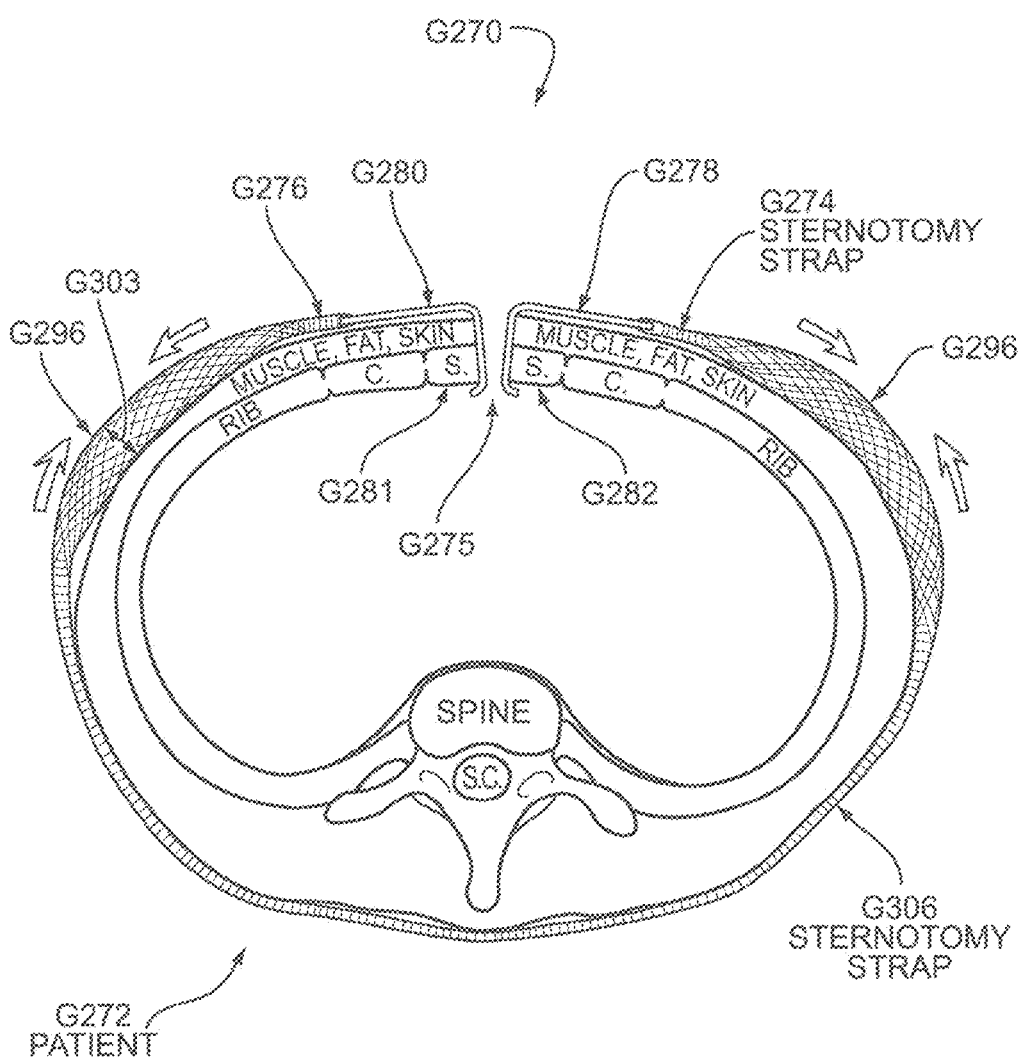
FIG. 85 shows another embodiment of a retractor for sternotomy comprising retractor blades pulled by the two ends of a strap that wraps around a patient and inflatable balloons for generating tension.

FIGS. 84 and 85 show another embodiment of a tension strap retractor G270 adapted for sternotomy. FIG. 84 shows a front view of tension strap retractor G270, and FIG. 85 shows a cross-sectional view through a patient's body G272. Tension strap retractor G270 simply wraps around behind the back of the patient G272 and automatically orients to open up an incision G275 that bisects the sternum into two halves G281 and G282. Retractor blades G278 and G280 reach into and/or around the margin of the incision G275, pulling back on sternum halves G281, G282. Tension strap retractor G270 pulls along the surface of the body of the patient G272. In this arrangement, the straps G274, G276 and G306 of the tension strap retractor G290 load the body wall such that straps G274, G276 and G306 remain aligned with the body wall and, thus, with the retraction forces for opening incision G275.

For tension strap retractor G270, the straps can be any thin and strong fabric, such as nylon webbing, that can resist tension. The straps can develop tension via a pull strap with sliding buckle, a ratchet pull, a winch, or by direct shortening of the fibers of the strap (for example by using shape memory alloy for the fibers). To this end, the strap might be fibrous netting surrounding pressure bladders G296, for example elastomer balloons residing within two-layer (or hollow) nylon webbing. In this case, the netting can be formed of fibers that run helically around the strap G276, G278, and G306 as a whole. In this example, the trajectory of the helical fibers forms an angle with respect to the path of the main strap; the angle can be very low (10 to 30 degrees) to facilitate developing significant force when the bladders G296 are inflated. Retraction forces can be generated by inflation alone if desired. Inflating the pressure bladders G296 would swell them, developing tension in the straps G276, G278, and G306, and so loading the retractor blades G278 and G280. The swollen bladders G296 can also provide a moment enhancer G303 (i.e., a stand-off) to reduce the magnitude of the tension that must be developed to create the forces sufficient to operate the tension strap retractor G290. Alternately, the stand-off G303 function might be achieved more directly by placing pads, pillows, blocks, or other compression-resisting members between the straps G276, Gs78, and G306 and the body of the patient G272. Saddles and pads can be added to the straps G274, G276 and G306 to distribute loading of the straps over the patient's body G272, or to concentrate the loads in particular areas, for example those areas that can withstand more concentrated pressure.

Another advantage of the tension strap retractor G270 is that it offers greater access to the surgical field because it has few components near the surgical field and these components lay close to the body of the patient G272 with tension strap retractor G270 having an extremely low profile, perhaps projecting no taller than 2 or 3 millimeters above the skin of the patient.

Figure 86:
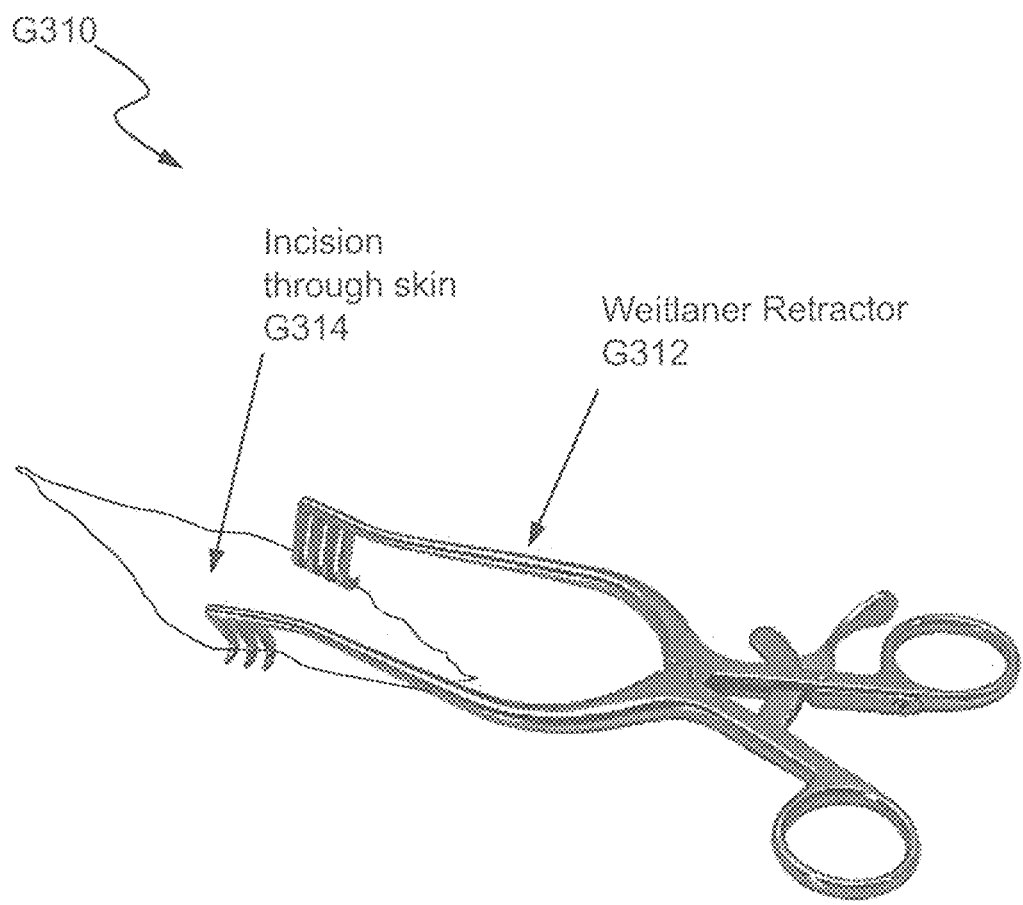
FIG. 86 shows an example of a Weitland retractor in the prior art for retracting skin inserted into an incision in the skin.

Tension strap retractors G290 can also be used for nonthoracic surgery. A common use of retractors, such as a Weitland retractor G312 (see FIG. 86) is to pull open an incision through the skin G314 to provide access to the anatomy beneath the skin for plastic surgery, orthopedic surgery, neurosurgery, and others. Retraction of the skin frequently requires only small forces, but conventional retractors in the prior art, such as a Weitland retractor G312, are typically scissor-like devices made of steel and are heavy, thereby interfering with surgical access and exerting unnecessary loads, especially during the second phase of retraction.

Figure 87:
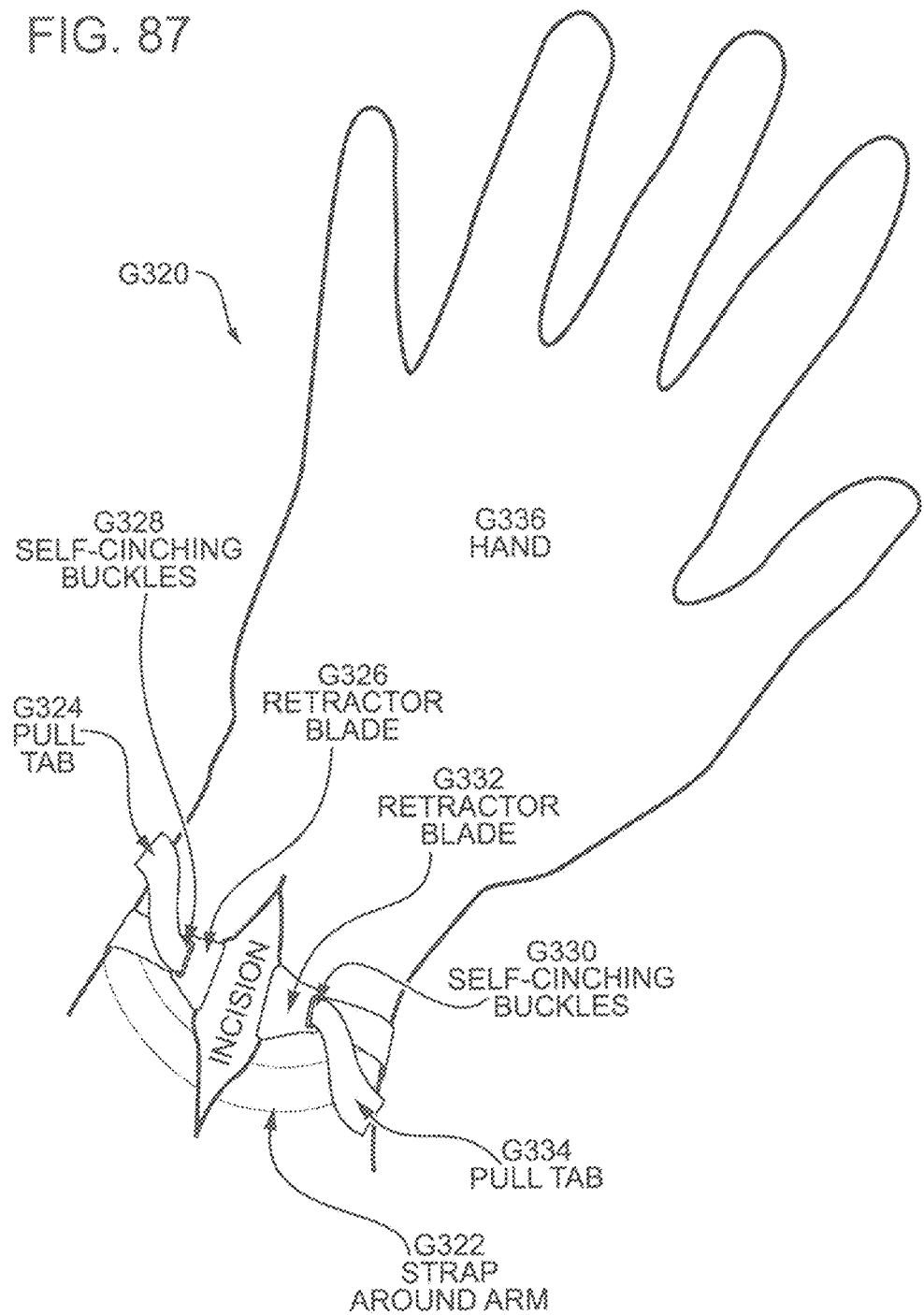
FIG. 87 shows another embodiment of a retractor comprising retractor blades pulled by straps that wrap around the patient's wrist and having pull tabs for generating retraction forces.

FIG. 87 shows a tension strap retractor G320 that is small and lightweight to, for example, open the skin on an arm for vascular surgery. The tension for retraction of the retractor blades G326 and G332 can be generated by pull tabs G324 and G334 that pull the strap G322 through a self-cinching buckle G328 and G330. Alternatively, tension could be generated by pulling the strap through a loop and then securing back onto the strap with Velcro.

H. Hard Tissue Engagers

Retractors, by their very nature, are typically made of rigid stainless steel to withstand the stresses of forcing open incision, including incisions through rigid structures like rib cages. Rib cages are themselves made largely of rigid bone and built to withstand the stresses of human locomotion or lifting large loads. The ribs, as it happens, are intermingled with several much softer tissues, including muscles which provide actuation for breathing and modifying posture, connective tissues which transmit forces from one rib to another and to the spinal column, vessels and arteries which supply nutrients and remove waste products, nerves providing signaling to and from the spinal chord; and all these are covered with skin and adipose tissues. During a thoracotomy in which a surgeon inserts the retractor blades and then cranks to spread the patient's ribs apart, the muscles apposed to those ribs and the nerves running along the surface of those ribs are often damaged when compressed between the rigid rib and the metal blades of the retractor. The soft tissues, supposedly protected by the ribs, are instead caught in the middle when the retractor blades push against the bones during retraction.

Figure 88A:
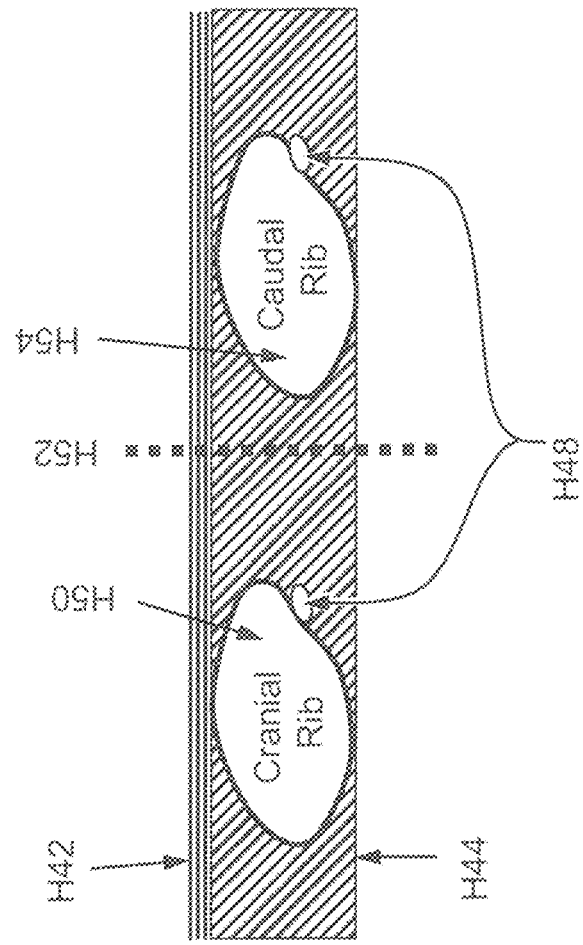
FIGS. 88A and 88B shows the anatomy of a chest wall around an incision for a thoracotomy.

In more detail, our ribs lie in a closely packed row deep under the skin, spaced about as far apart as they are wide, forming serial bony bars embedded in the muscle and other soft tissues that the ribs in turn support. As shown in FIG. 88A, running under the skin H42, cranial rib H46 and caudal rib H47 are roughly oval in cross section with the long axis of the oval aligned more-or-less parallel to the surface of the skin H42. (The following description uses the terms "caudal" H45 and "cranial" H43, which refer to relative position in the body, with cranial being closer to the head and caudal being closer to the feet.) Intercostal tissues H44, which are mostly muscle and connective tissues, span the space between the cranial margin H54 of the caudal rib H47 and the caudal margin H50 of the cranial rib H46. A delicate bundle of nerves and arteries (the neurovascular bundle H48, which includes the intercostal nerve, lays just inside the caudal margin of each rib H46, H47.

Surgeons, aware that the neurovascular bundle H48 can be easily damaged, prepare to insert the retractor by slicing the intervening intercostal tissues H44 closer to the cranial margin H54 of the caudal rib H47. This lessens the probability of accidentally cutting the neurovascular bundle H48 during the incision, and it provides a pad of muscle on the caudal margin H50 of the rib H46 that is cranial to the incision H52, in order to protect the neurovascular bundle H48.

Figure 88B:
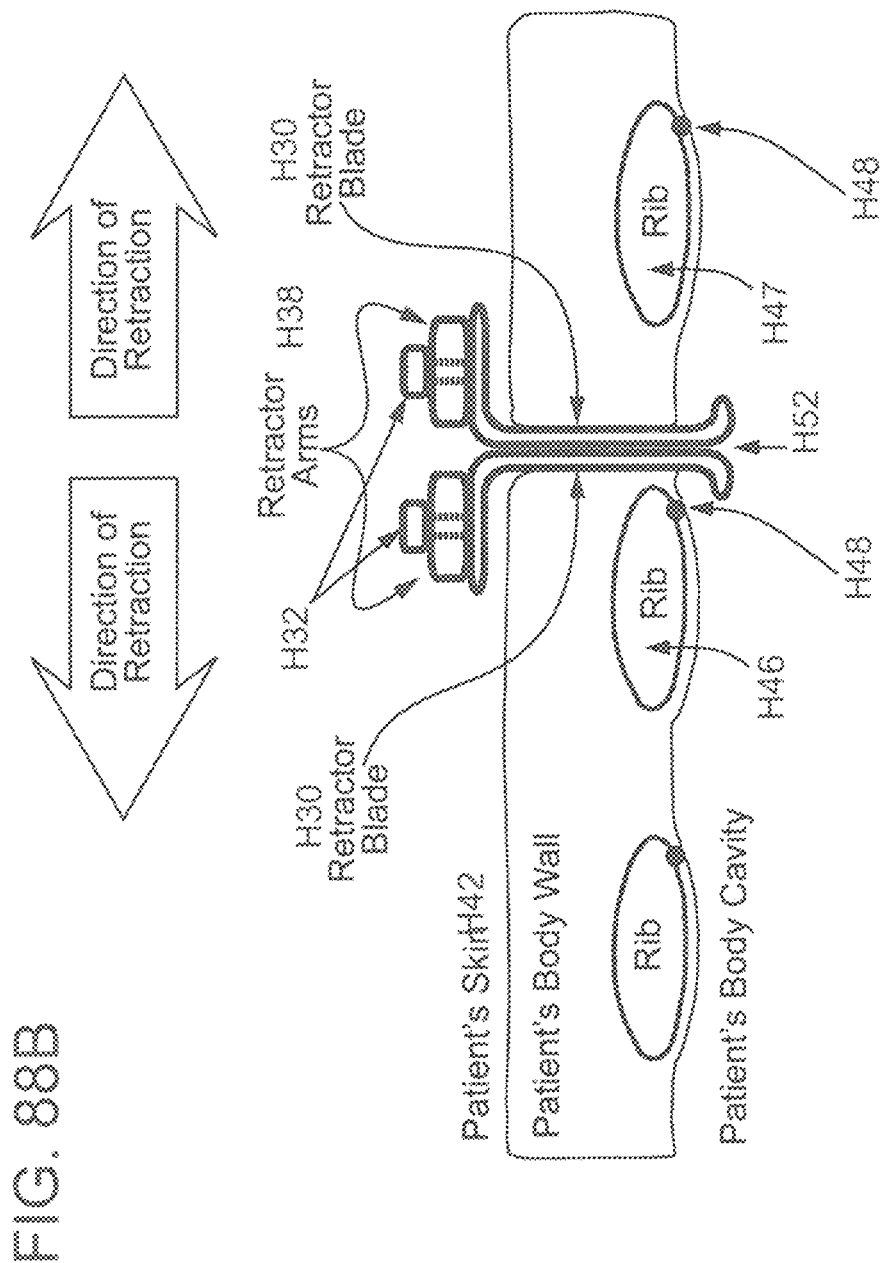

As shown in FIG. 88B, the retractor is inserted into the incision H52, with retractor blades H30 positioned to push against the two ribs H46 and H48. Retractor blades H30 are attached to retractor arms H32 by fasteners H38 such that retraction pries apart the ribs H46, H47 when retraction arms H32 separate during the first phase of retraction.

Figure 89:
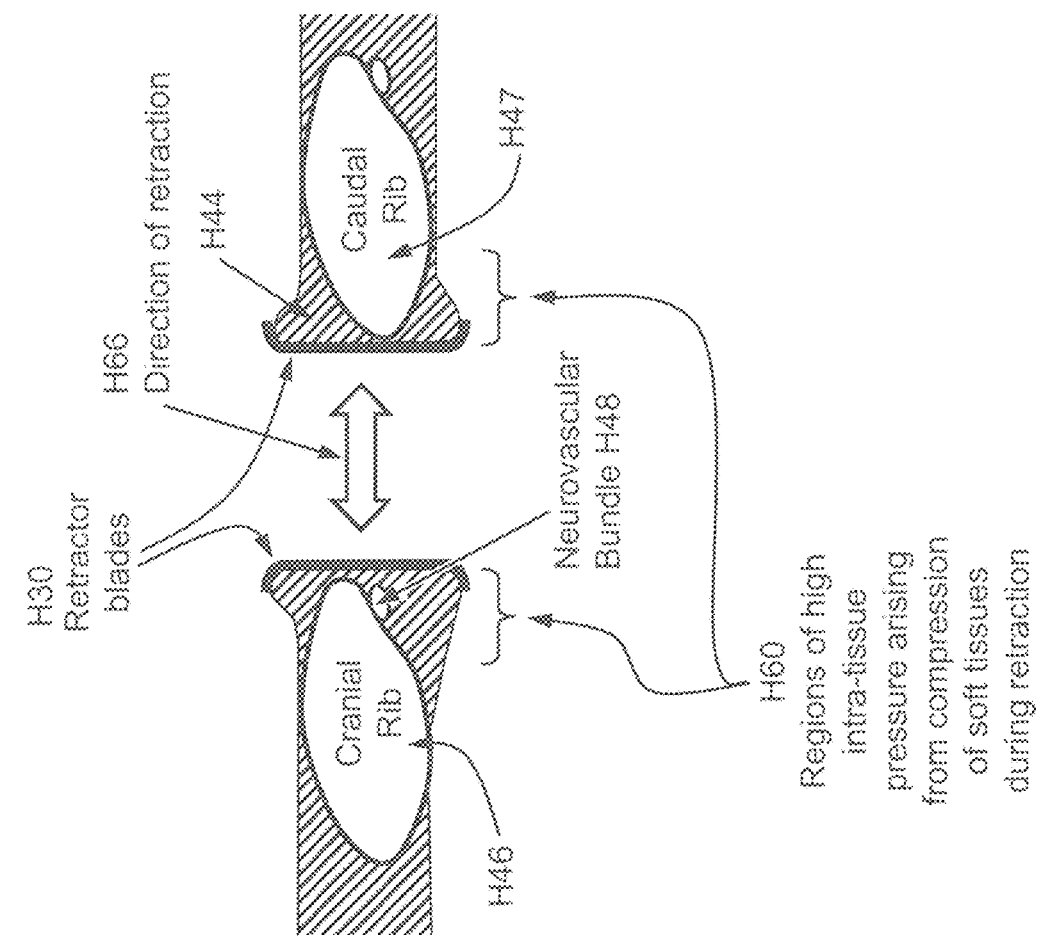
FIG. 89 shows the deformation of the tissues of the chest wall by retractor blades during a thoracotomy.
Figure 90:
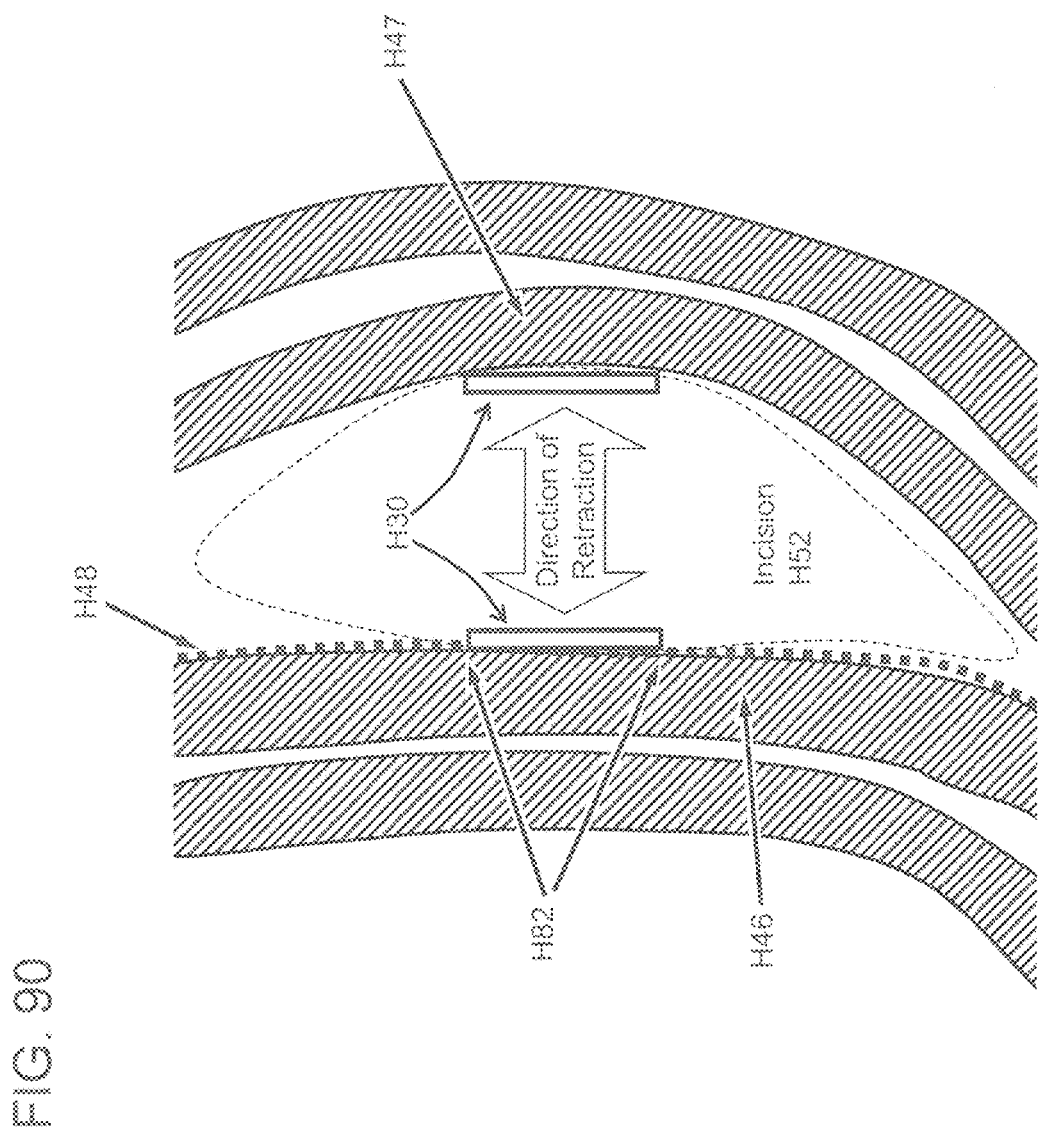
FIG. 90 shows pinch points generated by retractor blades on the ribs and neurovascular bundle during a thoracotomy.
Figure 91:
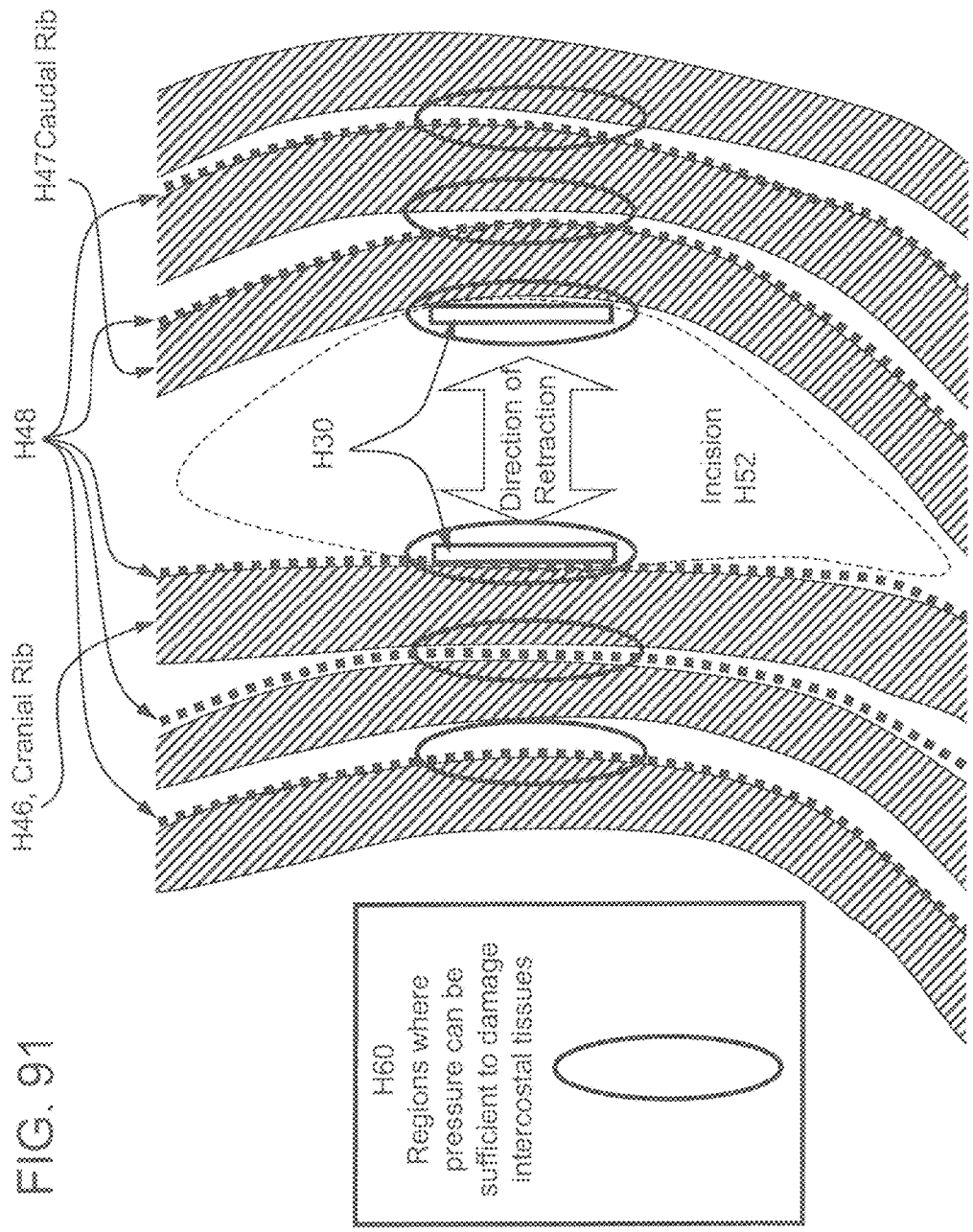
FIG. 91 shows regions of potential damage to tissues caused by elevated tissue pressure during thoracotomy.

Damage to the neurovascular bundle H48, nevertheless, occurs. As depicted in FIGS. 89 and 90. FIG. 89 shows a cross-sectional view, and FIG. 90 shows a top view. Regions of high pressure H60 are created in the intercostal tissues H44 that are compressed between the ribs H46, H47 and the hard retractor blades H30. The pressures are large, owing to the large forces used to separate the ribs. Subsequently, tissues are mechanically crushed. The neurovascular bundle H48 can be pinched, especially at pinch points H82 created by the edges (i.e., corners) of the blades H30 where they intersect the ribs H46 and H47. The tissue pressures underlying the retractor blades H30 can be sufficiently high to block both blood flow through the vessels of neurovascular bundle H48 and perfusion of all this tissue underlying the retractor blades H30. Lack of perfusion causes anoxia in theses tissues, which damages all tissues, especially nerves. Additionally, movement of ribs H46, H47 during retraction can be sufficiently large that a rib H46, H47 can impinge on the adjacent rib further from the incision, as shown in FIG. 91. Again, the resulting regions of high tissue pressure H60 between ribs can be sufficiently large that intercostal tissues H44, including the intercostal nerves in neurovascular bundles H48, can be damaged one or even several ribs removed from the incision (Rogers, Henderson et al. 2002).

The regions of high pressure H60 and the pinch points H82 are established during the first phase of retraction and are then sustained during the second phase of retraction for the duration of the surgical procedure, which can often be hours.

Damage to intercostal tissues caused by the regions of high pressure H60 and by pinch points H82 is thought to underlie much of the pain caused by thoracotomies, especially damage to the intercostal nerves of the neurovascular bundles H48. Thoracotomies are considered one of the most painful of all surgical procedures. Pain is always intense for days after surgery and, unfortunately, can last for months to years, and sometimes is permanent. The long-lasting pain after a thoracotomy has led to the identification of a "post-thoracotomy pain syndrome".

This great pain following thoracotomies, and the associated morbidity and mortality, are the main drivers for alternatives to these open-chest procedures, including minimally invasive surgery (MIS). While many MIS procedures have been developed, such as mini-thoracotomies, endoscopic surgeries, and the like, their adoption rates have been low.

An improved retractor blade that decreases tissue damage during retraction, especially to the intercostal nerve, would be of great benefit. It would reduce post-operative pain while retaining full surgical access.

To these ends, we disclose apparatus and methods for attaining favorable alignments and positive engagements with a patient's hard tissues, for example bones (e.g. ribs) or teeth. With the various embodiments of the present invention one can rapidly and assuredly apply forces sufficient to displace or deform the patient's tissues for medical procedures while entirely avoiding compressing, crushing, or compromising adjacent soft tissues, thus preventing post-surgical pain.

Figure 92B:
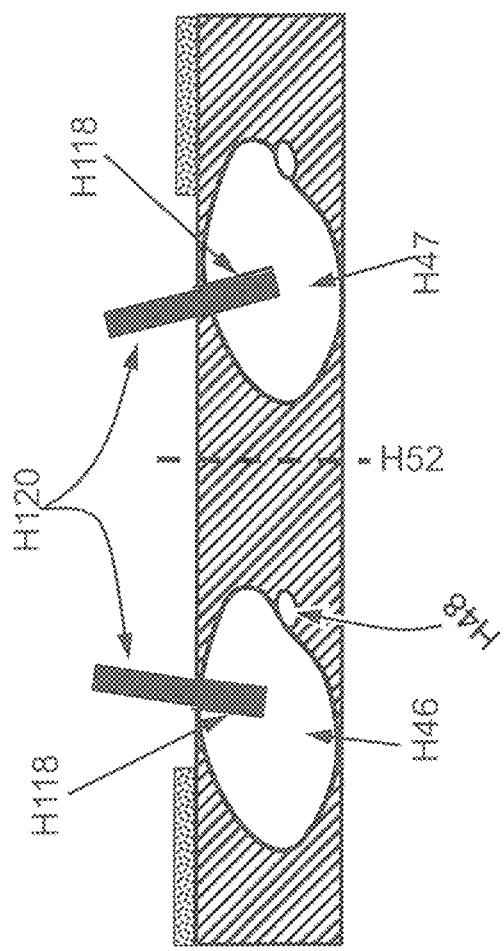

In one embodiment shown in FIG. 92A and FIG. 92B, holes H118 are drilled from above into the ribs H46 and H47 and rigid posts H120 are inserted into these holes to serve as anchors for the retractor. Holes H118 can be drilled at an angle H119 such that, after the posts H130 are inserted, the posts possess an angle with respect to the axis of loading to ensure the posts don't slip out of the holes during retraction. The posts H120 can be made such that they snugly fit into the holes H118 to ensure good purchase in the bone of ribs H46 and H47. Optionally, the posts H120 can possess threads and be screwed into position in the ribs H46 and H47 to ensure good purchase in the bone of ribs H46 and H47. A jig can be used when drilling the holes to ensure appropriate angle, depth, and position of the holes H118.

As shown in FIG. 92C, the posts H120, after placement in the holes H118 drilled in the ribs H46 and H47, are then used as secure anchors for retractor arms H100 that push against the posts H120 to move the ribs H46 and H47 without pushing on soft tissue. The posts H120 can be used for closing the incision as well.

Figure 93:
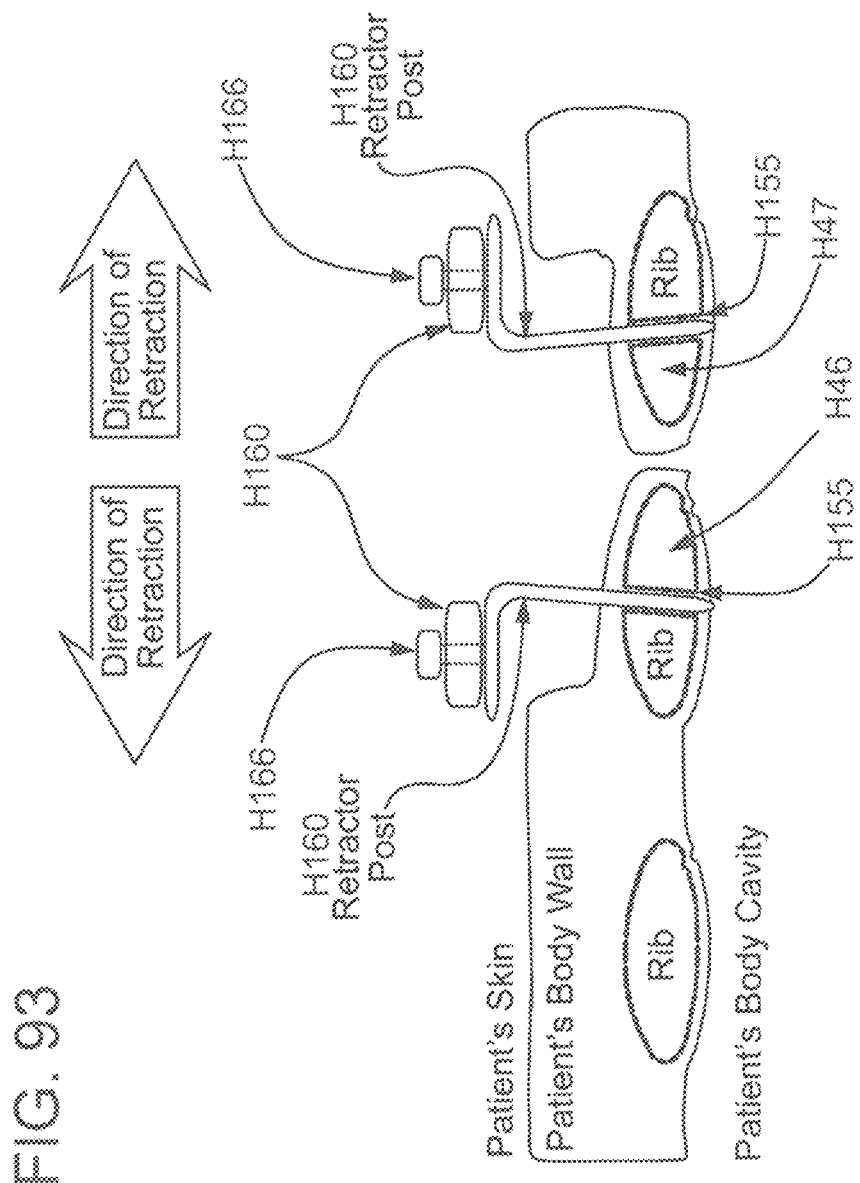
FIG. 93 shows another embodiment of a retractor comprising posts that engage the arms of the retractor.

Another embodiment is shown in FIG. 93. The posts H160 are attached by mechanical fasteners H166 to the retractor arms H170. Also, the holes H155 are drilled all the way through the ribs H46, H47. Note that different depths of the holes H155, including holes that pass through the ribs H46, H47, can be used with any configuration of posts H160. Note, also, that when the holes H155 are drilled all the way through the ribs H46, H47, holes H155 can be used during closing, whereby sutures pass through the holes H155, running from caudal rib H47 to caudal rib H46 to re-appose the ribs and to secure them into position. (It is prior art that such holes are drilled specifically for re-apposing and securing the ribs with sutures, but the holes are not used for retraction.)

Figure 94A:
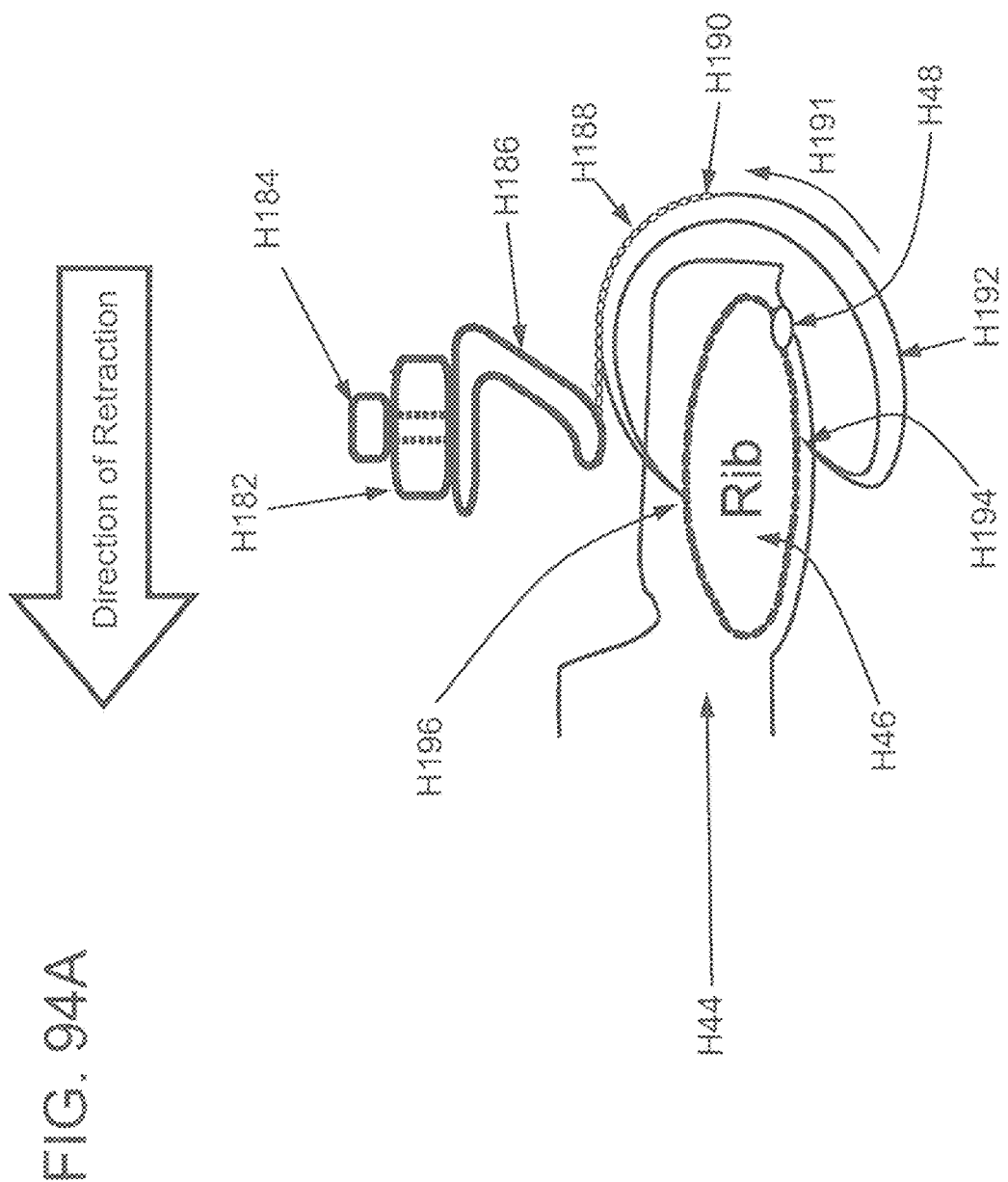
FIGS. 94A and 94B show another embodiment of a retractor comprising clips that grasp the ribs and attach to the arms of a retractor.
Figure 94B:
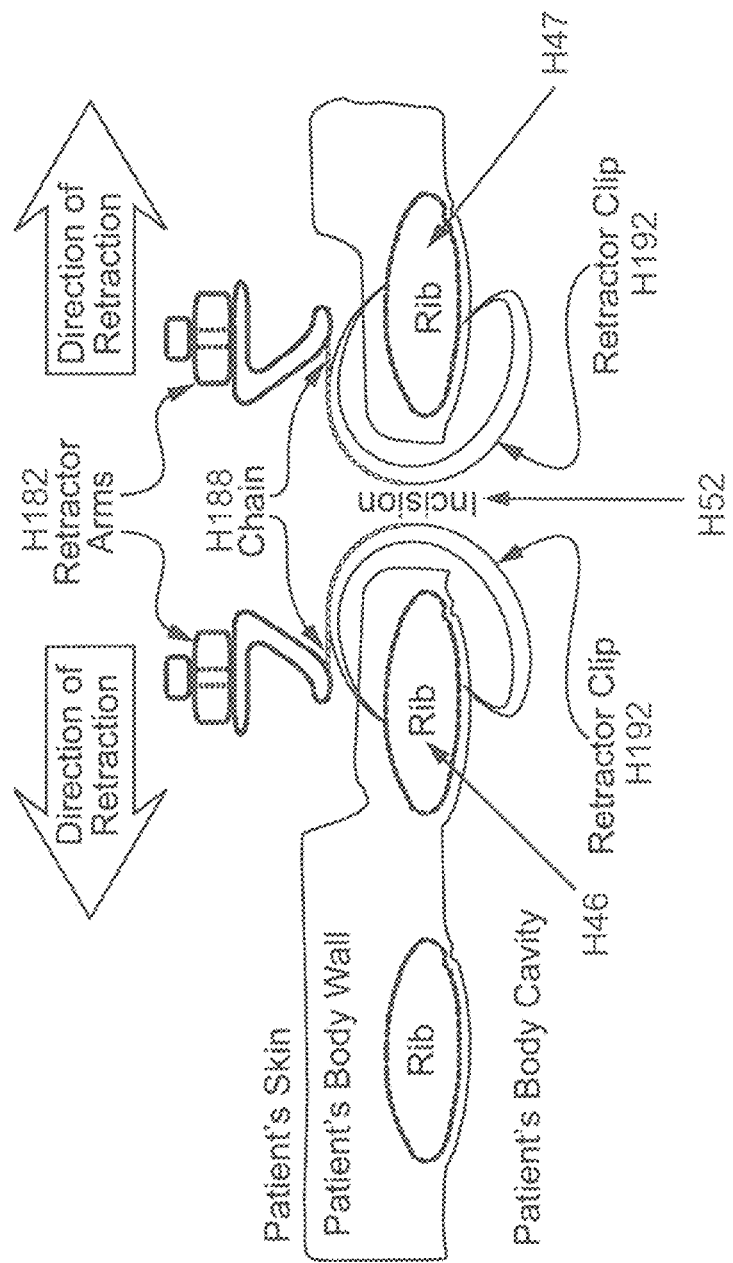

FIGS. 94A and 94B show another embodiment of a device to engage ribs but for which holes need not be drilled. Rather, elastic circumferentially surrounding clips H192 can be attached to the ribs H46, H47 such that each rib H46, H47 is firmly clasped without exerting pressure on soft tissues H44 surrounding ribs H46, H47. As shown in FIG. 94A, clip H192 possesses points, or spikes, including a top spike H196 that engages the outer surface of the rib H46 and a bottom spike H194 that engages the inner surface of the rib H46. The spikes H194 and H196 automatically seat onto or into the surface of the bone (i.e., rib H46), crucially, away from the neurovascular bundle H48. The clip H192 is attached to a descenders H186 that are attached to retractor arm H182 by mechanical fasteners H184. Descender H186 descends from the retractor arm H182. Clip H192 is attached to descender H186 by a flexibly bendable, tensily stiff element, such as cable or chain H188, which runs tangentially around and attaches to the clip H192 at point H190. Clip H192 is hooked into, and so loads, the ribs H180. The clip H192 possesses a roughly even radius that is a function of the tension in the chain H188, that is, the radial distance separating the clip H192 from the surface of the rib H46 changes as the tension in the chain H188 changes. Use of descender H186 ensures an advantageous angle for pulling on the chain H188 around the circumference of the clip H192. When the spikes H194 and H196 are loaded for retraction of the rib H46, by tension on the chain H188, the resulting torque on the clip H192 acts as if to rotate the entire clip H192. But, since the clip's H192 rotation is largely restrained by the spikes H194 and H196 inserted onto or into the surface of the rib H46, the torque instead causes the clip H192 to "rise up on tiptoes," i.e., the elastic circumferential clip H192 increases its radius away from the surface of rib H180, doing so by angling the spikes H194 and H196 and firmly driving the spikes H194 and H196 into the bone H46, thereby more securely engaging with the rib H46. Bottom spike H194 effectively serves as a pivot point for the clip H192 which, when combined with rotation H191 of the clip H192, forces the top spike H196 into the bone H46. Thus, slippage of the clip H192 is prevented by the spikes H194 and H196, and sufficient force can be exerted on the rib H46 to achieve retraction without loading the soft tissues H44, including the neurovascular bundle H48.

As shown in FIG. 94B, clips are placed on the both ribs H46 and H47 on both sides of the incision H52, and retraction moves the ribs apart.

Figure 95B:
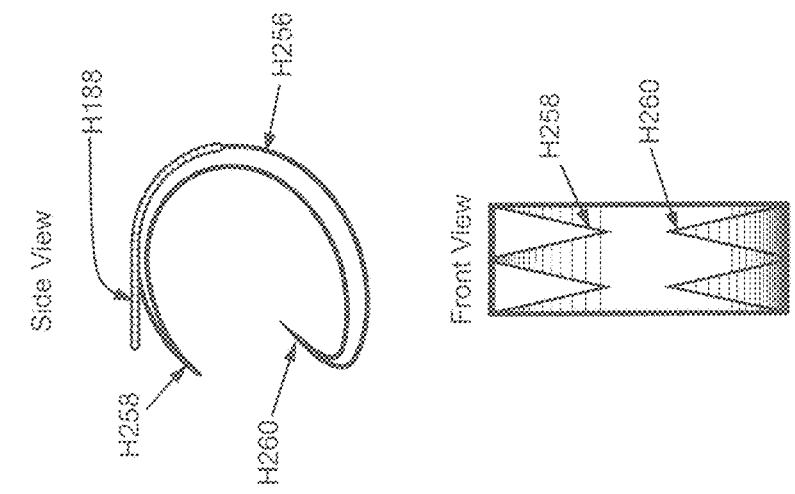
FIGS. 95A and 95B show embodiments of retractor clips having one or two spikes, respectively, for engaging the ribs.
Figure 95A:
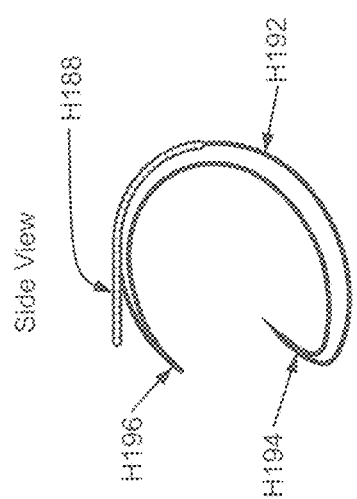
Figure 96:
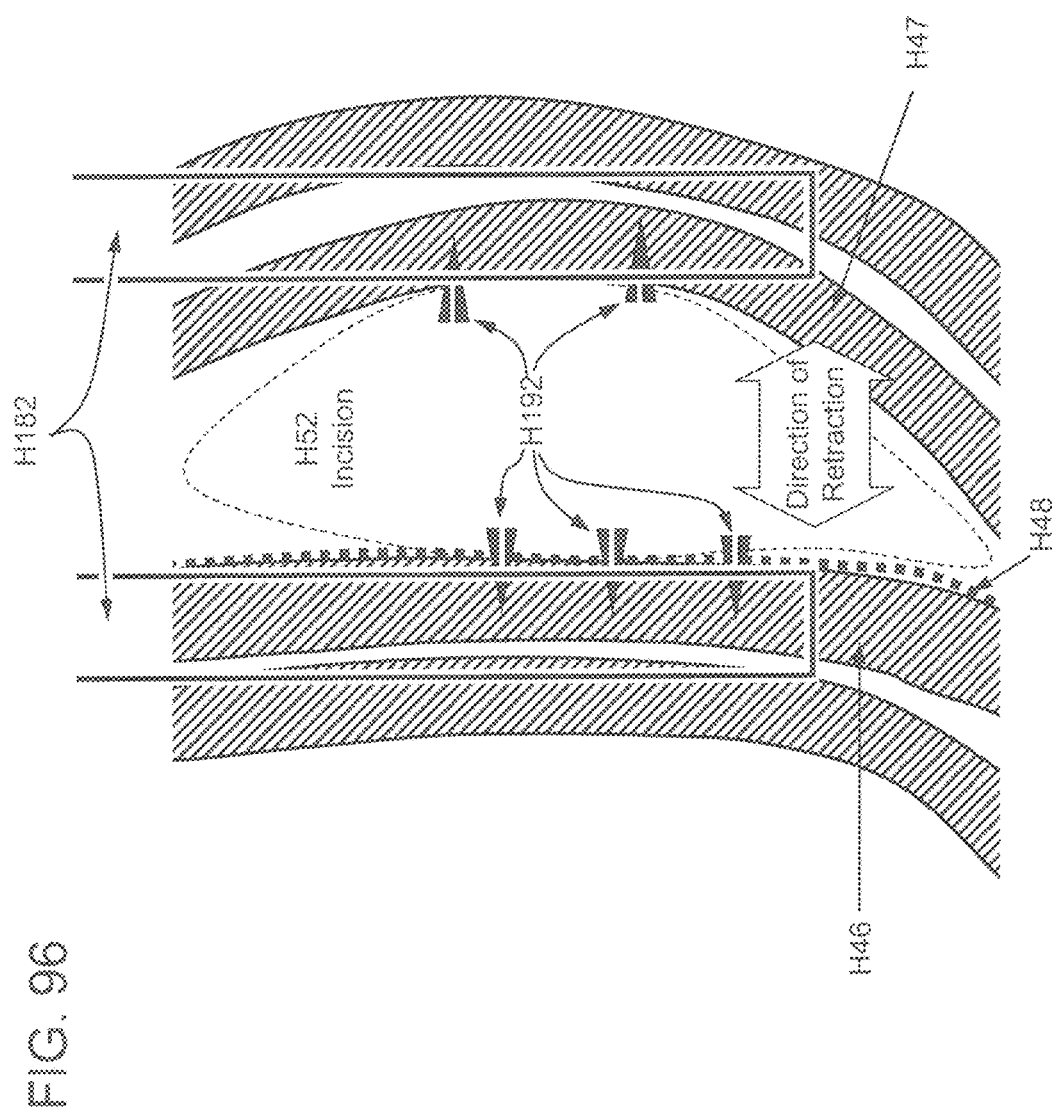
FIG. 96 shows a top view of another embodiment of a retractor comprising two retractor arms and multiple clips for engaging the ribs for a thoracotomy.

FIGS. 95A and 95B illustrate different configurations of spikes on clips to achieve more secure engagement with the rib. FIG. 95A shows a clip H192 like those in FIGS. 94A and 94B. Clip H192 has single spikes H194, H196. Alternatively, FIG. 95B shows that a clip H256 can have multiple spikes on each end, double spikes H258 and H260 in this example, which distribute loading of the spikes H188 on a rib and also prevent sideways rolling of the clip H256 if chain H188 should pull a bit sideways.

Clips H192 and H256 are positioned after the intercostal incision is made, and then the chains H188 are attached to the descender H186. Similarly, the chains H188, or other tensile element, can be attached to the descender H186 with sufficient length of chain H188 to provide slack during placement of the clip H192 or H256. After placement of the clip H192 or H256, the slack is then removed before retraction commences. Removal of the slack can be by any of several one-way slip attachments, such as a ratcheting cable tie or "zip tie" as offered for sale by Nelco, Inc. of Pembroke, Mass.

FIG. 95 illustrates the placement of one or more clips to distribute loading along the ribs during retraction. Multiple single spike clips H192 are placed on each rib H46 and H47, possibly with different numbers on each rib H46 and H47. Multiple clips H192 are attached to retractor arms H182 and are, thus, spaced along the rib margin facing the incision H52. When retractor arms H182 move apart during retraction, the multiple clips distribute loading of the rib to decrease the chance of rib fracture.

Figure 97A:
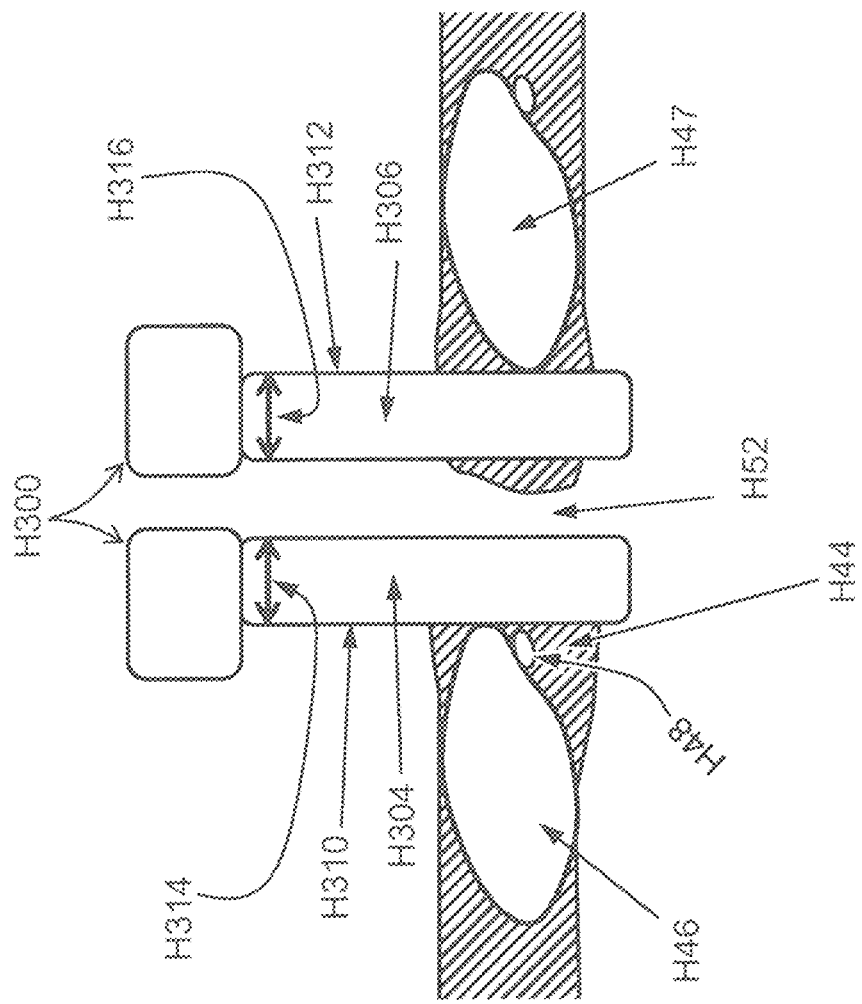
FIGS. 97A through 97D show the top and side views of another embodiment of a retractor comprising two retractor arms having descender posts for engaging ribs, and two side views of a descender posts having hooks and rotatable mounts.
Figure 97B:
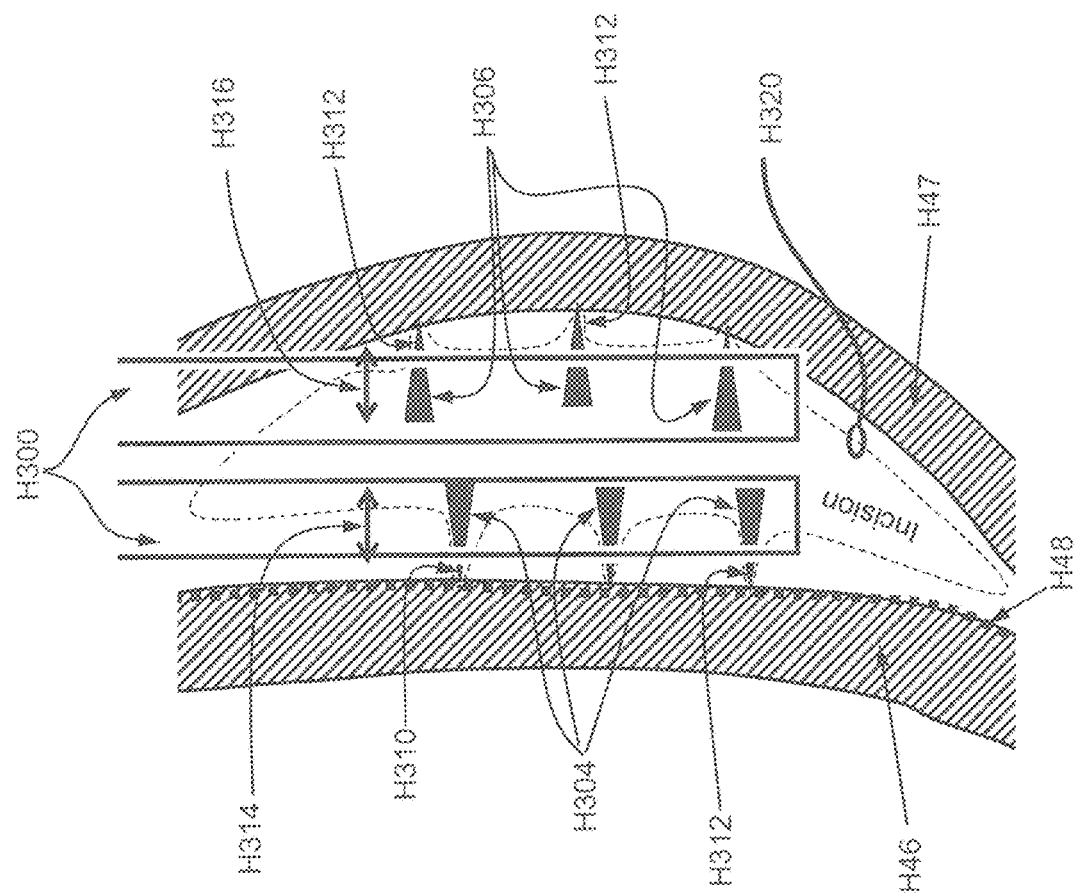
Figure 97C:
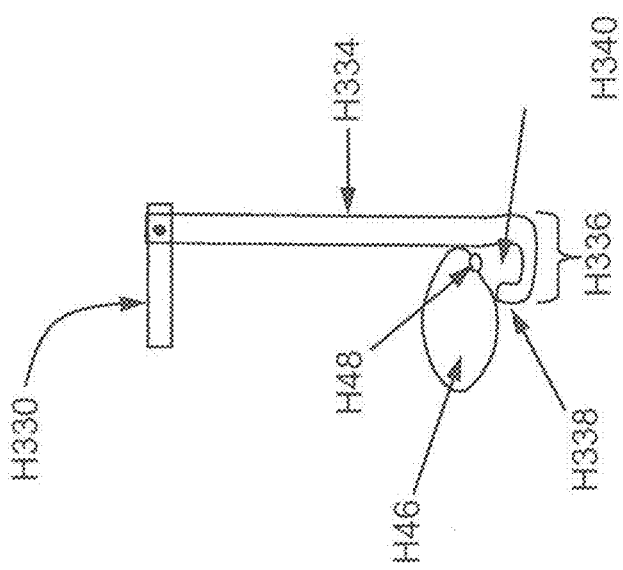

FIGS. 97A through 97D show another embodiment of a device that engages the ribs directly, minimizing trauma to intercostal tissues. FIG. 97A shows a side view and FIG. 97B shows a top view. A device can cut through soft tissues H44 to abut hard tissues. The cut through the soft tissues is a small trauma relative to the compressive loading of a larger retractor blade. Retractor arms H300 can have descender posts attached, a first descender post H304 abutting cranial rib H46 and a second descender post H306 abutting caudal rib H47. Descender posts H304 and H306 can have their positions adjusted (arrows H314 and H316) closer or farther from the centerline of the incision H52 (i.e., left-right in FIGS. 97A and 97B) to permit automatic balancing of loads as disclosed in Section F. Descender posts H304 and H306 can have sharpened edges H310 and H312, respectively, that face the ribs H46 and H47, respectively, such that the descender posts H304 and H306 can penetrate laterally through the margin of soft intercostal tissues H44 to abut the ribs H46 and H47 directly. Thus, rather than crush the intercostal tissue, descender posts H304 and H306 slice into the intercostal tissues H44. Because descender post H302 has a vertically straight margin oriented towards the cranial rib H46, descender post H302 can abut the cranial rib H46, but does not impinge on the neurovascular bundle H48 that lies just underneath the caudal edge of the cranial rib H46 (see FIG. 97A). The sharp edges H310, H312 of descender posts H304, H306 can be serrated, or possess other structures to engage the ribs, to prevent the descender post H304, H306 from slipping off the rib H46, H47. Alternatively, FIG. 97C shows a different descender post H334 descending from retractor arm H330. Descender arm H334 has a retraction hook H336 to facilitate positioning against the rib H46 and to prevent slipping. Preferably, such structures include appropriate stand-offs H338 and curvature such as to create a hollow H340 to avoid impinging on the neurovascular bundle H48.

Figure 97D:
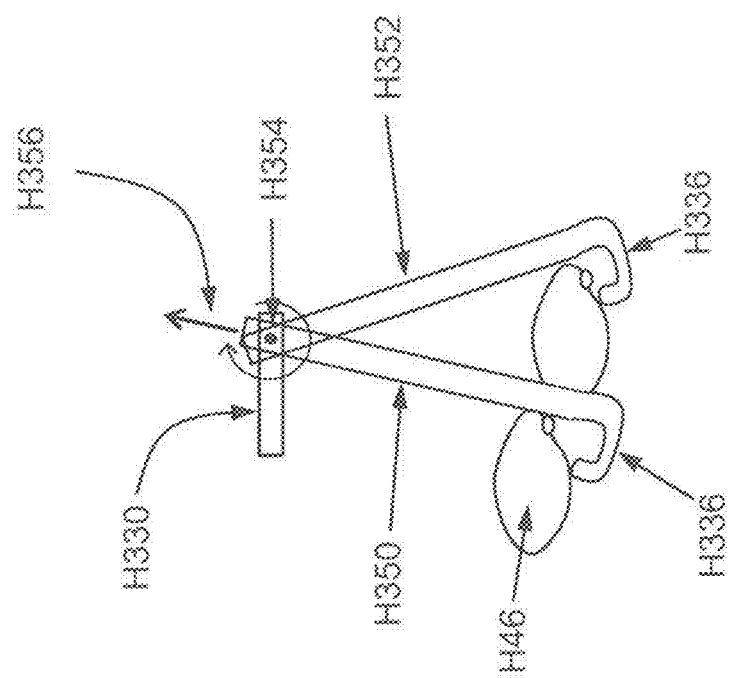

Descender posts can be mounted to the retractor arms such that their positions can be adjusted left-right (indicated by arrows H314 and H316 in FIGS. 97A and 97B), variably pushing through the soft tissues H44 at the margins H320 of the incision H52 to accommodate curvature of the ribs H46, H47 and thereby ensure distribution of loads on the ribs H46, H47. Any of the embodiments disclosed in Section F are appropriate. Additionally, as shown in FIG. 97D, a retractor arm H330 can have descender posts H350 and H352 attached by lockable, telescoping, rotatable mounts H354. Thus, after the descender posts H350 and H352 have been placed into an incision, each descender post H350 or H352 can be swung up against the rib H46, telescoped by a motion shown by arrow H356 to bring the hook H336 into contact with the bottom of the rib H46, and then locked into position.

Figure 98A:
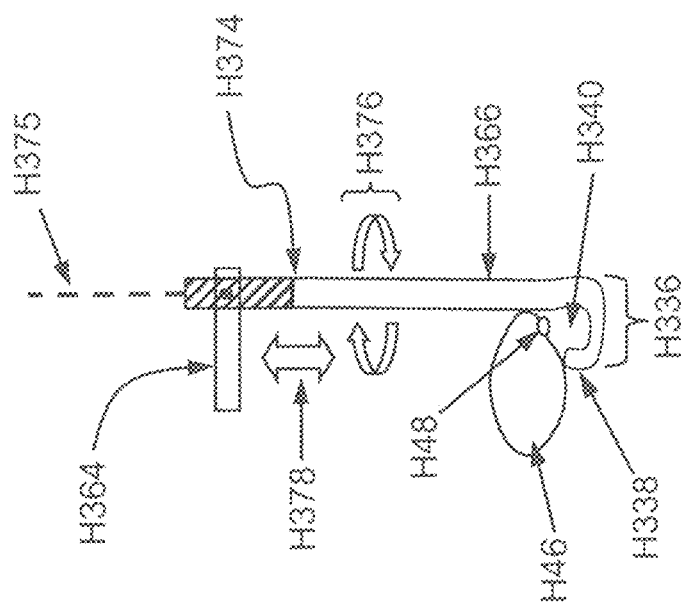

Refer now to FIGS. 98A and 98B which show another embodiment using retraction hooks that have an additional degree of freedom of motion facilitating placement onto the rib. FIG. 98A shows a side view, and FIG. 98B presents a top view showing the steps of placing the retraction hook onto the rib. Consider FIG. 98A, a descender post has a shaft H366 that attaches to retractor arm H364 via swivel joint H374. Shaft H366 has a Retraction hook H336, including a stand-off H338, that extends under the rib H46 and forms a hollow H340 to avoid contact with or compression of neurovascular bundle H48. Swivel joint H374 permits rotation H376 of shaft H366 around an axis of rotation H375 parallel to the axis of the shaft of the descender post H366 (as shown in FIG. 983A). As shown in FIG. 98B, Step 1 (block 390), the retraction hook H336 on shaft H366 can be aligned such that, before insertion into the incision H52, the retraction hook H336 is parallel to both the rib H46 and the incision H52. In Step 2 (block 392) of FIG. 98B, after insertion into the incision H52, the retraction hook H336 can be rotated to position the retraction hook H336 under the rib H46. Additionally, the length of the shaft H366, or the distance between the retraction hook H336 and the retractor arm H364, can be adjusted (arrow H378), as shown in FIG. 98A, to further permit positioning of the retraction hook H336 relative to the rib H46.

Figure 99:
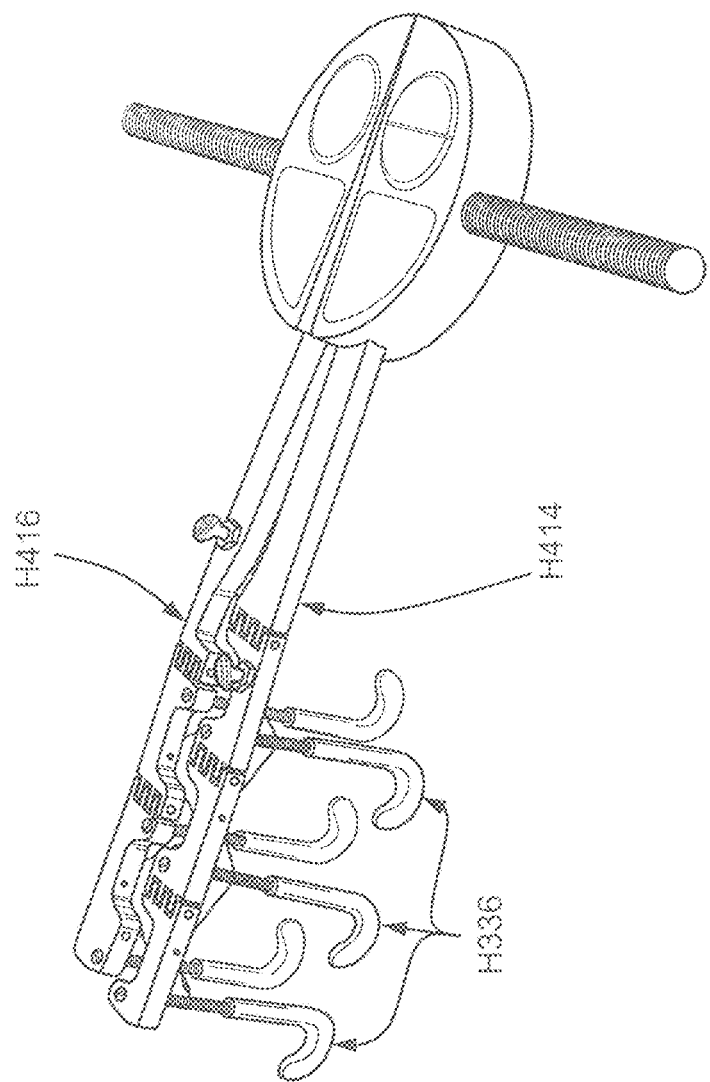
FIG. 99 shows a 3D model of a retractor having descender posts with hooks rotatably mounted on retractor arms.

FIG. 99 shows a three-dimensional working model of a retractor H412 equipped with first and second retractor arms H414 and H416, respectively, each having three (3) descender post shafts H366 with rotatable, height-adjustable, retraction hooks H336.

Figure 100:
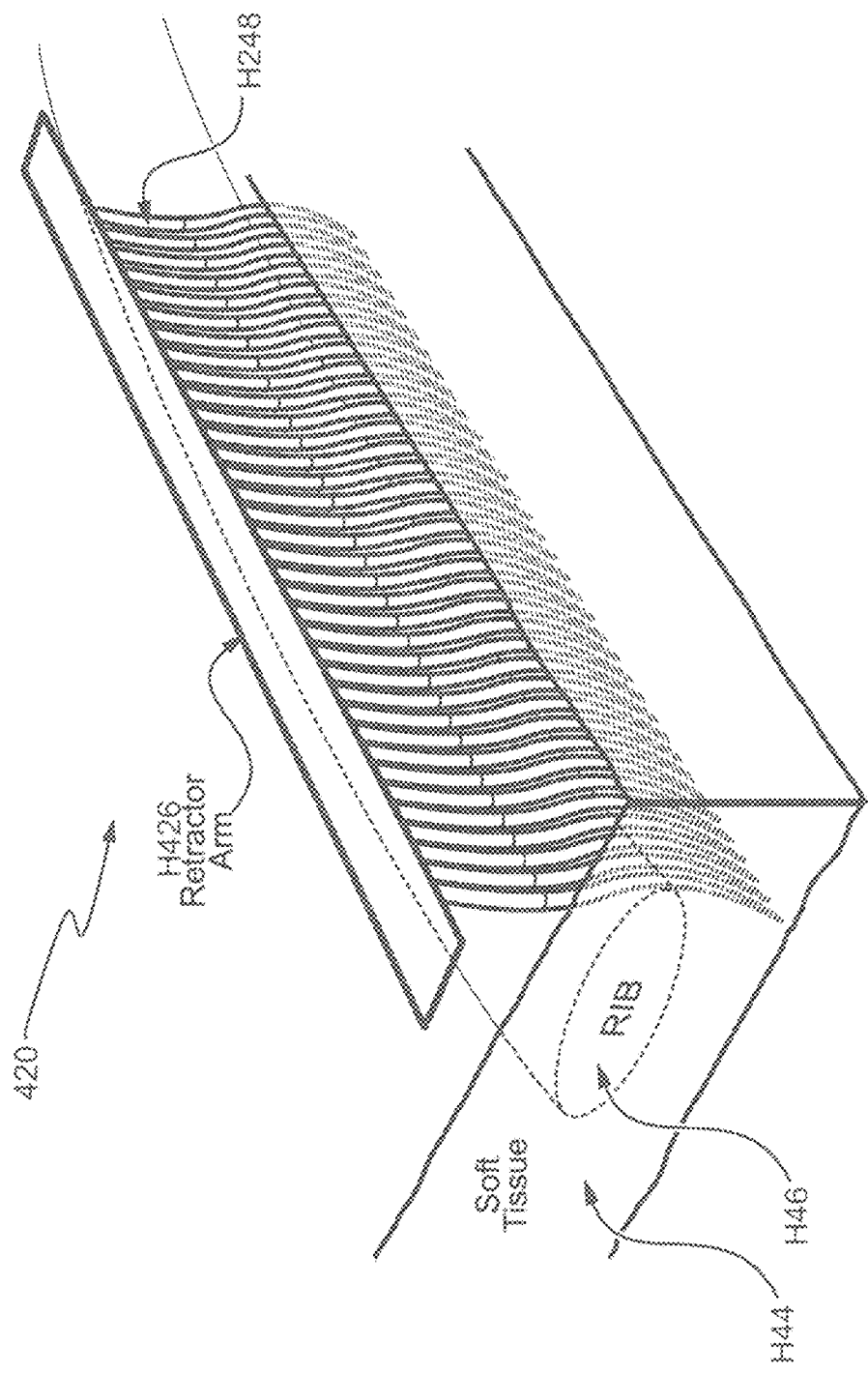
FIG. 100 shows another embodiment of a retractor arm comprising an arm and a plurality of descender posts for engaging a rib.

FIG. 100 discloses yet another embodiment having a plurality of descender posts to distribute loads on a rib. Descender posts H428 can be very thin, each not capable of displacing the rib H46, but with several arrayed in parallel on retractor arm H426 such that, combined, descender posts H428 can displace the rib H46. Descender posts H428 can be, for example, stiff wires arrayed into a comb that can be placed against the rib H46. The descender posts H428 can be sufficiently sharp on their ends that they are placed by piercing the soft tissues H44 next to the rib H46. The positions of the descender posts H428 can be independently adjustable, or they can be flexible such that they automatically seat against the rib. As also shown in FIG. 100, the shape of the descender posts H428 can be such that they press against the rib H46 without impinging on the space below it, thus again avoiding loading the neurovascular bundle residing in the soft tissues H44 there. Any number of hard tissue engagers can be arrayed to avoid crushing, damaging, or traumatizing any soft tissues associated with a hard tissue.

Figure 101E:
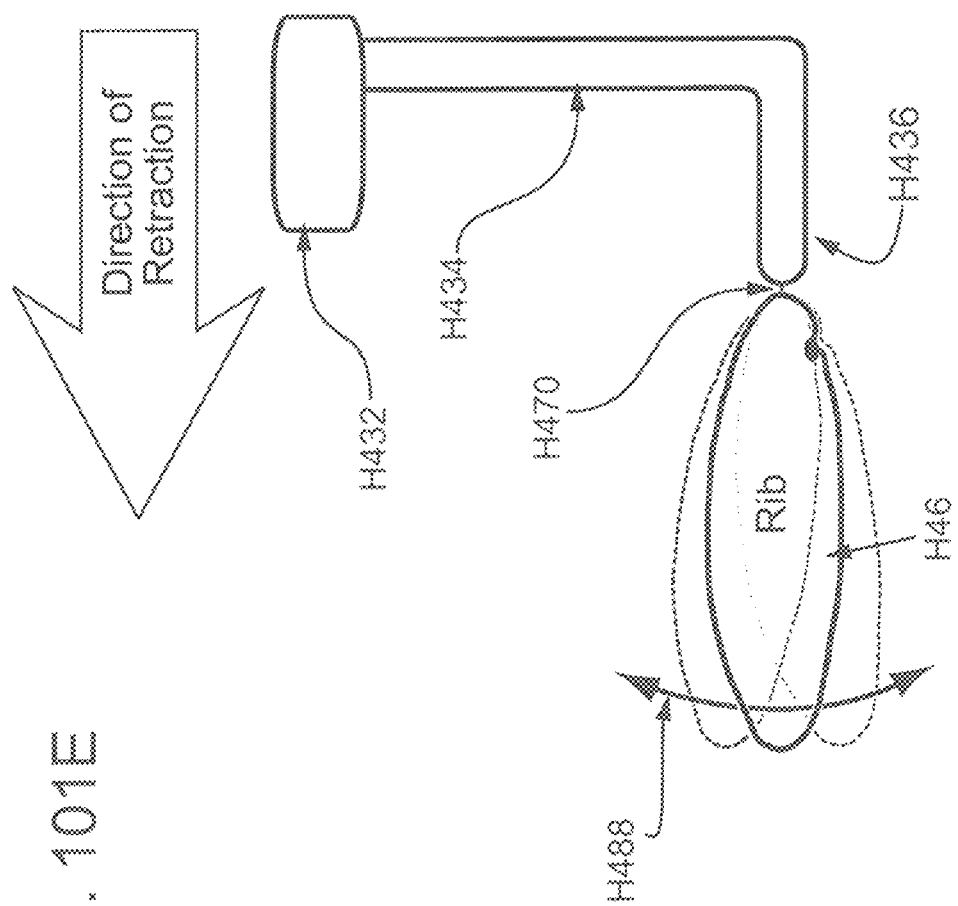

FIGS. 101A through 101E show another embodiment of a device for engaging a hard tissue, like a rib, without damaging neighboring soft tissues. Retractor arm 432 has a descender post H434 with a turn or bend H435 going to a projection H436 that engages the rib H46. The projection H436 is thin and pointed such that it easily penetrates the soft tissues H44 adjacent to the rib H46. The projection H436 can include a tip H442 with a sharp point to engage the edge of the rib H46 such that projection H436 of the descender post H434 firmly engages rib H46 but does not touch the neurovascular bundle H48. As shown in FIGS. 101B through 101D, the sharp point of tip H442 can be configured such that it pierces only the surface of the rib H46 to prevent slipping, but can not pierce further. For example, as depicted in FIG. 101C, the tip H442 of the projection H436 can terminate with a spike H470 that penetrates the rib H46, but the tip of the projection itself H442 it too dull to further penetrate the rib H46. As shown in FIG. 101D, the tip H442 can have multiple spikes H472 to ensure engagement of the rib H46. As shown in FIG. 101E, projection H436 is depicted engaging the rib H46 with a spike H470, which ensures engagement of projection H436 with rib H46 even as rib H46 moves (shown by arrow H488).

Figure 102:
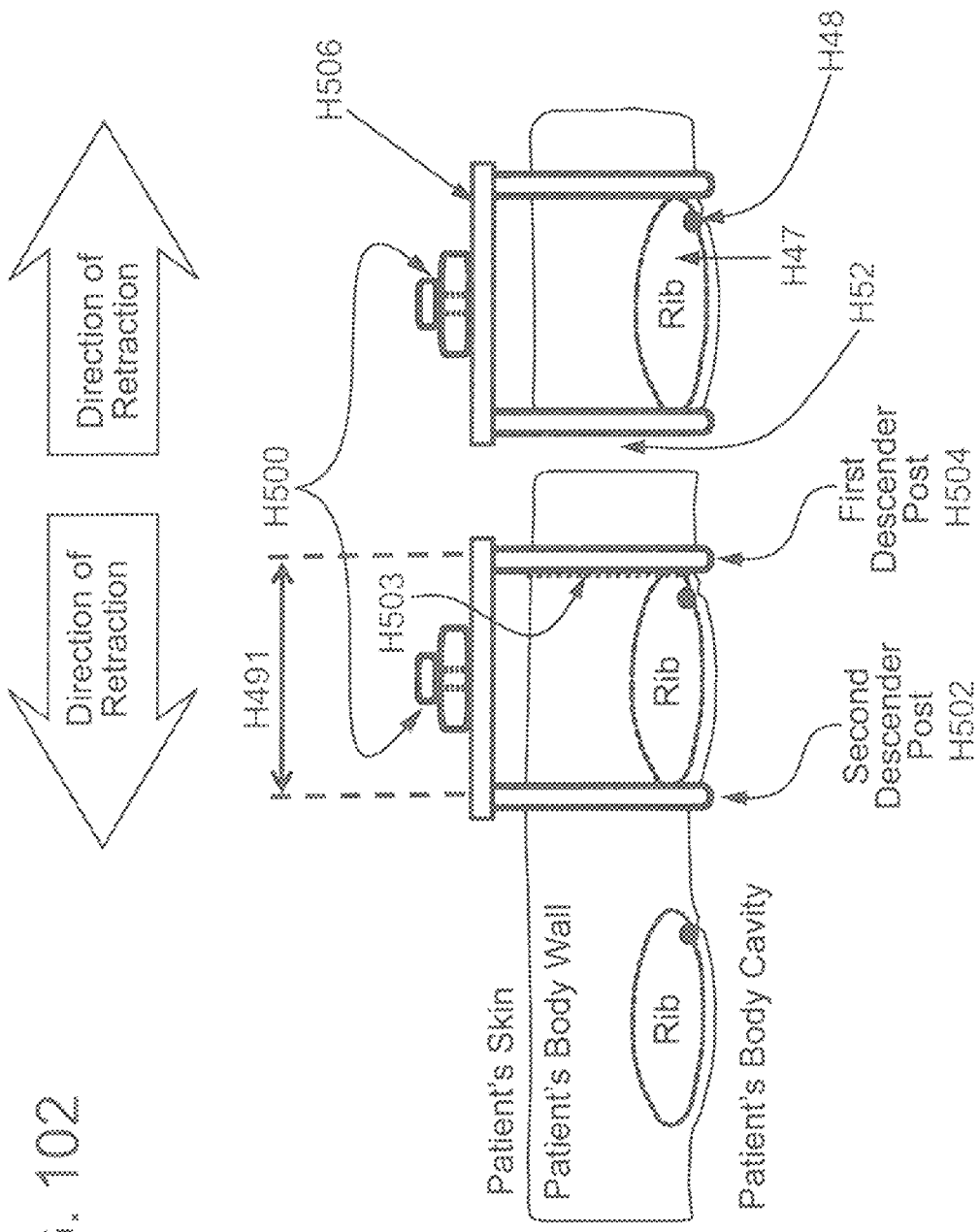
FIG. 102 shows another embodiment of a retractor comprising two retractor arms each having a first and a second descender post for engaging a rib.

FIG. 102 shows a section view of a thoracotomy performed by another embodiment in which the rib is firmly grasped on both sides to permit deterministic control of its motion, i.e. the position and orientation of the rib is always controlled. Retractor arms H500 each have a spacer bar H506 to which are attached paired descender posts H502 and H504. The paired descender posts H502 and H504 engage both sides of the ribs (for example, H46). The directions of retraction (i.e., rib spreading) are shown by arrows. Both descender posts H502 and H504 are straight and engage the ribs H46 laterally. The sides of the descender posts H502 and H504 can have serrations H503 where they engage the ribs to reduce slipping of the descender posts H502 and H504 on the ribs H46. The distance H491 separating the paired descender posts H504 and H502 can be adjustable to permit positioning the paired descender posts H502 and H504 firmly against the margins of rib H46 thereby accommodating variations in cranial-caudal width of rib H46. This embodiment allows a retractor to firmly grasp the rib H46, permitting deterministic control of rib position throughout retraction.

Figure 103:
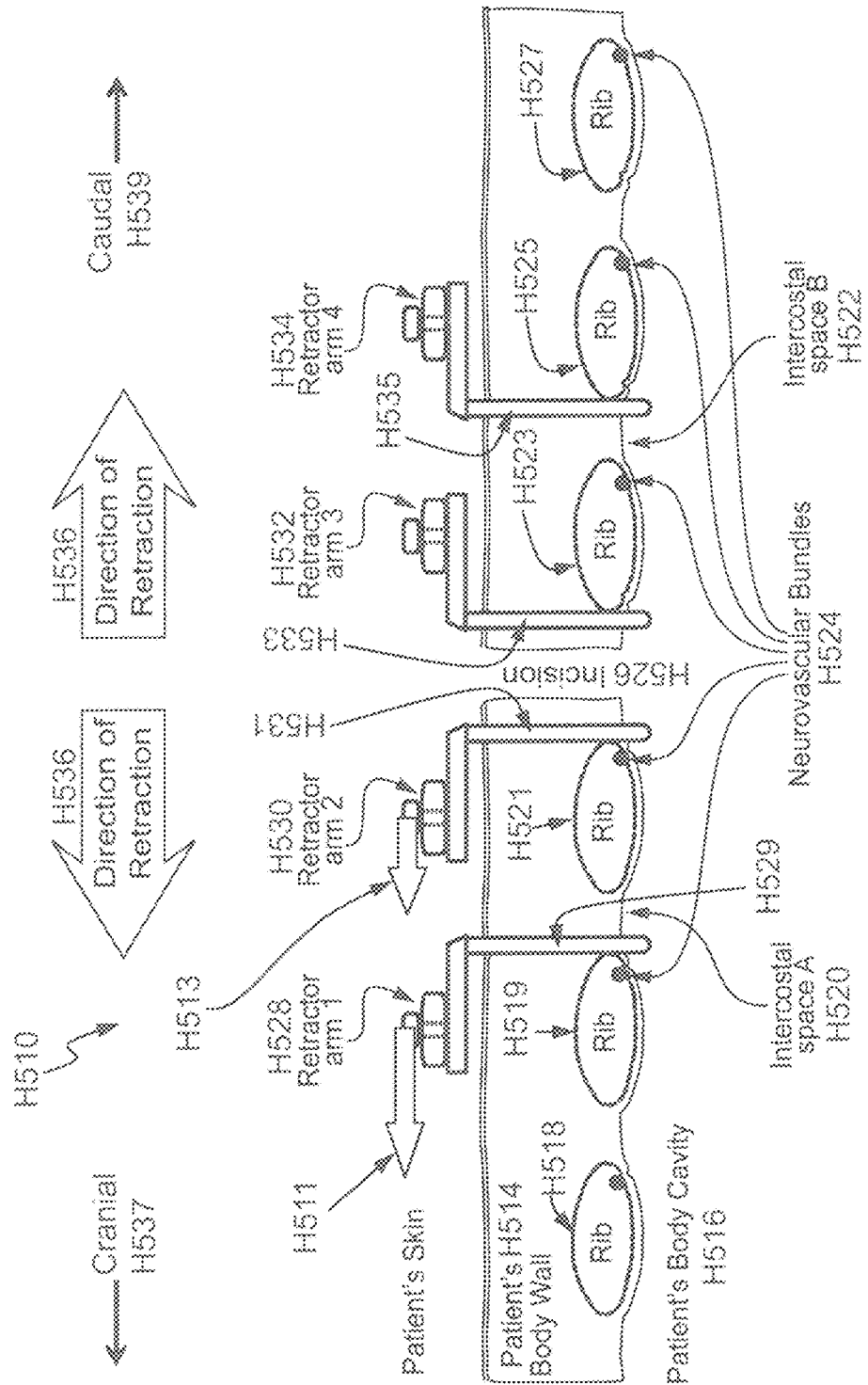
FIG. 103 shows another embodiment of a retractor comprising multiple arms, each having descender posts and configured to engage multiple ribs on each side of a thoracotomy incision.

Referring now to FIG. 103, a retractor H510 can also engage ribs H519 and H525 further from the incision H526, in addition to the ribs H521 and H523 adjacent to the incision. As shown in FIG. 103, a retractor H510 can possess a plurality of retractor arms (H528, H530, H532 and H534), each equipped with descender posts (H529, H531, H533 and H535, respectively). The retractor arms H528, H530, H532 and H534 can have coordinated motion, with respect to one another, that includes different speeds such that the retractor arms H528, H530, H532 and H534 each effect a different displacement over the same time. For example, retractor arms 1 (H528) and 2 (H530) form a pair on one side (the cranial side, H537) of the incision H526, and both retractor arms 1 (H528) and retractor arms 2 (H530) can move in the same direction of retraction (H536), but the displacement (H511) of retractor arm 1 H528 can be less than the displacement (H513) for retractor arm 2 H530 (e.g., retractor arm 1 can move more slowly than retractor arm 2). (Retractor arms 3 H532 and 4 H534 can, similarly, form a pair on the opposite, or caudal H539, side of the incision H526.) This varying displacement of the retractor arms reduces the pressure in intercostal space A H520 and intercostal space B H522 (and their respective neurovascular bundles, grouped H524) arising from ribs H518, H519 and H521 (cranially) and H523, H25 and H527 (caudally) impinging on one another during retraction.

Figure 104A:
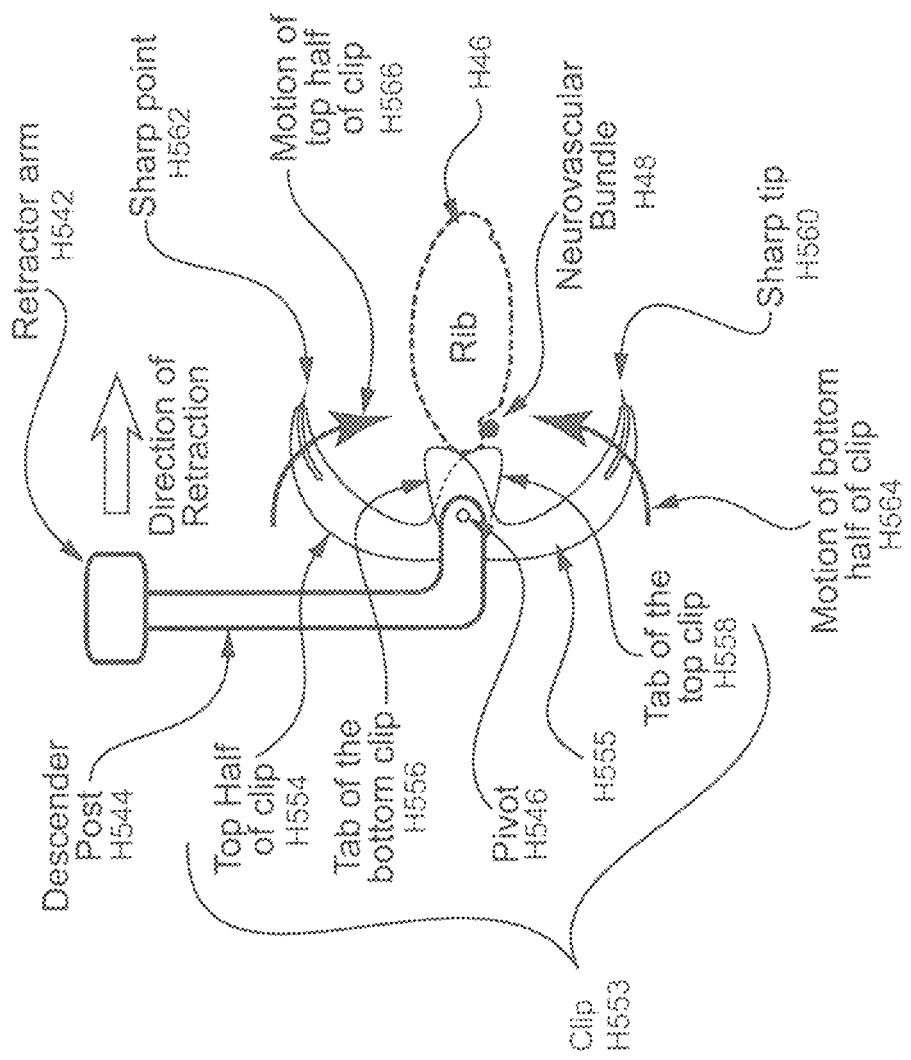
FIGS. 104A through 104C shows another embodiment of a descender post comprising a post with clips on one end, wherein the clips close on a rib when pushed against the rib.
Figure 104B:
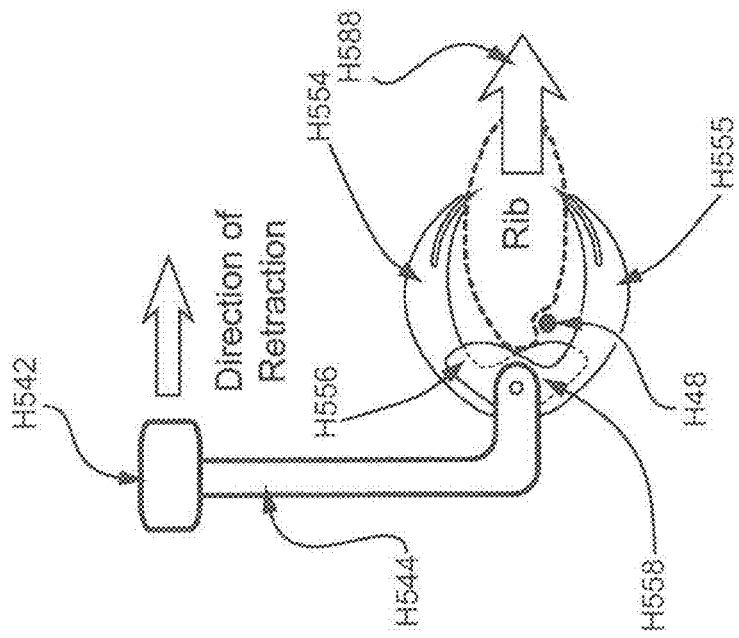
Figure 104C:
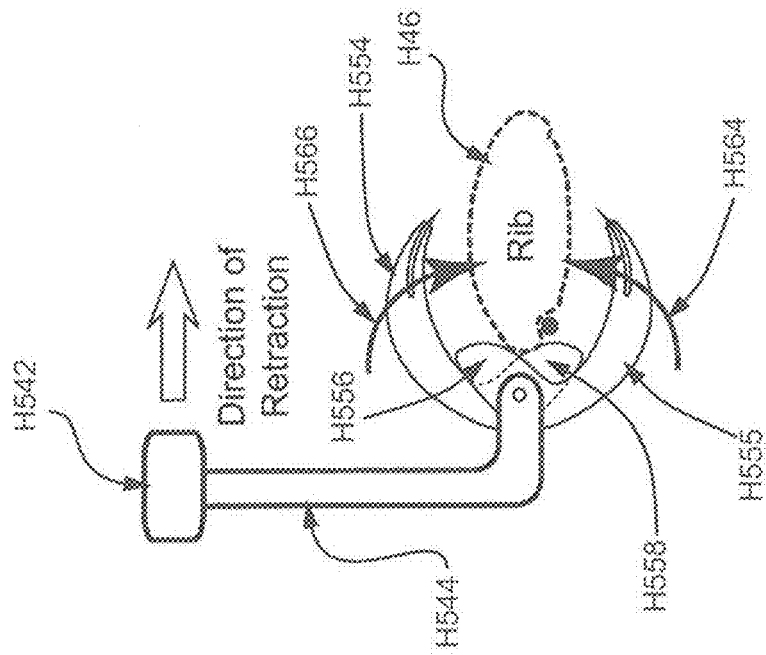

FIGS. 104A, 104B and 104C show another embodiment in which an articulating clip is used to grasp a rib without compressing neighboring soft tissues. FIGS. 104A through 104C show an action sequence of an articulated clip H553 meeting, closing, and locking down onto a rib H46. In the sequence, a descender post H544 is fitted with a moveable, deeply curved, articulated clip H553 having a top half jaw H554 and a bottom half jaw H555 attached by a pivot H546 to the descender post H544. Each half H554 and H555 possesses a sharp point H562 and H560, respectively, for engaging the rib H46, and a tab (one tab, H556, projects up and is associated with the bottom clip half H555, and another tab, H558, projects down and is associated with the top clip half, H554. The clip halves H554 and H555 can be spring-loaded such that they stay open (with jaws spread wide) before loading (i.e., before contacting the rib H46). The clip half tabs H556 and H558 are cams shaped so as to generate a torque when the descender post H544 with all associated components is pushed against the rib H46. When the rib H46 impinges on the clip half tabs H556 and H558, each tab is pushed apart and away from the other, causing each half of the clip H554 and H555 to rotate in the opposite direction (i.e., the top half clip H554 comes down and the bottom half clip H555 comes up), thus using the force applied by the rib H46 to bring the sharp points H560 and H562 into position against the rib H46 to forcefully secure it. The shapes of tabs H556 and H558 cooperate with that of the clip jaw halves H554 and H555 such that a space is created protecting the neurovascular bundle H48 from any contact while retraction proceeds. The sharp points H560 and H562 are configured such that they penetrate only the surface of the rib H46, far behind the neurovascular bundle H48 as the descender post H544 is pushed more firmly against the rib H46. Thus, further force (or travel) of the descender post H544 against the rib H46 is born by the sharp points H560 and H562 loaded into hard, resistant bone, and not just the tabs H556 and H558, thereby limiting any pressure exerted by the tabs against the soft tissues adjacent to the rib H46 and, thus, protecting the neurovascular bundle H48.

J. Compensating for Retractor Deformation

Many biological tissues are very rigid. For example, rib cages are made of rigid bone connected by numerous ligaments, muscles, and tendons—strong enough to withstand the stresses of human locomotion or lifting large loads. Thus, the forces required to deform these tissues during procedures such as sternotomy or thoracotomy are significant. We have measured forces of up to 500 N during thoracotomies and 250 N during sternotomies on pigs weighing 50 to 60 kg. Forces on vertebral distractors are also large.

Retractors, by their very nature, are typically made of rigid stainless steel to withstand the stresses of forcing open rib cages. However, retractors deform under load. Deformation of a typical Finochietto-style retractor (e.g. a Finochietto, see FIG. 2, Burford, Ankeney, or other thoracic retractor) is primarily of two types—the arms bend and twist. Deformation of the retractor is more complex, e.g. including bending of the rack of the rack and pinion.

Figure 105A:
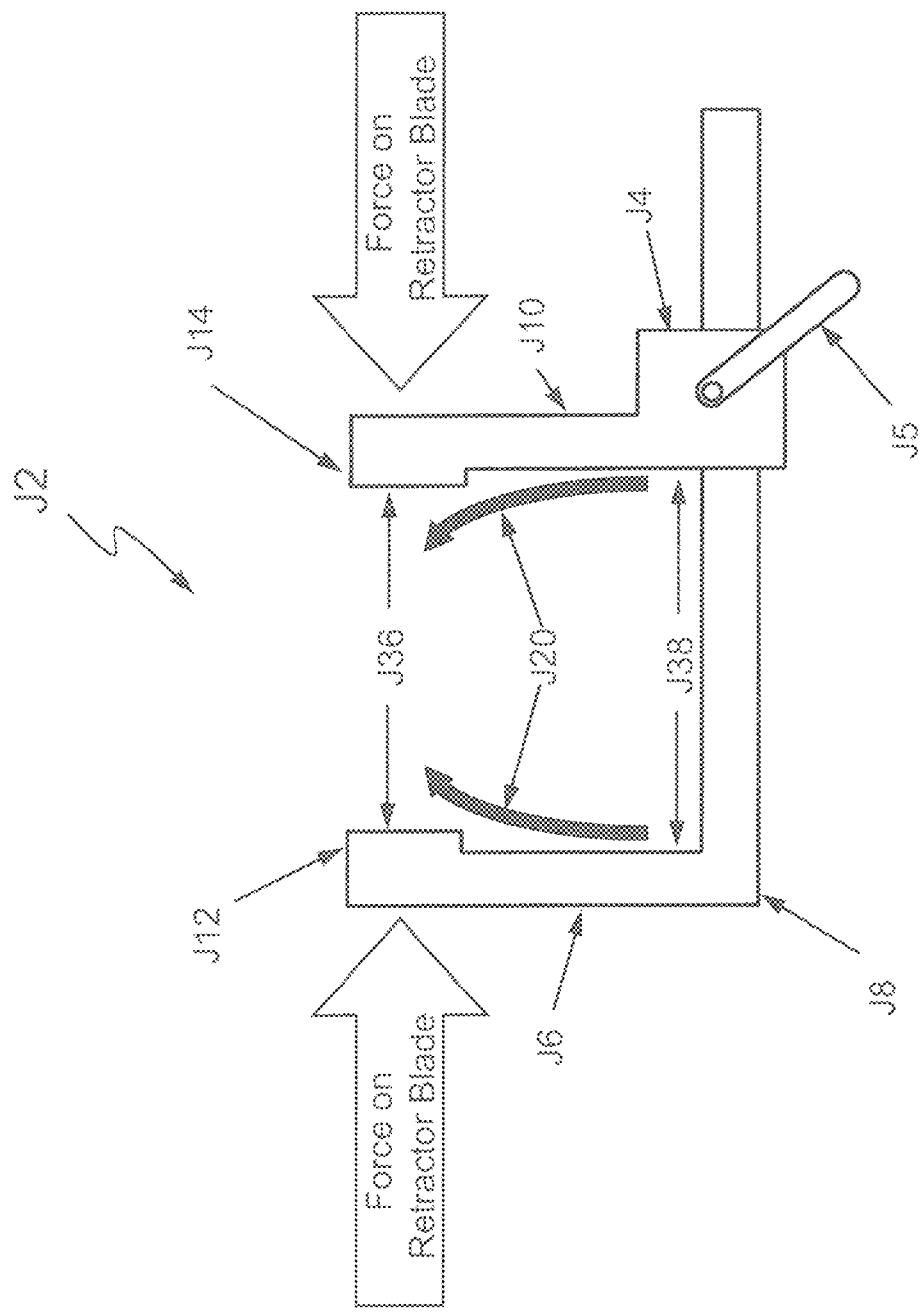
FIGS. 105A and 105B show the deformations under loading of a thoracic retractor in the prior art.

FIG. 105A shows the bending of the retractor arms J6, J10 of a Finochietto-style retractor J2 in the prior art when loaded during retraction. Retractor J2 has two retractor arms J6 and J10. Retractor arm J6 is fixed to the rack J8 of a rack-and-pinion drive J4 that is driven by a manual handle J5. Each retractor arm J6 and J10 has an attached retractor blade J12 and J14, respectively, that engages the patient's tissues during retraction. Bending J20 of the retractor arms J6 and J10 causes the distance J36 between the retractor blades J12, J14 to decrease, whereas the distance J38 between the retractor arms J6, J10 is not greatly effected.

Figure 105B:
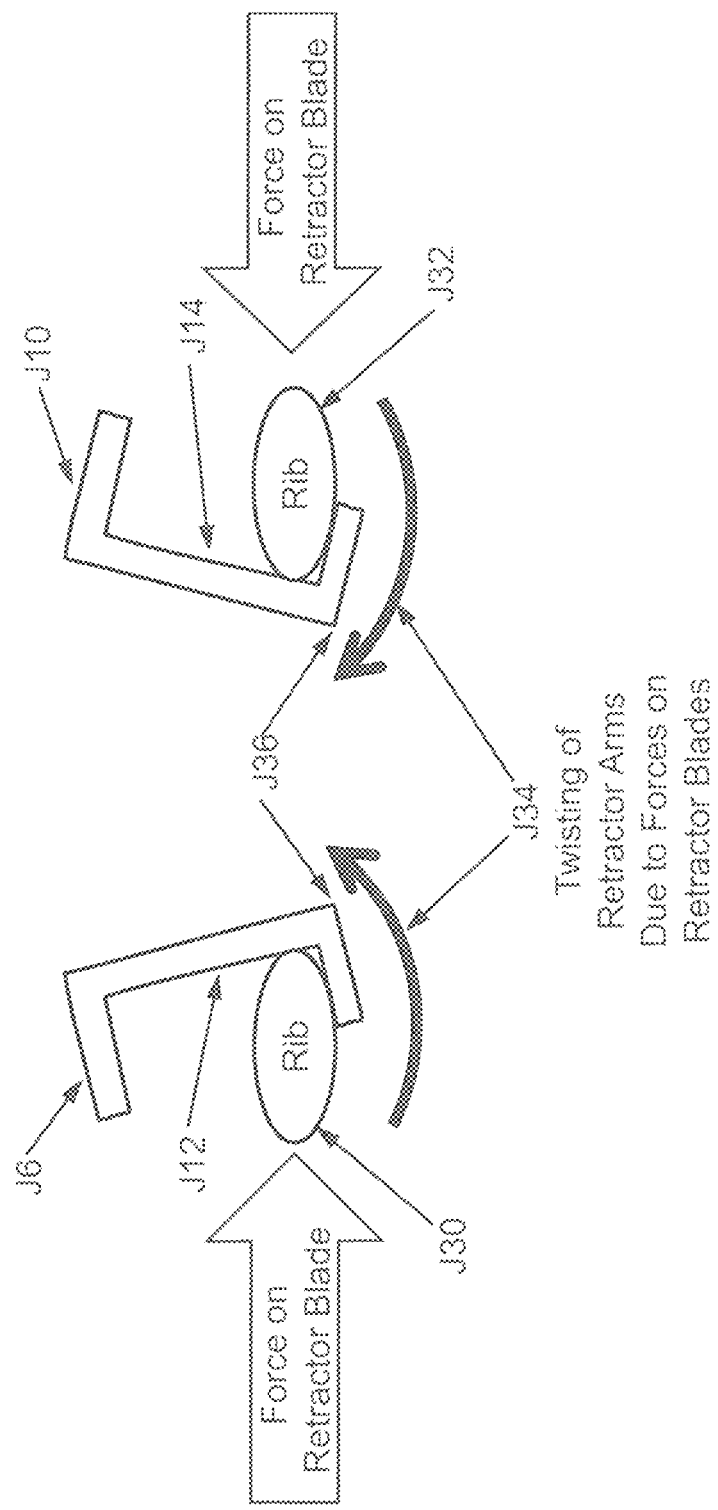

FIG. 105B shows twisting of the retractor arms J6, J10 of a Finochietto-style retractor J2 in the prior art when loaded during retraction. Retractor blades J12 and J14 push against ribs J30 and J32, respectively. The force on the retractor blades J12, J14 twists the retractor arms J6, J10, causing the distance J36 to decrease.

We have measured deformations, decreases of J36, of up to 2 cm when the retractor blades J12, J14 are first separated 10 cm and then loaded with 500 N; in other words, the retractor blades J12, J14 are forced together 20% of the separation J36 when loaded with forces seen in thoracotomies.

These deformations of the retractor J2 are elastic; the retractor J2 deforms like a spring under load. If the load decreases, the deformation of the retractor J2 decreases, and the retractor blades J12, J14 move further apart.

The tissues against which the retractor applies this load are viscoelastic. Unlike an elastic material, a viscoelastic material will continue to deform when loaded, even if the load is constant—it will exhibit creep.

This combination of an elastically deformed retractor J2 pushing against a viscoelastic material creates a problem. Consider a sternotomy, a surgeon retracts (first phase of retraction) to a desired opening of the incision and then stops (second phase of retraction), striving not to retract wider than necessary to reduce damage to the tissues of the chest. Many retractors are self-locking or have a lock mechanism designed to hold the incision at that desired opening during the second phase of retraction. However, the retractor J2 has deformed during the first phase of retraction, and now the elastic deformation of the retractor J2 continues to push against the viscoelastic materials of the chest during the second phase of retraction, causing the thoracic opening to further widen as the viscoelastic materials of the chest wall creep under the elastic force of the retractor. This results in an unnecessarily wide thoracic opening, increasing damage to the tissues of the chest wall. For example, cardiothoracic surgeons report that they will hear a "pop" or "snap" as a rib breaks, sometimes minutes after cessation of the first phase of retraction.

This problem is encountered whenever any surgical instrument or medical device is used to deform a biological tissue because biological tissues are viscoelastic. Examples include, but are not limited to, retraction of skin for access to subdermal tissues, distraction of vertebrae for surgeries on intervertebral discs or to manipulate vertebrae for fusion or for other fixation, separation of joints for surgery on cartilage or for joint replacement, forcing open an annulus or tube with an inflatable device, such as angioplasty, or any other procedure requiring deformation of a biological tissue.

We disclose apparatus and methods for deforming a patient's tissues to the degree defined by the physician, reducing any further deformation of the tissue after the desired deformation is attained, and, thereby, reducing the chances of unnecessary tissue trauma.

One solution to this problem is to make the retractor exceedingly rigid through the use of materials having large Young's modulus (e.g., titanium which is expensive) or by the use of members having large cross-sectional area (e.g., wide, thick members which adds weight to the retractor). This retractor will still deform elastically, but the elastic deformation of the retractor will be small, so it will impose only a short distance of creep on the tissues of the chest.

An alternative solution is a thoracic retractor that deforms elastically but the surgical opening is controlled by a servo-mechanism that maintains the opening at the point set by the surgeon. Thus, as the tissue begins to creep, causing the retractor blades to move apart elastically, the servo-mechanism causes the retractor to close slightly, thereby decreasing the elastic deformation of the retractor and applying only the force required to maintain the surgical opening at the point set by the surgeon.

Figure 106:
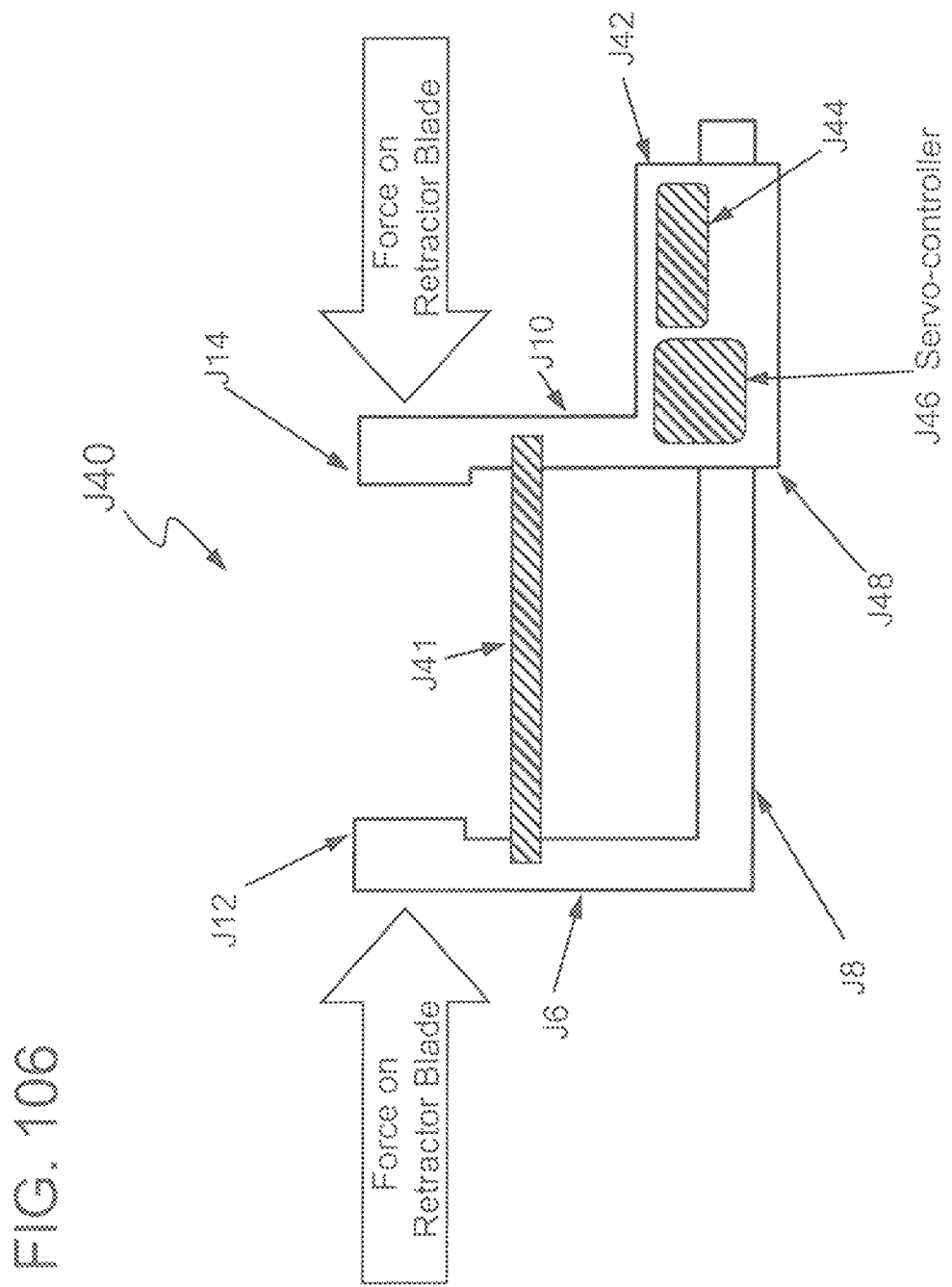
FIG. 106 shows an embodiment comprising a retractor having two opposing blades, a servo-motor, a servo-controller, and linear potentiometer.

FIG. 106 shows one embodiment in which the servo-mechanism controls the distance J36 between the retractor blades J12, J14 of a retractor J40. The servo-mechanism is comprised of a motor J44 that opens the retractor J40, a distance measuring device J41 that measures the surgical opening (e.g. a linear potentiometer), and a servo-controller J46 that receives the signal from the distance measuring device J41 and then adjusts the position of motor J44 to maintain the desired surgical opening, even as the tissue creeps. Any actuator that effects the deformation of the tissue (i.e. that powers the first phase of the retraction) can be used; thus, for the embodiment shown in FIG. 106, the actuator that opens the retractor J40 is also the actuator controlled by the servo-controller J44.

An alternative to direct measurement of the surgical opening for servo-control, as shown in FIG. 106, is to use the force-deformation relationship of the retractor (e.g. a spring constant or a force-deformation curve). During use of the retractor, the force on the retractor is measured with a force measuring device, and then the deformation of the retractor is determined from the measured force using the force-deformation relationship. This has the advantage that no measuring device is present in or near the surgical opening.

Figure 107:
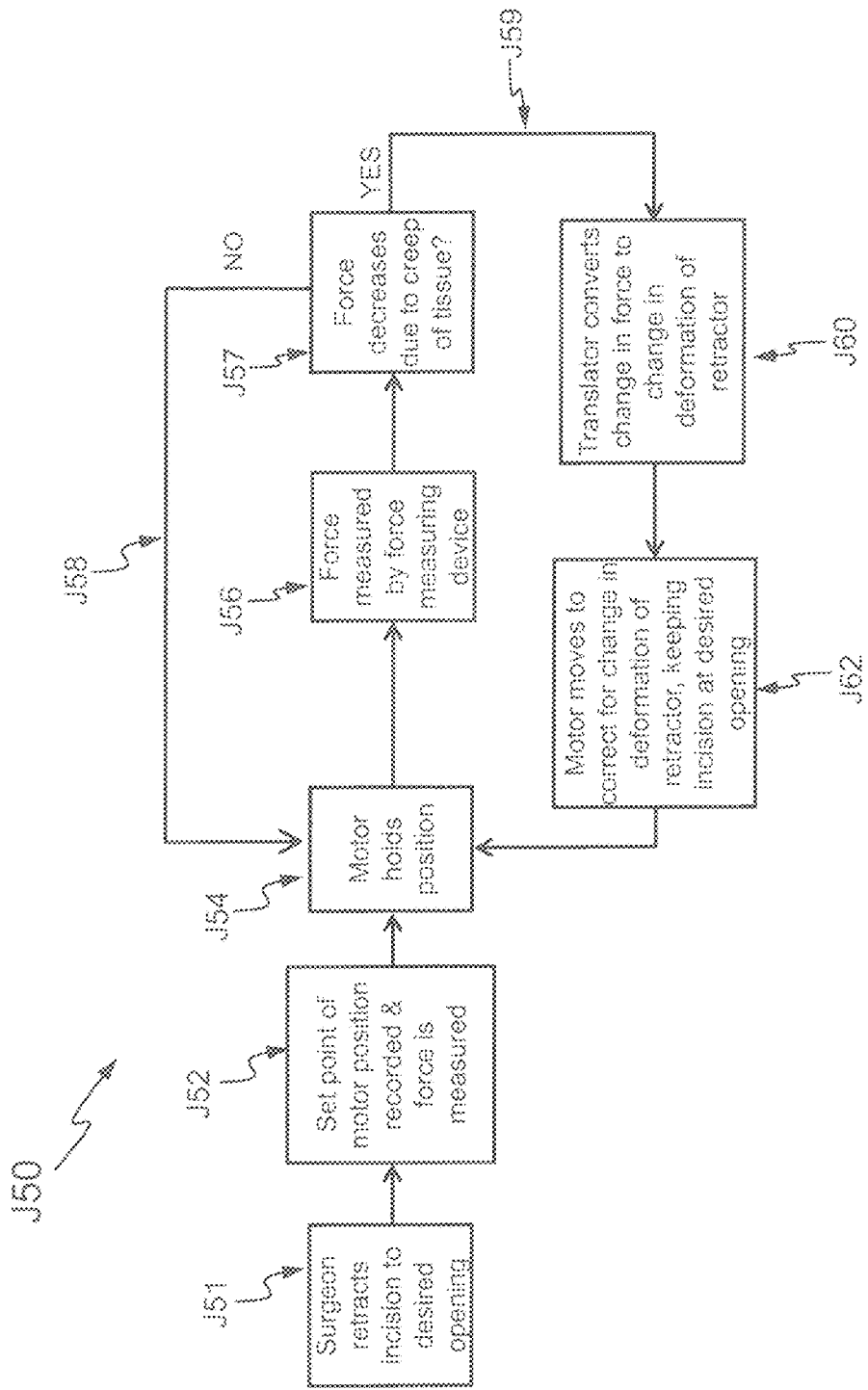
FIG. 107 shows an algorithm in which force on the retractor is used to determine and correct for deformation of the retractor when loaded.

FIG. 107 presents an algorithm J50 illustrating one way to implement a servo-mechanism that uses force measurement with a force-deformation relationship. A surgeon retracts to a desired opening (block J51) and then activates the servo-mechanism (block J52). The position of the motor is recorded by the servo-mechanism (block J52), the force on the retractor is measured (block J52), and the motor begins to hold position (block J54). Force is then measured continuously (block J56). If force remains constant, then the motor continues to hold position (decision at block J57 then to step J58). If force decreases (due to creep of the biological tissue) (block J57 then to step J59), then a translator (e.g. an electrical circuit, possibly including a microprocessor) uses the force-deformation relationship to convert the change in force on the retractor into a change in deformation of the retractor (block J60). The translator then instructs the motor to move to correct for the change in deformation, thereby keeping the surgical opening at the separation set by the surgeon (block J62) returning the feedback loop to block J54.

A similar algorithm can be used to correct for deformation throughout retraction. Thus, rather than correct for changes in deformation on entering the second phase of retraction, the algorithm can correct for deformation throughout both the first and second phases of retraction. With such an algorithm, the separation achieved by the retractor blades (i.e., distance J36) will then match the separation seen by the surgeon when looking at the retractor arms (i.e., distance J38). This algorithm also can be part of an automated retraction system to ensure that separations J36 intended by the automatic retraction system are, in fact, the separations achieved.

Figure 108:
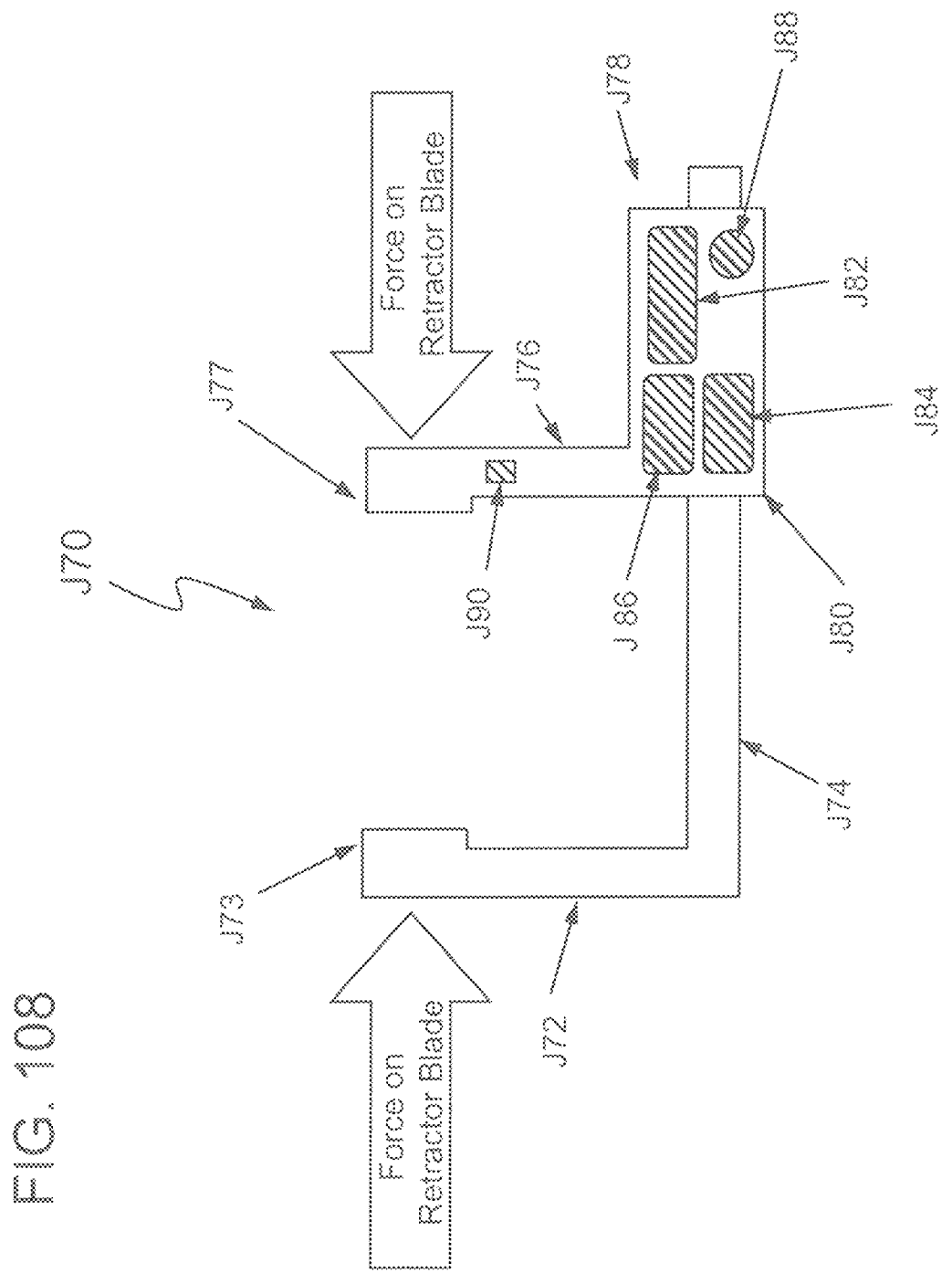
FIG. 108 shows an embodiment of a device for compensating for changes in retractor deformation comprising a force measuring device, a force-to-deformation translator, a servo-controller and a servo-motor.

FIG. 108 shows a retractor J70 that can control the distance J36 between the retractor blades J73, J77 by using servo-loop J78 that implements an algorithm such as algorithm J50. The retractor has a first retractor arm J72 and a second retractor arm J76 that is driven relative to the first retractor arm J72 by a motorized rack-and-pinion drive J78 comprised of a rack J74 attached to the first retractor arm J72 and a drive housing J80 attached to the second retractor arm J76. Retractor arms J72 and J76 have retractor blades J73 and J77, respectively. The drive housing J80 houses a servo-motor J84 and a servo-controller J86 that controls the servo-motor J84. The surgeon opens the retractor J70 by providing instructions to the servo-controller J86, for example with a rotating knob J88 that replaces the crank of a manual rack-and-pinion. A force measuring device J90, for example a strain gauge, is placed on the second retractor arm J76 to measure force on the retractor J70. A translator J82 in the drive housing J80 receives signals from the force measuring device J90 and implements the algorithm J50. Placement of the force measuring device and the translator can be at any of several locations, such as on the fixed retractor arm, but placement of all three components—servo-motor, translator, and force measuring device, on the moveable retractor arm simplifies the design.

Figure 109:
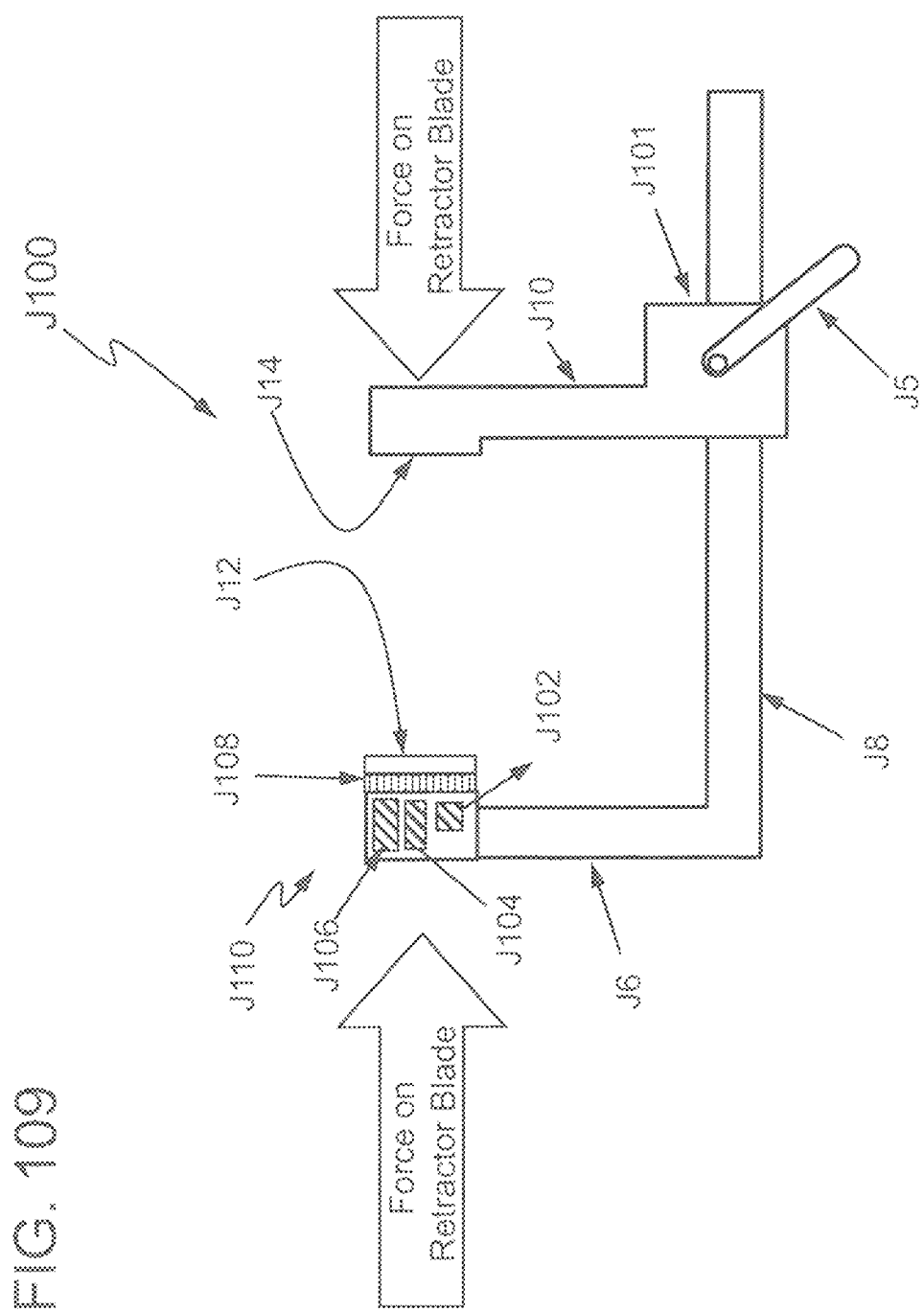
FIG. 109 shows an embodiment of a device for compensating for changes in retractor deformation comprising a force measuring device, a force-to-deformation translator, a servo-controller and a servo-motor in which all components fit onto one arm of the retractor.

FIG. 109 shows another retractor J100 that uses two actuators, a first actuator J101 to drive the first phase of retraction and a second actuator J108 to adjust for changes in deformation arising from creep in the tissues during the second phase of retraction. During the first phase of retraction the first actuator J101, a hand-cranked rack-and-pinion in this example, is used to by the surgeon. A second actuator J108 attached to one arm of the retractor J100, for example the first arm of the retractor J6, is controlled by a servo-mechanism J110 and is used to correct for changes in the deformation of the retractor J100 due to creep of the tissue during the second phase of retraction. A force measuring device J102, for example a strain gauge, measures force on the first retractor arm J6. A translator J104 detects changes in force, translates these to changes in the deformation of the retractor J100, and signals the servo-controller J106 to instruct the second actuator J108 to move and thereby remove the change in the surgical opening resulting from the change in the deformation of the retractor J100. The second actuator J108 can be a servo-motor, a voice coil, a hydraulic cylinder from which fluid is released to move the retractor blade J12, or any other actuator that can move the retractor blade J12 such that the retractor blade J12 moves closer to the opposing retractor blade J14 when a decrease in force on the retractor is detected by the translator. Such a device as shown in FIG. 109 can either be integrated into a retractor or be a component that attaches to an existing retractor.

K. A Thoracic Retractor Combining Elements of the Earlier Sections

FIGS. 110 through 114 present a thoracic retractor K2 used for thoracotomies. This thoracic retractor K2 combines components disclosed in earlier sections. Thoracic retractor K2 comprises two opposing retractor arms K4 and K6 attached to retraction driver K60.

Figure 111:
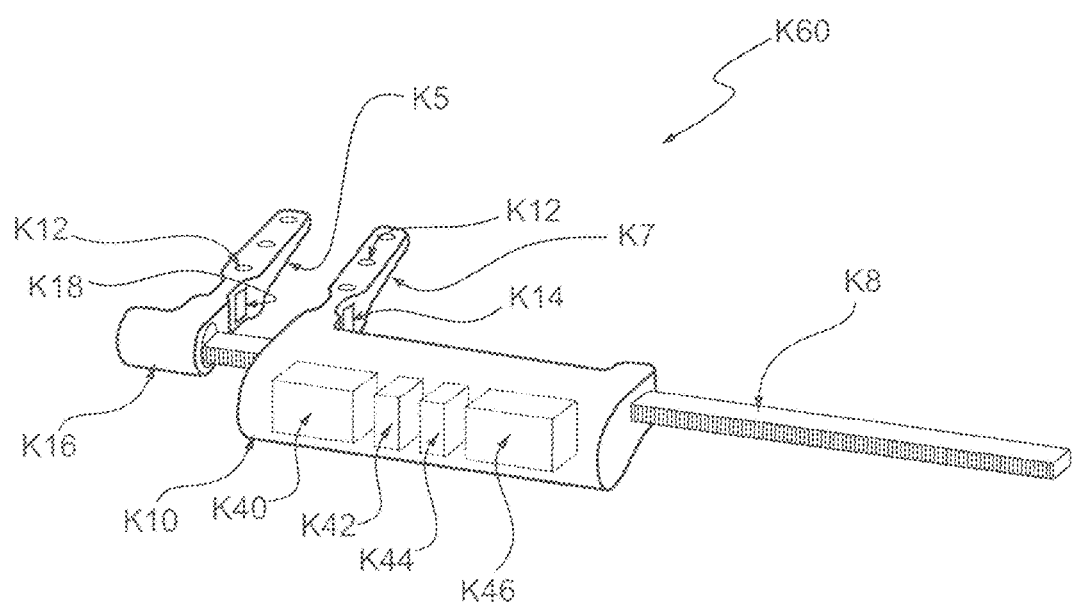
FIG. 111 shows an embodiment of a retraction driver.

FIG. 111 shows retraction driver K60. Retraction driver K60 comprises a motor-driven rack-and-pinion, with the pinion driven by a servo-motor K40 controlled by servo-controller K42 and powered by battery K44. Processor K46 receives input from strain gauge sensors K14 and K18 that measure the forces on the retractor arms K6 and K4, respectively. Strain gauge sensors K14 and K18 can be single gauges or multiple gauges located in multiple locations and arrayed in, for example, a full bridge configuration; additionally, strain gauge sensors K14 and K18 can be mounted where the strains in the underlying material are expected or designed to be large to increase the sensitivity of force measurement. Processor K46 is in communication with servo-controller K42 for automatic control of the servo-motor K40. Retractor arm K4 attaches to the rack K8 connector K5 via and then rotatable mount K16. Retractor arm K6 attaches to driver housing K10 via connector K7. The attachment of retractor arms K4 and K6 to connectors K5 and K7, respectively, is secured with fasteners K12. Examples of fasteners include screws, clips, or any other appropriate mechanical fastener.

Figure 112:
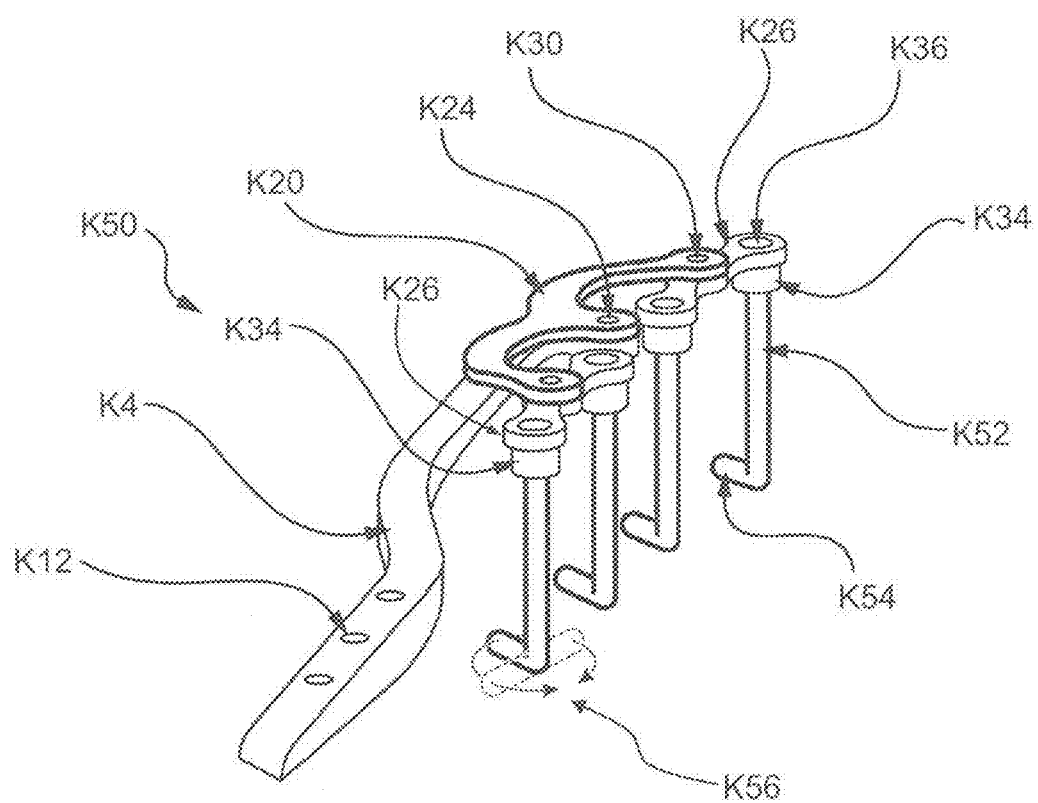
FIG. 112 shows an embodiment of a retractor arm assembly for a thoracotomy.

FIG. 112 shows retractor arm assembly K50 that attaches via retractor arm K4 to connector K5 to rotatable mount K16. A similar retractor arm assembly is attached via retractor arm K6 to driver housing K10. Retractor arm assembly K50 comprises retractor arm K4 which attaches to balance arm K20 via rotating mount K24; two daughter balance arms K26 which attach to balance arm K20 via rotating mounts K30; and two descender posts K52 each with hook K54 attaching to each daughter balance arm K26 via rotatable mount K34. Thus there are four descender posts K52 each with hook K54. Each descender post K52 is attached to the daughter balance arm K26 by rotatable mount K36 such that hook K54 rotates as shown in K56. Rotatable mount K36 can include a heavy sleeve K34 that reinforces the joint.

Figure 113:
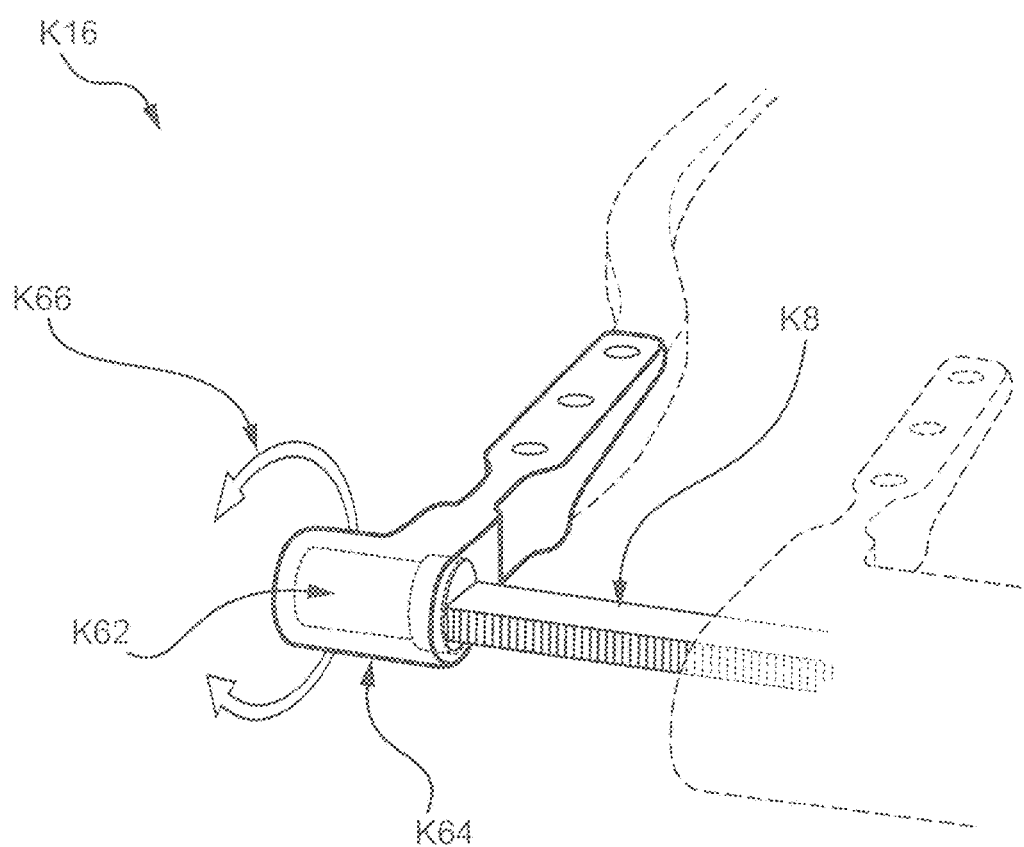
FIG. 113 shows an enlarged view of a rotatable mount on a thoracic retractor.

FIG. 113 shows an enlarged view of rotatable mount K16 which provides retractor arm assembly K50 an additional degree of rotational freedom, as disclosed in Section G. Rotatable mount K16 comprises rod K62 that is rigidly coupled to rack K8. Sleeve K64 is attached to rod K62 and secured by an E-clip (not shown). Rotatable mount K16, therefore, provides for rotation K66 of retractor arm assembly K50.

Figure 114:
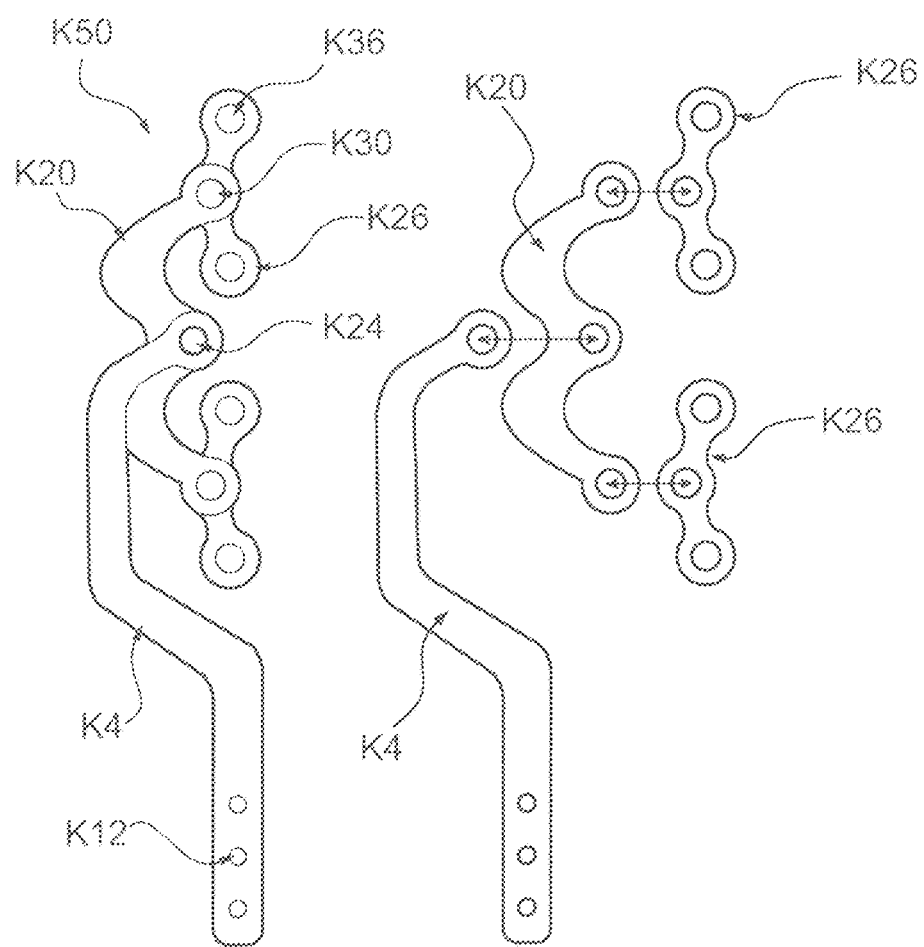
FIG. 114 shows the design of the balance arms of a retractor arm assembly.

FIG. 114 shows the shapes and sequence of attachment of retractor arm K4 to balance arm K20 and daughter balance arms K26 for retractor arm assembly K50. Rotatable mounts K24 and K30 can be made by connector pins; alternatively, rotatable bushings or bearings can be used. Rotatable mounts K24 and K30 can be made loose to provide some freedom of alignment out of the plane of the page of FIG. 114.

Connectors K5 and K7 can be replaced by appropriate snap-together fittings permitting the retractor arms K4 and K6 to be easily attached and removed. Furthermore, connectors K5 and K7 can include electrical connectors for transmission of power or electrical signals to electrical components on or connected to the retractor arms K4 and K6 or to different retractor arm assemblies K50. Such electrical components can include sensors, processors, motors or other actuators, data input interfaces, data or status indicators, or other advantageous electrical components.

Retractor assembly K50 is designed to distribute the forces along a rib during a thoracotomy. Other retractor assemblies designed for other procedures, such as a sternotomy, can be attached to rack K8 and to retraction driver K60, optionally with rotating mount K16a replaced by a rigid connection or other moveable mount.

Retractor arm assembly K50 can be a disposable component. Retractor arm assembly can include the battery K44, and if K50 is a disposable component, this would permit the attachment of a fresh battery for every use.

Figure 115:
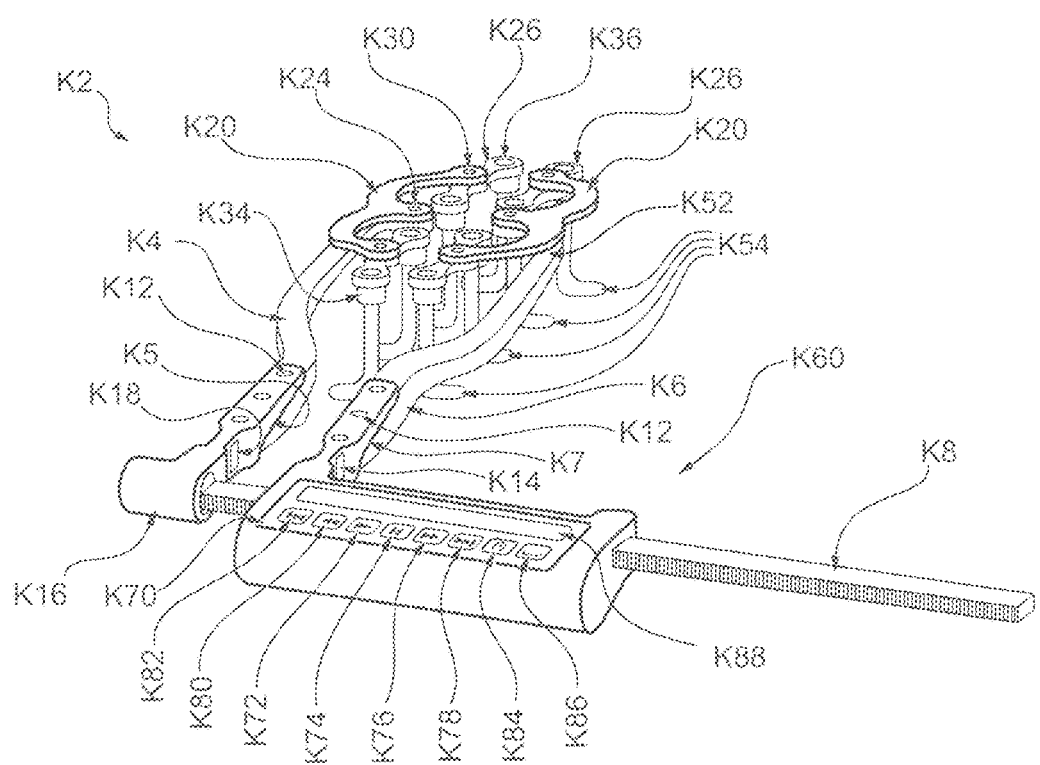
FIG. 115 shows an example of a user interface built into a thoracic retractor.

Instructions to the servo-controller K42 and processor K46 can be via a user interface that is integral to retraction driver K60. An example of a user interface is shown in FIG. 115. The interface can include a panel in which membrane buttons activate functions such as start retraction K72, pause retraction K74, fast forward or accelerate retraction K76, emergency open K78, rewind or reverse retraction K80, fully close the retractor K82, set duration for retraction K84, set distance of retraction K86, and a display K80 for showing information to the user, for example retraction progress with a progress bar, force on the retractor, or other information.

Figure 110:
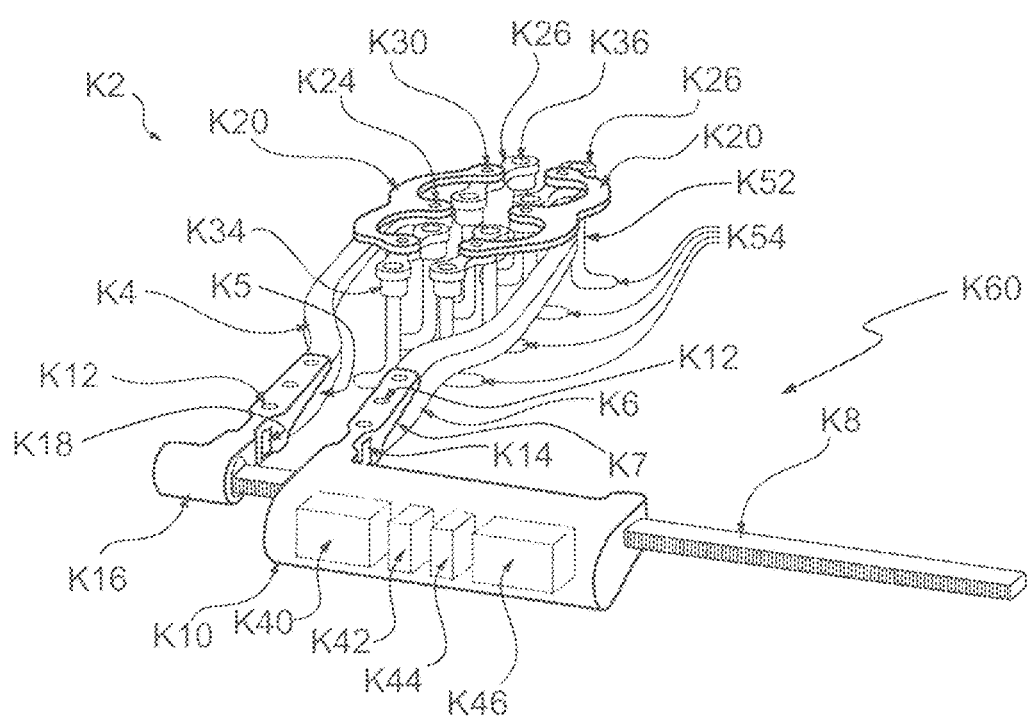
FIG. 110 shows an embodiment of a thoracic retractor.

The thoracic retractor K2 shown in FIG. 110 has been constructed to demonstrate selected embodiments described above and, specifically, to demonstrate functioning of the self-balancing retractor arms as described in Section F (e.g., see FIG. 55), the rotating retraction arm and retraction assembly as described in Section G (e.g. see FIG. 74), hook-shaped tissue engagers as described in Section H (e.g. FIG. 98), and automated retraction with detection of trauma as described in Section C (e.g. algorithm C300 in FIG. 42). Motor K40 is a model EC22 50W from Maxon Precision Motor Inc. The prototype does not have battery K44 or servo-controller K42 or processor K46 housed in driver housing K10. Rather, these functions are provided by an off-board power supply (16V, 4.5 A), servo-controller (EPOS 24/5 motor controller from Maxon Precision Motor, Inc), and computer connected by a cable. Strain gauges from Vishay Micro-Measurements, Inc. are placed at locations K14 and K18, arranged as full bridges, to measure forces on arms K6 and K4, respectively. Power to and signals from these strain gauges is provided by signal conditioners (Model OM-2-115 from 1-800-LoadCell), which then send signals to a data acquisition card (Model USB-6211 from National Instruments, Inc.) attached to a laptop computer. Custom software for motor control and data acquisition is written in LabVIEW from National Instruments, Inc.

Figure 116A:
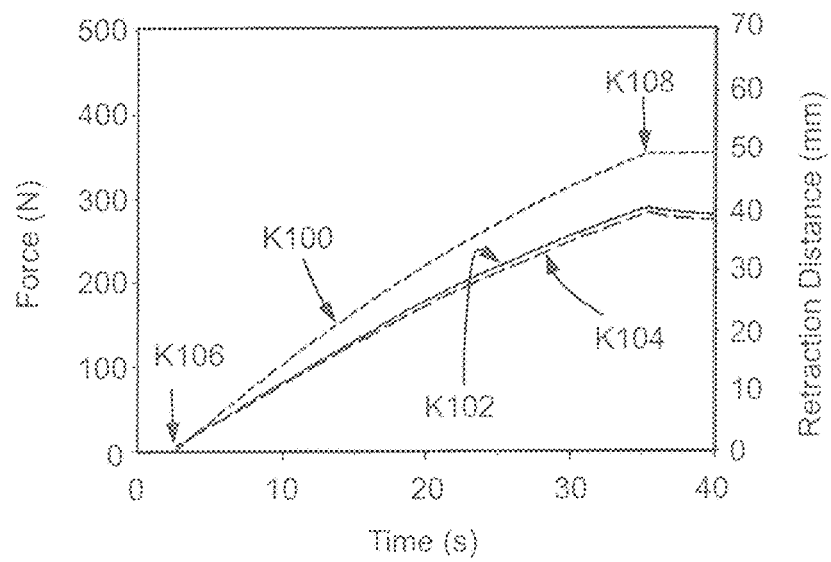
FIGS. 116A and 116B show force and displacement for two automated thoracotomy retractions performed with a prototype thoracic retractor.
Figure 116B:
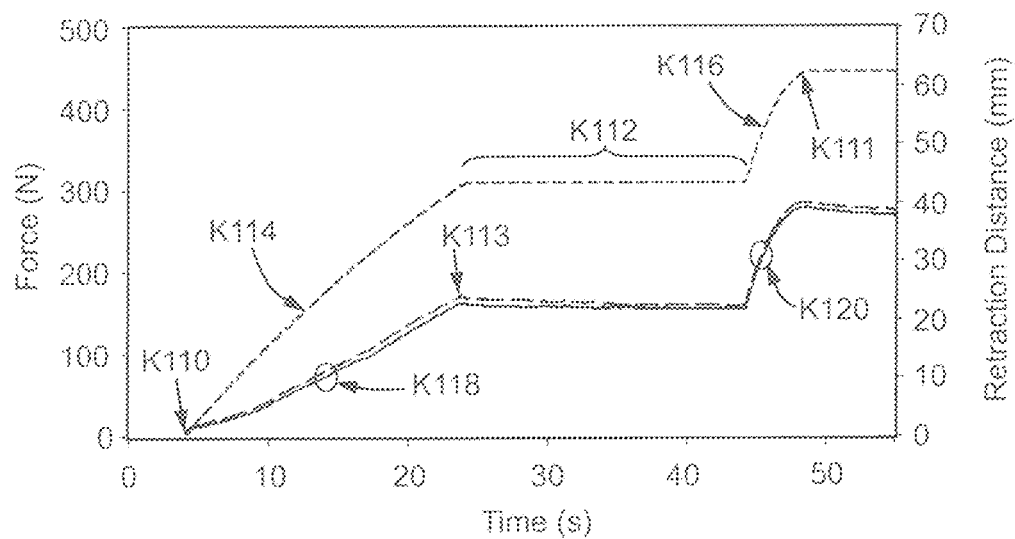

FIGS. 116A and 116B show retractions from two thoracotomies. These are fully automated retractions. The surgeon placed the retractor into the incision, rotated the hooks K54 on the descender posts K52 under the ribs, and then a remote operator initiated computer-controlled retraction—the computer controlled the rest of the retraction. The retraction trajectory was programmed to be parabolic (distance as a function of time, retraction speed initially higher, continuously decreasing throughout retraction, and approaching zero speed as full retraction is approached). The algorithm C300 described in FIG. 42 was used to automatically pause the retractor, thereby acting as a detector and automatic response to imminent tissue trauma. If a pause was triggered, then after the pause, the computer calculated a new parabolic trajectory starting at the current position and reaching the desired end point; for example, consider the retraction in FIG. 116B:

the desired endpoint was 62 mm;
retraction was to occur over 45 seconds;
a pause occurred at 43 mm after 20 seconds had elapsed, with the pause being 20 seconds long; thus
the remaining retraction distance (62–43=19 mm) was to be covered in (45–20–20)=5 seconds.

Alternate algorithms for desired endpoints, desired retraction duration, pause durations, and means of recalculating the trajectory after the pause can be used. Alternate algorithms could be:

Desired endpoint=50 mm; desired retraction duration=50 s; pause duration=15 s; if pause occurs in last 30 s of retraction, then set the pause duration to be equal to half the remaining time; or Desired endpoint=100 mm; desired retraction duration=2 minutes (120 seconds); pause duration=one-third of time remaining at the initiation of a pause.

The complexity of the algorithm is limited only by such things as the processing power of the processor K46, the numbers and types of sensors used, etc.

FIG. 116A shows the displacement K100 and forces on the right arm K102 and left arm K104 for a retraction to 50 mm over about 35 seconds. This retraction should be compared to a similar retraction performed with an instrumented Finochietto retractor (shown in FIG. 37) for retraction to 52 mm over about 50 seconds. Both retractions in FIGS. 37 and 116A were performed on the same animal. The retraction in FIG. 37 was at rib pair 4/5 on the left side, and the retraction in FIG. 116A was at rib pair 4/5 on the right side. Returning to FIG. 116A, retraction starts K106 at 2 seconds and follows a substantially parabolic trajectory, with retraction ending at K108. We have found that such substantially parabolic trajectories have less evidence of tissue trauma than other trajectories, such as linear trajectories or, as in FIG. 37, stepped trajectories. It is important to note several things:

(1) No pause was triggered.
(2) The maximum force generated during retraction was about 300 N, about 25% less than the 400 N observed with the instrumented Finochietto during retraction to 52 mm over 50 seconds (FIG. 37). This lower force of retraction is especially noteworthy because the more rapid retraction in FIG. 116A should have required more force than the slower retraction in FIG. 37.
(3) The forces on the two retractor arms are nearly equal, unlike the unequal forces seen on the retractor arms in FIG. 37.
(4) The force traces K102 and K104 in FIG. 116A are exceedingly smooth, unlike the extremely jagged traces seen in FIG. 37. Note that all the data presented in FIGS. 116 and 117 are raw data—the data are not smoothed, the traces are not fitted curves.

FIG. 116B shows another retraction with retractor K2. This retraction was at rib pair 5/6, right hand side, of the same animal as in FIGS. 37 and 116A. We performed multiple retractions on this rib pair, going to increasingly wider endpoints, in an attempt to get a pause to be initiated by the algorithm C300. FIG. 116B shows the third retraction which was to an endpoint of 62 mm over 45 seconds. Retraction started at K110 and ended at K111. A pause K112 was triggered by a negative-going spike (too small to see in this figure) at the point marked by the arrow K113 approximately 20 seconds after starting retraction. Retraction before the pause produced a very smooth displacement trace K114 and force traces (right and left arms collectively labeled K118). Only a small amount of force relaxation is evident in the pause. The retraction after the pause was very rapid, due to the short time allowed by the algorithm (about 5 seconds), but again produced a very smooth displacement trace K116 and force traces, right and left arms collectively numbered as K120.

It is noteworthy that the forces on the retractor relaxed only slightly during the pause in FIG. 116B and also at the end of the retractions in both FIGS. 116A and 116B, relative to the relaxation seen after each ½-rotation of the crank in FIG. 37. This indicates that slow, steady pulling permits force relaxation to occur simultaneously with retraction and, therefore, also indicates that there is an optimum retraction speed that maximizes force relaxation and thereby reduces forces during retraction. A substantially parabolic trajectory, as described above, provides such an optimal retraction.

Figure 117A:
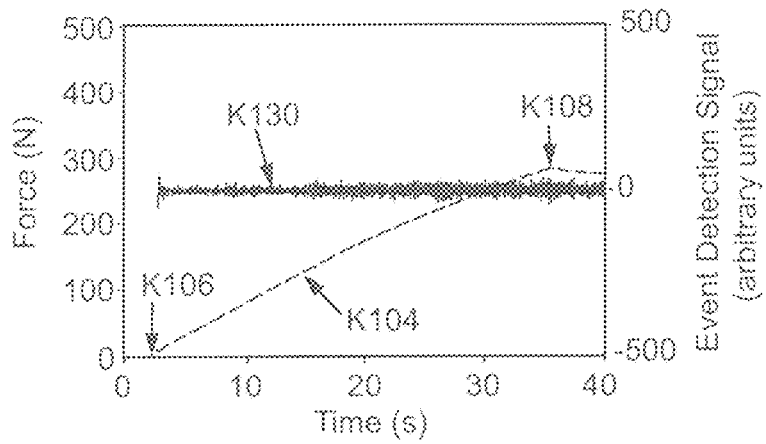
FIGS. 117A through 117C show the force on a left arm and an Event Detection Signal for the automated retractions shown in FIGS. 116A and 116B.
Figure 117B:
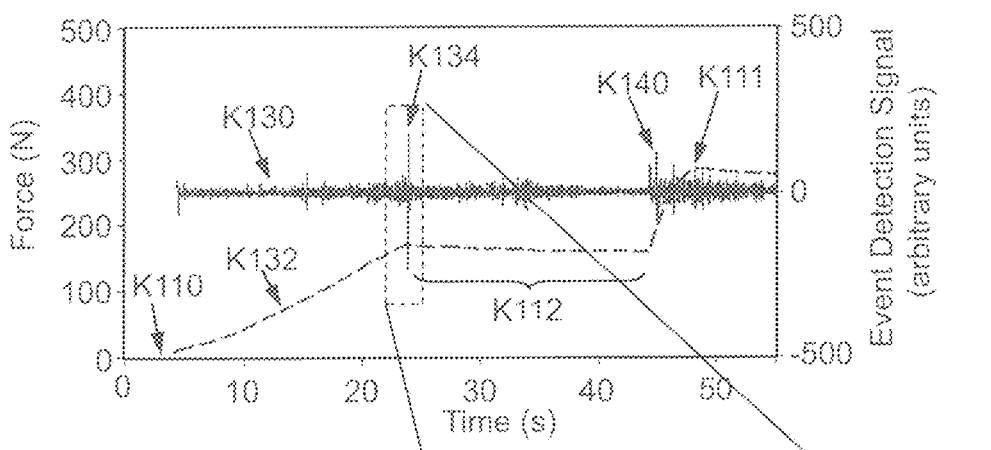
Figure 117C:
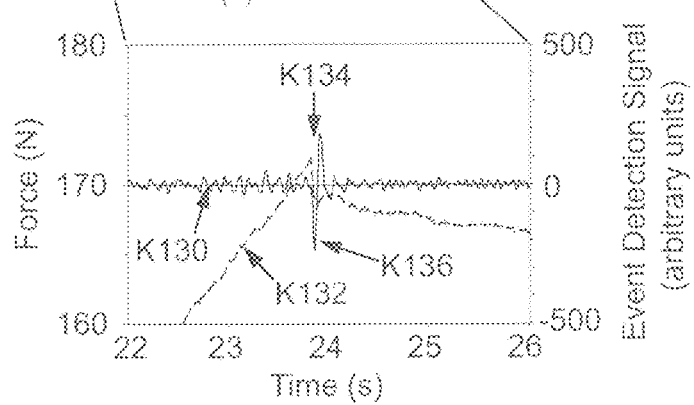

FIGS. 117A, 117B, and 117C present the same data from the retractions shown in FIGS. 116A and 116B, but show only force for the left retractor arm; these figures also show the second derivative of the force, $d^2F/dt^2$, referred to here as the Fracture Predicting Signal, FPS, where fracture can be of any tissue (e.g. rib, ligament, tendon, muscle) giving rise to tissue trauma.

FIG. 117A shows the retraction from FIG. 116A. Traces for both the FPS K130 and force K104 on the left retractor arm are presented. The FPS trace K130 is constant, with low noise, at zero throughout the retraction. There are no negative-going spikes and no increase in variance of the signal that would trigger a pause, so there was no pause in this retraction.

FIG. 117B shows the retraction from FIG. 116B. The force trace K132 is presented from the left retractor arm only. Here, there is a prominent event K134 at about 24 seconds that triggers the pause K112.

FIG. 117C shows the event K134 with an expanded scale. A small drop in the force K132 occurs in event K134, a decrease of only about 3N (~1% of the maximum retraction force during this retraction). This creates a negative going spike K136 in the FPS K130 that triggers the pause. Retraction stopped 0.2 seconds after the drop in force K132 (displacement trace not shown).

Returning to FIG. 117B, there is another event K140 in the FPS during retraction after the pause. This event was not sufficient to trigger a second pause, and retraction proceeded to completion K111.

L. Tissue Engagers: "Safe Tissue Retraction Elements for Thoracotomy" Introduction to the Problem Tissue Engagers (Safe Tissue Retraction Elements) for Thoracotomy Introduction to the Problem Every 15 seconds, a thoracic surgeon enters a patient's chest by spreading the space between two adjacent ribs. After choosing a location and slicing through the patient's intercostal musculature, the surgeon first (1) inserts the retractor's blades into the incision, then (2) ensures the retractor blades are parallel to and apposed to the incision's margins so that the blades will open along an axis (the retraction axis) lying perpendicular to the line of the incision, and (3) forcefully cranks open the retractor to widen the intercostal space.

Unfortunately, the design of thoracic retractors hasn't changed much in 75 years. Tissue trauma is common, including broken ribs, crushed nerves and vessels, and torn muscles, ligaments and cartilage. Knowing this, many surgeons preemptively cut nerves or remove rib sections in an attempt to confine the damage. Clearly there is a need for improvements to thoracic retractor design.

Issues with Current Thoracic Retractor Blade Designs

Today's thoracic retractors employ stiff retractor blades stamped out of stainless steel plate, usually rectangular and possessing fenestrations through the plate. They are minimally finished; in fact, the blades' corners are intentionally left sharp to bite into the exposed muscle tissue to prevent slippage under load. Further, the retractor blades possess wide, right-angled shelves at their tips (also with sharp corners), the better to catch hold of the incision's margins, to prevent the retractor blades' rising up and out of the incision as the ribs are spread open. With the retractor blades cranked together, closed for insertion, these shelves are much wider than the initial gap created by the incision through the intercostals. To insert the blades the surgeon must therefore force the wide edges of the shelves past the patient's freshly cut muscle, jamming that muscle against the patient's ribs. Once inserted, these retractor blades continue to damage tissues, for example, when the retractor blades are settled in place, sharp edges are adjacent to the fragile, respiring lungs. The aforementioned tissue trauma of then spreading the ribs leads to severe pain, prolonging the patient's recovery and trading quality of life for quantity. The resulting healthcare costs are unnecessarily high. Is this avoidable?

Solution

Physcient here discloses novel devices and methods in the field of Tissue Retraction Elements (TRE) enabling and improving the process of:
(1) Inserting a retractor's Tissue Retraction Elements into a thoracoscopic incision,
(2) Orienting and Settling those Tissue Retraction Elements into place against the margins of the thoracoscopic incision to be retracted, and
(3) Applying Force against those margins to expose the chest cavity.

We propose a device that is easy to insert without damaging the patient's tissues, that gently and securely self-orients and engages the tissues forming the margins of the patient's incision, and that safely applies force throughout the retraction process. Further, the improved Tissue Retraction Elements are also easier for the surgeon to use, are easier to remove, are self-adjusting and improve overall patient recovery. Surgeon, Patient and Hospital all benefit.

Inserting the Tissue Retraction Elements without Trauma

Figure 118:
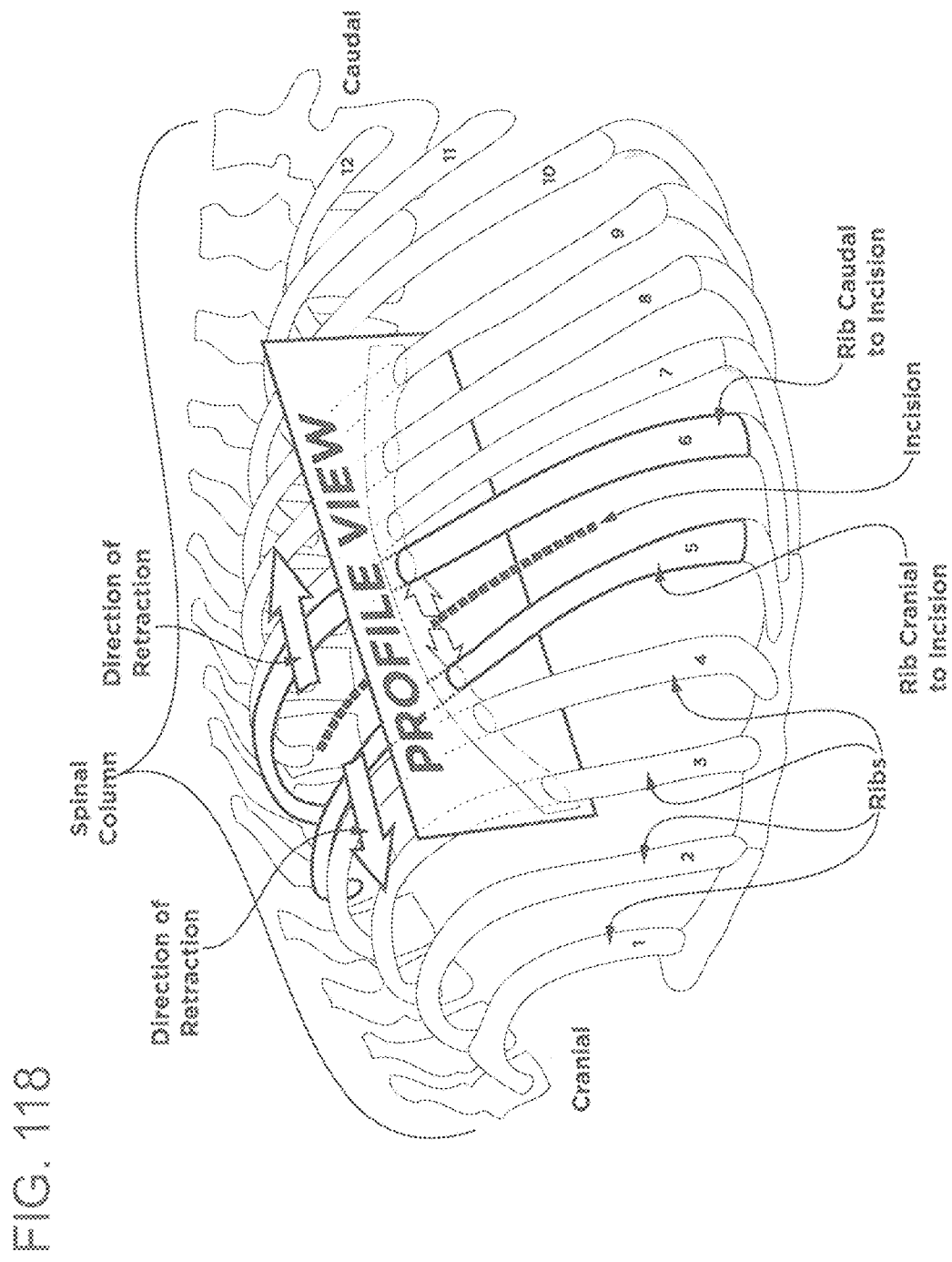
FIG. 118—A rib cage; inserted plane defines "profile" view.
Figure 119A:
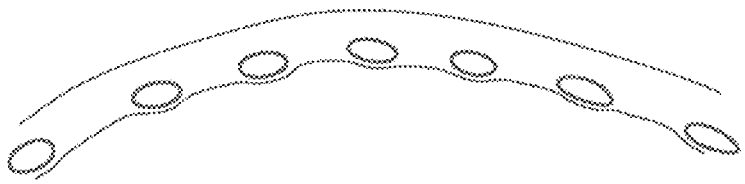
FIGS. 119A through 119C—Profile view from a rib cage.
Figure 119B:
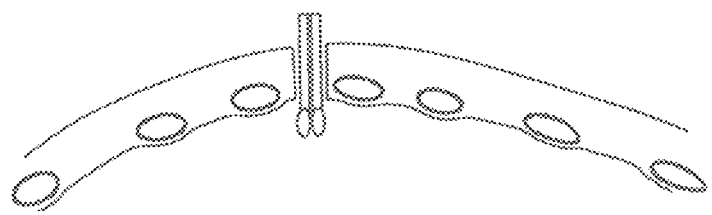
Figure 119C:
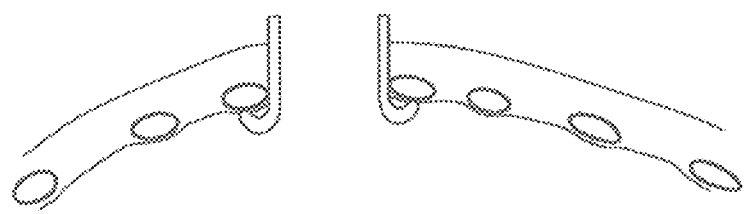

Physcient discloses here multiple devices and methods for inserting retraction elements of a thoracic retractor. The portion of the thoracic retractor that is to be inserted into the patient's chest cavity (hereinafter referred to as the Tissue Retraction Elements, or TRE) can possess certain attributes to prevent tissue trauma from insertion:

First, the TRE can be thin in profile ("profile" here defined as the plane view of the incision in section, see FIG. 118 and FIG. 119), so as not to spread or stretch the ribs apart as the device is inserted parallel to the incision. The TRE might also be thin enough in profile to avoid any contact with the freshly exposed margin of the patient's incision (FIG. 118).

Second, the TRE can possess an overall, grossly rounded shape, free of any corners, rectilinear portions, or other substantial protrusions that could catch hold of, impinge on, slice, cut, dig into, pierce, hook into, grab or otherwise injure tissues on the way in, i.e., during the insertion step (FIG. 119).

FIGS. 120A-120I show various embodiments of exemplary TREs. FIG. 120*a* shows a thin Tissue Retraction Element in profile view. FIG. 120B1 shows an example of a Tissue Retraction Element with a square shape of the prior art. FIG. 120B2 shows an exemplary Tissue Retraction Element with a polished surface.

Third, the surface or surfaces of the TRE can be free of fine projections, surface imperfections, edges, mold lines, or textures; the TRE can be polished smooth, for example as shiny and smooth as glass, to more easily slide easily into place without friction or impediment (FIG. 120C).

Fourth, the TRE can be constructed all or in part of a very low friction material, so as to minimize shearing of the exposed margins of the incision should any contact occur during insertion (FIG. 120D).

Fifth, the TRE can be lubricated, to reduce friction between the TRE and the patient's tissues even further (FIG. 120E-G). Any number of lubricants could be used, including FDA-cleared lubricants. The lubricants could be applied to the surface of the TRE during the procedure or before (for example during factory-packaging the TRE in a sterile bag) (FIG. 120E), or the device could be designed so that lubricants emerge from the TRE (FIG. 120F). Further, the TRE could be coated or made with a substance that, when contacting the wet surfaces of the freshly exposed margins of the patient's incision, creates there a lubricant or lubricating effect (FIG. 120G). For example, the TRE can incorporate a hydrogel that takes up water and becomes slippery.

Sixth, the TRE can move, flex, bend, or otherwise behave in a compliant manner (FIGS. 120H-I). Since the patient's tissues are diverse and include some highly flexible, compliant tissues, the TRE can itself be constructed all or in part of an elastomer, rubber or other soft, compliant material, so as to give way upon contact with the patient's tissues (FIG. 120H). The Young's modulus of the compliant material can be substantially similar to one or more of the patient's tissues. For example, the modulus of the TRE could be close to the modulus of the freshly exposed muscle, to match the muscle's shearing behavior, preventing steep shear gradients there. The modulus of the TRE (or a portion thereof) might also be made lower than, or greater than, the exposed tissues so as to give way, or push and guide, as is deemed appropriate. Any number of FDA-cleared polymers might be used, including plasticizers for varying their modulus. Alternatively, the TRE might include a substantially rigid component(s) working in concert with a compliant component(s) (FIG. 120I), for example associated with joints. Further, the compliant component might not be in direct contact with the patient's tissue.

Seventh, a TRE could be capable of changing shape. While a thin or flattened profile permits easy entry into the patient's incision, a TRE designed solely for easy entry might not be optimal for engaging nor holding the patient's tissues under load. The TRE can be designed to be capable of changing shape from a first, thin profile favoring easy insertion to another, subsequent, second profile favoring securely retracting the patient's tissues. The shape change can be achieved any number of ways. We'll describe at least two here.

Articulated Joints—Finger

One embodiment (FIGS. 121-126C) of a shape-changing Tissue Retraction Element is an Articulated Safety Finger (ASF). The ASF mimics the structure of the surgeon's own fingers (FIG. 121), which were likely the first "retractors" employed. The ASF can be constructed with substantially rigid, jointed segments (i.e., "bones") held together by a compliant sheath (i.e., a "skin") and actuated by a cable (i.e., "tendon") (FIG. 122). The cable can be very stiff in tension, or it may be designed to be somewhat compliant to permit some accommodation of the load of the patient's tissues on the Articulated Safety Finger.

The ASF starts out straight, for insertion (FIG. 123). Once inserted, the tendon can pull on the segments (FIG. 124A) to flex them until the tip of the Articulated Safety Finger rests against the inside of the patient's rib (FIG. 124B). FIG. 125 shows an embodiment of the Articulated Safety Finger ready for retraction.

The ASF's cable (i.e., tendon) could be designed to automatically pull and flex the ASF as a part of the insertion or retraction process, or the action of the cable could be under the manual control of the surgeon (FIG. 126A-C, showing a surgeon pushing the Finger Flexing Lever). See also FIG. 127 for a more detailed drawing of the parts of the ASF's Finger Flexing Handle (aka Finger Flexing Lever). See FIG. 128 for a depiction of one way the Finger Flexing Handle (Lever) can drive the cable motion.

The flexing action and proportions of the ASF can be designed to automatically create a gap that avoids applying any force to the neurovascular bundle (refer again to FIG. 122).

Further, Settling the Tissue Retraction Elements into Place without Trauma

Swinging Safety Fingers

Another embodiment (FIGS. 129-130B) of a shape-changing Tissue Retraction Element is a Swinging Safety Finger (SSF) (oblique view, FIG. 129). Designed without any sharp surfaces or projections, the SSF starts out folded flat in profile for easy insertion (FIG. 130A). One advantage of the SSF is that the surface area of the tissue retraction elements that are projecting down into the incision can be designed to make the SSF TRE respond to initial loading (e.g., near the beginning of the rib retraction process) by automatically reorienting the SSF TRE to present a new profile shape designed to safely engage and capture the tissues as a part of the retraction process (FIG. 130B). This reorientation can occur within the space of the incision and can involve SSF TRE rotation about one or more axes. This rotation can be passive, driven by rib retraction, or it can be actively controlled.

One way for the SSF TRE to accomplish automatic, passive reorientation is (1) to arrange an axis (about which a SSF TRE might swing, called a swing axis) oriented and projecting substantially up and out of the chest cavity, and (2) arranging a substantial majority of the area of the tissue retraction element to be located both within the depth of the incision (and so impinging upon the surface of the margin of the incision) and located some distance to one side of a line drawn from the swing axis perpendicular to the retraction axis (FIG. 131). The portion of the SSF TRE that contains the actual joint about which the SSF TRE swings can be located up out of the incision (for example, above the skin). Looking down into the incision, the deep, off-center portion of the SSF TRE thus forms a moment arm with its fulcrum at the swing axis.

Refer to the deployment sequence in FIGS. 132A-C. Before beginning rib retraction, the SSF TRE is oriented flat and parallel to the line of the incision for easy insertion (FIG. 132A). As the rib retraction process starts (FIG. 132B), the high, joint section passes freely and easily across the patient's skin, perpendicularly away from the incision and parallel to the retraction axis. At the same time, however, the margin of the incision resists passage of the deeper, flat area of the SSF TRE. Given the moment created by the off-center portion of the SSF TRE, the resistance of the tissue causes the entire TRE to swing backwards about the swing joint as retraction proceeds. The SSF TRE will swing through whatever angle that that design permits. If the motion about the SSF TRE joint is unrestricted, the force of the oncoming chest wall tissues means that the whole SSF TRE will naturally swing through an angle of around 90 degrees, until the deep portion of the SSF TRE trails directly behind the SSF TRE joint (FIG. 132C), pointing back at the incision. Note that the amount of SSF TRE rotation can be limited to any arbitrary angle by providing limit stops in the swing joint, by providing progressive resistance of a compliant element associated with the SSF TRE, by providing a SSF shape that reaches torque equilibrium with the patient's tissues at a chosen angle, or any other rotation or torque-limiting means.

The shape of the deep portion of the SSF can be so designed so that as it reorients as it swings about the swing joint, it presents the impinging chest wall tissues with a profile that changes over time (FIGS. 133A-F). During initial retraction, such a changing profile can automatically guide the relative positions of the SSF TRE and the patient's rib, gradually developing a safe hold on the rib while protecting the neurovascular bundle throughout.

Ribs rotate about their attachments to the spine and sternum, presenting a challenge to avoiding contact with the neurovascular bundle. Addressing this, another important element of our design can include a gap that avoids applying pressure to the neurovascular bundle regardless of the relative rotations of the rib and SSF TRE (FIG. 134). Such a gap can be formed by the space between a curved, descending SSF TRE shaft and a substantially flattened, or oblate spheroid fingertip mounted near the end of the shaft, making it impossible for the neurovascular bundle to impinge on the SSF TRE. The shape of such a space preserves a gap for the neurovascular bundle regardless of the orientation of the patient's rib as it contacts the SSF TRE. Even more, this shape preserves a protective gap for the neurovascular bundle over a wide range of rib sizes (i.e., patient sizes).

Still further, if a SSF TRE shaft is curved in a first plane, such a fingertip might or might not be oriented substantially in that same plane (FIG. 135). When retraction begins, a deviation of the oblate spheroid fingertip from the plane of the curve of the SSF TRE shaft can be advantageous. For example the rounded, blunt limb of the oblate spheroid fingertip can be oriented to impinge very early (i.e., at very low SSF TRE swing angles) upon the underside of the near margin of the adjacent rib, keeping the oblate spheroid fingertip low and the rib high right from the start, thus immediately presenting the protective gap to the neurovascular bundle even at very low degrees of SSF TRE rotation.

So, the SSF TRE incorporates a first, flat profile shape for easy insertion, a further, second SSF TRE profile shape providing mechanically automatic reorienting to the patient's tissues, and a final, achieved SSF TRE profile shape that gently and safely applies force to the patient's tissues without impinging upon the neurovascular bundle under load.

Yet another feature of our device is that the SSF TRE can be designed so that the tissue retraction elements are gathered up by, guided by, or contained within a compliant, elastic, flexible sheath, for example an elastomeric cover (above). One advantage of including a rubber sheath would be that the re-orientable tissue retraction elements are managed easily in a flat, thin form during handling in an operating room, as the surgeon inserts the tissue retraction elements. Another advantage is that a compliant material can keep the surfaces of the SSF TRE smooth. Still another advantage of a compliant sheath is that, if resilient, the SSF TRE automatically re-flattens itself upon removing it from the patient's incision, making the process of completing the surgery faster and easier.

Helical Shape Rotates on Oblique Axis to Grab Tissues

The Tissue Retraction Element, all or in part, can be substantially helical, creating a Helical Tissue Retraction Element (HTRE) (FIG. 136A). The advantage of the HTRE shape is that a helix (or a portion thereof) can present to the incision a nearly straight, thin first profile shape in a first rotational position, and a curving, grasping, or engaging profile shape when in a second rotational position. The helically shaped TRE might be designed to rotate from the first rotational position to the second rotational position under the influence of the forces experienced in the retraction process. This can be facilitated by off-center loading as above, so that automatic reorienting is achieved as retraction begins.

The axis of rotation can be arbitrarily oblique, as desired. Further, helical shapes are naturally gradually curved, so that the transition from a first profile orientation to a second profile orientation can be extremely smooth, gradual and without sudden changes in aspect or loading to the patient's tissues.

Still further, a smooth, helical TRE form can be designed so that all or a part of the process of inserting the tissue retraction elements into the incision automatically reorients the HTRE (FIGS. 136B and 136C). To facilitate this, the radius of curvature of such a helix forming the HTRE need not be constant over its depth. For example, if the lower, more vertical portion of an HTRE (with a small radius and a high pitch angle) presents a thin profile shape to the incision, so easing insertion (FIG. 136B), the overall helical form can be such that the upper portion of that HTRE (with a larger radius and lower pitch angle) smoothly impinges on the margin of the incision to drive HTRE rotation from a first rotational position to a second rotational position (FIG. 136C).

Tissue Retraction Elements on an Improved Thoracic Retractor

FIG. 137 shows some improved Tissue Retraction Elements as mounted on an automated thoracic retractor L50. The retractor L50 is motorized and automated. Tissue engagers L60 are for thoracotomy. A hand-held controller L70 communicates with retractor body L80 through cable L90.

FIG. 138 shows an embodiment of a complete retractor L00 for reducing the trauma to ribs during retraction for thoracotomy. Retractor L100 comprises a linear drive element L05 aligned with the direction of retraction L10. Retractor L00 has a first arm L15 and a second arm L20 oriented substantially perpendicular to the direction of retraction L10 with at least one of the arms L15 and L20 being moveable along linear drive element L05. For the purposes of this discussion two axes are important: first, the direction of retraction L10 and a vertical axis L11 that is approximately normal to a plane that is parallel with the skin of a patient. Each arm L15 and L20 have a self-balancing tissue engager associated with each arm. The two arms and associated self-balancing tissue engagers presented here are symmetrical, with the two self-balancing tissue engagers being mirror images, but asymmetrical assemblies can be made. Due to the symmetry here, description of only one arm and balancing assembly will suffice.

Consider first arm L15 in FIG. 139. Self-balancing tissue engager L25 comprises a first rotatable joint L105 that joins arm L15 to first balance bar L110 such that the middle L115 of first balance bar L110 attaches to the end L120 of arm L15. First rotatable joint L105 thus permits rotation about an axis L125 that is oriented approximately perpendicular to the direction of retraction L10 and approximately parallel to normal axis L11. First balance bar L110 has a first end L130 and a second end L135. Two second rotary joints L140 are located on first balance bar L110, with a second rotary joint L140 being placed at each of the two ends, first end L130 and second end L135, of balance bar L110. Both second rotary joints L140 permit rotation about an axis L145 that is oriented approximately perpendicular to the direction of retraction L10 and approximately parallel to normal axis L11. A second balance bar L150 attaches at its middle L155 to each of the rotary joints L140 on first end L130 and on second end L135 of first balance bar L110. Two third rotary joints L160 are located on second balance bar L150, with a third rotary joint L160 being placed at each of the two ends, first end L165 and second end L170, of second balance bar L150. Both third rotary joints L160 permit rotation about an axis L175 that also is oriented approximately perpendicular to the direction of retraction L10 and approximately parallel to normal axis L11. A descender post L180 attaches to third rotatory joints L160 as shown in FIG. 140 to permit rotation L185 of descender post L180 in the incision of the patient.

Note that there are, thus, four descender posts L180 in each self-balancing tissue engager L25. The combination of rotary joints L105, L140, and L160 with the first and second balance arms L110 and L150, respectively, creates a doubletree as described in Section F—Self-balancing Retractor Blades. Thus, the first balance bar L110 is a doubletree balance bar and the second balance bars L150 are swingletrees.

FIG. 140 shows a descender post L180 having a unique shape that enables sure engagement of a rib L205 without touching the neurovascular bundle L210. The cranial direction is the direction of retraction L10. Rib L205 is the cranial-most rib at the incision. Descender post L180 pushes against caudal margin L215 of rib L205 to retract rib L205. Descender post L180 comprises an elongate member L220 having a first end L225 and a second end L230, a first rib-forcing surface L235 adjacent to second end L230, a hook element L240 disposed adjacent the second end L230 of the elongate member L220, the hook element L240 comprising a first hook end L245 and a second hook end L250, and a second rib-forcing surface L255 between first hook end L245 second hook end L250, thereby defining a gap region L260 between the first rib-forcing surface L235 and the second rib-forcing surface L255. The gap region L260 is concave and possesses a length L265 along the direction of retraction L10 configured to place the second rib-forcing surface L255 substantially away from the neurovascular bundle L210.

The placement of second rib-forcing surface L255 should be such that second rib-forcing surface L255 contacts the bottom of rib L205 somewhere in the mid-region along the chord L270 of the rib L205, from approximately 20% to 80% from the caudal margin L215 of rib L205. This placement is important to ensure that neurovascular bundle L210 is positioned in the gap region L260 such that no part of descender post L180 contacts or in any ways exerts a force on neurovascular bundle L210. A descender post L180 on the opposite side of the incision retracting a caudal rib (not shown) does not have this consideration because the neurovascular bundle L210 is not on the cranial margin L280 of a rib. Nevertheless, descender posts L180 work well for the caudal rib, too.

FIG. 141 shows a descender post having a different shape, being more hook-shaped, like the descender post shown in FIG. 98A. FIG. 141 is a photograph from a thoracotomy in a 50 kg pig. It is clear in this picture there is a large gap region and that the neurovascular bundle is not being touched.

The axis of rotation L175 of third rotary joint L160 is shown in FIG. 140 and is positioned at the first end L225 of elongate member L220. Rotation about axis L175 causes first rib-forcing surface L235 to swing through an arc having substantial radius L275. FIG. 139 shows a descender post L180 in two positions, position L300 with the descender post aligned approximately perpendicular to the direction of retraction L10 and position L310 with the descender post L180 aligned approximately parallel to the direction of retraction L10. Position L310 is the deployed position, the position the descender post L180 assumes during retraction. Position L300 is the undeployed position. If all descender posts are in position L300, then the hook element L240 aligns approximately parallel with the incision, easing insertion between the ribs. This is the situation depicted in FIG. 130A. As retraction commences, the force at first rib forcing surface L235 causes descender post L180 to rotate into position L310. Thus descender posts L180 in self-balancing tissue engager L25 can self-deploy. The surgeon can insert both self-balancing tissue engagers into the incision with hook elements L240 of all descender posts L180 aligned approximately perpendicular to the direction of retraction (and thus parallel with the margins of the two ribs adjacent the incision). When retraction commences, the force applied to the first rib-forcing surfaces L235 on all descender posts L180 on both sides of the incision causes all descender posts L180 to automatically rotate into the deployed position L310 with second rib-forcing surface L255 coming into proper position under the rib, as depicted in FIG. 130B.

An elastic element can be added to self-balancing tissue engager L25 both to hold all components (balance arms and descender posts) in their undeployed position L300. This makes retractor L00 easier to handle. When the retractor is loaded, the elastic element only lightly opposes the forces at first rib-forcing surfaces, allowing the descender posts L180 to rotate into position L310 and the balance arms to balance the forces on the descender posts L180. Furthermore, when retraction is released, the elastic element will exert a light force to return the descender posts L180 to their undeployed position L300 facilitating removal from the incision. The elastic element can include simple rubber bands or other elastomeric components deployed at joints. Alternately, an elastomeric layer could be placed over the entire self-balancing tissue engager L25, such as would occur on coating the self-balancing tissue engager during a dip or molding process.

Elastomeric components can also be placed at the rib-forcing surfaces to pad the rib at those surfaces. These pads can be soft, but the pad at the first rib-forcing surface L235 should not be so thick as to deform into the gap region L260 and apply pressure to the neurovascular bundle L210.

The embodiments set forth herein are examples and are not intended to encompass the entirety of the invention. Many modifications and embodiments of the inventions set forth herein will come to mind to one skilled in the art to which these inventions pertain having the benefit of the teaching presented in the foregoing descriptions and the associated drawings. Therefore, it is to be understood that the inventions are not to be limited to the specific embodiments disclosed and that modifications and other embodiments are intended to be included within the scope of the appended claims. Although specific terms are used herein, they are used in a generic and descriptive sense only and not for the purposes of limitation.

REFERENCES

Baisden, C. E., L. V. Greenwald, et al. (1984). "Occult rib fractures and brachial plexus injury following median sternotomy for open-heart operations." Ann Thorac Surg 38(3): 192-194.

Bolotin, G., G. D. Buckner, et al. (2007). "A novel instrumented retractor to monitor tissue-disruptive forces during lateral thoracotomy." J Thorac Cardiovasc Surg 133 (4): 949-954.

Bonfils-Roberts, E. A. (1972). "The Rib Spreader: A Chapter in the History of Thoracic Surgery." Chest 61(5): 469-474.

Brown, M. D. and D. C. Holmes (1990). Apparatus and method for measuring spinal instability. U.S. Pat. No. 4,899,761

Buckner, G. D. and G. Bolotin (2006). Force-determining retraction device and associated method. US. Application 20060025656.

Chaudhuri, O., S. H. Parekh, et al. (2007). "Reversible stress softening of actin networks." Nature 445(7125): 295-298.

Dorfmann, A., B. A. Trimmer, et al. (2007). "A constitutive model for muscle properties in a soft-bodied arthropod." Journal of The Royal Society Interface 4(13): 257-269.

Erdogan, M., A. Erdogan, et al. (2005). "Prospective, Randomized, Placebo-controlled Study of the Effect of TENS on postthoracotomy pain and pulmonary function." World J Surg 29(12): 1563-1570.

Fleck, C. and D. Eifler (2003). "Deformation behaviour and damage accumulation of cortical bone specimens from the equine tibia under cyclic loading." J Biomech 36(2): 179-189.

Greenwald, L. V., C. E. Baisden, et al. (1983). "Rib fractures in coronary bypass patients: radionuclide detection." Radiology 148(2): 553-554.

Horgan, C. O., R. W. Ogden, et al. (2004). "A theory of stress softening of elastomers based on finite chain extensibility." Proceedings of the Royal Society A: Mathematical, Physical and Engineering Sciences 460(2046): 1737-1754.

Huszar, G. B. (1984). Method for determining the extensibility of selected non-excised tissue of the uterine cervix, ear or skin. U.S. Pat. No. 4,432,376

Kirton, R. S., A. J. Taberner, et al. (2004). "Strain softening behaviour in nonviable rat right-ventricular trabeculae, in the presence and the absence of butanedione monoxime." Exp Physiol 89(5): 593-604.

Kirton, R. S., A. J. Taberner, et al. (2004). "Strain softening is not present during axial extensions of rat intact right ventricular trabeculae in the presence or absence of 2,3-butanedione monoxime." Am J Physiol Heart Circ Physiol 286(2): H708-715.

Leveque, J.-L., L. Rasseneur, et al. (1981). Method of and apparatus for measurement of at least one mechanical property of an elastic material. U.S. Pat. No. 4,297,884

Lewis, R. J. (2007, 19 Jun. 2007). "The advent of VATS." In My Opinion. CTSNet, from http://www.ctsnet.org/sections/newsandviews/inmyopinion/articles/article-62.html.

Long, J. H., Jr. (1992). "Stiffness and damping forces in the intevertebral joints of blue marlin (Makaira nigricans)." J. exp. Biol. 162: 131-155.

Long, J. H., Jr., D. A. Pabst, et al. (1997). "Locomotor design of dolphin vertebral columns: bending mechanics and morphology of Delphinus delphis." J Exp Biol 200(1): 65-81.

McEwen, J. A., G. F. Auchinleck, et al. (1993). Advanced surgical retractor. US. Provenzano, P., R. Lakes, et al. (2001). "Nonlinear ligament viscoelasticity." Ann Biomed Eng 29(10): 908-914.

Rogers, M. L., L. Henderson, et al. (2002). "Preliminary findings in the neurophysiological assessment of intercostal nerve injury during thoracotomy." Eur J Cardiothorac Surg 21(2): 298-301.

Speich, J. E., L. Borgsmiller, et al. (2005). "ROK-induced cross-link formation stiffens passive muscle: reversible strain-induced stress softening in rabbit detrusor." Am J Physiol Cell Physiol 289(1): C12-21.

Vander Salm, T. J., B. S. Cutler, et al. (1982). "Brachial plexus injury following median sternotomy. Part II." J Thorac Cardiovasc Surg 83(6): 914-917.

Vanderby, R. and P. P. Provenzano (2003). "Collagen in connective tissue: from tendon to bone." J Biomech 36(10): 1523-1527.

Vincent, J. F. V. (1975). "Locust Oviposition: Stress Softening of the Extensible Intersegmental Membranes." Proceedings of the Royal Society of London. Series B, Biological Sciences (1934-1990) 188(1091): 189-201.

Wainwright, S. A., W. D. Biggs, et al. (1976). Mechanical Design in Organisms. New York, John Wiley & Sons.

Weisman, G., M. H. Pope, et al. (1980). "Cyclic loading in knee ligament injuries." Am J Sports Med 8(1): 24-30.

Woo, S. L.-Y., T. T. Manson, et al. (1999). Mechanical Testing of Ligaments and Tendons. Animal Models in Orthopaedic Research. Y. H. An and R. J. Friedman, CRC Press: 175-196.

Woodring, J. H., J. M. Royer, et al. (1985). "Upper rib fractures following median sternotomy." Ann Thorac Surg 39(4): 355-357.

Yin, L. and D. M. Elliott (2004). "A biphasic and transversely isotropic mechanical model for tendon: application to mouse tail fascicles in uniaxial tension." J Biomech 37(6): 907-916.

What is claimed is:

1. An automated control device for assisting a surgeon performing a procedure in which a patient's tissue is being deformed, comprising:
at least one tissue engager adapted to engage a patient's tissue;
a sensor configured to produce a first signal based on the deformation of the patient's tissue; and
an automated control system configured to adjust input from all the surgeon during the procedure based on a state of the patient's tissue during the procedure and to control the at least one tissue engager to deform the patient's tissue based on the first signal received from the sensor,
wherein the automated control system comprises a processor containing software instructions that, when executed by the processor, cause the automated control system to:
receive the first signal from the sensor during the procedure:
perform a plurality of measurements during the procedure based on the first signal over time:
calculate a variance in the plurality of measurements over an interval of time preceding an instantaneous measurement of the first signal, wherein the variance is a statistical distribution of amplitude of the plurality of measurements during the interval of time preceding the instantaneous measurement of the first signal;
compare the instantaneous measurement of the first signal to the calculated variance in the plurality of measurements over the interval of time preceding the instantaneous measurement;
detect the state of the patient's tissue based on the comparison; and
adjust, at least in part, a motion of the at least one tissue engager based on the detected state of the patient's tissue based on the comparison.

2. The automated control device of claim 1, wherein the processor containing software instructions that, when executed by the processor, cause the automated control system to predict a trauma to the patient's tissue based on the detected state.

3. The automated control device of claim 1, wherein the first signal comprises a force of deformation of the patient's tissue.

4. The automated control device of claim 1, wherein the plurality of measurements are comprised of a plurality of first time derivatives of the first signal.

5. The automated control device of claim 1, wherein the plurality of measurements are comprised of second time derivatives of the first signal.

6. The automated control device of claim 1, wherein the at least one tissue engager is configured to oscillate the patient's tissue.

7. The automated control device of claim 1, wherein the variance is comprised of a root-mean-square of the plurality of measurements.

8. The automated control device of claim 1, wherein the processor containing software instructions that, when executed by the processor, cause the automated control system to:
compare a ratio between the variance in the plurality of measurements and the instantaneous measurement; and
detect the state of the patient's tissue based on the comparison exceeding a threshold value, $T\_v$.

9. The automated control device of claim 1, wherein the automated control system has a sensitivity setting, $T\_s$, for detecting an onset of tissue trauma.

10. The automated control device of claim 8, wherein the processor containing software instructions that, when executed by the processor, cause the automated control system to alter deformation of the patient's tissue when the threshold value, $T\_V$, is exceeded.

11. The automated control device of claim 8, wherein the threshold value, $T\_v$, is configured to be determined by the surgeon performing the procedure.

12. The automated control device of claim 9, wherein the sensitivity setting, $T\_s$, is configured to be determined by the surgeon performing the procedure.

13. The automated control device of claim 10, wherein the processor containing software instructions that, when executed by the processor, cause the automated control system to alter the deformation of the patient's tissue by oscillating loading of the patient's tissue.

14. The automated control device of claim 13, wherein the processor containing software instructions that, when executed by the processor, cause the automated control system to modify the oscillation of the at least one tissue engager loading the patient's tissue.

15. The automated control device of claim 6, wherein the at least one tissue engager is configured to induce small scale failure of the patient's tissue, avoiding catastrophic failure of the patient's tissue.

16. The automated control device of claim 6, wherein the at least one tissue engager is configured to measure properties of the patient's tissue.

17. The automated control device of claim 16, wherein the measured properties of the patient's tissue comprise a tissue state signal.

18. The automated control device of claim 17, wherein the tissue state signal is used to guide additional manipulations of the patient's tissue.

19. The automated control device of claim 1, further comprising at least one motor configured to control the at least one tissue engager to deform the patient's tissue.

20. The automated control device of claim 19, wherein the at least one motor is controlled at least in part by the automated control system.

* * * * *